United States Patent
Berrebi-Bertrand et al.

(10) Patent No.: US 9,029,357 B2
(45) Date of Patent: May 12, 2015

(54) BENZAZOLE DERIVATIVES AS HISTAMINE H4 RECEPTOR LIGANDS

(71) Applicant: Bioprojet, Paris (FR)

(72) Inventors: Isabelle Berrebi-Bertrand, Pace (FR); Xavier Billot, Rennes (FR); Thierry Calmels, Melesse (FR); Marc Capet, Melesse (FR); Denis Danvy, Yvetot (FR); Stéphane Krief, Rennes (FR); Olivier Labeeuw, Fougeres (FR); Jeanne-Marie Lecomte, Paris (FR); Nicolas Levoin, Mordelles (FR); Xavier Ligneau, Saint Gregoire (FR); Philippe Robert, Pace (FR); Jean-Charles Schwartz, Paris (FR)

(73) Assignee: Bioprojet, Paris (FR)

( * ) Notice: Subject to any disclaimer, the term of this patent is extended or adjusted under 35 U.S.C. 154(b) by 0 days.

(21) Appl. No.: 14/317,024

(22) Filed: Jun. 27, 2014

(65) Prior Publication Data

US 2015/0004181 A1    Jan. 1, 2015

Related U.S. Application Data

(62) Division of application No. 13/825,989, filed as application No. PCT/EP2011/066782 on Sep. 27, 2011, now Pat. No. 8,802,664.

(30) Foreign Application Priority Data

Sep. 27, 2010    (EP) .................................... 10306038

(51) Int. Cl.

| | | |
|---|---|---|
| A61K 31/506 | (2006.01) |
| A61K 31/428 | (2006.01) |
| A61K 31/454 | (2006.01) |
| A61K 31/4545 | (2006.01) |
| A61K 31/496 | (2006.01) |
| A61K 31/5377 | (2006.01) |
| C07D 417/14 | (2006.01) |
| C07D 401/12 | (2006.01) |
| C07D 405/14 | (2006.01) |
| C07D 417/12 | (2006.01) |
| A61K 45/06 | (2006.01) |
| C07D 401/14 | (2006.01) |
| C07D 401/04 | (2006.01) |
| C07D 417/04 | (2006.01) |

(52) U.S. Cl.
CPC ............ *C07D 417/14* (2013.01); *C07D 401/12* (2013.01); *C07D 405/14* (2013.01); *C07D 417/12* (2013.01); *A61K 31/428* (2013.01); *A61K 31/454* (2013.01); *A61K 31/4545* (2013.01); *A61K 31/496* (2013.01); *A61K 31/5377* (2013.01); *A61K 45/06* (2013.01); *C07D 401/14* (2013.01); *A61K 31/506* (2013.01); *C07D 401/04* (2013.01); *C07D 417/04* (2013.01)

(58) Field of Classification Search
CPC . A61K 31/506; A61K 31/428; A61K 31/454; A61K 31/4545; A61K 31/496; A61K 31/5377
USPC ........ 514/210.21, 321, 367, 322, 318, 253.09
See application file for complete search history.

(56) References Cited

PUBLICATIONS

Deng et al., Organic Letters (2002), 4(23), 4017-4020.*

* cited by examiner

*Primary Examiner* — Niloofar Rahmani
(74) *Attorney, Agent, or Firm* — Stephen J. Weyer, Esq.; Stites & Harbison, PLLC.

(57) ABSTRACT

The present patent application concerns new ligands of the H4-receptor, their process of preparation and their therapeutic use.

9 Claims, No Drawings

BENZAZOLE DERIVATIVES AS HISTAMINE H4 RECEPTOR LIGANDS

This application is a divisional of application Ser. No. 13/825,989, filed May 21, 2013 (which is hereby incorporated by reference).

The present patent application concerns new ligands of the H4-receptor, their process of preparation and their therapeutic use.

Until recently, the pro-inflammatory actions of histamine were thought to be essentially mediated by the H1 receptor and H1 receptor antagonists have found large therapeutic applications in allergic manifestations like the anaphylactic shock, allergic rhinitis, dermatitis, pruritus, etc.

However these drugs essentially prevent the occurrence of major symptoms of these manifestations without modifying clearly the progressive development of the inflammatory process leading to chronic diseases like asthma in which, however, histamine release from mast-cells might represent an important trigger (reviewed in Galli et al, Nature, 2008, 454, 445).

The recent discovery of the histamine H4 receptor (H4R) has modified this landscape (reviewed in Thurmond et al, Nature Rev. Drug Disc., 2008, 7, 41). The H4R belongs to the superfamily of G-protein coupled heptahelical receptors and is expressed on the plasma membranes of a variety of immunocompetent/inflammatory cells, e.g. eosinophils, basophils, mast-cells or dendritic cells. The H4R has a chimiotactic role, controlling the afflux of e.g. mast-cells or eosinophils to inflammatory sites that is elicited by histamine release and, thereby plays a major role in the development of chronic inflammatory disorders. It also controls the activity of eosinophils and some classes of lymphocytes. Blockade of the H4R by antagonists or inverse agonists should therefore constitute a novel therapeutic approach in diseases like asthma, emphysema, allergic rhinitis, nasal congestion, bronchitis, chronic obstructive pulmonary disease, dermatitis, arthritis, psoriasis, colitis, etc. in which they could be used alone or in association with already used other classes of anti-inflammatory medications, namely H1R antagonists. In addition the utilisation of H4R antagonists/inverse agonists is also of potential interest in a variety of autoimmune diseases e.g. type I diabetes, Crohn's disease, multiple sclerosis, lupus, etc. . . . . The itch-preventing effect of some H4R antagonists in a rodent model (Bell et al, Br J Pharmacol, 2004, 142, 374) also suggests the use of these agents in pruritus, a manifestation only imperfectly controlled by available medications, namely H1R antagonists.

H4R antagonists/inverse agonists have not yet reached clinical uses and there is therefore a need for compounds displaying high potency and safety. In the present application a novel chemical class of H4R ligands is disclosed.

The instant invention thus relates to novel benzazoles derivatives as H4 receptor ligands, to their preparation and to their application in therapeutics.

According to a first object, the present invention concerns new compounds of formula (I):

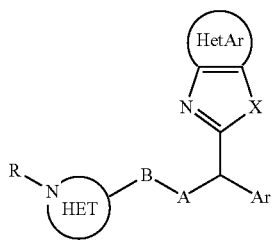

(I)

wherein:
X represents NR', S or O;
HetAr represents a phenyl or heteroaryl, optionally substituted with one or more substituents chosen from halogen, OR''' alkyl, cyano, NR''R''', —COR'', —COOR'', —CONR''R''', aryl, -alkylaryl;
R represents a lower alkyl or H;
R' represents H, lower alkyl, alkoxyalkyl or alkoxycarbonyl;
R'', R''' identical or different independently represent H or alkyl;
HET representing a non aromatic monocyclic heterocycle containing at least one nitrogen atom, which is linked to R;
B represents a single bond or an -alkyl- group;
A represents O, NH or S;
Ar is a mono or polycyclic aromatic or a mono or polycyclic heteroaromatic which can be optionally substituted with one or more of:
halo; azido; cyano; hydroxy; nitro;
alkyl; alkoxy; alkylsulfanyl; alkenyl; alkynyl; alkenyloxy; alkenyloxy; alkenylsulfanyl; alkynylsulfanyl; cycloalkoxy; cycloalkylalkyl;
whose alkyl, alkenyl, alkynyl or cycloalkyl part can be substituted with one or more of halo, hydroxy, polyhydroxy, alkoxy, hydroxyalkoxy, cyano, amino, aminoalkyl, alkylamino, dialkylamino, aminoalkylamino, aminoalkylaminocarbonyl, alkoxycarbonylamino, diarylmethylimino (where aryl is optionally substituted with one or more of hydroxy or halo), cycloalkenylimino (where cylalkenyl is optionally substituted with one or more of alkyl, OH), alkylsulfanyl, alkylsulfinyl, alkylsulfonyl, cycloalkyl, polycycloalkyl, cycloalkenyl, polycycloalkenyl, guanidino, alkylcarbonylguanidino, acylguanidino, cyanoguanidino, alkoxycarbonylguanidino, alkoxycarbonyl, alkoxycarbonylalkylamino, alkoxycarbonylalkylcycloalkyl, alkoxycarbonylheterocyclyl, aminocarbonyl, alkylaminocarbonyl, alkylcarbonyl, alkylcarbonylalkoxy, aryloxy, arylsulfanyl, arylsulfinyl, arylsulfonyl, heteroaryl, heterocyclyl (heterocyclyl being optionally substituted with one or more of oxo, amino, imino), heteroaryloxy, heterocyclyloxy, heteroarylamino, heterocyclylamino, hydrazinocarbonyl, hydroxyalkylcycloalkyl, N-alkyl(thioureido), phthalimido, ureido, oxocycloalkenylamino substituted with amino, carbamimidoylheterocyclyl;
amino; alkylamino; alkylcarbonyl; alkoxycarbonyl; alkylsulfanyl; alkylsulfinyl; alkylsulfonyl; alkylsulfonyloxy whose alkyl can be substituted with one or more of halo;
aminocarbonyl which can be N-substituted with one or two of alkyl, aryl, arylalkyl;
aryl; arylalkyl; aryloxy; arylalkoxy; arylalkylamino; arylalkylsulfanyl; heteroaryl; heteroaryloxy
whose (hetero)aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, alkylsulfinyl, alkylsulfonyl, nitro, cyanoalkyl, or fused with a non aromatic heterocycle;
heterocyclyl; heterocyclyloxy; heterocyclylalkoxy
whose heterocycle can be substituted with one or more of halogenoalkyl, acylamino, acyloxy, amino, alkyl, alkylamino, dialkylamino, aminoalkyl, oxo, carbamimidoyl, halo, hydroxy, hydroxyalkyl, hydroxymethyl, alkoxcarbonyl; or
fused with a non aromatic heterocycle (optionally substituted with one or more of halogens) or carbocycle;

as well as their enantiomers, diastereomers, mixtures thereof and pharmaceutically acceptable salts, tautomers, hydrates and solvates.

Unless specified otherwise, the terms used hereabove or hereafter have the meaning ascribed to them below:

"Halo" or "halogen" refers to fluorine, chlorine, bromine or iodine atom.

Halogenoalkyl refers to a C1-C9-alkyl moiety wherein one or more hydrogen atoms and refers in particular to perhaloalkyl.

"Perhaloalkyl" represents a C1-C9-alkyl moiety wherein all hydrogen atoms are substituted with same or different halogen atoms, for example, —CF₃, —CHF₂, —CCl₃, —CF₂Cl, —CH₂Cl, —CH₂CF₂—CF₃.

"Perhaloalkoxy" represents a perhaloalkyl linked via an oxygen atom, for example, —O—CF₃, —O—CHF₂, —O—CH₂CF₃.

"Alkyl" represents an aliphatic-hydrocarbon group which may be straight or branched having 1 to 20 carbon atoms in the chain unless specified otherwise. Preferred alkyl groups have 1 to 12 carbon atoms, more preferably have 1 to 6 carbon atoms in the chain; lower alkyls have preferably 1 to 4 carbon atoms. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alkenyl" refers to an aliphatic hydrocarbon group containing a carbon-carbon double bond and which may be straight or branched having 2 to 15 carbon atoms in the chain unless specified otherwise. Preferred alkenyl groups have 2 to 12 carbon atoms in the chain; and more preferably about 2 to 6 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkynyl" refers to an aliphatic hydrocarbon group containing a carbon-carbon triple bond and which may be straight or branched having 2 to 15 carbon atoms in the chain unless specified otherwise. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methyl-1-butynyl, n-pentynyl, 4,4-dimethyl-2-pentynyl, heptynyl, octynyl and decynyl.

"Carbocycle" refers to a saturated or saturated on unsaturated non aromatic mono- or multicyclic hydrocarbon ring system of 3 to 10 carbon atoms, preferably of 4 to 10 carbon atoms.

"Cycloalkyl" refers to a saturated non-aromatic mono- or multicyclic hydrocarbon ring system of 3 to 10 carbon atoms, preferably of 4 to 10 carbon atoms. Preferred ring sizes of rings of the ring system include 4 to 6 ring atoms. Exemplary monocyclic cycloalkyl include cyclopropyl, cyclobutyl, cyclopentyl, cyclohexyl, cycloheptyl, and the like. Exemplary multicyclic cycloalkyl include 1-decalin, norbornyl, adamant-(1- or 2-)yl.

"Aryl" refers to an aromatic monocyclic or multicyclic hydrocarbon ring system of 6 to 14 carbon atoms, preferably of 6 to 10 carbon atoms. Exemplary aryl groups include phenyl, naphthyl, indenyl, phenanthryl, biphenyl.

The terms "heterocycle" or "heterocyclic" refer to a saturated or partially unsaturated non aromatic stable 3 to 14, preferably 5 to 10-membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in the *Handbook of Chemistry and Physics,* 76th Edition, CRC Press, Inc., 1995-1996, pages 2-25 to 2-26, the disclosure of which is hereby incorporated by reference. Preferred non aromatic heterocyclic include, but are not limited to oxetanyl, tetrahydrofuranyl, dioxolanyl, tetrahydropyranyl, dioxanyl, pyrrolidinyl, piperidyl, morpholinyl, imidazolidinyl, pyranyl. Preferred saturated heterocycles are chosen from tetrahydrofuranyl, dioxolanyl, tetrahydropyranyl, dioxanyl, pyrrolidinyl, piperidyl, morpholinyl, imidazolidinyl, more preferably tetrahydrofuranyl, dioxolanyl, tetrahydropyranyl.

The term "heteroaryl" refers to a 5 to 14, preferably 5 to 10 membered aromatic mono-, bi- or multicyclic ring wherein at least one member of the ring is a hetero atom. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl.

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Alkyl", "cycloalkyl", "alkenyl", "alkynyl", "aryl", "heteroaryl", "heterocycle" also refers to the corresponding "alkylene", "cycloalkylene", "alkenylene", "alkynylene", "arylene", "heteroarylene", "heterocyclene" which are formed by the removal of two hydrogen atoms.

As used herein, "carbamimidoyl" also refers to "amidino".

A first group of compounds according to the invention may be defined as follows:

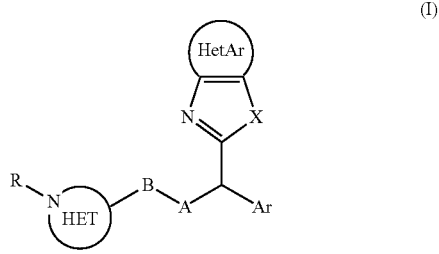

(I)

wherein:

X represents NR' or S;

HetAr represents a phenyl, optionally substituted with one or more substituents chosen from hydrogen, halogen, amino, alkyl;

R represents H or a lower alkyl;

R' represents H, alkyl, alkoxyalkyl, alkoxycarbonyl;

HET representing a non aromatic 5 or 6 membered heterocycle containing one nitrogen atom, which is linked to R;

B represents a single bond or a —CH₂— group;

A represents O, NH or S;

Ar is a thienyl, phenyl or naphtyl or 5 to 6 membered heteroaromatic where the phenyl can be optionally substituted with one or more of:

halo; azido; cyano; hydroxy; nitro; alkyl;

alkoxy; alkylsulfanyl; alkenyl; alkenylsulfanyl; alkynyl; alkenyloxy; alkenyloxy; cycloalkoxy; cyloalkylalkyl whose alkyl, alkenyl, alkynyl or cycloalkyl part can be substituted with one or more of halo, hydroxy, alkoxy, hydroxyalkoxy, cyano, amino, aminoalkyl, alkylamino, aminoalkylamino, dialkylamino, aminoalkylaminocarbonyl, alkoxycarbonylamino, diarylmethylimino (where aryl is optionally substituted with one or more of hydroxy or halo), cycloalkenylimino (where cylalkenyl is optionally substituted with one or more of alkyl, OH), alkylsulfanyl, alkylsulfonyl, cycloalkyl, (poly)cycloalkenyl, guanidino, alkylcarbonylguanidino, acylguanidino, alkoxycarbonylguanidino, alkoxycarbonyl, alkoxycarbonylalkylamino, alkoxycarbonylheterocyclyl, aminocarbonyl, alkylaminocarbonyl, alkylcarbonyl, alkylcarbonylalkoxy, aryloxy, arylsulfonyl, heteroaryl, heterocyclyl (heterocyclyl being optionally substituted with one or more of oxo, amino, imino), heterocyclylamino, hydrazinocarbonyl, N-alkyl(thioureido), phthalimido, ureido, oxocycloalkenylamino substituted with amino, carbamimidoylheterocyclyl;

amino; alkylamino; alkylcarbonyl; alkoxycarbonyl; alkylsulfanyl; alkylsulfonyl; alkylsulfonyloxy whose alkyl can be substituted with one or more of halo;

aminocarbonyl which can be N-substituted with one or two of alkyl, aryl, arylalkyl;

aryl; arylalkyl; aryloxy; arylalkoxy; arylalkylsulfanyl; heteroaryl; heteroaryloxy whose (hetero)aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, nitro, cyanoalkyl, or is fused with a non aromatic heterocycle;

heterocyclyloxy; heterocyclylalkoxy; heterocyclyl whose heterocycle can be substituted with one or more of halo, halogenoalkyl, acylamino, acyloxy, amino, alkyl, alkylamino, dialkylamino, aminoalkyl, oxo, carbamimidoyl, hydroxy, hydroxyalkyl; or fused with a non aromatic heterocycle (optionally substituted with one or more of halogens) or carbocycle;

as well as their enantiomers, diastereomers, mixtures thereof and pharmaceutically acceptable salts, tautomers, hydrates and solvates.

Further group of compounds are those of formula (I) where:

X represents NH or S; and/or
HetAr represents a phenyl; and/or
R represents methyl; and/or
HET represents a piperidine or pyrrolidine; and/or
HET represents a piperidine; and/or
B represents a single bond; and/or
A represents 0 or NH;
Ar is a phenyl which can be optionally substituted with one or more of:

halo; azido; cyano; hydroxy; nitro; alkyl;
alkoxy; alkylsulfanyl; alkenyl; alkynyl; alkenyloxy; alkenyloxy;

whose alkyl; alkenyl or alkynyl part can be substituted with one or more of halo, hydroxy, alkoxy, hydroxyalkoxy, cyano, amino, alkylamino, aminoalkylamino, alkylsulfanyl, alkylsulfonyl, cycloalkyl, (poly)cycloalkenyl, guanidino, acylguanidino, alkoxycarbonylguanidino, alkoxycarbonyl, alkoxycarbonylalkylamino, alkoxycarbonylheterocyclyl, aminocarbonyl, alkylaminocarbonyl, alkylcarbonyl, alkylcarbonylalkoxy, aryloxy, arylsulfonyl, heteroaryl, heterocyclyl, heterocyclylamino, hydrazinocarbonyl, N-alkyl(thioureido), phthalimido, ureido, oxocycloalkenylamino substituted with amino, carbamimidoylheterocyclyl;

amino; alkylamino; alkylcarbonyl; alkoxycarbonyl; alkylsulfanyl; alkylsulfonyl; alkylsulfonyloxy whose alkyl can be substituted with one or more of halo;

aminocarbonyl which can be N-substituted with one or two of alkyl, aryl, arylalkyl;

aryl; aryloxy; arylalkoxy; arylalkylsulfanyl; heteroaryl whose aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, nitro, cyanoalkyl, or is fused with a non aromatic heterocycle;

heterocyclyloxy; heterocyclylalkoxy whose heterocycle can be substituted with one or more of acylamino, acyloxy, amino, alkyl, carbamimidoyl, hydroxy, hydroxyalkyl; or fused with a non aromatic heterocycle;

as well as their enantiomers, diastereomers, mixtures thereof and pharmaceutically acceptable salts, tautomers, hydrates and solvates.

In particular, the compounds of formula (I) may be chosen from those of formula (I') below:

(I')

and (I") below:

(I")

where
Ar is defined as above; and/or
i is 0, 1, 2, or 3; and/or
j is 0, 1, 2, or 3; and/or
Y is chosen from halo, hydroxy, alkyl, perhalogenoalkyl, alkoxy; and/or
Z is chosen from halo, hydroxy, alkyl, alkoxy.
More particularly, in formula (I') and (I"):
i is 1, 2 or 3 and Y is chosen from halo, hydroxy, alkyl, perhalogenoalkyl, alkoxy; and/or
j is 0.

In one preferred embodiment, the present invention provides a compound selected from the group consisting of:
2-[(1-methylpiperidin-4-yloxy)phenylmethyl]benzothiazole
2-[(1-methylpyrrolidin-3-yloxy)phenylmethyl]benzothiazole
2-[(4-fluorophenyl)(1-methylpiperidin-4-yloxy)methyl]benzothiazole
2-[(4-chlorophenyl)(1-methylpiperidin-4-yloxy)methyl]benzothiazole
2-[(3-fluorophenyl)(1-methylpiperidin-4-yloxymethyl]benzothiazole
2-[(2-fluorophenyl)(1-methylpiperidin-4-yloxy)methyl]benzothiazole
2-[(1-methylpiperidin-4-yloxy)-p-tolylmethyl]benzothiazole
2-[(1-methylpiperidin-4-yloxy)(m-tolyl)methyl]benzothiazole (benzothiazol-2-yl-phenylmethyl)(1-methylpiperidin-4-yl)amine
2-[(2,3-dihydrobenzo[1,4]dioxin-6-yl)(1-methylpiperidin-4-yloxy)methyl]benzothiazole
2-[(3-methoxyphenyl)(1-methylpiperidin-4-yloxy)methyl]benzothiazole
2-[(2,4-difluorophenyl)(1-methylpiperidin-4-yloxy)methyl]benzothiazole
2-[(1-methylpiperidin-4-yloxy)thiophen-2-ylmethyl]benzothiazole
2-[(4-methoxyphenyl)(1-methylpiperidin-4-yloxy)methyl]benzothiazole
2-[(3,5-difluorophenyl)(1-methylpiperidin-4-yloxy)methyl]benzothiazole
2-[(1-methylpiperidin-4-yloxy)thiophen-3-ylmethyl]benzothiazole
2-[(1-methylpiperidin-4-yloxy)naphthalen-1-ylmethyl]benzothiazole
2-[(1-methylpiperidin-4-yloxy)naphthalen-2-ylmethyl]benzothiazole
2-[(1-methylpiperidin-4-yloxy)(5-methylthiophen-2-yl)methyl]benzothiazole
2-[benzo[1,3]dioxol-5-yl(1-methylpiperidin-4-yloxy)methyl]benzothiazole
[(benzothiazol-2-yl)(m-tolyl)methyl](1-methylpiperidin-4-yl)amine
2-[(3-allyloxyphenyl)(1-methylpiperidin-4-yloxy)methyl]benzothiazole
2-[(1-methylpiperidin-4-yloxy)(3-trifluoromethoxyphenyl)methyl]benzothiazole
2-[(1-methylpiperidin-4-yloxy)(4-trifluoromethoxyphenyl)methyl]benzothiazole
[benzothiazol-2-yl(3-methoxyphenyl)methyl](1-methylpiperidin-4-yl)amine
2-[(1-methylpiperidin-4-yloxy)(3-propoxy-phenyl)methyl]benzothiazole
2-[(3-bromo-phenyl)(1-methylpiperidin-4-yloxy)methyl]benzothiazole
2-[(1-methylpiperidin-4-yloxy)(3-phenoxy-phenyl)methyl]benzothiazole
5-methyl-2-[(1-methylpiperidin-4-yloxy)phenylmethyl]benzothiazole
2-[(1-methylpiperidin-4-yloxy)phenylmethyl]-1H-benzimidazole
2-[(1-methylpiperidin-4-yloxy)(3-trifluoromethylphenyl)methyl]benzothiazole
2-[(2,3-dihydrobenzofuran-5-yl)(1-methylpiperidin-4-yloxy)methyl]benzothiazole
5-fluoro-2-[(1-methylpiperidin-4-yloxy)phenylmethyl]benzothiazole
2-[(4-fluoro-3-methylphenyl)(1-methylpiperidin-4-yloxy)methyl]benzothiazole
[benzothiazol-2-yl(4-fluoro-3-methyl-phenyl)methyl](1-methylpiperidin-4-yl)amine
(benzothiazol-2-yl-p-tolylmethyl)(1-methylpiperidin-4-yl)amine
[(benzofuran-2-yl)(benzothiazol-2-yl)methyl](1-methylpiperidin-4-yl)amine
2-[(3-fluoro-5-methylphenyl)(1-methylpiperidin-4-yloxy)methyl]benzothiazole
[(1H-benzimidazol-2-yl)phenylmethyl](1-methylpiperidin-4-yl)amine
2-[(3-fluoro-5-methoxyphenyl)(1-methylpiperidin-4-yloxy)methyl]benzothiazole
2-[(3-iodophenyl)(1-methylpiperidin-4-yloxy)methyl]benzothiazole
[benzothiazol-2-yl(3-propoxyphenyl)methyl](1-methylpiperidin-4-yl)amine
[benzothiazol-2-yl(3-fluoro-5-methoxyphenyl)methyl](1-methylpiperidin-4-yl)amine
[benzothiazol-2-yl(3-fluoro-5-methylphenyl)methyl](1-methylpiperidin-4-yl)amine
2-[(3-benzyloxyphenyl)(1-methylpiperidin-4-yloxy)methyl]benzothiazole
2-[benzofuran-5-yl(1-methylpiperidin-4-yloxy)methyl]benzothiazole
2-[(3-ethoxyphenyl)(1-methylpiperidin-4-yloxy)methyl]benzothiazole
[benzothiazol-2-yl(3-iodophenyl)methyl](1-methylpiperidin-4-yl)amine
2-[(1-methylpiperidin-4-yloxy)(3-propoxyphenyl)methyl]-1H-benzimidazole
[(1H-benzimidazol-2-yl)(3-propoxyphenyl)methyl](1-methylpiperidin-4-yl)amine
2-[(3-iodophenyl)(1-methylpiperidin-4-yloxy)methyl]-1H-benzimidazole
(benzothiazol-2-ylpyridin-3-ylmethyl)(1-methylpiperidin-4-yl)amine
2-[biphenyl-3-yl(1-methylpiperidin-4-yloxy)methyl]benzothiazole
{3'-[benzothiazol-2-yl(1-methylpiperidin-4-yloxymethyl]biphenyl-3-yl}methanol
2-[(3-isopropoxyphenyl)(1-methylpiperidin-4-yloxy)methyl]benzothiazole
[benzothiazol-2-yl(3-propoxyphenyl)methyl](1-methylpiperidin-4-yl)amine
[benzothiazol-2-yl(3-propoxyphenyl)methyl](1-methylpiperidin-4-yl)amine
[benzothiazol-2-yl(1H-pyrrol-2-yl)methyl](1-methylpiperidin-4-yl)amine
[(1H-benzimidazol-2-yl)(3-trifluoromethylphenyl)methyl](1-methylpiperidin-4-yl)amine
[(1H-benzimidazol-2-yl)(3-trifluoromethoxyphenyl)methyl](1-methylpiperidin-4-yl)amine
[(1H-benzimidazol-2-yl)(3-ethylphenyl)methyl](1-methylpiperidin-4-yl)amine
3-[benzothiazol-2-yl(1-methylpiperidin-4-yloxy)methyl]phenol
2-[(1-methylpiperidin-4-yloxy)(3-pyridin-3-ylphenyl)methyl]benzothiazole
[(1H-benzimidazol-2-yl)(3-bromophenyl)methyl](1-methylpiperidin-4-yl)amine
[(1H-benzimidazol-2-yl)(3-benzyloxyphenyl)methyl](1-methylpiperidin-4-yl)amine
[(1H-benzimidazol-2-yl)(3-isopropylphenyl)methyl](1-methylpiperidin-4-yl)amine

[(1H-benzimidazol-2-yl)(3-isobutoxyphenyl)methyl](1-methylpiperidin-4-yl)amine
{(1H-benzimidazol-2-yl)[3-(3-methylbutoxy)phenyl]methyl}(1-methylpiperidin-4-yl)amine
[(1H-benzimidazol-2-yl)(3-butoxyphenyl)methyl](1-methylpiperidin-4-yl)amine
[(1H-benzimidazol-2-yl)(3-methoxyphenyl)methyl](1-methylpiperidin-4-yl)amine
trifluoromethanesulfonic acid 3-[benzothiazol-2-yl(1-methylpiperidin-4-yloxy)methyl]phenyl ester
trifluoromethanesulfonic acid 3-[benzothiazol-2-yl(1-methylpiperidin-4-yloxy)methyl]phenyl ester
[(1H-benzimidazol-2-yl)(3-cyclohexyl methoxyphenyl)methyl](1-methylpiperidin-4-yl)amine
[(1H-benzimidazol-2-yl)(3-fluorophenyl)methyl](1-methylpiperidin-4-yl)amine
[(1H-benzimidazol-2-yl)(3-methylsulfanylphenyl)methyl](1-methylpiperidin-4-yl)amine
[(1H-benzimidazol-2-yl)(3-hexylphenyl)methyl](1-methylpiperidin-4-yl)amine
[(1H-benzimidazol-2-yl)(3-isopropoxyphenyl)methyl](1-methylpiperidin-4-yl)amine
2-[(3-bromophenyl)(1-methylpiperidin-4-yloxy)methyl]-1H-benzimidazole
3'-[benzothiazol-2-yl(1-methylpiperidin-4-yloxy)methyl]biphenyl-3-ylamine
2-[(3-butylphenyl)(1-methylpiperidin-4-yloxy)methyl]benzothiazole
2-[biphenyl-3-yl(1-methylpiperidin-4-yloxy)methyl]-1H-benzimidazole
[benzothiazol-2-yl(3-bromophenyl)methyl](1-methylpiperidin-4-yl)amine
[(1H-benzimidazol-2-yl)(3-ethoxyphenyl)methyl](1-methylpiperidin-4-yl)amine
[(1H-benzimidazol-2-yl)(m-tolyl)methyl](1-methylpiperidin-4-yl)amine
[(1H-benzimidazol-2-yl)(3-phenoxyphenyl)methyl](1-methylpiperidin-4-yl)amine
{3'-[(1H-benzimidazol-2-yl)(1-methylpiperidin-4-yloxy)methyl]biphenyl-3-yl}methanol
3'-[(1H-benzimidazol-2-yl)(1-methylpiperidin-4-yloxy)methyl]biphenyl-3-ylamine
[benzothiazol-2-yl(3-isopropoxyphenyl)methyl](1-methylpiperidin-4-yl)amine
2-[(1-methylpiperidin-4-yloxy)(3-pyridin-3-ylphenyl)methyl]-1H-benzimidazole
1-{3-[(1H-benzimidazol-2-yl)(1-methylpiperidin-4-ylamino)methyl]phenyl}ethanone
[benzothiazol-2-yl(3-butoxyphenyl)methyl](1-methylpiperidin-4-yl)amine
2-[(3-butoxyphenyl)(1-methylpiperidin-4-yloxy)methyl]benzothiazole
[benzothiazol-2-yl(3-cyclohexylmethoxyphenyl)methyl](1-methylpiperidin-4-yl)amine
[(1H-benzimidazol-2-yl)biphenyl-3-ylmethyl](1-methylpiperidin-4-yl)amine
[(1H-benzimidazol-2-yl)(3-pentyloxyphenyl)methyl](1-methylpiperidin-4-yl)amine
2-[(2'-methoxybiphenyl-3-yl)(1-methylpiperidin-4-yloxy)methyl]benzothiazole
2-[(1-methylpiperidin-4-yloxy)(3'-nitrobiphenyl-3-yl)methyl]benzothiazole
{3'-[benzothiazol-2-yl(1-methylpiperidin-4-yloxy)methyl]biphenyl-3-yl}acetonitrile
2-[(3'-methoxybiphenyl-3-yl)(1-methylpiperidin-4-yloxy)methyl]benzothiazole
2-[(4'-methoxybiphenyl-3-yl)(1-methylpiperidin-4-yloxy)methyl]benzothiazole
[benzothiazol-2-yl(3-benzyloxyphenyl)methyl](1-methylpiperidin-4-yl)amine
(benzothiazol-2-ylbiphenyl-3-ylmethyl)(1-methylpiperidin-4-yl)amine
{(1H-benzimidazol-2-yl)[3-(4-fluorobenzyloxy)phenyl]methyl}(1-methylpiperidin-4-yl)amine
[(1H-benzimidazol-2-yl)(3-benzylsulfanylphenyl)methyl](1-methylpiperidin-4-yl)amine
{(1H-benzimidazol-2-yl)[3-(3-fluorobenzyloxy)phenyl]methyl}(1-methylpiperidin-4-yl)amine
{(1H-benzimidazol-2-yl)[3-(2-phenoxyethoxy)phenyl]methyl}(1-methylpiperidin-4-yl)amine
[benzothiazol-2-yl(3-benzylsulfanylphenyl)methyl](1-methylpiperidin-4-yl)amine
1-{3'-[(1H-benzimidazol-2-yl)(1-methylpiperidin-4-yloxy)methyl]biphenyl-4-yl}ethanone
2-[(3'-fluoro-biphenyl-3-yl)(1-methylpiperidin-4-yloxy)methyl]-1H-benzimidazole
1-{3'-[(1H-benzimidazol-2-yl)(1-methylpiperidin-4-yloxy)methyl]biphenyl-3-yl}ethanone
[benzothiazol-2-yl(3-methylsulfanylphenyl)methyl](1-methylpiperidin-4-yl)amine
[(3-allyloxyphenyl)(1H-benzimidazol-2-yl)methyl](1-methylpiperidin-4-yl)amine
{(1H-benzimidazol-2-yl)[3-(2-fluorobenzyloxy)phenyl]methyl}(1-methylpiperidin-4-yl)amine
2-[(1-methylpiperidin-4-yloxy)(2'-methylsulfanylbiphenyl-3-yl)methyl]-1H-benzimidazole
2-[(4'-fluorobiphenyl-3-yl)(1-methylpiperidin-4-yloxy)methyl]-1H-benzimidazole
2-[(1-methylpiperidin-4-yloxy)(3'-methylsulfanylbiphenyl-3-yl)methyl]-1H-benzimidazole
2-[(3-iodophenyl)(1-methylpiperidin-4-yloxy)methyl]benzothiazole
2-[(3-iodophenyl)(1-methylpiperidin-4-yloxy)methyl]benzothiazole
2-[(1-methylpiperidin-4-yloxy)(4'-trifluoromethylbiphenyl-3-yl)methyl]-1H-benzimidazole
{(1H-benzimidazol-2-yl)[3-(tetrahydropyran-2-yloxy)phenyl]methyl}(1-methylpiperidin-4-yl)amine
2-[(2'-chlorobiphenyl-3-yl)(1-methylpiperidin-4-yloxy)methyl]-1H-benzimidazole
2-[(3',4'-dichlorobiphenyl-3-yl)(1-methylpiperidin-4-yloxy)methyl]-1H-benzimidazole
{3'-[(1H-benzimidazol-2-yl)(1-methylpiperidin-4-yloxy)methyl]biphenyl-2-yl}methanol
{(1H-benzimidazol-2-yl)[3-(4-methoxybenzyloxy)phenyl]methyl}(1-methylpiperidin-4-yl)amine
{(1H-benzimidazol-2-yl)[3-(3-methoxybenzyloxy)phenyl]methyl}(1-methylpiperidin-4-yl)amine
3-[(1H-benzimidazol-2-yl)(1-methylpiperidin-4-ylamino)methyl]phenol
{3'-[benzothiazol-2-yl(1-methylpiperidin-4-yloxy)methyl]biphenyl-2-yl}methanol
2-[(1-methylpiperidin-4-yloxy)(3'-methylsulfanylbiphenyl-3-yl)methyl]benzothiazole
{(1H-benzimidazol-2-yl)[3-(2-methylbenzyloxy)phenyl]methyl}(1-methylpiperidin-4-yl)amine
{(1H-benzimidazol-2-yl)[3-(4-methylbenzyloxy)phenyl]methyl}(1-methylpiperidin-4-yl)amine
[(1H-benzimidazol-2-yl)(3-nitrophenyl)methyl](1-methylpiperidin-4-yl)amine
[(3-azidophenyl)(1H-benzimidazol-2-yl)methyl](1-methylpiperidin-4-yl)amine 2-[(3',4'-dichlorobiphenyl-3-yl)(1-methylpiperidin-4-yloxy) methyl]benzothiazole
{(1H-benzimidazol-2-yl)[3-(2-ethoxyethoxy)phenyl]methyl}(1-methylpiperidin-4-yl)amine
[(1H-benzimidazol-2-yl)(3-pent-4-enyloxyphenyl)methyl](1-methylpiperidin-4-yl)amine
2-[(4'-fluorobiphenyl-3-yl)(1-methylpiperidin-4-yloxy)methyl]benzothiazole
2-[(2'-fluorobiphenyl-3-yl)(1-methylpiperidin-4-yloxy)methyl]benzothiazole
{3'-[(1H-benzimidazol-2-yl)(1-methylpiperidin-4-yloxy) methyl]biphenyl-4-yl}carbamic acid tert-butyl ester
2-[(3'-fluorobiphenyl-3-yl)(1-methylpiperidin-4-yloxy)methyl]benzothiazole
2-[(1-methylpiperidin-4-yloxy)(4'-trifluoromethylbiphenyl-3-yl)methyl]benzothiazole
2-[(1-methylpiperidin-4-yloxy)(2',3',4'-trifluorobiphenyl-3-yl)methyl]benzothiazole
2-[(2'-fluorobiphenyl-3-yl)(1-methylpiperidin-4-yloxy)methyl]-1H-benzimidazole
{3'-[benzothiazol-2-yl(1-methylpiperidin-4-yloxy)methyl] biphenyl-4-yl}carbamic acid tert-butyl ester
[(1H-benzimidazol-2-yl)(3-furan-2-ylphenyl)methyl](1-methylpiperidin-4-yl)amine
[(1H-benzimidazol-2-yl)(3-but-3-enyloxyphenyl)methyl](1-methylpiperidin-4-yl)amine
{(1H-benzimidazol-2-yl)[3-(4-methylpentyloxy)phenyl] methyl}(1-methylpiperidin-4-yl)amine
2-[(1-methylpiperidin-4-yloxy)(3-pyrazol-1-ylphenyl)methyl]benzothiazole
2-[(3-benzylsulfanylphenyl)(1-methylpiperidin-4-yloxy) methyl]benzothiazole
{(1H-benzimidazol-2-yl)[3-(2,5-difluoro-benzyloxy)phenyl]methyl}(1-methylpiperidin-4-yl)amine
2-[(3-benzylsulfanylphenyl)(1-methylpiperidin-4-yloxy) methyl]-1H-benzimidazole
2-[(2-chlorophenyl)(1-methylpiperidin-4-yloxy)methyl]-1H-benzimidazole
2-[(3-ethylphenyl)(1-methylpiperidin-4-yloxy)methyl]benzothiazole
2-[(3-ethylsulfanylphenyl)(1-methylpiperidin-4-yloxy)methyl]-1H-benzimidazole
{3-[(1H-benzimidazol-2-yl)(1-methylpiperidin-4-yloxy) methyl]phenylsulfanyl}acetic acid methyl ester
2-[(3-fluorophenyl)(1-methylpiperidin-4-yloxy)methyl]-1H-benzimidazole
2-[[3-(2,5-difluorobenzyloxy)phenyl](1-methylpiperidin-4-yloxy)methyl]benzothiazole
2-{3-[(1H-benzimidazol-2-yl)(1-methylpiperidin-4-yloxy) methyl]phenylsulfanyl}ethanol
2-{3-[benzothiazol-2-yl(1-methylpiperidin-4-yloxy)methyl] phenylsulfanyl}ethanol
2-[(3-ethylsulfanylphenyl)(1-methylpiperidin-4-yloxy)methyl]benzothiazole
{3-[benzothiazol-2-yl(1-methylpiperidin-4-yloxy)methyl] phenylsulfanyl}acetic acid methyl ester
2-[[3-(2,3-difluorobenzyloxy)phenyl](1-methylpiperidin-4-yloxy)methyl]benzothiazole
{(1H-benzimidazol-2-yl)[3-(2,3-difluoro-benzyloxy)phenyl]methyl}(1-methylpiperidin-4-yl)amine
2-[[3-(2-fluoroethoxy)phenyl](1-methylpiperidin-4-yloxy) methyl]benzothiazole
2-[(1-methylpiperidin-4-yloxy)(m-tolyl)methyl]-1H-benzimidazole
5,6-dichloro-2-[(1-methylpiperidin-4-yloxy)phenyl-methyl]-1H-benzimidazole
5-fluoro-2-[(1-methylpiperidin-4-yloxy)phenyl-methyl]-1H-benzimidazole
2-[(2-fluorophenyl)(1-methylpiperidin-4-yloxy)methyl]-1H-benzimidazole
2-[(1-methylpiperidin-4-yloxy)(3-pent-4-enyloxy-phenyl) methyl]benzothiazole
2-{(1-methylpiperidin-4-yloxy)[3-(4,4,4-trifluoro-butoxy) phenyl]methyl}benzothiazole
5-bromo-2-[(1-methylpiperidin-4-yloxy)phenyl-methyl]-1H-benzimidazole
2-[[3-(3-fluorobenzyloxy)phenyl](1-methylpiperidin-4-yloxy)methyl]benzothiazole
3-[(1H-benzimidazol-2-yl)(1-methylpiperidin-4-yloxy)methyl]benzonitrile
2-[[3-(furan-2-ylmethylsulfanyl)phenyl](1-methylpiperidin-4-yloxy)methyl]-1H-benzimidazole
((1H-benzimidazol-2-yl)-{3-[3-(2-methyl-[1,3]dioxolan-2-yl)-propoxy]phenyl}methyl)(1-methylpiperidin-4-yl) amine
{(1H-benzimidazol-2-yl)[3-(4,4,4-trifluoro-butoxy)phenyl] methyl}(1-methylpiperidin-4-yl)amine
2-[[3-(3-fluoropropoxy)phenyl](1-methylpiperidin-4-yloxy) methyl]benzothiazole
2-[(1-methylpiperidin-4-yloxy)-p-tolyl-methyl]-1H-benzimidazole
2-{(1-methylpiperidin-4-yloxy)[3-(3,3,3-trifluoro-propoxy) phenyl]methyl}benzothiazole
2-[(4-fluorophenyl)(1-methylpiperidin-4-yloxy)methyl]-1H-benzimidazole
{(1H-benzimidazol-2-yl)[3-(2-fluoro-ethoxy)phenyl]methyl}(1-methylpiperidin-4-yl)amine
((1H-benzimidazol-2-yl)-{3-[2-(6,6-dimethyl-bicyclo [3.1.1]hept-2-en-2-yl)ethoxy]phenyl}methyl)(1-methylpiperidin-4-yl)amine
2-[(1-methylpiperidin-4-yloxy)(4'-trifluoromethoxy-biphenyl-3-yl)methyl]-1H-benzimidazole
2-[(4'-methoxybiphenyl-3-yl)(1-methylpiperidin-4-yloxy) methyl]-1H-benzimidazole
2-[(3-benzo[1,3]dioxol-5-ylphenyl)(1-methylpiperidin-4-yloxy)methyl]-1H-benzimidazole
2-[[3-(3-methoxybenzyloxy)phenyl](1-methylpiperidin-4-yloxy)methyl]benzothiazole
5-{3-[benzothiazol-2-yl(1-methylpiperidin-4-yloxy)methyl] phenoxy}pentan-2-one
2-{(1-methylpiperidin-4-yloxy)[3-(3-trifluoromethyl-benzyloxy)phenyl]methyl}benzothiazole
4-[benzothiazol-2-yl(3-bromo-phenyl)methoxy]-1,1-dimethylpiperidinium
2-(3-{3-[(1H-benzimidazol-2-yl)(1-methylpiperidin-4-yloxy)methyl]phenyl}prop-2-ynyl)isoindole-1,3-dione
3-{3-[(1H-benzimidazol-2-yl)(1-methylpiperidin-4-yloxy) methyl]phenyl}prop-2-yn-1-ol
4-{3-[(1H-benzimidazol-2-yl)(1-methylpiperidin-4-yloxy) methyl]phenyl}but-3-yn-1-ol
5-{3-[(1H-benzimidazol-2-yl)(1-methylpiperidin-4-yloxy) methyl]phenyl}pent-4-yn-1-ol
2-[(1-methylpiperidin-4-yloxy)-o-tolyl-methyl]-1H-benzimidazole
3-{3-[(1H-benzimidazol-2-yl)(1-methylpiperidin-4-yloxy) methyl]phenyl}prop-2-ynylamine
2-[(3-ethynylphenyl)(1-methylpiperidin-4-yloxy)methyl]-1H-benzimidazole
2-{(1-methylpiperidin-4-yloxy)[3-(3-nitro-benzyloxy)phenyl]methyl}benzothiazole
3-[benzothiazol-2-yl(1-methylpiperidin-4-yloxy)methyl] benzonitrile 2-{(1-methylpiperidin-4-yloxy)[3-(1H-[1,2,3]triazol-4-yl)phenyl]methyl}-1H-benzimidazole
3-[benzothiazol-2-yl(1-methylpiperidin-4-yloxy)methyl]benzoic acid methyl ester
2-[(1-methylpiperidin-4-yloxy)phenyl-methyl]-3H-benzimidazol-4-ylamine
2-[(1-methylpiperidin-4-yloxy)(3-methylsulfanyl-phenyl)methyl]benzothiazole
2-[(1-methylpiperidin-4-yloxy)(3-methylsulfanyl-phenyl)methyl]-1H-benzimidazole
2-[(3-methanesulfonylphenyl)(1-methylpiperidin-4-yloxy)methyl]benzothiazole
2-[(4-bromophenyl)(1-methylpiperidin-4-yloxy)methyl]-1H-benzimidazole
3-{3-[benzothiazol-2-yl(1-methylpiperidin-4-yloxy)methyl]phenyl}acrylic acid tert-butyl ester
3-[benzothiazol-2-yl(1-methylpiperidin-4-yloxy)methyl]benzoic acid ethyl ester
{3-[benzothiazol-2-yl(1-methylpiperidin-4-yloxy)methyl]phenyl}methanol
3-{3-[benzothiazol-2-yl(1-methylpiperidin-4-yloxy)methyl]phenyl}propionic acid tert-butyl ester
2-[[3-(2-benzenesulfonylvinyl)phenyl](1-methylpiperidin-4-yloxy)methyl]benzothiazole
2-[(1-methylpiperidin-4-yloxy)phenyl-methyl]-3H-benzimidazol-4-ol
[benzothiazol-2-yl(4'-methoxy-biphenyl-3-yl)methyl](1-methylpiperidin-4-yl)amine
2-[[3-(2-methanesulfonylvinyl)phenyl](1-methylpiperidin-4-yloxy)methyl]benzothiazole
2-[(2-chloro-4-methylphenyl)(1-methylpiperidin-4-yloxy)methyl]-1H-benzimidazole
5-{3-[benzothiazol-2-yl(1-methylpiperidin-4-yloxy)methyl]phenyl}pyrimidin-2-ol
2-[(3-tert-butylsulfanylphenyl)(1-methylpiperidin-4-yloxy)methyl]-1H-benzimidazole
2-[(1-methylpiperidin-4-yloxy)(3-pyrimidin-5-yl-phenyl)methyl]benzothiazole
3-{3-[benzothiazol-2-yl(1-methylpiperidin-4-yloxy)methyl]phenyl}acrylonitrile
2-[(1-methylpiperidin-4-yloxy)(3-vinyl-phenyl)methyl]benzothiazole
3-[benzothiazol-2-yl(1-methylpiperidin-4-yloxy)methyl]-N-benzyl-N-methylbenzamide
3-[benzothiazol-2-yl(1-methylpiperidin-4-yloxy)methyl]-N-propylbenzamide
2-[(2,4-difluorophenyl)(1-methylpiperidin-4-yloxy)methyl]-1H-benzimidazole
[(1H-benzimidazol-2-yl)(4'-methoxy-biphenyl-3-yl)methyl](1-methylpiperidin-4-yl)amine
3-[benzothiazol-2-yl(1-methylpiperidin-4-yloxy)methyl]-N-methyl-N-phenylbenzamide
3-[(1H-benzimidazol-2-yl)(1-methylpiperidin-4-yloxy)methyl]phenylamine
2-[(3-chlorophenyl)(1-methylpiperidin-4-yloxy)methyl]-1H-benzimidazole
2-[(4-chlorophenyl)(1-methylpiperidin-4-yloxy)methyl]-1H-benzimidazole
3-{3-[benzothiazol-2-yl(1-methylpiperidin-4-yloxy)methyl]phenyl}prop-2-yn-1-ol
3-{3-[benzothiazol-2-yl(1-methylpiperidin-4-yloxy)methyl]phenoxymethyl}-phenylamine
2-{3-[benzothiazol-2-yl(1-methylpiperidin-4-yloxy)methyl]phenylsulfanyl}ethanol
2-{3-[benzothiazol-2-yl(1-methylpiperidin-4-yloxy)methyl]phenylsulfanyl}ethanol
2-[(3-azidophenyl)(1-methylpiperidin-4-yloxy)methyl]-1H-benzimidazole
2-{(1-methylpiperidin-4-yloxy)[3-(2-pyrazin-2-yl-ethylsulfanyl)phenyl]methyl}-1H-benzimidazole
2-{(1-methylpiperidin-4-yloxy)[3-(2-pyrazin-2-yl-ethylsulfanyl)phenyl]methyl}benzothiazole
{3-[benzothiazol-2-yl(1-methylpiperidin-4-yloxy)methyl]phenyl}benzyl-amine
3-{3-[(1H-benzimidazol-2-yl)(1-methylpiperidin-4-yloxy)methyl]phenylsulfanyl}-3-methyl-butan-1-ol
4-{3-[benzothiazol-2-yl(1-methylpiperidin-4-yloxy)methyl]phenyl}but-3-yn-1-ol
5-{3-[benzothiazol-2-yl(1-methylpiperidin-4-yloxy)methyl]phenyl}pent-4-yn-1-ol
4-{3-[benzothiazol-2-yl(1-methylpiperidin-4-yloxy)methyl]phenyl}butan-1-ol
(1-{3-[benzothiazol-2-yl(1-methylpiperidin-4-yloxy)methyl]phenylsulfanylmethyl}-cyclopropyl)acetic acid methyl ester
2-{(1-methylpiperidin-4-yloxy)[3-(2-[1,2,3]triazol-2-yl-ethylsulfanyl)phenyl]methyl}benzothiazole
2-{(1-methylpiperidin-4-yloxy)[3-(2-[1,2,3]triazol-1-yl-ethylsulfanyl)phenyl]methyl}benzothiazole
3-{3-[benzothiazol-2-yl(1-methylpiperidin-4-yloxy)methyl]phenylsulfanyl}-3-methyl-butan-1-ol
2-[(1-methylpiperidin-4-yloxy)(3-morpholin-4-yl-phenyl)methyl]benzothiazole
2-{3-[benzothiazol-2-yl(1-methylpiperidin-4-yloxy)methyl]phenoxy}ethanol
2-[(1-methylpiperidin-4-yloxy)(3-vinyl-phenyl)methyl]-1H-benzimidazole
3-{3-[(1H-benzimidazol-2-yl)(1-methylpiperidin-4-yloxy)methyl]phenylsulfanyl}propan-1-ol
1-{3-[(1H-benzimidazol-2-yl)(1-methylpiperidin-4-yloxy)methyl]phenylsulfanyl}propan-2-ol
4-{3-[(1H-benzimidazol-2-yl)(1-methylpiperidin-4-yloxy)methyl]phenylsulfanyl}butan-1-ol
2-{3-[(1H-benzimidazol-2-yl)(1-methylpiperidin-4-yloxy)methyl]phenylsulfanyl}ethylamine
2-{(1-methylpiperidin-4-yloxy)[3-(2-methylsulfanyl-ethoxy)phenyl]methyl}benzothiazole
2-[(1-methylpiperidin-4-yloxy)(2-trifluoromethoxy-phenyl)methyl]-1H-benzimidazole
2-[(1-methylpiperidin-4-yloxy)-p-tolylmethyl]-1H-benzimidazole
2-[(1-methylpiperidin-4-yloxy)-p-tolyl-methyl]-1H-benzimidazole
3-{3-[benzothiazol-2-yl(1-methylpiperidin-4-yloxy)methyl]phenylsulfanyl}propan-1-ol
1-{3-[benzothiazol-2-yl(1-methylpiperidin-4-yloxy)methyl]phenylsulfanyl}propan-2-ol
4-{3-[benzothiazol-2-yl(1-methylpiperidin-4-yloxy)methyl]phenylsulfanyl}butan-1-ol
2-(1-{3-[(1H-benzimidazol-2-yl)(1-methylpiperidin-4-yloxy)methyl]phenylsulfanylmethyl}-cyclopropyl)ethanol
3-{3-[benzothiazol-2-yl(1-methylpiperidin-4-yloxy)methyl]phenoxy}propan-1-ol
2-{3-[benzothiazol-2-yl(1-methylpiperidin-4-yloxy)methyl]phenylsulfanyl}-N-methylacetamide
2-{(1-methylpiperidin-4-yloxy)[3-(2H-pyrazol-3-yl)phenyl]methyl}benzothiazole
2-[(3-bromo-4-methylphenyl)(1-methylpiperidin-4-yloxy)methyl]-1H-benzimidazole
2-[(2-bromophenyl)(1-methylpiperidin-4-yloxy)methyl]-1H-benzimidazole 2-{3-[benzothiazol-2-yl(1-methylpiperidin-4-yloxy)methyl]
  phenylsulfanyl}acetamide
{3-[benzothiazol-2-yl(1-methylpiperidin-4-yloxy)methyl]
  phenylsulfanyl}acetic acid hydrazide
2-{(1-methylpiperidin-4-yloxy)[3-(pyridin-4-ylmethoxy)
  phenyl]methyl}benzothiazole
4-{3-[benzothiazol-2-yl(1-methylpiperidin-4-yloxy)methyl]
  phenoxy}butan-1-ol
2-[[3-(furan-2-ylmethoxy)phenyl](1-methylpiperidin-4-
  yloxy)methyl]benzothiazole
2-(1-{3-[benzothiazol-2-yl(1-methylpiperidin-4-yloxy)me-
  thyl]phenylsulfanylmethyl}-cyclopropyl)ethanol
2-{3-[benzothiazol-2-yl(1-methylpiperidin-4-yloxy)methyl]
  phenylsulfanyl}ethylamine
1-{3-[benzothiazol-2-yl(1-methylpiperidin-4-yloxy)methyl]
  benzyloxy}propan-2-one
2-{3-[benzothiazol-2-yl(1-methylpiperidin-4-yloxy)methyl]
  phenoxy}ethylamine
2-[(1-methylpyrrolidin-3-yloxy)phenyl-methyl]-1H-benz-
  imidazole
[(1H-benzimidazol-2-yl)-p-tolyl-methyl](1-methylpiperi-
  din-4-yl)amine
2-[(3-ethylsulfanyl-4-methylphenyl)(1-methylpiperidin-4-
  yloxy)methyl]-1H-benzimidazole
1-(3-{3-[benzothiazol-2-yl(1-methylpiperidin-4-yloxy)me-
  thyl]phenyl}prop-2-ynyloxy)-propan-2-one
1-(3-{3-[benzothiazol-2-yl(1-methylpiperidin-4-yloxy)me-
  thyl]phenyl}prop-2-ynyloxy)-propan-2-ol
2-[[3-(2-methoxyethoxy)phenyl](1-methylpiperidin-4-
  yloxy)methyl]benzothiazole
N-(2-{3-[(1H-benzimidazol-2-yl)(1-methylpiperidin-4-
  yloxy)methyl]phenylsulfanyl}ethyl)guanidine
(2-{3-[benzothiazol-2-yl(1-methylpiperidin-4-yloxy)me-
  thyl]phenoxy}ethyl)methyl-amine
2-[(1-methylpiperidin-4-yloxy)(3-trifluoromethoxy-phenyl)
  methyl]-1H-benzimidazole
2-[(2-chlorophenyl)(1-methylpiperidin-4-yloxy)methyl]
  benzothiazole
4-{3-[benzothiazol-2-yl(1-methylpiperidin-4-yloxy)methyl]
  phenyl}but-3-ynylamine
2-{(1-methylpiperidin-4-yloxy)[3-(pyridin-2-ylmethoxy)
  phenyl]methyl}benzothiazole
2-{(1-methylpiperidin-4-yloxy)[3-(pyridin-3-ylmethoxy)
  phenyl]methyl}benzothiazole
2-[(3-Cyclohexylmethoxyphenyl)(1-methylpiperidin-4-
  yloxy)methyl]benzothiazole
4-{3-[(1H-benzimidazol-2-yl)(1-methylpiperidin-4-yloxy)
  methyl]phenyl}but-3-ynylamine
5-{3-[benzothiazol-2-yl(1-methylpiperidin-4-yloxy)methyl]
  phenyl}pent-4-ynylamine
3-{3-[(1H-benzimidazol-2-yl)(1-methylpiperidin-4-yloxy)
  methyl]phenylsulfanyl}propane-1,2-diol
5-{3-[benzothiazol-2-yl(1-methylpiperidin-4-yloxy)methyl]
  phenyl}pentylamine
2-{3-[benzothiazol-2-yl(1-ethyl-piperidin-4-yloxy)methyl]
  phenoxy}ethylamine
2-{3-[(1H-benzimidazol-2-yl)(1-methylpiperidin-4-yloxy)
  methyl]phenoxy}ethylamine
6-{3-[benzothiazol-2-yl(1-methylpiperidin-4-yloxy)methyl]
  phenylsulfanyl}hexan-1-ol
4-{3-[(1H-benzimidazol-2-yl)(1-methylpiperidin-4-yloxy)
  methyl]phenyl}butylamine
5-{3-[(1H-benzimidazol-2-yl)(1-methylpiperidin-4-yloxy)
  methyl]phenyl}pent-4-ynylamine
6-{3-[(1H-benzimidazol-2-yl)(1-methylpiperidin-4-yloxy)
  methyl]phenylsulfanyl}hexan-1-ol
3-{3-[benzothiazol-2-yl(1-methylpiperidin-4-yloxy)methyl]
  phenyl}prop-2-ynylamine
2-[benzo[1,3]dioxol-5-yl(1-methylpiperidin-4-yloxy)me-
  thyl]-1H-benzimidazole
(2-{3-[(1H-benzimidazol-2-yl)(1-methylpiperidin-4-yloxy)
  methyl]phenylsulfanyl}ethyl)-urea
(2-{3-[(1H-benzimidazol-2-yl)(1-methylpiperidin-4-yloxy)
  methyl]phenylsulfanyl}ethyl)(4,5-dihydro-thiazol-2-yl)
  amine
2-[(2,3-dihydrobenzo[1,4]dioxin-6-yl)(1-methylpiperidin-
  4-yloxy)methyl]-1H-benzimidazole
4-{3-[benzothiazol-2-yl(1-methylpiperidin-4-yloxy)methyl]
  phenoxy}butylamine
N-(2-{3-[benzothiazol-2-yl(1-methylpiperidin-4-yloxy)me-
  thyl]phenylsulfanyl}ethyl)guanidine
3-{3-[(1H-benzimidazol-2-yl)(1-methylpiperidin-4-yloxy)
  methyl]phenyl}propylamine
N-tert-butoxycarbonyl-N'-(2-{3-[(benzothiazol-2-yl)(1-me-
  thylpiperidin-4-yloxy)methyl]phenylsulfanyl}ethyl)
  guanidine
5-{3-[benzothiazol-2-yl(1-methylpiperidin-4-yloxy)methyl]
  phenylsulfanyl}pentylamine
2-[{3-[2-(1-methyl-1H-imidazol4-yl)ethyl]phenyl}(1-meth-
  ylpiperidin-4-yloxy)methyl]benzothiazole
N-tert-butoxycarbonyl-N'-(4-{3-[(1H-benzimidazol-2-yl)
  (1-methylpiperidin-4-yloxy)methyl]phenyl}but-3-ynyl)
  guanidine
N-(4-{3-[(1H-benzimidazol-2-yl)(1-methylpiperidin-4-
  yloxy)methyl]phenyl}butyl)guanidine
N-tert-butoxycarbonyl-N'-(4-{3-[(1H-benzimidazol-2-yl)
  (1-methylpiperidin-4-yloxy)methyl]phenyl}butyl)guani-
  dine
2-{(1-methylpiperidin-4-yloxy)[3-(pyridin-2-ylmethoxy)
  phenyl]methyl}-1H-benzimidazole
3-{3-[benzothiazol-2-yl(1-methylpiperidin-4-yloxy)methyl]
  phenoxy}propylamine
5-{3-[(1H-benzimidazol-2-yl)(1-methylpiperidin-4-yloxy)
  methyl]phenyl}pentylamine
N-tert-butoxycarbonyl-N'-(3-{3-[(1H-benzimidazol-2-yl)
  (1-methylpiperidin-4-yloxy)methyl]phenyl}propyl)
  guanidine
3-{3-[benzothiazol-2-yl(1-methylpiperidin-4-yloxy)methyl]
  phenylsulfanyl}propylamine
2-{(1-methylpiperidin-4-yloxy)[3-(4-[1,2,3]triazol-2-yl-bu-
  toxy)phenyl]methyl}benzothiazole
2-{(1-methylpiperidin-4-yloxy)[3-(4-[1,2,4]triazol-1-yl-bu-
  toxy)phenyl]methyl}benzothiazole
(2-{3-[(1H-benzimidazol-2-yl)(1-methylpiperidin-4-yloxy)
  methyl]phenylsulfanyl}ethyl)(4,5-dihydro-1H-imidazol-
  2-yl)amine
N-(2-{3-[(1H-benzimidazol-2-yl)(1-methylpiperidin-4-
  yloxy)methyl]phenylsulfanyl}ethyl)-N'-cyanoguanidine
6-{3-[benzothiazol-2-yl(1-methylpiperidin-4-yloxy)methyl]
  phenyl}hex-5-ynylamine
N-(3-{3-[(1H-benzimidazol-2-yl)(1-methylpiperidin-4-
  yloxy)methyl]phenyl}propyl)guanidine
N-(3-{3-[(1H-benzimidazol-2-yl)(1-methylpiperidin-4-
  yloxy)methyl]phenyl}propyl)guanidine
2-{(1-methylpiperidin-4-yloxy)[3-(4-morpholin-4-yl-bu-
  toxy)phenyl]methyl}benzothiazole
(1-{3-[benzothiazol-2-yl(1-methylpiperidin-4-yloxy)me-
  thyl]phenyl}pyrrolidin-2-yl)methanol
(1-{3-[benzothiazol-2-yl(1-methylpiperidin-4-yloxy)me-
  thyl]phenyl}pyrrolidin-2-yl)methanol
6-{3-[benzothiazol-2-yl(1-methylpiperidin-4-yloxy)methyl]
  phenyl}hexylamine 4-{3-[(1H-benzimidazol-2-yl)(1-methylpiperidin-4-yloxy)
methyl]phenylsulfanyl}butylamine
3-{3-[(1H-benzimidazol-2-yl)(1-methylpiperidin-4-yloxy)
methyl]phenoxy}propylamine
4-(2-{3-[benzothiazol-2-yl(1-methylpiperidin-4-yloxy)methyl]phenoxy}ethyl)piperazine-1-carboxylic acid tert-butyl ester
4-(2-{3-[benzothiazol-2-yl(1-methylpiperidin-4-yloxy)methyl]phenoxy}ethyl)piperazine-1-carboxylic acid tert-butyl ester
2-{(1-methylpiperidin-4-yloxy)[3-(2-piperazin-1-ylethoxy)phenyl]methyl}benzothiazole
4-{3-[(1H-benzimidazol-2-yl)(1-methylpiperidin-4-yloxy)methyl]phenoxy}butylamine
2-{(1-methylpiperidin-4-yloxy)[3-(4-morpholin-4-yl-butoxy)phenyl]methyl}-1H-benzimidazole
2-{(1-methylpiperidin-4-yloxy)[3-(4-piperidin-1-yl-butoxy)phenyl]methyl}-1H-benzimidazole
2-[(2-fluoro-3-iodophenyl)(1-methylpiperidin-4-yloxy)methyl]-1H-benzimidazole
N-tert-butoxycarbonyl-N'-(3-{3-[(1H-benzimidazol-2-yl)(1-methylpiperidin-4-yloxy)methyl]phenyl}pentyl)guanidine
N-tert-butoxycarbonyl-N'-(3-{3-[(1H-benzimidazol-2-yl)(1-methyl piperidin-4-yloxy)methyl]phenyl}prop-2-ynyl)guanidine
6-{3-[(1H-benzimidazol-2-yl)(1-methylpiperidin-4-yloxy)methyl]phenyl}hex-5-ynylamine
2-{(1-methylpiperidin-4-yloxy)[3-(1,2,3,6-tetrahydro-pyridin-4-yl)phenyl]methyl}-1H-benzimidazole
N-tert-butoxycarbonyl-N'-(5-{3-[(benzothiazol-2-yl)(1-methylpiperidin-4-yloxy)methyl]phenyl}pent-5-ynyl)guanidine
N-(5-{3-[benzothiazol-2-yl(1-methylpiperidin-4-yloxy)methyl]phenyl}pent-4-ynyl)guanidine
N-tert-butoxycarbonyl-N'-(6-{3-[(benzothiazol-2-yl)(1-methylpiperidin-4-yloxy)methyl]phenyl}hex-5-ynyl)guanidine
N-(6-{3-[benzothiazol-2-yl(1-methylpiperidin-4-yloxy)methyl]phenyl}hex-5-ynyl)guanidine
4-(4-{3-[(1H-benzimidazol-2-yl)(1-methylpiperidin-4-yloxy)methyl]phenoxy}butyl)piperazine-1-carboxylic acid tert-butyl ester
6-{3-[(1H-benzimidazol-2-yl)(1-methylpiperidin-4-yloxy)methyl]phenyl}hexylamine
N-tert-butoxycarbonyl-N'-(6-{3-[(1H-benzimidazol-2-yl)(1-methylpiperidin-4-yloxy)methyl]phenyl}hex-5-ynyl)guanidine
N-(6-{3-[(1H-benzimidazol-2-yl)(1-methylpiperidin-4-yloxy)methyl]phenyl}hex-5-ynyl)guanidine
1-(2-{3-[(1H-benzimidazol-2-yl)(1-methylpiperidin-4-yloxy)methyl]phenylsulfanyl}ethyl)-3-isopropyl-thiourea
2-{(1-methylpiperidin-4-yloxy)[3-(3-[1,2,4]triazol-1-yl-propoxy)phenyl]methyl}benzothiazole
2-{(1-methylpiperidin-4-yloxy)[3-(3-[1,2,3]triazol-2-yl-propoxy)phenyl]methyl}benzothiazole
2-{(1-methylpiperidin-4-yloxy)[3-(3-morpholin-4-yl-propoxy)phenyl]methyl}benzothiazole
4-(3-{3-[benzothiazol-2-yl(1-methylpiperidin-4-yloxy)methyl]phenoxy}propyl)piperazine-1-carboxylic acid tert-butyl ester
2-{3-[(1H-benzimidazol-2-yl)(1-methylpiperidin-4-yloxy)methyl]-2-fluoro-phenylsulfanyl}ethylamine
4-{3-[(1H-benzimidazol-2-yl)(1-methylpiperidin-4-yloxy)methyl]phenyl}-3,6-dihydro-2H-pyridine-1-carboxamidine
2-[[3-(2-chloroethoxy)phenyl](1-methylpiperidin-4-yloxy)methyl]benzothiazole
N-(6-{3-[(1H-benzimidazol-2-yl)(1-methylpiperidin-4-yloxy)methyl]phenyl}hexyl)guanidine
2-{(1-methylpiperidin-4-yloxy)[3-(2-piperidin-1-yl-ethoxy)phenyl]methyl}-1H-benzimidazole
N-tert-butoxycarbonyl-N'-(5-{3-[(1H-benzimidazol-2-yl)(1-methyl piperidin-4-yloxy)methyl]phenyl}pent-4-ynyl)guanidine
N-(5-{3-[(1H-benzimidazol-2-yl)(1-methylpiperidin-4-yloxy)methyl]phenyl}pent-4-ynyl)guanidine
4-{3-[benzothiazol-2-yl(1-methylpiperidin-4-yloxy)methyl]phenylsulfanyl}butylamine
4-(3-{3-[(1H-benzimidazol-2-yl)(1-methylpiperidin-4-yloxy)methyl]phenoxy}propyl)piperazine-1-carboxylic acid tert-butyl ester
(2-{3-[(1H-benzimidazol-2-yl)(1-methylpiperidin-4-yloxy)methyl]phenoxy}ethylamino)acetic acid tert-butyl ester
4-(5-{3-[benzothiazol-2-yl(1-methylpiperidin-4-yloxy)methyl]phenoxy}pentyl)piperazine-1-carboxylic acid tert-butyl ester
N-(6-{3-[benzothiazol-2-yl(1-methylpiperidin-4-yloxy)methyl]phenyl}hexyl)guanidine
N-tert-butoxycarbonyl-N'-(6-{3-[(1H-benzimidazol-2-yl)(1-methylpiperidin-4-yloxy)methyl]phenyl}hexyl)guanidine
N-(5-{3-[benzothiazol-2-yl(1-methylpiperidin-4-yloxy)methyl]phenyl}pentyl)guanidine
4-{3-[benzothiazol-2-yl(1-methylpiperidin-4-yloxy)methyl]phenyl}butylamine
[[3-(4-aminobutoxy)phenyl](1H-benzimidazol-2-yl)methyl](1-methylpiperidin-4-yl)amine
3-{3-[(1H-benzimidazol-2-yl)(1-methylpiperidin-4-yloxy)methyl]phenylsulfanyl}propylamine
4-(2-{3-[(1H-benzimidazol-2-yl)(1-methylpiperidin-4-yloxy)methyl]phenoxy}ethyl)piperazine-1-carboxylic acid tert-butyl ester
(2-{3-[benzothiazol-2-yl(1-methylpiperidin-4-yloxy)methyl]phenoxy}ethylamino)acetic acid tert-butyl ester
5-{3-[benzothiazol-2-yl(1-methylpiperidin-4-yloxy)methyl]phenoxy}pentylamine
N-(4-{3-[benzothiazol-2-yl(1-methylpiperidin-4-yloxy)methyl]phenyl}but-3-ynyl)guanidine
N-(3-{3-[benzothiazol-2-yl(1-methylpiperidin-4-yloxy)methyl]phenyl}prop-2-ynyl)guanidine
N-(4-{3-[benzothiazol-2-yl(1-methylpiperidin-4-yloxy)methyl]phenyl}butyl)guanidine
(5-{3-[benzothiazol-2-yl(1-methylpiperidin-4-yloxy)methyl]phenoxy}pentylamino)acetic acid tert-butyl ester
2-[(1-methylpiperidin-4-yloxy)(3-piperidin-4-ylethynyl-phenyl)methyl]-1H-benzimidazole
2-{(1-methylpiperidin-4-yloxy)[3-(piperidin-4-ylmethoxy)phenyl]methyl}benzothiazole
2-{(1-methylpiperidin-4-yloxy)[3-(piperidin-3-ylmethoxy)phenyl]methyl}benzothiazole
2-[[3-(1-methylpiperidin-3-ylmethoxy)phenyl](1-methylpiperidin-4-yloxy)methyl]benzothiazole
2-[(1-methylpiperidin-4-yloxy)(3-piperidin-3-ylethynyl-phenyl)methyl]-1H-benzimidazole
5-{3-[(1H-benzimidazol-2-yl)(1-methylpiperidin-4-yloxy)methyl]phenylsulfanyl}pentylamine
2-{(1-methylpiperidin-4-yloxy)[3-(pyrrolidin-3-yloxy)phenyl]methyl}benzothiazole
2-{(1-methylpiperidin-4-yloxy)[3-(pyrrolidin-3-yloxy)phenyl]methyl}benzothiazole
5-{3-[benzothiazol-2-yl(1-methylpiperidin-4-yloxy)methyl]phenyl}pent-4-en-1-ol 3-amino-4-(2-{3-[(1H-benzimidazol-2-yl)(1-methylpiperidin-4-yloxy)methyl]phenylsulfanyl}ethylamino)-cyclobut-3-ene-1,2-dione
[[3-(6-aminohex-1-ynyl)phenyl](1H-benzimidazol-2-yl)methyl](1-methylpiperidin-4-yl)amine
{[3-(4-aminobutoxy)phenyl]benzothiazol-2-yl-methyl}(1-methylpiperidin-4-yl)amine
2-[(3-azetidin-3-ylethynylphenyl)(1-methylpiperidin-4-yloxy)methyl]-1H-benzimidazole
5-{3-[(1H-benzimidazol-2-yl)(1-methylpiperidin-4-yloxy)methyl]phenyl}pent-4-en-1-ol
5-{3-[benzothiazol-2-yl(1-methylpiperidin-4-yloxy)methyl]phenyl}pent-4-en-1-ol
4-(5-{3-[(1H-benzimidazol-2-yl)(1-methylpiperidin-4-yloxy)methyl]phenoxy}pentyl)piperazine-1-carboxylic acid tert-butyl ester
2-[[3-(2-azetidin-3-ylethyl)phenyl](1-methylpiperidin-4-yloxy)methyl]-1H-benzimidazole
N-(4-{3-[(1H-benzimidazol-2-yl)(1-methylpiperidin-4-yloxy)methyl]phenyl}but-3-ynyl)guanidine
4-{3-[(1H-benzimidazol-2-yl)(1-methylpiperidin-4-yloxy)methyl]phenyl}piperidine-1-carboxamidine
2-{(1-methylpiperidin-4-yloxy)[3-(2-piperidin-2-yl-ethylsulfanyl)phenyl]methyl}-1H-benzimidazole
2-{(1-methylpiperidin-4-yloxy)[3-(2-piperidin-4-yl-ethyl)phenyl]methyl}-1H-benzimidazole
N-(5-{3-[(1H-benzimidazol-2-yl)(1-methylpiperidin-4-yloxy)methyl]phenyl}pentyl)guanidine
2-[{3-[3-(3H-imidazol-4-yl)propylsulfanyl]phenyl}(1-methylpiperidin-4-yloxy)methyl]-1H-benzimidazole
N-tert-butoxycarbonyl-N'-(4-{3-[(benzothiazol-2-yl)(1-methylpiperidin-4-yloxy)methyl]phenyl}but-3-ynyl)guanidine
5-{3-[(1H-benzimidazol-2-yl)(1-methylpiperidin-4-yloxy)methyl]phenoxy}pentylamine
N-acetyl-N'-(2-{3-[(1H-benzimidazol-2-yl)(1-methylpiperidin-4-yloxy)methyl]phenylsulfanyl}ethyl)guanidine
2-[[3-(azetidin-3-yloxy)phenyl](1-methylpiperidin-4-yloxy)methyl]benzothiazole
1-{3-[benzothiazol-2-yl(1-methylpiperidin-4-yloxy)methyl]phenyl}azetidin-3-ol
(1-{3-[benzothiazol-2-yl(1-methylpiperidin-4-yloxy)methyl]phenyl}pyrrolidin-3-yl)methanol
1-{3-[benzothiazol-2-yl(1-methylpiperidin-4-yloxy)methyl]phenyl}piperidin-4-ylamine
1-{3-[benzothiazol-2-yl(1-methylpiperidin-4-yloxy)methyl]phenyl}pyrrolidin-3-ol
1-{3-[benzothiazol-2-yl(1-methylpiperidin-4-yloxy)methyl]phenyl}pyrrolidin-3-ol
N-(1-{3-[benzothiazol-2-yl(1-methylpiperidin-4-yloxy)methyl]phenyl}pyrrolidin-3-yl)acetamide
2-[[3-(5-imidazol-1-ylpent-1-ynyl)phenyl](1-methylpiperidin-4-yloxy)methyl]-1H-benzimidazole
2-{(1-methylpiperidin-4-yloxy)[3-(5-pyrazol-1-yl-pent-1-ynyl)phenyl]methyl}-1H-benzimidazole
1-{3-[benzothiazol-2-yl(1-methylpiperidin-4-yloxy)methyl]phenyl}piperidin-4-ol
2-[{3-[2-(1H-imidazol-4-yl)ethyl]phenyl}(1-methylpiperidin-4-yloxy)methyl]-1H-benzimidazole
acetic acid 1-{3-[benzothiazol-2-yl(1-methylpiperidin-4-yloxy)methyl]phenyl}piperidin-4-yl ester
2-[(3-bromo-phenyl)(1-methyl-pyrrolidin-3-ylmethoxy)methyl]-1H-benzimidazole
2-{(1-methylpiperidin-4-yloxy)[3-(piperidin-4-yloxy)phenyl]methyl}benzothiazole
2-{(1-methylpiperidin-4-yloxy)[3-(5-[1,2,3]triazol-2-yl-pent-1-ynyl)phenyl]methyl}-1H-benzimidazole
2-{(1-methylpiperidin-4-yloxy)[3-(5-[1,2,3]triazol-1-yl-pent-1-ynyl)phenyl]methyl}-1H-benzimidazole
N-(3-{3-[(1H-benzimidazol-2-yl)(1-methylpiperidin-4-yloxy)methyl]phenyl}prop-2-ynyl)guanidine
N1-(5-{3-[(1H-benzimidazol-2-yl)(1-methylpiperidin-4-yloxy)methyl]phenoxy}pentyl)butane-1,4-diamine
{[3-(6-aminohex-1-ynyl)phenyl]benzothiazol-2-yl-methyl}(1-methylpiperidin-4-yl)amine
5-{3-[(1H-benzimidazol-2-yl)(1-methylpiperidin-4-yloxy)methyl]phenyl}pent-4-enylamine
4-{3-[benzothiazol-2-yl(1-methylpiperidin-4-yloxy)methyl]phenoxy}but-2-en-1-ol
1-{3-[benzothiazol-2-yl(1-methylpiperidin-4-yloxy)methyl]phenyl}pyrrolidin-3-ylamine
2-[(2,5-difluorophenyl)(1-methylpiperidin-4-yloxy)methyl]-1H-benzimidazole
2-[(2-fluoro-5-iodo-phenyl)(1-methylpiperidin-4-yloxy)methyl]-1H-benzimidazole
3-{3-[(1H-benzimidazol-2-yl)(1-methylpiperidin-4-yloxy)methyl]phenylethynyl}azetidine-1-carboxamidine
4-{3-[(5-fluoro-1H-benzimidazol-2-yl)(1-methylpiperidin-4-yloxy)methyl]phenylsulfanyl}butan-1-ol
2-{3-[(5-fluoro-1H-benzimidazol-2-yl)(1-methylpiperidin-4-yloxy)methyl]phenylsulfanyl}ethylamine
1-{3-[benzothiazol-2-yl(1-methylpiperidin-4-yloxy)methyl]phenyl}pyrrolidin-3-ylamine
2-[[3-(3-fluoropyrrolidin-1-yl)phenyl](1-methylpiperidin-4-yloxy)methyl]benzothiazole
4-{3-[benzothiazol-2-yl(1-methylpiperidin-4-yloxy)methyl]phenoxy}but-2-enylamine
2-[(2-fluoro-5-trifluoromethoxyphenyl)(1-methylpiperidin-4-yloxy)methyl]-1H-benzimidazole
2-[(2-fluoro-5-trifluoromethoxyphenyl)(1-methylpiperidin-4-yloxy)methyl]-1H-benzimidazole (enantiomer A)
2-[(2-fluoro-5-trifluoromethoxyphenyl)(1-methylpiperidin-4-yloxy)methyl]-1H-benzimidazole (enantiomer B)
N-(2-aminoethyl)-2-{3-[(1H-benzimidazol-2-yl)(1-methylpiperidin-4-yloxy)methyl]phenylsulfanyl}acetamide
N-(2-{3-[(5-fluoro-1H-benzimidazol-2-yl)(1-methylpiperidin-4-yloxy)methyl]phenylsulfanyl}ethyl)guanidine
2-(5-{3-[(5-fluoro-1H-benzimidazol-2-yl)(1-methylpiperidin-4-yloxy)methyl]phenyl}pent-4-ynyl)isoindole-1,3-dione
6-{3-[(5-fluoro-1H-benzimidazol-2-yl)(1-methylpiperidin-4-yloxy)methyl]phenyl}hex-5-ynylamine oxalate
4-{3-[(5-fluoro-1H-benzimidazol-2-yl)(1-methylpiperidin-4-yloxy)methyl]phenylsulfanyl}butylamine oxalate
N-(3-{3-[(1H-benzimidazol-2-yl)(1-methylpiperidin-4-yloxy)methyl]phenylsulfanyl}propyl)guanidine, dihydrochloride
1-{3-[benzothiazol-2-yl(1-methylpiperidin-4-yloxy)methyl]phenyl}pyrrolidin-3-one, oxalate
N-(4-{3-[(1H-benzimidazol-2-yl)(1-methylpiperidin-4-yloxy)methyl]phenylsulfanyl}butyl)guanidine, dihydrochloride
5-{3-[(1H-benzimidazol-2-yl)(1-methylpiperidin-4-yloxy)methyl]phenylsulfanyl}pentan-1-ol
N-(2-{3-[(1H-benzimidazol-2-yl)(1-methylpiperidin-4-yloxy)methyl]phenylsulfanyl}ethyl)-N-(2,2-dimethylpropionyl)guanidine
2-[(1-methylpiperidin-4-yloxy)(4-nitrophenyl)methyl]-1H-benzimidazole
2-{(1-methylpiperidin-4-yloxy)[3-(pyridin-3-yloxy)phenyl]methyl}benzothiazole, oxalate
2-[(3-bromophenyl)(1-methylpyrrolidin-3-ylmethoxy)methyl]-5-fluoro-1H-benzimidazole, oxalate 4-[(1H-benzimidazol-2-yl)(1-methylpiperidin-4-yloxy)methyl]aniline
4-[(1H-benzimidazol-2-yl)(piperidin-4-yloxy)methyl]aniline, hydrochloride
N-(2-amino-ethyl)-2-{3-[(5-fluoro-1H-benzimidazol-2-yl)(1-methylpiperidin-4-yloxy)methyl]phenylsulfanyl}acetamide
1-{3-[benzothiazol-2-yl(1-methylpiperidin-4-yloxy)methyl]phenyl}-3-trifluoromethylpyrrolidin-3-ol, oxalate
2-[[3-(4,5-dihydro-1H-imidazol-2-ylmethylsulfanyl)phenyl](1-methylpiperidin-4-yloxy)methyl]-1H-benzimidazole
2-[[3-(4,5-dihydro-1H-imidazol-2-ylmethylsulfanyl)phenyl](1-methylpiperidin-4-yloxy)methyl]-5-fluoro-1H-benzimidazole
2-[(3-bromophenyl)(1-methylpiperidin-4-yloxy)methyl]-5,6-difluoro-1H-benzimidazole
2-[(3-iodophenyl)(1-methylpiperidin-4-yloxy)methyl]-1-methyl-1H-benzimidazole, dioxalate
2-amino-5-{3-[(1H-benzimidazol-2-yl)(1-methylpiperidin-4-yloxy)methyl]phenylsulfanylmethyl}-1,5-dihydroimidazol-4-one
2-[(3-bromophenyl)(1-methylpiperidin-4-yloxy)methyl]-5,6,7-trifluoro-1H-benzimidazole
1-(2-ethoxyethyl)-2-[(3-iodophenyl)(1-methylpiperidin-4-yloxy)methyl]-1H-benzimidazole, dioxalate
3-[(1H-benzimidazol-2-yl)(1-methylpiperidin-4-yloxy)methyl]benzaldehyde
4-{3-[(1H-benzimidazol-2-yl)(1-methylazetidin-3-ylmethoxy)methyl]phenylsulfanyl}butylamine, oxalate
2-[(2-fluoro-5-trifluoromethoxyphenyl)(1-methylpiperidin-4-yloxy)methyl]benzoxazole, oxalate
{3-[(1H-benzimidazol-2-yl)(1-methylpiperidin-4-yloxy)methyl]phenyl}methanol. dimethylsulfoxonium ylide of 3-bromophenylacetic acid methyl ester
2-[(2-fluoro-4-methylphenyl)(1-methylpiperidin-4-yloxy)methyl]-1H-benzimidazole, enantiomer B
2-[(2,6-difluoro-3-methoxyphenyl)(1-methylpiperidin-4-yloxy)methyl]-1H-benzimidazole
ethyl (6-{3-[(1-methyl-1H-benzimidazol-2-yl)(1-methylpiperidin-4-yloxy)methyl]phenyl}hex-5-ynyl)carbamate, oxalate
2-[(1H-indol-6-yl)(1-methylpiperidin-4-yloxy)methyl]-1H-benzimidazole, oxalate
2-[benzo[b]thiophen-6-yl(1-methylpiperidin-4-yloxy)methyl]-1H-benzimidazole, oxalate
2-[(2,6-difluoro-4-methylphenyl)(1-methylpiperidin-4-yloxy)methyl]-1H-benzimidazole, enantiomer B
2-[(1H-benzimidazol-2-yl)(1-methylpiperidin-4-yloxy)methyl]phenol
2-[(1H-benzimidazol-2-yl)hydroxymethyl]phenol
2-[(6-{3-[(1H-benzimidazol-2-yl)(1-methylpiperidin-4-yloxy)methyl]-4-fluorophenyl}hex-5-ynylimino)phenylmethyl]phenol
5-(6-{3-[(1H-benzimidazol-2-yl)(1-methylpiperidin-4-yloxy)methyl]-4-fluorophenyl}hex-5-ynylimino)-2-methylcyclopent-1-enol
2-[(3-bromophenyl)(1-methylpiperidin-4-yloxy)methyl]-1H-benzimidazole, enantiomer B
5-{3-[(1H-benzimidazol-2-yl)(1-methylpiperidin-4-yloxy)methyl]phenyl}pent-4-ynylamine, enantiomer A
5-{3-[(1H-benzimidazol-2-yl)(1-methylpiperidin-4-yloxy)methyl]phenyl}pent-4-ynylamine, enantiomer B
2-[(3-bromophenyl)(1-methylpiperidin-4-yloxy)methyl]-5-fluoro-1H-benzimidazole, enantiomer A
2-[(3-bromophenyl)(1-methylpiperidin-4-yloxy)methyl]-5-fluoro-1H-benzimidazole, enantiomer B
2-[(1H-benzimidazol-2-yl)(1-methylpiperidin-4-yloxy)methyl]-4-methylphenol
2-[(1H-benzimidazol-2-yl)(1-methylpiperidin-4-yloxy)methyl]phenol enantiomer A
2-[(1H-benzimidazol-2-yl)(1-methylpiperidin-4-yloxy)methyl]phenol enantiomer B
6-[(1H-benzimidazol-2-yl)(1-methylpiperidin-4-yloxy)methyl]-2-fluoro-3-methylphenol enantiomer A
6-[(1H-benzimidazol-2-yl)(1-methylpiperidin-4-yloxy)methyl]-2-fluoro-3-methylphenol enantiomer B
6-[(1H-benzimidazol-2-yl)(1-methylpiperidin-4-yloxy)methyl]-2,3-difluorophenol enantiomer A
6-[(1H-benzimidazol-2-yl)(1-methylpiperidin-4-yloxy)methyl]-2,3-difluorophenol enantiomer B
5-{3-[(1H-benzimidazol-2-yl)(1-methylpiperidin-4-yloxy)methyl]-4-fluorophenyl}pent-4-ynylamine, dioxalate
3-{3-[benzothiazol-2-yl(1-methylpiperidin-4-yloxy)methyl]phenoxy}cyclopentylamine, oxalate
2-{[3-(3-fluoropyrrolidin-1-yl)phenyl](1-methylpiperidin-4-yloxy)methyl}benzothiazole, oxalate
5-{3-[(5-fluoro-1H-benzimidazol-2-yl)(1-methylpyrrolidin-3-ylmethoxy)methyl]phenyl}pent-4-ynylamine, oxalate
2-[(3-bromophenyl)(1-methylpyrrolidin-3-ylmethoxy)methyl]benzothiazole, oxalate (one epimer)
2-[(3-bromophenyl)(1-methylpyrrolidin-3-ylmethoxy)methyl]benzothiazole, oxalate (50/50 mixture of two epimers)
2-{(1-methylpiperidin-4-yloxy)[3-(octahydrocyclopenta[c]pyrrol-5-yloxy)phenyl]methyl}benzothiazole, dioxalate
(1-{3-[benzothiazol-2-yl(1-methylpiperidin-4-yloxy)methyl]phenyl}pyrrolidin-3-yl)methylamine, dioxalate
4-{3-[(5,6-difluoro-1H-benzimidazol-2-yl)(1-methylpiperidin-4-yloxy)methyl]phenylsulfanyl}butan-1-ol
2-{3-[benzothiazol-2-yl(1-methylpiperidin-4-yloxy)methyl]phenyl}octahydrocyclopenta[c]pyrrol-5-ylamine, dioxalate
2-{[3-(3-fluoropropoxy)phenyl](1-methylpiperidin-4-yloxy)methyl}-1H-benzimidazole, oxalate
2-{[3-(2-fluoroethoxy)phenyl](1-methylpiperidin-4-yloxy)methyl}-1H-benzimidazole, oxalate
4-{3-[benzothiazol-2-yl(1-methylpiperidin-4-yloxy)methyl]phenoxy}cyclohexylamine, oxalate
6-{3-[(1-methyl-1H-benzimidazol-2-yl)(1-methylpiperidin-4-yloxy)methyl]phenyl}hex-5-ynylamine, dioxalate
1-{3-[benzothiazol-2-yl(1-methylpiperidin-4-yloxy)methyl]phenyl}pyrrolidin-2-ylmethylamine, oxalate
(1-{3-[benzothiazol-2-yl(1-methylpiperidin-4-yloxy)methyl]phenyl}pyrrolidin-3-yl)(methyl)amine, oxalate
(1-{3-[benzothiazol-2-yl(1-methylpiperidin-4-yloxy)methyl]phenyl}pyrrolidin-3-yl)(dimethyl)amine, oxalate
2-{[3-(5-methylhexahydropyrrolo[3,4-c]pyrrol-2-yl)phenyl](1-methylpiperidin-4-yloxy)methyl}benzothiazole, dioxalate
2-[(2-fluoro-5-methoxyphenyl)(1-methylpiperidin-4-yloxy)methyl]-1H-benzimidazole, oxalate
3-[(1H-benzimidazol-2-yl)(1-methylpiperidin-4-yloxy)methyl]-4-fluorophenol, oxalate
2-{[2-fluoro-5-(2-fluoroethoxy)phenyl](1-methylpiperidin-4-yloxy)methyl}-1H-benzimidazole, oxalate
2-[(2-fluoro-5-methylphenyl)(1-methylpiperidin-4-yloxy)methyl]-1H-benzimidazole, oxalate
4-{3-[(1-methylpiperidin-4-yloxy)(5,6,7-trifluoro-1H-benzimidazol-2-yl)methyl]phenylsulfanyl}butylamine, oxalate
4-{3-[(5,6-difluoro-1H-benzimidazol-2-yl)(1-methylpiperidin-4-yloxy)methyl]phenylsulfanyl}butylamine, oxalate 6-(3-{[1-(2-ethoxyethyl)-1H-benzimidazol-2-yl](1-methylpiperidin-4-yloxy)methyl}phenyl)hex-5-ynylamine, dioxalate
6-(3-{[1-(2-methoxyethyl)-1H-benzimidazol-2-yl](1-methylpiperidin-4-yloxy)methyl}phenyl)hex-5-ynylamine, dioxalate
2-{[3-(3-fluoropropylsulfanyl)phenyl](1-methylpiperidin-4-yloxy)methyl}-1H-benzimidazole, dioxalate
5-fluoro-2-[(2-fluoro-5-trifluoromethoxyphenyl)(1-methylpiperidin-4-yloxy)methyl]-1H-benzimidazole, oxalate
4,5,6-trifluoro-2-[(2-fluoro-5-trifluoromethoxyphenyl)(1-methylpiperidin-4-yloxy)methyl]-1H-benzimidazole
5,6-difluoro-2-[(2-fluoro-5-trifluoromethoxyphenyl)(1-methylpiperidin-4-yloxy)methyl]-1H-benzimidazole
2-{[2-fluoro-5-(2,2,2-trifluoroethoxy)phenyl](1-methylpiperidin-4-yloxy)methyl}-1H-benzimidazole
2-[(2,6-difluoro-4-methylphenyl)(1-methylpiperidin-4-yloxy)methyl]-1H-benzimidazole
2-[(2-chloro-5-trifluoromethoxyphenyl)(1-methylpiperidin-4-yloxy)methyl]-1H-benzimidazole, oxalate
2-[(2-fluoro-5-trifluoromethoxyphenyl)(1-methylpiperidin-4-yloxy)methyl]benzothiazole, oxalate
2-[(4-chloro-2,6-difluorophenyl)(1-methylpiperidin-4-yloxy)methyl]-1H-benzimidazole
7-fluoro-2-[(2-fluoro-5-trifluoromethoxyphenyl)(1-methylpiperidin-4-yloxy)methyl]-1H-benzimidazole, oxalate
2-[(2,6-difluoro-4-methylphenyl)(1-methylpiperidin-4-yloxy)methyl]benzothiazole, oxalate
2-[(4-chloro-2,6-difluorophenyl)(1-methylpiperidin-4-yloxy)methyl]benzothiazole, oxalate
2-[(3-ethoxy-2,6-difluorophenyl)(1-methylpiperidin-4-yloxy)methyl]-1H-benzimidazole
2-[(2,6-difluoro-4-methylphenyl)(1-methylpiperidin-4-yloxy)methyl]benzoxazole, oxalate
2-[(1-methylpiperidin-4-yloxy)(4-trifluoromethylphenyl)methyl]-1H-benzimidazole
2-[(2-fluoro-4-trifluoromethylphenyl)(1-methylpiperidin-4-yloxy)methyl]-1H-benzimidazole
2-[(2,4-dimethylphenyl)(1-methylpiperidin-4-yloxy)methyl]-1H-benzimidazole
2-[(3-methoxyphenyl)(1-methylpiperidin-4-yloxy)methyl]-1H-benzimidazole
2-[chroman-7-yl(1-methylpiperidin-4-yloxy)methyl]-1H-benzimidazole
2-[(2-fluoro-4-methylphenyl)(1-methylpiperidin-4-yloxy)methyl]benzoxazole, oxalate
2-[(3,5-bis-trifluoromethylphenyl)(1-methylpiperidin-4-yloxy)methyl]-1H-benzimidazole, oxalate
5-fluoro-2-[(2-fluoro-4-methylphenyl)(1-methylpiperidin-4-yloxy)methyl]-1H-benzimidazole
2-[(2,3-difluoro-4-methylphenyl)(1-methylpiperidin-4-yloxy)methyl]-1H-benzimidazole
2-[(3-chloro-4-methylphenyl)(1-methylpiperidin-4-yloxy)methyl]-1H-benzimidazole
ethyl 2-[(2-fluoro-5-trifluoromethoxyphenyl)(1-methylpiperidin-4-yloxy)methyl]benzimidazole-1-carboxylate, oxalate
2-[(3-fluoro-4-methylphenyl)(1-methylpiperidin-4-yloxy)methyl]-1H-benzimidazole
2-[(5-bromo-2-fluorophenyl)(1-methylpiperidin-4-yloxy)methyl]-1H-benzimidazole
6-{3-[(1H-benzimidazol-2-yl)(1-methylpiperidin-4-yloxy)methyl]-4-fluorophenyl}hex-5-ynylamine, oxalate
5-{4-fluoro-3-[(5-fluoro-1H-benzimidazol-2-yl)(1-methylpiperidin-4-yloxy)methyl]phenyl}pent-4-ynylamine
ethyl (5-{3-[(1H-benzimidazol-2-yl)(1-methylpiperidin-4-yloxy)methyl]-4-fluorophenyl}pent-4-ynyl)carbamate
2-[(1H-benzimidazol-2-yl)(1-methylpiperidin-4-yloxy)methyl]-4-chlorophenol
ethyl (5-{4-fluoro-3-[(5-fluoro-1H-benzimidazol-2-yl)(1-methylpiperidin-4-yloxy)methyl]phenyl}pent-4-ynyl)carbamate
2-[(1H-benzimidazol-2-yl)(1-methylpiperidin-4-yloxy)methyl]-4-trifluoromethoxyphenol
2-[(1H-benzimidazol-2-yl)(1-methylpiperidin-4-yloxy)methyl]-4-fluorophenol
2-[(1H-benzimidazol-2-yl)(1-methylpiperidin-4-yloxy)methyl]-4-methoxyphenol
2-[(1H-benzimidazol-2-yl)(1-methylpiperidin-4-yloxy)methyl]-5-methylphenol
2-[(1H-benzimidazol-2-yl)(1-methylpiperidin-4-yloxy)methyl]-4-bromophenol
2-[(1H-benzimidazol-2-yl)(1-methylpiperidin-4-yloxy)methyl]-4-ethoxyphenol
2-[(1H-indol-7-yl)(1-methylpiperidin-4-yloxy)methyl]-1H-benzimidazole
2-[(1H-benzimidazol-2-yl)(1-methylpiperidin-4-yloxy)methyl]-4,6-difluorophenol
2-[(1H-benzimidazol-2-yl)(1-methylpiperidin-4-yloxy)methyl]-4,6-dichlorophenol
2-[(1H-benzimidazol-2-yl)(1-methylpiperidin-4-yloxy)methyl]-6-fluorophenol
2-[(1H-benzimidazol-2-yl)(1-methylpiperidin-4-yloxy)methyl]-3-fluorophenol
2-[(1H-benzimidazol-2-yl)(1-methylpiperidin-4-yloxy)methyl]-4,5-difluorophenol
2-[(1H-benzimidazol-2-yl)(1-methylpiperidin-4-yloxy)methyl]-5-fluorophenol
2-[(1H-benzimidazol-2-yl)(1-methylpiperidin-4-yloxy)methyl]-5-chlorophenol
2-[(1H-benzimidazol-2-yl)(1-methylpiperidin-4-yloxy)methyl]-6-methylphenol
2-[(1H-benzimidazol-2-yl)(1-methylpiperidin-4-yloxy)methyl]-4-methylsulfanylphenol
2-[(1H-benzimidazol-2-yl)(1-methylpiperidin-4-yloxy)methyl]-4-ethylsulfanylphenol
3-[(1H-benzimidazol-2-yl)(1-methylpiperidin-4-yloxy)methyl]biphenyl-4-ol
2-[(1H-benzimidazol-2-yl)(1-methylpiperidin-4-yloxy)methyl]-4-tert-butyl phenol
2-[(1H-benzimidazol-2-yl)(1-methylpiperidin-4-yloxy)methyl]-4-propylphenol
2-[(1H-benzimidazol-2-yl)(1-methylpiperidin-4-yloxy)methyl]-6-methoxyphenol
2-[(1H-benzimidazol-2-yl)(1-methy-piperidin-4-yloxy)methyl]-3-fluoro-5-methylphenol
2-[(1H-benzimidazol-2-yl)(1-methylpiperidin-4-yloxy)methyl]-3-chlorophenol
2-[(1H-benzimidazol-2-yl)(1-methylpiperidin-4-yloxy)methyl]-6-fluoro-4-ethylphenol
2-[(1H-benzimidazol-2-yl)(1-methylpiperidin-4-yloxy)methyl]-4-benzylphenol
2-[(1H-benzimidazol-2-yl)(1-methylpiperidin-4-yloxy)methyl]-4-trifluoromethylphenol
2-[(1H-benzimidazol-2-yl)(1-methylpiperidin-4-yloxy)methyl]-4-chloro-6-fluorophenol
2-[(1H-benzimidazol-2-yl)(1-methylpiperidin-4-yloxy)methyl]-5-fluoro-3-methylphenol
6-[(1H-benzimidazol-2-yl)(1-methylpiperidin-4-yloxy)methyl]-2-fluoro-3-methylphenol
6-[(1H-benzimidazol-2-yl)(1-methylpiperidin-4-yloxy)methyl]indan-5-ol
2-[(1H-benzimidazol-2-yl)(1-methylpiperidin-4-yloxy)methyl]-4-propoxyphenol 2-[(1H-benzimidazol-2-yl)(1-methylpiperidin-4-yloxy)methyl]-4-(1-methyl-1-phenylethyl)phenol
2-[(1H-benzimidazol-2-yl)(1-methylpiperidin-4-yloxy)methyl]-4-(2-fluoroethoxy)phenol
2-[(1H-benzimidazol-2-yl)(1-methylpiperidin-4-yloxy)methyl]-4-(3-fluoropropoxy)phenol
2-[(1H-benzimidazol-2-yl)(1-methylpiperidin-4-yloxy)methyl]-4-fluoro-6-methylphenol
2-[(1H-benzimidazol-2-yl)(1-methylpiperidin-4-yloxy)methyl]-6-fluoro-4-methoxyphenol
2-[(1H-benzimidazol-2-yl)(1-methylpiperidin-4-yloxy)methyl]-4-phenoxyphenol
2-[(1H-benzimidazol-2-yl)(1-methylpiperidin-4-yloxy)methyl]-4-fluoro-6-methoxyphenol
2-[(1H-benzimidazol-2-yl)(1-methylpiperidin-4-yloxy)methyl]-4,5-dimethylphenol
2-[(1H-benzimidazol-2-yl)(1-methylpiperidin-4-yloxy)methyl]-4-(3-fluoropropylsulfanyl)phenol
2-[(1H-benzimidazol-2-yl)(1-methylpiperidin-4-yloxy)methyl]-4-fluoro-5-methylphenol
2-[(1H-benzimidazol-2-yl)(1-methylpiperidin-4-yloxy)methyl]-4-(2-fluoroethylsulfanyl)phenol
3-[(1H-benzimidazol-2-yl)(1-methylpiperidin-4-yloxy)methyl]-2-hydroxybiphenyl
2-[(1H-benzimidazol-2-yl)(1-methylpiperidin-4-yloxy)methyl]-6-ethylphenol
2-[(1H-benzimidazol-2-yl)(1-methylpiperidin-4-yloxy)methyl]-5-trifluoromethylphenol
2-[(1H-benzimidazol-2-yl)(1-methylpiperidin-4-yloxy)methyl]-4-hydroxyphenol
2-[(1H-benzimidazol-2-yl)(1-methylpiperidin-4-yloxy)methyl]-5,6,7,8-tetrahydro-1-naphthol
2-[(1H-benzimidazol-2-yl)(1-methylpiperidin-4-yloxy)methyl]-6-trifluoromethoxyphenol
2-[(1H-benzimidazol-2-yl)(1-methylpiperidin-4-yloxy)methyl]-5-trifluoromethoxyphenol
6-[(1H-benzimidazol-2-yl)(1-methylpiperidin-4-yloxy)methyl]-2-fluoro-3,4-dimethylphenol
6-[(1H-benzimidazol-2-yl)(1-methylpiperidin-4-yloxy)methyl]-3-fluoro-2-methylphenol
6-[(1H-benzimidazol-2-yl)(1-methylpiperidin-4-yloxy)methyl]-2,4-difluoro-3-methylphenol
6-[(1H-benzimidazol-2-yl)(1-methylpiperidin-4-yloxy)methyl]-2,3-difluorophenol
(1-{3-[benzothiazol-2-yl(1-methylpiperidin-4-yloxy)methyl]phenyl}-azetidin-3-yl)dimethylamine, oxalate
1-{3-[(1H-benzimidazol-2-yl)(1-methylpiperidin-4-yloxy)methyl]phenyl}pyrrolidin-3-ol, oxalate
2-{(1-methylpiperidin-4-yloxy)[3-(pyrrolidin-3-yloxy)phenyl]methyl}-1H-benzimidazole, dioxalate
2-[(5-chloro-2-fluorophenyl)(1-methylpiperidin-4-yloxy)methyl]-1H-benzimidazole, oxalate
2-[(2-fluoro-5-trifluoromethylphenyl)(1-methylpiperidin-4-yloxy)methyl]-1H-benzimidazole, oxalate
6-{3-[(1-ethyl-1H-benzimidazol-2-yl)(1-methylpiperidin-4-yloxy)methyl]phenyl}hex-5-ynylamine, oxalate
2-[(2-fluoro-5-methoxyphenyl)(1-methylpyrrolidin-3-ylmethoxy)methyl]-1H-benzimidazole, oxalate
2-[(1-methylpiperidin-4-yloxy)(3-trifluoromethylsulfanylphenyl)methyl]-1H-benzimidazole, oxalate
2-[(4-fluoro-3-trifluoromethoxyphenyl)(1-methylpiperidin-4-yloxy)methyl]-1H-benzimidazole, oxalate
2-[(2-fluoro-5-propoxyphenyl)(1-methylpiperidin-4-yloxy)methyl]-1H-benzimidazole, oxalate
4-[(1H-benzimidazol-2-yl)(1-methylpiperidin-4-yloxy)methyl]phenol
2-{[3-(3,3-difluoropyrrolidin-1-yl)phenyl](1-methylpiperidin-4-yloxy)methyl}-1H-benzimidazole, dioxalate
2-{[3-(5-fluorohexahydrocyclopenta[c]pyrrol-2-yl)phenyl](1-methylpiperidin-4-yloxy)methyl}benzothiazole, dioxalate
6-{3-[(1H-benzimidazol-2-yl)(1-methylpiperidin-4-yloxy)methyl]phenylsulfanyl}hexylamine, oxalate
5-{3-[(1H-benzimidazol-2-yl)(1-methylpiperidin-4-yloxy)methyl]phenylsulfanylmethyl}oxazolidin-2-one
N-(6-{3-[(1H-benzimidazol-2-yl)(1-methylpiperidin-4-yloxy)methyl]phenylsulfanyl}hexyl)guanidine, dihydrochloride
4-{3-[(1H-benzimidazol-2-yl)(1-methylpiperidin-4-yloxy)methyl]phenylsulfanyl}but-2-enylamine
4-{3-[(1H-benzimidazol-2-yl)(1-methylpiperidin-4-yloxy)methyl]phenylsulfanyl}but-2-enylamine, oxalate
N-(2-{3-[(1H-benzimidazol-2-yl)(1-methylpiperidin-4-yloxy)methyl]phenylsulfanyl}ethyl)-N-isobutyrylguanidine
3-{3-[(1H-benzimidazol-2-yl)(1-methylpiperidin-4-yloxy)methyl]phenyl}allylamine
cis-2-{3-[(1H-benzimidazol-2-yl)(1-methylpiperidin-4-yloxy)methyl]phenylsulfanylmethyl}cyclopropylmethylamine
N-(3-{3-[(1H-benzimidazol-2-yl)(1-methylpiperidin-4-yloxy)methyl]phenyl}allyl)guanidine, trihydrochloride
2-[(azetidin-3-ylmethoxy)(3-bromophenyl)methyl]-1H-benzimidazole
2-[(3-bromophenyl)(1-methylazetidin-3-ylmethoxy)methyl]-1H-benzimidazole
2-[(2,6-difluorophenyl)(1-methylpiperidin-4-yloxy)methyl]-1H-benzimidazole
2-[(2-fluoro-4-methylphenyl)(1-methylpiperidin-4-yloxy)methyl]-1H-benzimidazole
2-[(5-ethylsulfanyl-2-fluorophenyl)(1-methylpiperidin-4-yloxy)methyl]-1H-benzimidazole
2-[(azetidin-3-ylmethoxy)(2-fluoro-5-trifluoromethoxyphenyl)methyl]-1H-benzimidazole, oxalate
2-[(2-fluoro-5-trifluoromethoxyphenyl)(1-methylazetidin-3-ylmethoxy)methyl]-1H-benzimidazole, oxalate
2-[(3-ethylsulfanyl-2,6-difluorophenyl)(1-methylpiperidin-4-yloxy)methyl]-1H-benzimidazole
2-[(2,2-difluorobenzo[1,3]dioxol-5-yl)(1-methylpiperidin-4-yloxy)methyl]-1H-benzimidazole
2-[(piperidin-4-yloxy)thiophen-3-ylmethyl]-1H-benzimidazole
2-[(1-methylpiperidin-4-yloxy)thiophen-3-ylmethyl]-1H-benzimidazole
2-[(piperidin-4-yloxy)thiophen-2-ylmethyl]-1H-benzimidazole
2-[(1-methylpiperidin-4-yloxy)thiophen-2-ylmethyl]-1H-benzimidazole as well as their enantiomers, diastereomers, mixtures thereof and pharmaceutically acceptable salts, free forms, tautomers, hydrates and solvates.

The compounds of formula (I) can comprise one or more asymmetric carbon atoms. They can therefore exist in the form of enantiomers or diastereoisomers. These enantiomers and diastereoisomers, as well as their mixtures, including racemic mixtures, form part of the invention.

The compounds of the invention may also comprise tautomeric forms which are all encompassed by the present invention. In particular, in formula (I), the group:

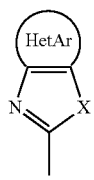

may have tautomeric forms such as when HetAr is a phenyl and X is N, leading to 1H-benzimidazole which is a tautomer of 3H-benzimidazole. A representative example is illustrated below:

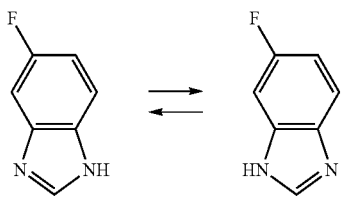 [SMILES: Fc1ccc2[nH]cnc2c1 ; Fc1ccc2nc[nH]c2c1]

The compounds of formula (I) can be provided in the form of a free base or in the form of addition salts with acids, which also form part of the invention.

These salts are advantageously prepared with pharmaceutically acceptable acids, but salts with other acids, useful for example for the purification or for the isolation of the compounds of formula (I), also form part of the invention.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propanoic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

The compounds of the general formula (I) having geometrical and stereomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, keto, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride;

alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, methylcyclohexane, toluene and xylene; amides, such as N,N-dimethylformamide; alcohols such as ethanol and methanol and ethers, such as diethyl ether, methyl tert-butyl ether, methyl cyclopentyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is another object of the present invention.

Compounds of formula (I) where A=O can be prepared by etherification of compound of formula (II):

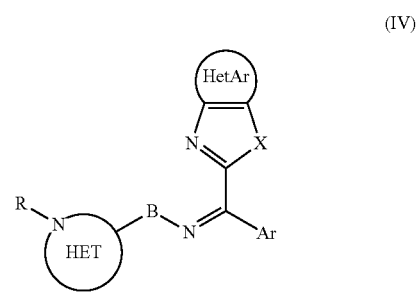

(II)

in which X, HetAr and Ar are as defined in general formula (I)

with a compound of formula (III):

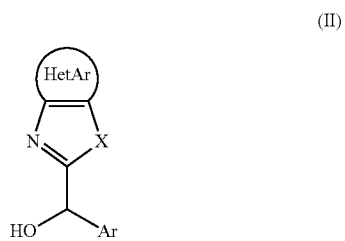

(III)

in which R, HET and B are as defined in general formula (I)

This etherification reaction can be performed in acidic medium (toluenesulfonic acid, methanesulfonic acid) in an inert solvent (toluene, dichlorobenzene, dichloroethane) at a temperature between room temperature and about 160° C.

Compounds of formula (II) can be prepared by condensing a benzothiazole or a benzimidazole derivative with an aldehyde ArCHO, by condensing an organometallic derivative ArMetal with an optionally substituted benzimidazole-2-carboxaldehyde or an optionally substituted benzothiazole-2-carboxaldehyde, or by condensing a hydroxy acid ArCHOHCOOH with an optionally substituted ortho-phenylenediamine or an optionally substituted 2-aminothiophenol or 2-aminophenol Compounds of formula (I) wherein A=NH can be prepared by reduction of compound of formula (IV):

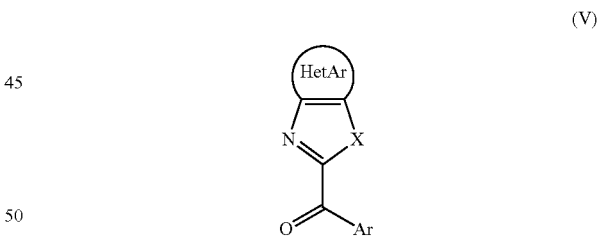

(IV)

in which R, HET, B, X, HetAr and Ar are as defined in general formula (I)

This reduction can be performed by hydrogenation with dihydrogen or transfer hydrogenation (formic acid, formic acid/triethylamine, ammonium formate) in the presence of a catalyst (palladium on charcoal) in an inert solvent (methanol, ethanol, ethyl acetate) at a temperature comprised between room temperature and about 150° C.

Compounds of formula (IV) in which R, HET, B, X, HetAr and Ar are as defined in general formula (I) can be prepared by condensing compound of formula (V):

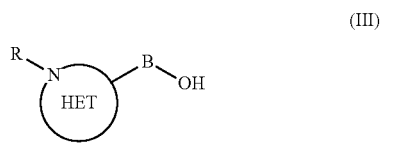

(V)

in which X, HetAr and Ar are as defined in general formula (I)

with an amine

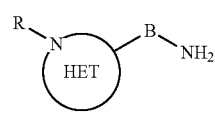

This condensation can be performed in the presence of an acid (titanium tetraisopropoxide) in an inert solvent (tetrahydrofurane) at a temperature comprised between room temperature and reflux of the medium.

Compounds of formula (V) in which X, HetAr and Ar are as defined in general formula (I) can be prepared by oxidizing compound of formula (II) in which X, HetAr and Ar are as defined in general formula (I).

This oxidation can be performed with an oxidizing agent (potassium permanganate, barium permanganate, manganese dioxide) in an inert solvent (dioxane, acetonitrile) at a temperature comprised between room temperature and reflux of the medium.

Compounds of formula (I) where A=NH can be prepared by condensation of compound of formula (II):

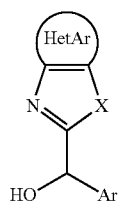

(II)

in which X, HetAr and Ar are as defined in general formula (I)
with an amine

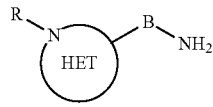

This condensation can be performed in the presence of a transition metal catalyst such as dichloro(pentamethylcyclopentadienyl)iridium(III) dimer, in the presence of a base such as sodium hydrogenocarbonate in an inert solvent such as toluene at a temperature comprised between about 80 and 150° C.

Alternatively, compounds of formula (I) in which A and X are NH can be prepared by condensing an organometallic reagent ArM onto a compound of formula (VI):

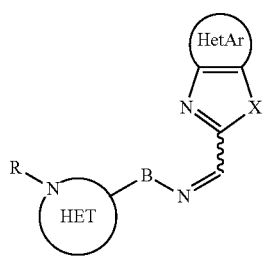

(VI)

in which R, HET, B, HetAr and Ar are as defined in general formula (I)

This addition can be performed by adding a Grignard reagent onto an imine in an inert solvent (tetrahydrofurane) at a temperature comprised between room temperature and reflux of the medium.

Compounds of formula (VI) in which R, HET, B, HetAr and Ar are as defined in general formula (I) can be prepared by condensing an optionally substituted benzimidazole-2-carboxaldehyde or heteroaryl fused imidazole-2-carboxaldehyde with an amine

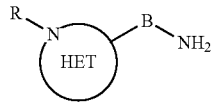

This condensation can be performed in the presence of molecular sieves or other dehydrating agent in an inert solvent (ethanol) at a temperature comprised between 40° C. and the refluxing temperature. A Dean Stark apparatus can also be used.

Alternatively, compounds of formula (I) in which A=O can be prepared by alkylation of compound of formula (VII):

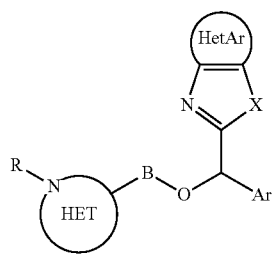

(VII)

in which HET, B, X, HetAr and Ar are as defined in general formula (I)

This alkylation can be performed by reductive method using a carbonylated compound and a reducing agent such as a borohydride, a cyanoborohydride, a triacetoxyborohydride, hypophosphonous acid, formic acid, formic acid/triethylamine or hydrogen, a catalyst such as palladium can be added for this transformation when hydrogen or hydrogen donnors are used.

Compounds of formula (VII) can be prepared by deprotection of compound of formula (VIII):

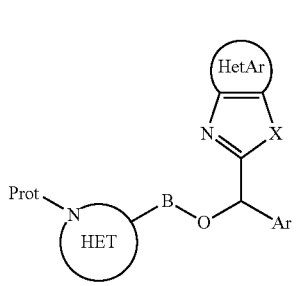

(VIII)

in which HET, B, X, HetAr and Ar are as defined in general formula (I) and Prot is a protecting group of the nitrogen atom.

When Prot is a tert-butoxycarbonyl group, the transformation is usually performed in acidic medium such a trifluoroacetic diluted with dichloromethane or in a solvent (ethyl acetate, ethanol, isopropanol) containing HCl. Preferably, this deprotection is performed at a temperature between 0° C. and the refluxing temperature of the medium.

Compounds of formula (VIII) in which HET, B, X, HetAr and Ar are as defined in general formula (I) and Prot is a protecting group of the nitrogen atom can be prepared using the general methods described above.

Alternatively, compounds of formula (VIII) in which A=O and HET, B, X, HetAr and Ar are as defined in general formula (I) and Prot is a protecting group of the nitrogen atom can be prepared by condensing an acid of formula (IX):

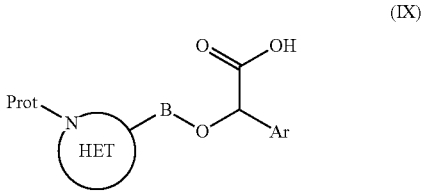
(IX)

in which HET, B and Ar are as defined in general formula (I) and Prot is a protecting group of the nitrogen atom, with an optionally substituted ortho-phenylenediamine or an optionally substituted 2-aminothiophenol.

This condensation can be performed by reacting the two compounds in acidic medium, or by first forming the amide bond with usual bond forming reagents, then dehydrating in acidic medium (acetic acid, hydrochloric acid) at a temperature comprised between room temperature and reflux.

Acids of formula (IX) in which HET, B and Ar are as defined in general formula (I) and Prot is a protecting group of the nitrogen atom can be prepared by hydrolysis of their esters. This hydrolysis can be performed in basic medium or in acidic medium at a temperature comprised between 0° C. and reflux of the medium.

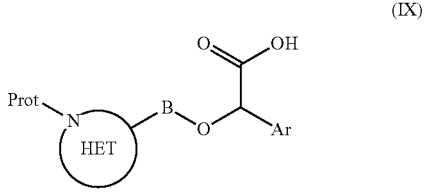
(IX)

Esters of the acid of formula (IX) in which HET, B, X and Ar are as defined in general formula (I) and Prot is a protecting group of the nitrogen atom can be prepared by condensing an ester of the acid (X)

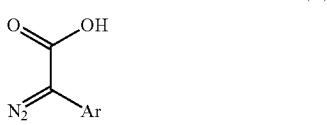
(X)

with an alcohol

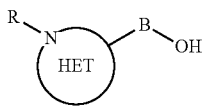

This condensation can be performed in the presence of a metal catalyst such as rhodium acetate dimer in an inert solvent such a dichloromethane or dichloroethane, at a temperature comprised between 0° C. and reflux of the medium.

Esters of the acid of formula (X) can be prepared from esters of an acid ArCH2COOH with a diazo transfer reagent such as tosylazide in the presence of a base such as 1,8-diazabicyclo[5.4.0]undec-7-ene in an inert solvent such as acetonitrile at a temperature comprised between −20° C. and 40° C.

Furthermore, compounds of formula (I) can be prepared from compounds of formula (I) by group interconversion or group transformation. Such reaction include, but are not limited to, reaction on aromatic or heteroaromatic groups such as halogen exchange reaction, Sonogashira reaction, Heck reaction, Suzuki reaction, sulfide condensation, triflate displacement with grignard reagents, copper catalysed ether formation, metal catalysed amine aromatic substitution, aromatic carbonylation reaction; reaction on reactive groups such as acylation, alcoxycarbonylation of nitrogen containing groups such as amines, amidines, guanidines; substitution of hydroxy with nucleophile (Mitsunobu reaction or activation and nucleophilic substitution); hydrogenation of unsaturation (alkenyl to alkyl, alkynyl to alkenyl, alkynyl to alkyl); Staudinger reduction of azido group.

The process of the invention may comprise the additional step of isolating the desired compound of formula (I).

The starting products and/or reagents may be commercially available, or may be readily prepared by the skilled person by applying or adapting the procedures disclosed in the experimental part below.

According to a still further object, the present invention is also concerned with pharmaceutical compositions comprising a compound of formula (I) as defined above with a pharmaceutically acceptable excipient.

The compounds of the invention are antagonists and/or inverse agonists of H4 R. The pharmaceutical compositions and compounds of the invention may thus be useful for use in the treatment and/or prevention of a disease associated with $H_4$ dysfunction, such as inflammatory disorders.

Said disease includes adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy induced airway responses, allergic rhinitis, viral rhinitis, non-allergic rhinitis, perennial and seasonal rhinitis, conjunctivitis, nasal congestion, allergic congestion; disorders of the genito-urinary tract such as female and male sexual dysfunction, overactive bladder conditions, urinary incontinence, bladder overactivity, benign prostate hyperplasia and lower urinary tract symptoms; dermatological diseases such as dermatitis and psoriasis and treatment of itchy skin; diseases of the cardiovascular system including thromboembolic diseases, atherosclerosis, myocardial infarction, angina pectoris, myocardial ischaemia and arrhythmia, peripheral arterial occlusive diseases, pulmonary embolisms or deep venous thromboses, hypotension, pulmonary hypertension, malignant hypertension, cardiac insufficiency, heart or kidney failure, stroke and renal dysfunction; diseases of the gastrointestinal tract including inflammatory bowel disease, Crohn's disease, ulcerative colitis; autoimmune diseases including rheumatoid arthritis, multiple sclerosis; cancer; pain; lymphatic diseases.

According to a further object, the present invention also concerns a combination of a compound of the invention with one or more therapeutic agent(s) selected from:

Histamine $H_1$, $H_2$ or $H_3$ receptor antagonists,
Leukotriene antagonists,
5-Lipoxygenase (5-LO) inhibitors or 5-lipoxygenase activating protein (FLAP) antagonists
$CX_1$- and $\alpha_2$-adrenoceptor agonist vasoconstrictor sympathomimetic agents for decongestant use
Xanthines, such as theophylline and aminophylline Non-steroidal antiinflammatories, such as sodium cromoglycate and nedocromil sodium Ketotifen COX-1 inhibitors (NSAIDs) and COX-2 selective inhibito Immunosuppressants mucolytics or anti-tussive agents More particularly, the present invention also concerns combinations comprising a compound of formula (I) of the invention with a H1R antagonist, such as cetirizine, desloratadine, bepotastine or doxepin.

According to a still further object, the present invention is also concerned with a compound of formula (I) for the above conditions to be administered to a patient in the need thereof.

According to a still further object, the present invention also concerns the methods of treatment comprising administering an effective amount of a compound of the invention for treating and/or preventing the above conditions or disorders.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day. A preferred daily dose for adult humans includes 1, 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably, the unit dose range is from 1 to 500 mg administered one to four times a day, and even more preferably from 1 mg to 300 mg, once a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches or ocular administration, or intravaginal or intra-uterine administration, particularly in the form of pessaries or by rectal administration.

The compositions may conveniently be administered in unit dosage form and may be prepared by any of the methods well known in the pharmaceutical art, for example, as described in Remington: *The Science and Practice of Pharmacy*, $20^{th}$ ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or *acacia*, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

Other features of the invention will become apparent in the course of the following description of exemplary embodiments that are given for illustration of the invention and not intended to be limiting thereof.

EXAMPLES

Melting points are determinated on Büchi capillary melting point apparatus.

Proton NMR spectra are recorded on a Bruker 250 MHz NMR instrument. Deuterochloroform is used as solvent unless otherwise stated. The chemicals shifts δ are expressed in ppm. The following abbreviations are used to denote signal patterns: s=singlet, d=doublet, t=triplet, q=quadruplet, m=multiplet, ms=massif. The coupling contents are expressed in Hz. The spectra recorded are consistent with the proposed structures.

TLC are performed on 0.25 mm silica gel F254 plates.

Example 1

2-[(1-methylpiperidin-4-yloxy)phenylmethyl]benzothiazole

1A

A mixture of benzothiazol-2-ylphenylmethanol (0.36 g), 4-hydroxy-1-methylpiperidine (0.17 g) and para-toluenesulfonic acid (0.57 g) in toluene (22 mL) is heated overnight in a Dean-Stark apparatus. The mixture is cooled back to room temperature and poured into water, alcalinised with 1N sodium hydroxide and extracted twice with ethyl acetate. Pooled organic extracts are washed with brine, dried over magnesium sulfate and concentrated. The residue is purified by column chromatography over silica gel (gradient dichloromethane/methanol from 98/2 to 90/10) to give 2-[(1-methylpiperidin-4-yloxy)phenylmethyl]benzothiazole melting at 115° C.

1B

A solution of benzothiazole (1.35 g) in tetrahydrofurane (10 mL) in a dried round bottom balloon is cooled at −70° C. A solution of butyl lithium (4.1 mL) is added and the mixture stirred for 15 minutes. Benzaldehyde (1.03 mL) diluted with tetrahydrofurane (10 mL) is then added. The mixture is stirred at −70° C. for 1 h, allowed to warm to −20° C. and quenched with saturated aqueous ammonium chloride solution. The mixture is extracted with ethyl acetate. Organic extracts are pooled, dried over magnesium sulfate and concentrated under reduced pressure. Trituration of the residue with diisopropyl oxide affords benzothiazol-2-ylphenylmethanol.

TLC (heptane/ethyl acetate 1/1) Rf=0.57

Further examples can be prepared according to the described general methods:

| Example | Product | General methods | Melting point |
|---|---|---|---|
| 2 | 2-[(1-methylpyrrolidin-3-yloxy)phenylmethyl]-benzothiazole, oxalate | 1A, 1B | 120° C. |
| 3 | 2-[(4-fluorophenyl)(1-methylpiperidin-4-yloxy)methyl]benzothiazole, oxalate | 1A, 1B | 192° C. |
| 4 | 2-[(4-chlorophenyl)(1-methylpiperidin-4-yloxy)methyl]benzothiazole, oxalate | 1A, 1B | 147-148° C. |
| 5 | 2-[(3-fluorophenyl)(1-methylpiperidin-4-yloxymethyl]benzothiazole, oxalate | 1A, 1B | 167-170° C. |
| 6 | 2-[(2-fluorophenyl)(1-methylpiperidin-4-yloxy)methyl]benzothiazole, oxalate | 1A, 1B | 178-179° C. |
| 7 | 2-[(1-methylpiperidin-4-yloxy)-p-tolylmethyl]benzothiazole, oxalate | 1A, 1B | 177° C. |
| 8 | 2-[(1-methylpiperidin-4-yloxy)(m-tolyl)methyl]benzothiazole, oxalate | 1A, 1B | 177° C. |
| 10 | 2-[(2,3-dihydrobenzo[1,4]dioxin-6-yl)(1-methylpiperidin-4-yloxy)methyl]benzothiazole, hydrochloride | 1A, 1B | 71° C. |
| 11 | 2-[(3-methoxyphenyl)(1-methylpiperidin-4-yloxy)methyl]benzothiazole, hydrochloride | 1A, 1B | 182° C. |
| 12 | 2-[(2,4-difluorophenyl)(1-methylpiperidin-4-yloxy)methyl]benzothiazole, dioxalate | 1A, 1B | 182° C. |
| 14 | 2-[(4-methoxyphenyl)(1-methylpiperidin-4-yloxy)methyl]benzothiazole, dihydrochloride | 1A, 1B | 72° C. |
| 15 | 2-[(3,5-difluorophenyl)(1-methylpiperidin-4-yloxy)methyl]benzothiazole, oxalate | 1A, 1B | 165° C. |

Following compounds are prepared using general methods described in Example 1:

| Example | Product |
|---|---|
| 9 | (benzothiazol-2-yl-phenylmethyl)(1-methylpiperidin-4-yl)amine |
| | ¹H NMR: 8.00 (d, 1H), 7.90 (d, 1H), 7.55-7.35 (m, 2H), 7.32 (d, 1H), 7.10 (d, 1H), 6.98 (d, 1H), 6.17 (s, 1H), 3.80-3.65 (m, 1H), 2.80-2.65 (m, 2H), 2.29 (s, 3H),), 2.28-2.15 (m, 2H), 2.10-1.80 (m, 4H) |
| 13 | 2-[(1-methylpiperidin-4-yloxy)thiophen-2-ylmethyl]benzothiazole |
| | ¹H NMR: 7.95 (d, 1H), 7.84 (d, 1H), 7.52 (m, 2H), 7.50-7.25 (m, 5H), 5.44 (s, 1H), 3.88-3.75 (m, 2H), 3.65-3.50 (m, 1H), 2.24 (s, 3H),), 2.15-1.85 (m, 4H), 1.65-1.35 (m, 2H) |
| 23 | 2-[(1-methylpiperidin-4-yloxy)(3-trifluoromethoxyphenyl)methyl]benzothiazole, oxalate |
| | ¹H NMR (DMSO-d⁶): 7.99 (d, 1H), 7.87 (d, 1H), 7.55-7.35 (m, 5H), 7.27-7.15 (m, 1H), 6.11 (s, 1H), 3.95-3.80 (m, 1H), 3.50-3.00 (m, 6H), 2.79 (s, 3H),), 2.20-1.70 (m, 4H), |

Example 16

16A

A mixture of (benzothiazol-2-yl)(thien-3-yl)methanol (0.247 g), 4-hydroxy-1-methylpiperidine (0.115 g) and para-toluenesulfonic acid (0.27 g) in dichloroethane (20 mL) is heated for 4H in a Dean-Stark apparatus. The mixture is concentrated under reduced pressure and the residue taken up in ethyl acetate. The organic phase is washed with water, dried over magnesium sulfate and concentrated. The residue is purified by column chromatography over silica gel (gradient dichloromethane/methanol from 100/0 to 95/5). Salification with oxalic acid in acetone gives -[(1-methylpiperidin-4-yloxy)thiophen-3-ylmethyl]benzothiazole oxalate melting at 174° C.

16B (benzothiazol-2-yl)(thien-3-yl)methanol is prepared according to general method 1B.

Example 21

21A

A solution of [(benzothiazol-2-yl)(m-tolyl)methylene](1-methylpiperidin-4-yl)amine (0.45 g) in methanol (30 mL) containing 10% palladium on charcoal (0.1 g) is stirred under dihydrogene (1 atm) at room temperature for 3 h. The suspension is filtered over clarcel and concentrated under reduced pressure. The residue is dissolved in acetone (2 mL) and mixed with a solution of oxalic acid (76 mg) in acetone (2 mL). A precipitate forms which is filtered, rinsed with acetonitrile and diethyl ether and dried under vacuum to afford [(benzothiazol-2-yl)(m-tolyl)methyl](1-methylpiperidin-4-yl)amine dioxalate melting at 127° C.

21B

To a solution of (benzothiazol-2-yl)(m-tolyl)methanone (1.06 g) and 4-amino-1-methylpiperidine (0.456 g) in tetrahydrofurane (4 mL) is added titanium tetraisopropoxide (1.42 g). The mixture is stirred at room temperature for 1 h, then polymethyl hydrosiloxane (1.2 mL) is added. The mixture is stirred for one day at room temperature, diluted with ethyl acetate (50 mL), hydolysed with 3N sodium hydroxide (30 mL). The organic phase is separated by decantation, washed with water, dried over magnesium sulfate and concentrated in vacuo. The residue is crystallised by triturration in diisopropyl oxide. A second crop can be obtained form the mother liquor by chromatography over silica gel (gradient dichloromethane/methanol from 98/2 to 95/5) to give [(benzothiazol-2-yl)(m-tolyl)methylene](1-methylpiperidin-4-yl)amine meting at 125° C.

21C

To a solution of (benzothiazol-2-yl)(m-tolyl)methanol (2.41 g) in dioxane (30 mL) is added manganese dioxide (1.2 molar equivalent). The mixture is stirred overnight at room temperature, then filtered over a clarcel pad. The filtrate is concentrated under reduced pressure. The residue is triturated in heptane and diisopropyl oxide to give (benzothiazol-2-yl)(m-tolyl)methanone

21D (benzothiazol-2-yl)(m-tolyl)methanol can be obtained as described in Example 1B.

Further examples can be prepared according to the described general methods:

| Example | Product | General methods | Melting point |
|---|---|---|---|
| 17 | 2-[(1-methylpiperidin-4-yloxy)naphthalen-1-ylmethyl]benzothiazole | 1A, 1B | 106.5° C. |
| 18 | 2-[(1-methylpiperidin-4-yloxy)naphthalen-2-ylmethyl]benzothiazole, dihydrochloride | 1A, 1B | 198° C. |
| 19 | 2-[(1-methylpiperidin-4-yloxy)(5-methylthiophen-2-yl)methyl]benzothiazole, oxalate | 16A, 1B | 174° C. |
| 20 | 2-[benzo[1,3]dioxol-5-yl(1-methylpiperidin-4-yloxy)methyl]benzothiazole, dihydrochloride | 1A, 1B | 110° C. |
| 24 | 2-[(1-methylpiperidin-4-yloxy)(4-trifluoromethoxyphenyl)methyl]benzothiazole, oxalate | 1A, 1B | 155° C. |
| 25 | [benzothiazol-2-yl(3-methoxyphenyl)methyl](1-methylpiperidin-4-yl)amine, dioxalate | 21A, 21B, 21C, 1B | 160° C. |
| 27 | 2-[(3-bromo-phenyl)(1-methylpiperidin-4-yloxy)methyl]benzothiazole | 1A, 1B | 99° C. |
| 28 | 2-[(1-methylpiperidin-4-yloxy)(3-phenoxy-phenyl)methyl]benzothiazole, oxalate | 1A, 1B | 92° C. |
| 29 | 5-methyl-2-[(1-methylpiperidin-4-yloxy)phenylmethyl]benzothiazole, oxalate | 1A, 1B | 175° C. |
| 30 | 2-[(1-methylpiperidin-4-yloxy)phenylmethyl]-1H-benzimidazole | 1A, 1B | 110° C. |
| 31 | 2-[(1-methylpiperidin-4-yloxy)(3-trifluoromethylphenyl)methyl]benzothiazole, hydrochloride | 1A, 1B | 61° C. |
| 34 | 2-[(4-fluoro-3-methylphenyl)(1-methylpiperidin-4-yloxy)methyl]benzothiazole, oxalate | 1A, 1B | 120° C. |
| 35 | [benzothiazol-2-yl(4-fluoro-3-methyl-phenyl)methyl](1-methylpiperidin-4-yl)amine, dioxalate | 1A, 1B | 160° C. |

-continued

| Example | Product | General methods | Melting point |
|---------|---------|-----------------|---------------|
| 36 | (benzothiazol-2-yl-p-tolylmethyl)(1-methylpiperidin-4-yl)amine, oxalate | 1A, 1B | 110° C. |
| 38 | 2-[(3-fluoro-5-methylphenyl)(1-methylpiperidin-4-yloxy)methyl]benzothiazole, oxalate | 1A, 1B | 170° C. |

Example 26

To a solution of 2-[(3-allyloxyphenyl)(1-methylpiperidin-4-yloxy)methyl]benzothiazole example 22 (250 mg) in ethanol (10 mL) is added 10% palladium on charcoal (25 mg). The mixture is stirred overnight under dihydrogen (1 atm) at room temperature, then filtrated over a clarcel pad. The filtrate is concentrated under reduced pressure to give the crude base which is converted to 2-[(1-methylpiperidin-4-yloxy)(3-propoxy-phenyl)methyl]benzothiazole, dihydrochloride melting at 59° C.

Following compounds are prepared using general methods described in example 1:

| Example | Product |
|---------|---------|
| 33 | 5-fluoro-2-[(1-methylpiperidin-4-yloxy)phenylmethyl]benzothiazole |

$^1$H NMR: 7.80 (dd, 1H), 7.65 (dd, 1H), 7.58-7.68 (m, 2H), 7.45-7.28 (m, 3H), 7.14 (dt, 1H), 5.89 (s, 1H), 3.80-3.60 (m, 1H), 2.90-2.72 (m, 2H), 2.38 (s, 3H), 2.15-1.70 (m, 6H)

Example 37

37A

Reduction of [(benzofuran-2-yl)(benzothiazol-2-yl)methylene](1-methylpiperidin-4-yl)amine as described in example 21A affords [(benzofuran-2-yl)(benzothiazol-2-yl)methyl](1-methylpiperidin-4-yl)amine oxalate melting at 125° C.

37B

To a solution of (benzofuran-2-yl)(benzothiazol-2-yl)methanone (1.4 g) and 4-amino-1-methylpiperidine (0.57 g) in tetrahydrofurane (8 mL) is added dropwise titanium tetraisopropoxide (1.78 g). The suspension is stirred for 24 h at room temperature, diluted with ethyl acetate and 1N sodium hydroxide. The precipitate is filtered over a clarcel pad and rinsed with ethyl acetate. The pooled filtrates are washed with saturated sodium chloride solution, dried and concentrated under reduced pressure. The residue is purified over silica gel (gradient dichloromethane/methanol from 100/0 to 90/10) to afford [(benzofuran-2-yl)(benzothiazol-2-yl)methylene](1-methylpiperidin-4-yl)amine.

37C (benzofuran-2-yl)(benzothiazol-2-yl)methanone can be prepared as described in example 21C.

37D (benzofuran-2-yl)(benzothiazol-2-yl)methanone can be prepared as described in example 1B.

Further examples can be prepared according to the described general methods:

| Example | Product | General methods | Melting point |
|---------|---------|-----------------|---------------|
| 39 | [(1H-benzimidazol-2-yl)phenylmethyl](1-methylpiperidin-4-yl)amine | 21A, 37B, 21C, 1B | 133° C. |
| 40 | 2-[(3-fluoro-5-methoxyphenyl)(1-methylpiperidin-4-yloxy)methyl]benzothiazole, oxalate | 1A, 1B | 145° C. |
| 41 | 2-[(3-iodophenyl)(1-methylpiperidin-4-yloxy)methyl]benzothiazole, oxalate | 1A, 1B | 165-170° C. |

Example 42

[benzothiazol-2-yl(3-propoxyphenyl)methyl](1-methylpiperidin-4-yl)amine

42A

Hydrogenation of [benzothiazol-2-yl(3-propoxyphenyl)methylene](1-methylpiperidin-4-yl)amine as described in example 21A gives [benzothiazol-2-yl(3-propoxyphenyl)methyl](1-methylpiperidin-4-yl)amine melting at 90° C.

42B

Condensation of benzothiazol-2-yl(3-propoxyphenyl)methanone with 4-amino-1-methylpiperidine as described in example 37B gives [benzothiazol-2-yl(3-propoxyphenyl)methylene](1-methylpiperidin-4-yl)amine.

42C

A mixture benzothiazol-2-yl(3-propoxyphenyl)methanol (1 g) and barium permanganate (0.95 g) in acetonitrile 15 mL) is refluxed for 30 minutes. The mixture is filtered over a clarcel pad, concentrated under reduced pressure and purified by column chromatography over silica gel (eluant heptane/ethyl acetate: 4/1) to give benzothiazol-2-yl(3-propoxyphenyl)methanone as a white crystalline solid.

42D

Benzothiazol-2-yl(3-propoxyphenyl)methanol can be prepared as described in example 1B.

Further examples can be prepared according to the described general methods:

| Example | Product | General methods | Melting point |
|---|---|---|---|
| 43 | [benzothiazol-2-yl(3-fluoro-5-methoxyphenyl)methyl](1-methylpiperidin-4-yl)amine, oxalate | 21A, 37B, 21C, 1B | 157° C. |
| 44 | [benzothiazol-2-yl(3-fluoro-5-methylphenyl)methyl](1-methylpiperidin-4-yl)amine | 21A, 37B, 21C, 1B | 102° C. |
| 45 | 2-[(3-benzyloxyphenyl)(1-methylpiperidin-4-yloxy)methyl]benzothiazole, oxalate | 1A, 1B | 52° C. |
| 46 | 2-[benzofuran-5-yl(1-methylpiperidin-4-yloxy)methyl]benzothiazole, oxalate | 1A, 1B | 153° C. |
| 47 | 2-[(3-ethoxyphenyl)(1-methylpiperidin-4-yloxy)methyl]benzothiazole, oxalate | 1A, 1B | 84° C. |
| 48 | [benzothiazol-2-yl(3-iodophenyl)methyl](1-methylpiperidin-4-yl)amine, oxalate | 21A, 37B, 21C, 1B | 188-195° C. |
| 49 | 2-[(1-methylpiperidin-4-yloxy)(3-propoxyphenyl)methyl]-1H-benzimidazole | 1A, 1B | 135° C. |
| 50 | [(1H-benzimidazol-2-yl)(3-propoxyphenyl)methyl](1-methylpiperidin-4-yl)amine | 21A, 37B, 21C, 1B | 143° C. |
| 51 | 2-[(3-iodophenyl)(1-methylpiperidin-4-yloxy)methyl]-1H-benzimidazole | 1A, 1B | 173.5° C. |
| 52 | (benzothiazol-2-ylpyridin-3-ylmethyl)(1-methylpiperidin-4-yl)amine | 21A, 37B, 42C, 1B | 109° C. |

53

A mixture of 2-[(3-iodophenyl)(1-methylpiperidin-4-yloxy)methyl]benzothiazole (200 mg), phenylboronic acid (70 mg), palladium acetate (4.8 mg) and 1,1-bis(diphenylphosphino)ferrocene is placed in a round-bottom flask and purged with argon. A 1M aqueous degassed solution of potassium carbonate (1.51 mL) and degassed tetrahydrofuran (2 mL) are introduced. The mixture is heated at 95° C. for 30 min, cooled back to room temperature and filtered over a celite pad. The cake is rinsed with ethyl acetate and water. The pooled phases are decanted. The organic phase is dried over magnesium sulfate and concentrated. The residue is purified by column chromatography (gradient dichloromethane/methanol from 98/2 to 90/10) to give the crude base which is then converted to the oxalate in acetone to give 2-[biphenyl-3-yl(1-methylpiperidin-4-yloxy)methyl]benzothiazole, oxalate as a beige amorphous solid.

$^1$H NMR (DMSO-d$^6$): 8.05 (d, 1H), 7.91 (d, 1H), 7.77 (s, 1H), 7.68-7.58 (m, 3H), 7.55-7.30 (m, 7H), 6.20 (s, 1H), 3.90-3.78 (m, 1H), 3.32-2.90 (m, 4H), 2.67 (s, 3H), 2.20-1.70 (m, 4H)

Following compounds are prepared analogously:

| Example | Product |
|---|---|
| 54 | {3'-[benzothiazol-2-yl(1-methylpiperidin-4-yloxymethyl]biphenyl-3-yl}methanol, oxalate |

$^1$H NMR (DMSO-d$^6$): 8.02 (d, 1H), 7.87 (d, 1H), 7.72 (s, 1H), 7.62-7.35 (m, 8H), 7.27 (d, 1H), 6.13 (s, 1H), 4.51 (s, 2H), 3.92-3.80 (m, 1H), 3.40-2.90 (m, 4H), 2.70 (s, 3H), 2.25-1.70 (m, 4H)

| | |
|---|---|
| 63 | 2-[(1-methylpiperidin-4-yloxy)(3-pyridin-3-ylphenyl)methyl]benzothiazole, oxalate |

$^1$H NMR (DMSO-d$^6$): 8.86 (d, 1H), 8.57 (dd, 1H), 8.09-8.00 (m, 2H), 7.92 (d, 1H), 7.84 (s, 1H), 7.73-7.63 (m, 1H), 7.58-7.37 (m, 5H), 6.21 (s, 1H), 3.92-3.78 (m, 1H), 3.40-2.95 (m, 4H), 2.70 (s, 3H), 2.25-1.75 (m, 4H)

| | |
|---|---|
| 79 | 3'-[benzothiazol-2-yl(1-methylpiperidin-4-yloxy)methyl]biphenyl-3-ylamine, oxalate |

$^1$H NMR (DMSO-d$^6$): 8.07 (d, 1H), 7.91 (d, 1H), 7.66 (s, 1H), 7.53-7.37 (m, 5H), 7.07 (t, 1H), 6.78 (s, 1H), 6.71 (d, 1H), 6.54 (d, 1H), 6.18 (s, 1H), 4.20-3.70 (m, 5H), 3.42-2.95 (m, 4H), 2.70 (s, 3H), 2.25-1.75 (m, 4H)

| | |
|---|---|
| 81 | 2-[biphenyl-3-yl(1-methylpiperidin-4-yloxy)methyl]-1H-benzimidazole |

$^1$H NMR: 12.38 (sl, 1H), 7.78 (s, 1H), 7.65-7.40 (m, 10H), 7.15-7.05 (m, 2H), 5.91 (s, 1H), 3.50-3.35 (m, 1H), 2.68-2.50 (m, 2H), 2.10 (s, 3H), 2.05-1.84 (m, 4H), 1.70-1.50 (m, 2H)

| | |
|---|---|
| 86 | {3'-[(1H-benzimidazol-2-yl)(1-methylpiperidin-4-yloxy)methyl]biphenyl-3-yl}methanol |

$^1$H NMR (DMSO-d$^6$): 12.37 (sl, 1H), 7.77 (s, 1H), 7.62-7.35 (m, 8H), 7.28 (d, 1H), 7.15-7.02 (m, 2H), 5.92 (s, 1H), 5.22 (t, 1H), 4.53 (d, 2H), 3.48-3.32 (m, 1H), 2.68-2.50 (m, 2H), 2.08 (s, 3H), 2.00-1.78 (m, 4H), 1.69-1.48 (m, 2H)

| | |
|---|---|
| 87 | 3'-[(1H-benzimidazol-2-yl)(1-methylpiperidin-4-yloxy)methyl]biphenyl-3-ylamine |

$^1$H NMR: 9.57 (sl, 1H), 7.82-8.68 (m, 1H), 7.67 (s, 1H), 7.55-7.35 (m, 4H), 7.30-7.15 (m, 3H), 6.94 (d, 1H), 6.85 (s, 1H), 6.67 (d, 1H), 5.92 (s, 1H), 3.85-3.50 (m, 3H), 2.80-2.75 (m, 2H), 2.27 (s, 3H), 2.25-1.65 (m, 6H)

| | |
|---|---|
| 89 | 2-[(1-methylpiperidin-4-yloxy)(3-pyridin-3-ylphenyl)methyl]-1H-benzimidazole |

$^1$H NMR: 9.62 (sl, 1H), 8.80 (d, 1H), 8.58 (dd, 1H), 7.83 (d, 1H), 7.80-7.65 (m, 2H), 7.55-7.20 (m, 7H), 5.96 (s, 1H), 3.70-3.55 (m, 1H), 2.85-2.70 (m, 2H), 2.30 (s, 3H), 2.25-1.65 (m, 6H)

| | |
|---|---|
| 96 | 2-[(2'-methoxybiphenyl-3-yl)(1-methylpiperidin-4-yloxy)methyl]benzothiazole |

$^1$H NMR: 8.02 (d, 1H), 7.88 (d, 1H), 7.74 (s, 1H), 7.55-7.25 (m, 7H), 7.08-6.95 (m, 2H), 5.99 (s, 1H), 3.77 (s, 3H), 3.75-3.65 (m, 1H), 2.82-2.68 (m, 2H), 2.29 (s, 3H), 2.29-2.15 (m, 2H), 2.10-1.80 (m, 4H)

| Example | Product |
|---|---|
| 97 | 2-[(1-methylpiperidin-4-yloxy)(3'-nitrobiphenyl-3-yl)methyl]benzothiazole |
| | ¹H NMR: 8.45 (d, 1H), 8.22 (d, 1H), 7.99 (d, 1H), 7.95-7.85 (m, 2H), 7.80 (s, 1H), 7.65-7.35 (m, 6H), 6.00 (s, 1H), 3.80-3.65 (m, 1H), 2.88-2.70 (m, 2H), 2.42-2.25 (m, 2H), 2.34 (s, 3H), 2.10-1.70 (m, 4H) |
| 99 | 2-[(3'-methoxybiphenyl-3-yl)(1-methylpiperidin-4-yloxy)methyl]benzothiazole |
| | ¹H NMR: 7.98 (d, 1H), 7.86 (d, 1H), 7.74 (s, 1H), 7.68-7.30 (m, 6H), 7.17 (d, 1H), 7.10 (d, 1H), 6.92 (d, 1H), 5.96 (s, 1H), 3.92-3.78 (m, 1H), 3.86 (s, 3H), 3.05-2.85 (m, 2H), 2.85-2.55 (m, 2H), 2.50 (s, 3H), 2.35-2.12 (m, 2H), 2.12-1.85 (m, 2H) |
| 100 | 2-[(4'-methoxybiphenyl-3-yl)(1-methylpiperidin-4-yloxy)methyl]benzothiazole, oxalate |
| | ¹H NMR: 8.06 (d, 1H), 7.91 (d, 1H), 7.71 (s, 1H), 7.50-7.30 (m, 7H), 7.02 (d, 2H), 6.18 (s, 1H), 3.92-3.78 (m, 1H), 3.77 (s, 3H), 3.45-2.90 (m, 4H), 2.70 (s, 3H), 2.12-1.72 (m, 4H) |
| 128 | 2-[(1-methylpiperidin-4-yloxy)(3'-methylsulfanylbiphenyl-3-yl)methyl]benzothiazole, oxalate |
| | ¹H NMR (DMSO d⁶): 8.07 (d, 1H), 7.92 (d, 1H), 7.78 (s, 1H), 7.62 (sl, 1H), 7.55-7.32 (m, 7H), 7.27 (sl, 1H), 6.20 (s, 1H), 3.45-3.30 (m, 1H), 3.30-2.82 (m, 4H), 2.67 (s, 3H), 2.47 (s, 3H), 2.25-1.75 (m, 4H) |
| 133 | 2-[(3',4'-dichlorobiphenyl-3-yl)(1-methylpiperidin-4-yloxy)methyl]benzothiazole |
| | ¹H NMR: 7.98 (d, 1H), 7.88 (d, 1H), 7.70 (s, 1H), 7.66 (d, 1H), 7.52-7.35 (m, 7H), 5.97 (s, 1H), 3.82-3.68 (m, 1H), 2.95-2.78 (m, 2H), 2.55-2.40 (m, 2H), 2.40 (s, 3H), 2.20-1.80 (m, 4H) |
| 136 | 2-[(4'-fluorobiphenyl-3-yl)(1-methylpiperidin-4-yloxy)methyl]benzothiazole |
| | ¹H NMR: 7.98 (d, 1H), 7.86 (d, 1H), 7.71 (s, 1H), 7.68-7.30 (m, 7H), 7.15 (d, 1H), 7.10 (d, 1H), 5.98 (s, 1H), 3.80-3.63 (m, 1H), 2.88-2.72 (m, 2H), 2.42-2.25 (m, 2H), 2.34 (s, 3H), 2.15-1.75 (m, 4H) |
| 137 | 2-[(2'-fluorobiphenyl-3-yl)(1-methylpiperidin-4-yloxy)methyl]benzothiazole |
| | ¹H NMR: 7.99 (d, 1H), 7.88 (d, 1H), 7.75 (s, 1H), 7.50-7.10 (m, 9H), 5.98 (s, 1H), 3.82-3.75 (m, 1H), 2.88-2.70 (m, 2H), 2.33 (s 3H), 2.40-2.20 (m, 2H), 2.12-1.85 (m, 4H) |

72

2-[(3-bromophenyl)(1-methylpiperidin-4-yloxy)methyl]-1H-benzimidazole

72A

A mixture of 1H-benzimidazol-2-yl(3-bromophenyl)methanol (12.9 g), 4-hydroxy-1-methylpiperidine (4.86 g) and para-toluenesulfonic acid (24 g) in chlorobenzene (60 mL) and N-methylpyrrolidone (6 mL) is heated under reflux for 120 h in a Dean Stark apparatus. Solvent is removed by evaporation. To the residue is added water which is made alcaline by addition of sodium hydroxide solution, then extracted with ethyl acetate. The pooled organic extracts are washed with water, treated with activated charcoal, dried over magnesium sulfate and concentrated under reduced pressure. The residue is triturated in diethyl ether to give 2-[(3-bromophenyl)(1-methylpiperidin-4-yloxy)methyl]-1H-benzimidazole.

72B

A mixture of (3-bromophenyl)hydroxyacetic acid (20 g) and ortho-phenylenediamine (9.36 g) in 5N aqueous hydrochloric solution (100 mL) is heated under reflux for 4 h and cooled back to room temperature. The precipitate is separated by filtration, rinsed with acetonitrile and dried under vacuum with phosphorus pentoxide et give 1H-benzimidazol-2-yl(3-bromophenyl)methanol as a white crystalline solid used without further purification.

72C

To a solution of 3-bromobenzaldehyde (18.5 g) in tetrahydrofuran (400 mL) is added trimethylsilylcyanide (10.9 g). Two drops of a 1M solution of tetrabutylammonium fluoride in tetrahydrofuran are added to the reaction mixture (a small exotherm is observed). After one hour at room temperature, solvent and volatiles are removed under reduced pressure. To the residual oil is added 6N aqueous hydrochloric acid (100 mL). The round-bottom flask is equipped with a Dean-Stark apparatus and the reaction mixture is heated to reflux for 3 hours while removing silanols.

The reaction mixture is cooled to 0° C. and a 10N sodium hydroxide solution is added dropwise to reach pH 1. The aqueous phase is extracted with ethyl acetate. The pooled organic phases are washed with brine; dried on magnesium sulphate and concentrated to dryness under reduced pressure. The residual solid is re-crystallized from hot toluene to give (3-bromophenyl)hydroxyacetic acid.

¹H NMR (DMSO-d⁶): 7.57 (t, 1H), (d, 1H), 7.45 (dt, 1H), 7.38 (s, 1H), 7.28 (t, 1H), 5.03 (s, 1H).

Following compounds are prepared using general methods 21A and 21B:

| Example | Product |
|---|---|
| 64 | [(1H-benzimidazol-2-yl)(3-bromophenyl)methyl](1-methylpiperidin-4-yl)amine |
| | ¹H NMR: 9.60 (sl, 1H), 7.75 (sl, 1H), 7.65 (s, 1H), 7.50-7.32 (m, 3H), 7.30-7.15 (m, 3H), 5.84 (s, 1H), 3.62-3.58 (m, 1H), 2.85-2.68 (m, 2H), 2.28 (s, 3H), 2.25-1.65 (m, 7H) |

Example 56

[benzothiazol-2-yl(3-propoxyphenyl)methyl](1-methylpiperidin-4-yl)amine enantiomer A A solution of racemic [benzothiazol-2-yl(3-propoxyphenyl)methyl](1-methylpiperidin-4-yl)amine (10 mg/mL) in a mixture of heptane/isopropanol (80/20) containing diethylamine (0.1%) is injected (20×100 µL) onto an analytical Chiralpak AD-H, 250×4.6 mm column. Elution is performed with a mixture of heptane/isopropanol (80/20) containing diethylamine (0.1%) at a flow of 1 mL/min. Products are detected at 220 nm.

47

The first enantiomer has a retention time of 6.7 min.
Collection affords [benzothiazol-2-yl(3-propoxyphenyl)methyl](1-methylpiperidin-4-yl)amine enantiomer A with a chromatographic enantiomeric purity of 92.6%.

Example 57

[benzothiazol-2-yl(3-propoxyphenyl)methyl](1-methylpiperidin-4-yl)amine enantiomer B The second enantiomer has a retention time of 8.2 min.
Collection affords [benzothiazol-2-yl(3-propoxyphenyl)methyl](1-methylpiperidin-4-yl)amine enantiomer B with a chromatographic enantiomeric purity of 98.8%.

Example 59

[(1H-benzimidazol-2-yl)(3-trifluoromethylphenyl)methyl](1-methylpiperidin-4-yl)amine

59A

To a solution of (1H-benzimidazol-2-ylmethylene)(1-methylpiperidin-4-yl)amine (70 mg) in tetrahydrofurane (3 mL) is added a 1.5M solution of 3-trifluoromethylphenylmagnesium bromide in tetrahydrofurane (0.77 mL) at room temperature. The mixture is then stirred at 40° C. for 1 h, hydrolyzed with water and extracted with ethyl acetate. The pooled organic extracts are washed with brine, dried over magnesium sulfate and concentrated under reduced pressure. The residue is purified by column chromatography (gradient dichloromethane/methanol/ammonia from 95/5/0.5 to 90/10/0.5) to give [(1H-benzimidazol-2-yl)(3-trifluoromethylphenyl)methyl](1-methylpiperidin-4-yl)amine as a yellow solid melting at 90° C.

59B

1H-Benzimidazole-2-carboxaldehyde (781 mg, can be prepared according to Fegy, K. Angewandte Chemie Int Ed, 1998, vol. 37, 1270-1273), 4-amino-1-methylpiperidine (781 mg) and 4 Å molecular sieves (15 g) in ethanol (100 mL) are heated under reflux for 4 h. The mixture is then filtered and the filtrate concentrated under reduced pressure to yield (1H-benzimidazol-2-ylmethylene)(1-methylpiperidin-4-yl)amine as a beige solid.

62

To a solution of 2-[(3-allyloxyphenyl)(1-methylpiperidin-4-yloxy)methyl]benzothiazole (example 22) (2.35 g) in tetrahydrofurane (40 mL) is added tetrakistriphenylphosphine-palladium (0.344 g). The mixture is stirred for 5 min at room temperature, then sodium borohydride (0.576 g) is added. The mixture is stirred for 20 h at room temperature, filtered over a clarcel pad. The pad is rinsed with ethyl acetate. Pooled organic phases are washed with aqueous ammonium chloride solution, then sodium hydrogenocarbonate, dried over magnesium sulfate and concentrated under reduced pressure. The residue is purified by three column chromatographies over silica gel (twice gradient heptane/ethyl acetate from 95/5 to 80/20, third eluant heptane/dichloromethane 5/1). Pooled fractions are concentrated under reduced pressure. The residue is dissolved in methanol, refluxed for 5 h and concentrated under reduced pressure. The residue is purified by column chromatography (gradient dichloromethane/methanol/ammonia from 100/0 to 90/10/1) to give 3-[benzothiazol-2-yl(1-methylpiperidin-4-yloxy)methyl]phenol as a beige solid melting at 201° C.

in the case of ketone-containing substituents, it is judicious to protect the carbonyl function (as an acetal for example) prior to the Grignard preparation Example 91

91A

A mixture of 4-amino-1-methylpiperidine (0.23 g), benzothiazol-2-yl(3-butoxyphenyl)methanol (0.63 g), sodium hydrogenocarbonate (2 mg) and dichloro(pentamethylcyclopentadienyl)iridium(III) dimer (8 mg) in toluene (3 mL) is heated in an autoclave at 110-120° C. for 66 hours. The mixture is purified by chromatography over silica gel (eluant dichloromethane/methanol: 98/2) to give the crude base, which is transformed to the oxalate in acetone to give [benzothiazol-2-yl(3-butoxyphenyl)methyl](1-methylpiperidin-4-yl)amine oxalate melting at 176° C.

91B

Benzothiazol-2-yl(3-butoxyphenyl)methanol can be obtained as described in example 1B.

Example 168

168A

2-[(1-methylpiperidin-4-yloxy)(3-pent-4-enyloxy-phenyl)methyl]benzothiazole, oxalate can be prepared as described in example 1A starting from benzothiazol-2-yl(3-pent-4-enyloxy-phenyl)methanol to get an orange solid melting at 75° C.

168B

Benzothiazol-2-yl(3-pent-4-enyloxy-phenyl)methanol can be prepared as follows: to a 1M solution of 3-pent-4-enyloxy-phenylmagnesium bromide in tetrahydrofurane (2.2 mL) diluted with the same solvent (6 mL) cooled at −50° C. is added benzothiazole-2-carboxaldehyde (326 mg). After stirring at −50° C. for 1 h, the mixture is allowed to warm at room temperature, then hydrolyzed with aqueous saturated ammonium chloride solution and extracted with ethyl acetate. The pooled organic extracts are dried over magnesium sulfate and concentrated under reduced pressure. The residue is purified by column chromatography (gradient heptane/ethyl acetate from 4/1 to 2/1) to give benzothiazol-2-yl(3-pent-4-enyloxy-phenyl)methanol as a yellow oil.

272

2-[(1-methylpyrrolidin-3-yloxy)phenyl-methyl]-1H-benzimidazole

272A

A mixture of (1H-benzimidazol-2-yl)phenylmethanol (611 mg) and 1-methyl-3-pyrrolidinol (263 mg) in methanesulfonic acid (1.3 mL) is heated for 4 hours in a sealed tube at a temperature close to 140° C. The mixture is cooled back to room temperature, poured into water which is then made alkaline with concentrated sodium hydroxide solution. The aqueous phase is extracted with ethyl acetate. Pooled extracts are dried over magnesium sulfate, concentrated under reduced pressure. The residue is purified by column chromatography over silica gel (gradient dichloromethane/methanol from 100/0 to 90/10) to give 2-[(1-methylpyrrolidin-3-yloxy)phenyl-methyl]-1H-benzimidazole melting at 53° C.

For the other examples prepared according this general procedure, it can be a good idea to rise the temperature progressively after having mixed the different reagents and to observe when etherification occurs. Once the right temperature has been found, reaction is continued up to adequate conversion.

272B

To a solution of 1-pyrrolidin-1-ylmethyl-1H-benzimidazole (5 g) in tetrahydrofurane (20 mL) cooled at a temperature close to −80° C., is added a 2.5M solution of butyl lithium in hexanes (10 mL). The mixture is stirred for 15 minutes. A solution of benzaldehyde (2.64 g) in tetrahydrofurane (20 mL) is added. The mixture is stirred at a temperature close to −80° C. for 1 hour, then at a temperature close to −20° C. for 2 hours. The reaction is quenched by addition of saturated ammonium chloride. The mixture is extracted with ethyl acetate. Pooled extracts are washed with brine, dried over magnesium sulfate and concentrated under reduced pressure. The residue is purified by column chromatography over silica gel (gradient dichloromethane/methanol from 100/0 to 90/10) to give (1H-benzimidazol-2-yl)phenylmethanol used without further purification.

1-Pyrrolidin-1-ylmethyl-1H-benzimidazole can be prepared as described by Katritzky, Alan R.; Aslan, Diana C.; Leeming, Peter; Steel, Peter J. Tetrahedron: Asymmetry, 1997, 8, p. 1491-1500.

Example 370

370A

A mixture of 2-[3-(2-chloroethoxy)phenyl](1-methylpiperidin-4-yloxy)methyl]-benzothiazole (625 mg), potassium iodide (332 mg), glycine tert-butyl ester, hydrochloride (503 mg) in triethylamine (630 µL) and N,N-dimethylformamide (20 mL) is heated overnight in a sealed tube at 70° C., then for 16 h at 90-100° C. The mixture is cooled back to room temperature, poured into crushed ice and concentrated sodium hydroxide solution. The aqueous phase is extracted with ethyl acetate. The pooled organic phases are washed with brine, dried over magnesium sulfate and concentrated under reduced pressure. The residue is purified by chromatography (gradient dichloromethane/methanol/ammonia from 100/0/0 to 90/10/1). The crude base is converted into its salt in acetone to give (2-{3-[benzothiazol-2-yl(1-methylpiperidin-4-yloxy)methyl]phenoxy}ethylamino)acetic acid tert-butyl ester, dioxalate melting at 136° C.

370B

2-[3-(2-chloroethoxy)phenyl](1-methylpiperidin-4-yloxy)methyl]benzothiazole can be obtained as described in example 272A.

370C benzothiazol-2-yl[3-(2-chloroethoxy)phenyl]methanol can be obtained as described in example 1B.

Example 371

371A

A mixture of 2-[[3-(5-azidopentyloxy)phenyl](1-methylpiperidin-4-yloxy)methyl]benzothiazole (0.13 g) and triphenylphosphine (0.11 g) in a mixture of tetrahydrofurane (3 mL) and water (2 drops) is heated at 70° C. overnight. Solvent is removed under reduced pressure. The residue is dissolved in ethyl acetate and 0.5N hydrochloric solution. The aqueous phase is washed with ethyl acetate, made alkaline with concentrated sodium hydroxide solution and extracted with ethyl acetate. The pooled extracts are washed with saturated sodium chloride solution, dried over magnesium sulfate, concentrated under reduced pressure. The residue is purified by column chromatography (gradient dichloromethane/methanol/ammonia from 100/0 to 90/10 1) and salified with oxalic acid to give 5-{3-[benzothiazol-2-yl(1-methylpiperidin-4-yloxy)methyl]phenoxy}pentylamine, oxalate melting at 141° C.

371B

A mixture of 2-[[3-(5-chloropentyloxy)phenyl](1-methylpiperidin-4-yloxy)-methyl]benzothiazole (200 mg) and sodium azide (85 mg) in dimethylsulfoxide (3 mL) is heated overnight at 70° C., then cooled back to room temperature. Water is added and the product is extracted with ethyl acetate. Pooled extracts are washed with water, then brine, dried over magnesium sulfate and concentrated under reduced pressure to give 2-[[3-(5-azidopentyloxy)phenyl](1-methyl-piperidin-4-yloxy)methyl]benzothiazole used without further purification.

371C

2-[[3-(5-chloropentyloxy)phenyl](1-methyl-piperidin-4-yloxy)methyl]benzothiazole can be prepared according to the procedures described in examples 272A and 1B.

Further examples can be prepared according to the described general methods:

| Example | Product | General methods | Melting point |
| --- | --- | --- | --- |
| 55 | 2-[(3-isopropoxyphenyl)(1-methylpiperidin-4-yloxy)methyl]benzothiazole, oxalate | 1A, 1B | 68° C. |
| 58 | [benzothiazol-2-yl(1H-pyrrol-2-yl)methyl](1-methylpiperidin-4-yl)amine | 21A, 21B, 42C, 1B | 125° C. |
| 60 | [(1H-benzimidazol-2-yl)(3-trifluoromethoxyphenyl)-methyl](1-methylpiperidin-4-yl)amine | 59A, 59B | 82° C. |
| 61 | [(1H-benzimidazol-2-yl)(3-ethylphenyl)methyl](1-methylpiperidin-4-yl)amine | 59A, 59B | 76° C. |
| 65 | [(1H-benzimidazol-2-yl)(3-benzyloxyphenyl)-methyl](1-methylpiperidin-4-yl)amine | 59A, 59B | 78° C. |

-continued

| Example | Product | General methods | Melting point |
|---|---|---|---|
| 66 | [(1H-benzimidazol-2-yl)(3-isopropylphenyl)-methyl](1-methylpiperidin-4-yl)amine | 59A, 59B | 82° C. |
| 67 | [(1H-benzimidazol-2-yl)(3-isobutoxyphenyl)-methyl](1-methylpiperidin-4-yl)amine | 59A, 59B | 99° C. |
| 68 | {(1H-benzimidazol-2-yl)[3-(3-methylbutoxy)-phenyl]methyl}(1-methylpiperidin-4-yl)amine | 59A, 59B | 70° C. |
| 69 | [(1H-benzimidazol-2-yl)(3-butoxyphenyl)methyl](1-methylpiperidin-4-yl)amine, oxalate | 59A, 59B | 137° C. |
| 70 | [(1H-benzimidazol-2-yl)(3-methoxyphenyl)-methyl](1-methylpiperidin-4-yl)amine | 59A, 59B | 182° C. |
| 73 | [(1H-benzimidazol-2-yl)(3-cyclohexylmethoxy-phenyl)methyl](1-methylpiperidin-4-yl)amine | 59A, 59B | 88° C. |
| 74 | [(1H-benzimidazol-2-yl)(3-fluorophenyl)methyl](1-methylpiperidin-4-yl)amine, oxalate | 59A, 59B | 155° C. |
| 75 | [(1H-benzimidazol-2-yl)(3-methylsulfanylphenyl)-methyl](1-methylpiperidin-4-yl)amine | 59A, 59B | 166° C. |
| 76 | [(1H-benzimidazol-2-yl)(3-hexylphenyl)methyl](1-methylpiperidin-4-yl)amine, oxalate | 59A, 59B | 115° C. |
| 77 | [(1H-benzimidazol-2-yl)(3-isopropoxyphenyl)-methyl](1-methylpiperidin-4-yl)amine | 59A, 59B | 75° C. |
| 83 | [(1H-benzimidazol-2-yl)(3-ethoxyphenyl)methyl](1-methylpiperidin-4-yl)amine | 59A, 59B | 74° C. |
| 84 | [(1H-benzimidazol-2-yl)(m-tolyl)methyl](1-methylpiperidin-4-yl)amine, oxalate | 59A, 59B | 132° C. |
| 85 | [(1H-benzimidazol-2-yl)(3-phenoxyphenyl)-methyl](1-methylpiperidin-4-yl)amine, oxalate | 59A, 59B | 144° C. |
| 88 | [benzothiazol-2-yl(3-isopropoxyphenyl)methyl](1-methylpiperidin-4-yl)amine, oxalate | 21A, 21B, 21C, 1B 168B | 96° C. |
| 90 | 1-{3-[(1H-benzimidazol-2-yl)(1-methylpiperidin-4-ylamino)methyl]phenyl}ethanone | 59A, 59B* | 198° C. |
| 92 | 2-[(3-butoxyphenyl)(1-methylpiperidin-4-yloxy)methyl]benzothiazole, oxalate | 1A, 1B | 135° C. |
| 93 | [benzothiazol-2-yl(3-cyclohexylmethoxyphenyl)-methyl](1-methylpiperidin-4-yl)amine, oxalate | 21A, 37B, 42C, 1B 168B | 98° C. |
| 94 | [(1H-benzimidazol-2-yl)biphenyl-3-ylmethyl](1-methylpiperidin-4-yl)amine | 59A, 59B | 98° C. |
| 95 | [(1H-benzimidazol-2-yl)(3-pentyloxyphenyl)-methyl](1-methylpiperidin-4-yl)amine, oxalate | 59A, 59B | 128° C. |
| 102 | (benzothiazol-2-ylbiphenyl-3-ylmethyl)(1-methylpiperidin-4-yl)amine, oxalate | 21A, 37B, 21C, 1B 168B | 112° C. |
| 103 | {(1H-benzimidazol-2-yl)[3-(4-fluorobenzyloxy)-phenyl]methyl}(1-methylpiperidin-4-yl)amine, oxalate | 59A, 59B | 140° C. |
| 104 | [(1H-benzimidazol-2-yl)(3-benzylsulfanylphenyl)-methyl](1-methylpiperidin-4-yl)amine, oxalate | 59A, 59B | 127° C. |
| 105 | {(1H-benzimidazol-2-yl)[3-(3-fluorobenzyloxy)phenyl]methyl}(1-methylpiperidin-4-yl)amine, oxalate | 59A, 59B | 116° C. |
| 106 | {(1H-benzimidazol-2-yl)[3-(2-phenoxyethoxy)-phenyl]methyl}(1-methylpiperidin-4-yl)amine, oxalate | 59A, 59B | 140° C. |
| 107 | [benzothiazol-2-yl(3-benzylsulfanylphenyl)-methyl](1-methylpiperidin-4-yl)amine, oxalate | 91A 168B | 50° C. |
| 108 | 1-{3'-[(1H-benzimidazol-2-yl)(1-methylpiperidin-4-yloxy)methyl]biphenyl-4-yl}ethanone, dioxalate | 53 | 115° C. |
| 109 | 2-[(3'-fluoro-biphenyl-3-yl)(1-methylpiperidin-4-yloxy)methyl]-1H-benzimidazole, dioxalate | 53 | 120° C. |
| 110 | 1-{3'-[(1H-benzimidazol-2-yl)(1-methylpiperidin-4-yloxy)methyl]biphenyl-3-yl}ethanone, dioxalate | 53 | 140° C. |
| 111 | [benzothiazol-2-yl(3-methylsulfanylphenyl)-methyl](1-methylpiperidin-4-yl)amine, oxalate | 91A 168B | 85° C. |
| 112 | [(3-allyloxyphenyl)(1H-benzimidazol-2-yl)methyl](1-methylpiperidin-4-yl)amine, oxalate | 59A, 59B | 125° C. |
| 113 | {(1H-benzimidazol-2-yl)[3-(2-fluorobenzyloxy)-phenyl]methyl}(1-methylpiperidin-4-yl)amine, oxalate | 59A, 59B | 118° C. |
| 114 | 2-[(1-methylpiperidin-4-yloxy)(2'-methylsulfanyl-biphenyl-3-yl)methyl]-1H-benzimidazole | 53 | 163° C. |
| 115 | 2-[(4'-fluorobiphenyl-3-yl)(1-methylpiperidin-4-yloxy)methyl]-1H-benzimidazole, oxalate | 53 | 100° C. |
| 116 | 2-[(1-methylpiperidin-4-yloxy)(3'-methylsulfanyl-biphenyl-3-yl)methyl]-1H-benzimidazole, dioxalate | 53 | 80° C. |

-continued

| Example | Product | General methods | Melting point |
|---|---|---|---|
| 119 | 2-[(1-methylpiperidin-4-yloxy)(4'-trifluoromethyl-biphenyl-3-yl)methyl]-1H-benzimidazole | 53 | 95° C. |
| 120 | {(1H-benzimidazol-2-yl)[3-(tetrahydropyran-2-yloxy)phenyl]methyl}(1-methylpiperidin-4-yl)amine | 59A, 59B | 97° C. |
| 121 | 2-[(2'-Chlorobiphenyl-3-yl)(1-methylpiperidin-4-yloxy)methyl]-1H-benzimidazole, oxalate | 53 | 130° C. |
| 122 | 2-[(3',4'-dichlorobiphenyl-3-yl)(1-methylpiperidin-4-yloxy)methyl]-1H-benzimidazole, oxalate | 53 | 150° C. |
| 123 | {3'-[(1H-benzimidazol-2-yl)(1-methylpiperidin-4-yloxy)methyl]biphenyl-2-yl}methanol | 53 | 107° C. |
| 124 | {(1H-benzimidazol-2-yl)[3-(4-methoxybenzyloxy)-phenyl]methyl}(1-methylpiperidin-4-yl)amine | 59A, 59B | 84° C. |
| 125 | {(1H-benzimidazol-2-yl)[3-(3-methoxybenzyloxy)-phenyl]methyl}(1-methylpiperidin-4-yl)amine, oxalate | 59A, 59B | 135° C. |
| 127 | {3'-[benzothiazol-2-yl(1-methylpiperidin-4-yloxy)methyl]biphenyl-2-yl}methanol, oxalate | 53 | 206-207° C. |
| 129 | {(1H-benzimidazol-2-yl)[3-(2-methylbenzyloxy)-phenyl]methyl}(1-methylpiperidin-4-yl)amine, oxalate | 59A, 59B | 121° C. |
| 130 | {(1H-benzimidazol-2-yl)[3-(4-methylbenzyloxy)-phenyl]methyl}(1-methylpiperidin-4-yl)amine | 59A, 59B | 87° C. |
| 132 | [(3-azidophenyl)(1H-benzimidazol-2-yl)methyl](1-methylpiperidin-4-yl)amine | 131, 231A, 231B | 202° C. |
| 138 | {3'-[(1H-benzimidazol-2-yl)(1-methylpiperidin-4-yloxy)methyl]biphenyl-4-yl}carbamic acid tert-butyl ester | 53 | 135° C. |
| 142 | 2-[(2'-fluorobiphenyl-3-yl)(1-methylpiperidin-4-yloxy)methyl]-1H-benzimidazole | 53 | 90° C. |
| 144 | [(1H-benzimidazol-2-yl)(3-furan-2-ylphenyl)methyl](1-methylpiperidin-4-yl)amine | 59A, 59B | 108° C. |
| 145 | [(1H-benzimidazol-2-yl)(3-but-3-enyloxyphenyl)-methyl](1-methylpiperidin-4-yl)amine | 59A, 59B | 71° C. |
| 146 | {(1H-benzimidazol-2-yl)[3-(4-methylpentyloxy)-phenyl]methyl}(1-methylpiperidin-4-yl)amine | 59A, 59B | 73° C. |
| 149 | {(1H-benzimidazol-2-yl)[3-(2,5-difluoro-benzyloxy)phenyl]methyl}(1-methylpiperidin-4-yl)amine, oxalate | 59A, 59B | 159° C. |
| 151 | 2-[(2-chlorophenyl)(1-methylpiperidin-4-yloxy)methyl]-1H-benzimidazole | 72A, 72B | 212° C. |
| 152 | 2-[(3-ethylphenyl)(1-methylpiperidin-4-yloxy)methyl]benzothiazole, oxalate | 1A, 168B | 123° C. |
| 155 | 2-[(3-fluorophenyl)(1-methylpiperidin-4-yloxy)methyl]-1H-benzimidazole | 72A, 72B, 72C | 93° C. |
| 161 | 2-[[3-(2,3-difluorobenzyloxy)phenyl](1-methylpiperidin-4-yloxy)methyl]benzothiazole, oxalate | 1A, 168B | 98° C. |
| 162 | {(1H-benzimidazol-2-yl)[3-(2,3-difluoro-benzyloxy)phenyl]methyl}(1-methylpiperidin-4-yl)amine | 59A, 59B | 151° C. |
| 163 | 2-[[3-(2-fluoroethoxy)phenyl](1-methylpiperidin-4-yloxy)methyl]benzothiazole, oxalate | 1A, 168B | 147° C. |
| 164 | 2-[(1-methylpiperidin-4-yloxy)(m-tolyl)methyl]-1H-benzimidazole | 72A, 72B, 72C | 119° C. |
| 166 | 5-fluoro-2-[(1-methylpiperidin-4-yloxy)phenylmethyl]-1H-benzimidazole | 165 | 134° C. |
| 167 | 2-[(2-fluorophenyl)(1-methylpiperidin-4-yloxy)methyl]-1H-benzimidazole | 72A, 72B, 72C | 181° C. |
| 169 | 2-{(1-methylpiperidin-4-yloxy)[3-(4,4,4-trifluoro-butoxy)phenyl]methyl}benzothiazole, oxalate | 1A, 168B | 115° C. |
| 170 | 5-bromo-2-[(1-methylpiperidin-4-yloxy)phenylmethyl]-1H-benzimidazole | 165 | 143° C. |
| 171 | 2-[[3-(3-fluorobenzyloxy)phenyl](1-methylpiperidin-4-yloxy)methyl]benzothiazole, oxalate | 1A, 168B | 65° C. |
| 174 | ((1H-benzimidazol-2-yl)-{3-[3-(2-methyl-[1,3]dioxolan-2-yl)-propoxy]phenyl}methyl)(1-methylpiperidin-4-yl)amine, oxalate | 59A, 59B* | 120° C. |
| 175 | {(1H-benzimidazol-2-yl)[3-(4,4,4-trifluoro-butoxy)phenyl]methyl}(1-methylpiperidin-4-yl)amine | 59A, 59B | 94° C. |
| 176 | 2-[[3-(3-fluoropropoxy)phenyl](1-methylpiperidin-4-yloxy)methyl]benzothiazole, oxalate | 1A, 1B | 72° C. |
| 177 | 2-[(1-methylpiperidin-4-yloxy)-p-tolyl-methyl]-1H-benzimidazole | 72A, 72B, 72C | 102° C. |
| 179 | 2-[(4-fluorophenyl)(1-methylpiperidin-4-yloxy)methyl]-1H-benzimidazole | 72A, 72B, 72C | 131° C. |

-continued

| Example | Product | General methods | Melting point |
|---|---|---|---|
| 180 | {(1H-benzimidazol-2-yl)[3-(2-fluoro-ethoxy)phenyl]methyl}(1-methylpiperidin-4-yl)amine, oxalate | 59A, 59B | 155° C. |
| 181 | ((1H-benzimidazol-2-yl)-{3-[2-(6,6-dimethyl-bicyclo[3.1.1]hept-2-en-2-yl)ethoxy]phenyl}methyl)(1-methylpiperidin-4-yl)amine, oxalate | 59A, 59B | 123° C. |
| 182 | 2-[(1-methylpiperidin-4-yloxy)(4'-trifluoro-methoxybiphenyl-3-yl)methyl]-1H-benzimidazole | 53 | 90° C. |
| 183 | 2-[(4'-methoxybiphenyl-3-yl)(1-methylpiperidin-4-yloxy)methyl]-1H-benzimidazole | 53 | 92° C. |
| 184 | 2-[(3-benzo[1,3]dioxol-5-ylphenyl)(1-methyl-piperidin-4-yloxy)methyl]-1H-benzimidazole | 53 | 95° C. |
| 185 | 2-[[3-(3-methoxybenzyloxy)phenyl](1-methyl-piperidin-4-yloxy)methyl]benzothiazole, oxalate | 1A, 168B | 77° C. |
| 186 | 5-{3-[benzothiazol-2-yl(1-methylpiperidin-4-yloxy)methyl]phenoxy}pentan-2-one, oxalate | 1A, 168B, * | 72° C. |
| 187 | 2-{(1-methylpiperidin-4-yloxy)[3-(3-trifluoromethyl-benzyloxy)phenyl]methyl}benzothiazole, oxalate | 1A, 168B | 80° C. |
| 190 | 3-{3-[(1H-benzimidazol-2-yl)(1-methylpiperidin-4-yloxy)methyl]phenyl}prop-2-yn-1-ol | 189 | 117-120° C. |
| 191 | 4-{3-[(1H-benzimidazol-2-yl)(1-methylpiperidin-4-yloxy)methyl]phenyl}but-3-yn-1-ol | 189 | 104-108° C. |
| 192 | 5-{3-[(1H-benzimidazol-2-yl)(1-methylpiperidin-4-yloxy)methyl]phenyl}pent-4-yn-1-ol | 189 | 85° C. |
| 193 | 2-[(1-methylpiperidin-4-yloxy)-o-tolyl-methyl]-1H-benzimidazole | 72A, 72B, 72C | 190° C. |
| 197 | 3-[benzothiazol-2-yl(1-methylpiperidin-4-yloxy)methyl]benzonitrile, oxalate | 72A, 1B | 75° C. |
| 204 | 2-[(4-bromophenyl)(1-methylpiperidin-4-yloxy)methyl]-1H-benzimidazole | 72A, 72B, 72C | 122° C. |
| 213 | 2-[(2-chloro-4-methylphenyl)(1-methylpiperidin-4-yloxy)methyl]-1H-benzimidazole, oxalate | 72A, 272B | 96° C. |
| 214 | 5-{3-[benzothiazol-2-yl(1-methylpiperidin-4-yloxy)methyl]phenyl}pyrimidin-2-ol | 53 | 170° C. |
| 216 | 2-[(1-methylpiperidin-4-yloxy)(3-pyrimidin-5-yl-phenyl)methyl]benzothiazole | 53 | 85° C. |
| 218 | 2-[(1-methylpiperidin-4-yloxy)(3-vinyl-phenyl)methyl]benzothiazole | 217 | 165° C. |
| 220 | 3-[benzothiazol-2-yl(1-methylpiperidin-4-yloxy)methyl]-N-propylbenzamide | 219 | 60° C. |
| 221 | 2-[(2,4-difluorophenyl)(1-methylpiperidin-4-yloxy)methyl]-1H-benzimidazole, oxalate | 72A, 272B | 106° C. |
| 222 | [(1H-benzimidazol-2-yl)(4'-methoxy-biphenyl-3-yl)methyl](1-methylpiperidin-4-yl)amine | 21A, 37B, 211B, 42C, 272B | 110° C. |
| 223 | 3-[benzothiazol-2-yl(1-methylpiperidin-4-yloxy)methyl]-N-methyl-N-phenylbenzamide, oxalate | 219 | 125° C. |
| 225 | 2-[(3-chlorophenyl)(1-methylpiperidin-4-yloxy)methyl]-1H-benzimidazole, oxalate | 72A, 272B | 158° C. |
| 226 | 2-[(4-chlorophenyl)(1-methylpiperidin-4-yloxy)methyl]-1H-benzimidazole, oxalate | 72A, 272B | 175° C. |
| 235 | 3-{3-[(1H-benzimidazol-2-yl)(1-methylpiperidin-4-yloxy)methyl]phenylsulfanyl}-3-methyl-butan-1-ol | 150 | 80° C. |
| 242 | 3-{3-[benzothiazol-2-yl(1-methylpiperidin-4-yloxy)methyl]phenylsulfanyl}-3-methyl-butan-1-ol, oxalate | 148 | 80° C. |
| 243 | 2-[(1-methylpiperidin-4-yloxy)(3-morpholin-4-yl-phenyl)methyl]benzothiazole, oxalate | 234 | 111° C. |
| 244 | 2-{3-[benzothiazol-2-yl(1-methylpiperidin-4-yloxy)methyl]phenoxy}ethanol, oxalate | 234 | 45° C. |
| 246 | 3-{3-[(1H-benzimidazol-2-yl)(1-methylpiperidin-4-yloxy)methyl]phenylsulfanyl}propan-1-ol | 150 | 97-99° C. |
| 247 | 1-{3-[(1H-benzimidazol-2-yl)(1-methylpiperidin-4-yloxy)methyl]phenylsulfanyl}propan-2-ol | 150 | 120-122° C. |
| 250 | 2-{(1-methylpiperidin-4-yloxy)[3-(2-methylsulfanyl-ethoxy)phenyl]methyl}benzothiazole, oxalate | 272A, 1B | 89° C. |
| 251 | 2-[(1-methylpiperidin-4-yloxy)(2-trifluoromethoxy-phenyl)methyl]-1H-benzimidazole | 72A, 272B | 193° C. |
| 261 | 2-[(3-bromo-4-methylphenyl)(1-methylpiperidin-4-yloxy)methyl]-1H-benzimidazole | 72A, 272B | 92° C. |
| 262 | 2-[(2-bromophenyl)(1-methylpiperidin-4-yloxy)methyl]-1H-benzimidazole | 72A, 272B | 213° C. |
| 265 | 2-{(1-methylpiperidin-4-yloxy)[3-(pyridin-4-ylmethoxy)phenyl]methyl}benzothiazole, oxalate | 258 | 101° C. |

-continued

| Example | Product | General methods | Melting point |
|---|---|---|---|
| 266 | 4-{3-[benzothiazol-2-yl(1-methylpiperidin-4-yloxy)methyl]phenoxy}butan-1-ol, oxalate | 258 | 63° C. |
| 267 | 2-[[3-(furan-2-ylmethoxy)phenyl](1-methylpiperidin-4-yloxy)methyl]benzothiazole, oxalate | 258 | 85° C. |
| 269 | 2-{3-[benzothiazol-2-yl(1-methylpiperidin-4-yloxy)methyl]phenylsulfanyl}ethylamine, dioxalate | 249, 149A | 80° C. |
| 271 | 2-{3-[benzothiazol-2-yl(1-methylpiperidin-4-yloxy)methyl]phenoxy}ethylamine | 371A, 371B, 272A, 1B | 76° C. |
| 273 | [(1H-benzimidazol-2-yl)-p-tolyl-methyl](1-methylpiperidin-4-yl)amine | 59A, 59C | 183° C. |
| 274 | 2-[(3-ethylsulfanyl-4-methylphenyl)(1-methylpiperidin-4-yloxy)methyl]-1H-benzimidazole, oxalate | 148, 272A, 272B | 142° C. |
| 277 | 2-[[3-(2-methoxyethoxy)phenyl](1-methylpiperidin-4-yloxy)methyl]benzothiazole, oxalate | 1A, 1B | 80° C. |
| 279 | (2-{3-[benzothiazol-2-yl(1-methylpiperidin-4-yloxy)methyl]phenoxy}ethyl)methyl-amine, dioxalate | 258 | 125° C. |
| 280 | 2-[(1-methylpiperidin-4-yloxy)(3-trifluoromethoxy-phenyl)methyl]-1H-benzimidazole, oxalate | 272A, 272B | 172° C. |
| 281 | 2-[(2-Chlorophenyl)(1-methylpiperidin-4-yloxy)methyl]benzothiazole, oxalate | 272A, 1B | 163° C. |
| 283 | 2-{(1-methylpiperidin-4-yloxy)[3-(pyridin-2-ylmethoxy)phenyl]methyl}benzothiazole, oxalate | 272A, 1B | 158° C. |
| 284 | 2-{(1-methylpiperidin-4-yloxy)[3-(pyridin-3-ylmethoxy)phenyl]methyl}benzothiazole, oxalate | 272A, 1B | 102° C. |
| 285 | 2-[(3-Cyclohexylmethoxyphenyl)(1-methylpiperidin-4-yloxy)methyl]benzothiazole, oxalate | 1A, 1B | 101° C. |
| 289 | 5-{3-[benzothiazol-2-yl(1-methylpiperidin-4-yloxy)methyl]phenyl}pentylamine, dihydrochloride | 293, 194 | 110° C. |
| 290 | 2-{3-[benzothiazol-2-yl(1-ethyl-piperidin-4-yloxy)methyl]phenoxy}ethylamine, dioxalate | 371A, 371B, 272A, 1B | 112° C. |
| 291 | 2-{3-[(1H-benzimidazol-2-yl)(1-methylpiperidin-4-yloxy)methyl]phenoxy}ethylamine | 371A, 371B, 272A, 272B | 90° C. |
| 292 | 6-{3-[benzothiazol-2-yl(1-methylpiperidin-4-yloxy)methyl]phenylsulfanyl}hexan-1-ol, oxalate | 148 | 80° C. |
| 300 | 2-[(2,3-dihydrobenzo[1,4]dioxin-6-yl)(1-methylpiperidin-4-yloxy)methyl]-1H-benzimidazole | 272A, 272B | 203° C. |
| 302 | N-(2-{3-[benzothiazol-2-yl(1-methylpiperidin-4-yloxy)methyl]phenylsulfanyl}ethyl)guanidine, hydrochloride | 278A, 249, 149A | 125° C. |
| 304 | N-tert-butoxycarbonyl-N'-(2-{3-[(benzothiazol-2-yl)(1-methylpiperidin-4-yloxy)methyl]phenylsulfanyl}ethyl)guanidine | 307A, 194A | 110° C. |
| 306 | 2-[{3-[2-(1-methyl-1H-imidazol-4-yl)ethyl]-phenyl}(1-methylpiperidin-4-yloxy)methyl]-benzothiazole, oxalate | 293, 194 | 80° C. |
| 310 | 2-{(1-methylpiperidin-4-yloxy)[3-(pyridin-2-ylmethoxy)phenyl]methyl}-1H-benzimidazole | 272A, 272B | 77° C. |
| 311 | 3-{3-[benzothiazol-2-yl(1-methylpiperidin-4-yloxy)methyl]phenoxy}propylamine, oxalate | 371A, 371B, 272A, 1B | 120° C. |
| 314 | 3-{3-[benzothiazol-2-yl(1-methylpiperidin-4-yloxy)methyl]phenylsulfanyl}propylamine, oxalate | 305A, 305B | 99° C. |
| 319 | 6-{3-[benzothiazol-2-yl(1-methylpiperidin-4-yloxy)methyl]phenyl}hex-5-ynylamine, oxalate | 194, 189 | 135° C. |
| 322 | 2-{(1-methylpiperidin-4-yloxy)[3-(4-morpholin-4-yl-butoxy)phenyl]methyl}benzothiazole,oxalate | 370A, 272A, 1B | 61° C. |
| 323 | (1-{3-[benzothiazol-2-yl(1-methylpiperidin-4-yloxy)methyl]phenyl}pyrrolidin-2-yl)methanol, oxalate | 258 | 76° C. |
| 324 | (1-{3-[benzothiazol-2-yl(1-methylpiperidin-4-yloxy)methyl]phenyl}pyrrolidin-2-yl)methanol, oxalate | 258 | 99° C. |
| 325 | 6-{3-[benzothiazol-2-yl(1-methylpiperidin-4-yloxy)methyl]phenyl}hexylamine, oxalate | 293, 194 | 115° C. |
| 326 | 4-{3-[(1H-benzimidazol-2-yl)(1-methylpiperidin-4-yloxy)methyl]phenylsulfanyl}butylamine, oxalate | 305A, 305B | 146° C. |
| 327 | 3-{3-[(1H-benzimidazol-2-yl)(1-methylpiperidin-4-yloxy)methyl]phenoxy}propylamine | 371A, 371B, 272A, 272B | 97° C. |
| 329 | 4-(2-{3-[benzothiazol-2-yl(1-methylpiperidin-4-yloxy)methyl]phenoxy}ethyl)piperazine-1-carboxylic acid tert-butyl ester, oxalate | 370A, 272A; 1B | 90° C. |
| 331 | 4-{3-[(1H-benzimidazol-2-yl)(1-methylpiperidin-4-yloxy)methyl]phenoxy}butylamine, oxalate | 371A, 371B, 272A, 272B | 115° C. |

-continued

| Example | Product | General methods | Melting point |
|---|---|---|---|
| 332 | 2-{(1-methylpiperidin-4-yloxy)[3-(4-morpholin-4-yl-butoxy)phenyl]methyl}-1H-benzimidazole, oxalate | 370A, 272A, 272B | 85° C. |
| 333 | 2-{(1-methylpiperidin-4-yloxy)[3-(4-piperidin-1-yl-butoxy)phenyl]methyl}-1H-benzimidazole, oxalate | 370A, 272A, 272B | 130° C. |
| 334 | 2-[(2-fluoro-3-iodophenyl)(1-methylpiperidin-4-yloxy)methyl]-1H-benzimidazole | 272A, 272B | 125° C. |
| 339 | N-tert-butoxycarbonyl-N'-(5-{3-[(benzothiazol-2-yl)(1-methylpiperidin-4-yloxy)methyl]phenyl}pent-5-ynyl)guanidine | 307A, 194A | 125° C. |
| 340 | N-(5-{3-[benzothiazol-2-yl(1-methylpiperidin-4-yloxy)methyl]phenyl}pent-4-ynyl)guanidine, hydrochloride | | 180° C. |
| 341 | N-tert-butoxycarbonyl-N'-(6-{3-[(benzothiazol-2-yl)(1-methylpiperidin-4-yloxy)methyl]phenyl}hex-5-ynyl)guanidine | 307A, 194A | 130° C. |
| 342 | N-(6-{3-[benzothiazol-2-yl(1-methylpiperidin-4-yloxy)methyl]phenyl}hex-5-ynyl)guanidine, hydrochloride | | 185° C. |
| 343 | 4-(4-{3-[(1H-benzimidazol-2-yl)(1-methylpiperidin-4-yloxy)methyl]phenoxy}butyl)piperazine-1-carboxylic acid tert-butyl ester | 370A, 272A, 272B | 64° C. |
| 348 | 2-{(1-methylpiperidin-4-yloxy)[3-(3-[1,2,4]triazol-1-yl-propoxy)phenyl]methyl}benzothiazole,oxalate | 315A, 272A, 1B | 60° C. |
| 349 | 2-{(1-methylpiperidin-4-yloxy)[3-(3-[1,2,3]triazol-2-yl-propoxy)phenyl]methyl}benzothiazole, oxalate (contains 23% of 1,2,3-triazol-1-yl compound) | 315A, 272A, 1B | 74° C. |
| 350 | 2-{(1-methylpiperidin-4-yloxy)[3-(3-morpholin-4-yl-propoxy)phenyl]methyl}benzothiazole, oxalate | 370A, 272A, 1B | 105° C. |
| 352 | 2-{3-[(1H-benzimidazol-2-yl)(1-methylpiperidin-4-yloxy)methyl]-2-fluorophenylsulfanyl}ethylamine | 423A, 150A, 272A, 272B | 204° C. |
| 354 | 2-[[3-(2-Chloroethoxy)phenyl](1-methylpiperidin-4-yloxy)methyl]benzothiazole, oxalate | 272A, 1B | 70° C. |
| 356 | 2-{(1-methylpiperidin-4-yloxy)[3-(2-piperidin-1-yl-ethoxy)phenyl]methyl}-1H-benzimidazole, oxalate | 370A, 272A, 272B | 160° C. |
| 360 | 4-(3-{3-[(1H-benzimidazol-2-yl)(1-methylpiperidin-4-yloxy)methyl]phenoxy}propyl)piperazine-1-carboxylic acid tert-butyl ester, oxalate | 370A, 272A, 272B | 140° C. |
| 362 | 4-(5-{3-[benzothiazol-2-yl(1-methylpiperidin-4-yloxy)methyl]phenoxy}pentyl)piperazine-1-carboxylic acid tert-butyl ester | 370A, 272A, 1B | 131° C. |
| 363 | N-(6-{3-[benzothiazol-2-yl(1-methylpiperidin-4-yloxy)methyl]phenyl}hexyl)guanidine, hydrochloride | 278A, 249, 149A | 90° C. |
| 364 | N-tert-butoxycarbonyl-N'-(6-{3-[(1H-benzimidazol-2-yl)(1-methylpiperidin-4-yloxy)methyl]phenyl}hexyl)guanidine | 307A, 194A | 90° C. |
| 365 | N-(5-{3-[benzothiazol-2-yl(1-methylpiperidin-4-yloxy)methyl]phenyl}pentyl)guanidine, hydrochloride | 278A, 249, 149A | 90° C. |
| 366 | 4-{3-[benzothiazol-2-yl(1-methylpiperidin-4-yloxy)methyl]phenyl}butylamine, dioxalate | 293, 194 | 100° C. |
| 367 | [[3-(4-aminobutoxy)phenyl](1H-benzimidazol-2-yl)methyl](1-methylpiperidin-4-yl)amine | 21A, 37B, 371B, 42C, 272B | 68° C. |
| 368 | 3-{3-[(1H-benzimidazol-2-yl)(1-methylpiperidin-4-yloxy)methyl]phenylsulfanyl}propylamine | 278A, 249, 149A | 126° C. |
| 369 | 4-(2-{3-[(1H-benzimidazol-2-yl)(1-methylpiperidin-4-yloxy)methyl]phenoxy}ethyl)piperazine-1-carboxylic acid tert-butyl ester, dioxalate | 370A, 272A; 1B | 92° C. |
| 373 | N-(3-{3-[benzothiazol-2-yl(1-methylpiperidin-4-yloxy)methyl]phenyl}prop-2-ynyl)guanidine, trihydrochloride | 278A, 249, 149A | 125° C. |
| 374 | N-(4-{3-[benzothiazol-2-yl(1-methylpiperidin-4-yloxy)methyl]phenyl}butyl)guanidine, trihydrochloride | 278A, 249, 149A | 120° C. |
| 375 | (5-{3-[benzothiazol-2-yl(1-methylpiperidin-4-yloxy)methyl]phenoxy}pentylamino)acetic acid tert-butyl ester, oxalate | 370A, 272A, 1B | 99° C. |
| 377 | 2-{(1-methylpiperidin-4-yloxy)[3-(piperidin-4-ylmethoxy)phenyl]methyl}benzothiazole, dioxalate | 423A, 258 | 90° C. |
| 378 | 2-{(1-methylpiperidin-4-yloxy)[3-(piperidin-3-ylmethoxy)phenyl]methyl}benzothiazole, dioxalate | 423A, 258 | 55° C. |
| 379 | 2-[[3-(1-methylpiperidin-3-ylmethoxy)phenyl](1-methylpiperidin-4-yloxy)methyl]benzothiazole, dioxalate | 165C, 423A, 258 | 76° C. |

-continued

| Example | Product | General methods | Melting point |
|---|---|---|---|
| 380 | 2-[(1-methylpiperidin-4-yloxy)(3-piperidin-3-ylethynylphenyl)methyl]-1H-benzimidazole | 376A, 189 | 97° C. |
| 381 | 5-{3-[(1H-benzimidazol-2-yl)(1-methylpiperidin-4-yloxy)methyl]phenylsulfanyl}pentylamine, oxalate | 305A, 305B | 140° C. |
| 382 | 2-{(1-methylpiperidin-4-yloxy)[3-(pyrrolidin-3-yloxy)phenyl]methyl}benzothiazole, dioxalate | 258 | 50° C. |
| 387 | {[3-(4-aminobutoxy)phenyl]benzothiazol-2-yl-methyl}(1-methylpiperidin-4-yl)amine | 21A, 37B, 371B, 42C, 1B | 67° C. |
| 388 | 2-[(3-azetidin-3-ylethynylphenyl)(1-methylpiperidin-4-yloxy)methyl]-1H-benzimidazole | 249, 293, 189 | 131° C. |
| 389 | 5-{3-[(1H-benzimidazol-2-yl)(1-methylpiperidin-4-yloxy)methyl]phenyl}pent-4-en-1-ol, oxalate | 384A, 53 | 125° C. |
| 391 | 4-(5-{3-[(1H-benzimidazol-2-yl)(1-methylpiperidin-4-yloxy)methyl]phenoxy}pentyl)piperazine-1-carboxylic acid tert-butyl ester, dioxalate | 370A, 72A, 272B | 101° C. |
| 392 | 2-[[3-(2-azetidin-3-ylethyl)phenyl](1-methylpiperidin-4-yloxy)methyl]-1H-benzimidazole | 249, 189 | 146° C. |
| 395 | 2-{(1-methylpiperidin-4-yloxy)[3-(2-piperidin-2-yl-ethylsulfanyl)phenyl]methyl}-1H-benzimidazole | 249, 149A | 164° C. |
| 399 | N-tert-butoxycarbonyl-N'-(4-{3-[(benzothiazol-2-yl)(1-methylpiperidin-4-yloxy)methyl]phenyl}but-3-ynyl)guanidine | 307A, 194A | 120° C. |
| 400 | 5-{3-[(1H-benzimidazol-2-yl)(1-methylpiperidin-4-yloxy)methyl]phenoxy}pentylamine, dioxalate | 371A, 371B, 72A, 272B | 111° C. |
| 402 | 2-[[3-(azetidin-3-yloxy)phenyl](1-methylpiperidin-4-yloxy)methyl]benzothiazole, dioxalate | 423A, 258 | 81° C. |
| 404 | (1-{3-[benzothiazol-2-yl(1-methylpiperidin-4-yloxy)methyl]phenyl}pyrrolidin-3-yl)methanol, oxalate | 403 | 106° C. |
| 405 | 1-{3-[benzothiazol-2-yl(1-methylpiperidin-4-yloxy)methyl]phenyl}piperidin-4-ylamine, dioxalate | 423A, 403 | 137° C. |
| 406 | 1-{3-[benzothiazol-2-yl(1-methylpiperidin-4-yloxy)methyl]phenyl}pyrrolidin-3-ol, oxalate | 403 | 103° C. |
| 407 | 1-{3-[benzothiazol-2-yl(1-methylpiperidin-4-yloxy)methyl]phenyl}pyrrolidin-3-ol, oxalate | 403 | 106° C. |
| 408 | N-(1-{3-[benzothiazol-2-yl(1-methylpiperidin-4-yloxy)methyl]phenyl}pyrrolidin-3-yl)acetamide, oxalate | 403 | 111° C. |
| 410 | 2-{(1-methylpiperidin-4-yloxy)[3-(5-pyrazol-1-yl-pent-1-ynyl)phenyl]methyl}-1H-benzimidazole, oxalate | 416A, 189 | 115° C. |
| 413 | acetic acid 1-{3-[benzothiazol-2-yl(1-methyl-piperidin-4-yloxy)methyl]phenyl}piperidin-4-yl ester, oxalate | 403 | 74° C. |
| 414 | 2-[(3-bromo-phenyl)(1-methylpyrrolidin-3-ylmethoxy)methyl]-1H-benzimidazole | 165C, 272A, 72B, 72C | 61° C. |
| 415 | 2-{(1-methylpiperidin-4-yloxy)[3-(piperidin-4-yloxy)phenyl]methyl}benzothiazole, dioxalate | 423A, 258 | 76° C. |
| 419 | N1-(5-{3-[(1H-benzimidazol-2-yl)(1-methyl-piperidin-4-yloxy)methyl]phenoxy}pentyl)butane-1,4-diamine, dioxalate | 423A, 370A, 72A, 272B | 162° C. |
| 420 | {[3-(6-aminohex-1-ynyl)phenyl]benzothiazol-2-yl-methyl}(1-methylpiperidin-4-yl)amine, oxalate | 386A, 275 | 80° C. |
| 422 | 4-{3-[benzothiazol-2-yl(1-methylpiperidin-4-yloxy)methyl]phenoxy}but-2-en-1-ol, oxalate | 258 | 73° C. |
| 424 | 2-[(2,5-difluorophenyl)(1-methylpiperidin-4-yloxy)methyl]-1H-benzimidazole | 272A, 272B | 140° C. |
| 425 | 2-[(2-fluoro-5-iodo-phenyl)(1-methylpiperidin-4-yloxy)methyl]-1H-benzimidazole, dioxalate | 272A, 272B | 175° C. |
| 427 | 4-{3-[(5-fluoro-1H-benzimidazol-2-yl)(1-methyl-piperidin-4-yloxy)methyl]phenylsulfanyl}butan-1-ol | 150 | 85° C. |
| 428 | 2-{3-[(5-fluoro-1H-benzimidazol-2-yl)(1-methyl-piperidin-4-yloxy)methyl]phenylsulfanyl}-ethylamine, dioxalate | 249, 149A | 85° C. |
| 429 | 1-{3-[benzothiazol-2-yl(1-methylpiperidin-4-yloxy)methyl]phenyl}pyrrolidin-3-ylamine, dioxalate | 423A, 423B | 137° C. |
| 430 | 2-[[3-(3-fluoropyrrolidin-1-yl)phenyl](1-methylpiperidin-4-yloxy)methyl]benzothiazole, oxalate | 423B | 70° C. |
| 431 | 4-{3-[benzothiazol-2-yl(1-methylpiperidin-4-yloxy)methyl]phenoxy}but-2-enylamine, dioxalate | 386A, 424A, 258 | 117° C. |

| Example | Product | General methods | Melting point |
|---------|---------|-----------------|---------------|
| 433 | 2-[(2-fluoro-5-trifluoromethoxyphenyl)(1-methylpiperidin-4-yloxy)methyl]-1H-benzimidazole | 272A, 272B | 95° C. |

*in the case of ketone-containing substituents, it is judicious to protect the carbonyl function (as an acetal for example) prior to the Grignard preparation

Example 434

2-[(2-fluoro-5-trifluoromethoxyphenyl)(1-methylpiperidin-4-yloxy)methyl]-1H-benzimidazole enantiomer A A solution of racemic 2-[(2-fluoro-5-trifluoromethoxyphenyl)(1-methylpiperidin-4-yloxy)methyl]-1H-benzimidazole (1 mg/mL) in a mixture of heptane/isopropanol (90/10) containing diethylamine (0.1%) is injected (10 µL) onto an analytical Chiralpak AD-H, 250×4.6 mm column. Elution is performed with a mixture of heptane/isopropanol (90/10) containing diethylamine (0.1%) at a flow of 1 mL/min. Products are detected at 220 nm.

The first enantiomer has a retention time of 6.9 min.

Collection affords 2-[(2-fluoro-5-trifluoromethoxyphenyl)(1-methylpiperidin-4-yloxy)methyl]-1H-benzimidazole enantiomer A with a chromatographic enantiomeric purity of 99.8%.

Example 435

2-[(2-fluoro-5-trifluoromethoxyphenyl)(1-methylpiperidin-4-yloxy)methyl]-1H-benzimidazole enantiomer B The second enantiomer has a retention time of 8.3 min.

Collection affords 2-[(2-fluoro-5-trifluoromethoxyphenyl)(1-methyl piperidin-4-yloxy)methyl]-1H-benzimidazole enantiomer B with a chromatographic enantiomeric purity of 96.8%.

Following compounds are prepared using general methods described in example 1:

| Example | Product |
|---------|---------|
| 78 | 2-[(3-bromophenyl)(1-methylpiperidin-4-yloxy)methyl]-1H-benzimidazole |

$^1$H NMR: 9.62 (sl, 1H), 7.85-7.70 (m, 1H), 7.65 (s, 1H), 7.50-7.35 (m, 3H), 7.30-7.15 (m, 3H), 5.84 (s, 1H), 3.65-3.50 (m, 1H), 2.85-2.65 (m, 2H), 2.28 (s, 3H), 2.25-1.60 (m, 6H)

80

2-[(3-butylphenyl)(1-methylpiperidin-4-yloxy)methyl]benzothiazole

80A

To a mixture of trifluoromethanesulfonic acid 3-[benzothiazol-2-yl(1-methylpiperidin-4-yloxy)methyl]phenyl ester (110 mg) and ferric acetylacetonate (4 mg) in a mixture of tetrahydrofurane (4.5 mL) and N-methylpyrrolidone (0.25 mL) cooled at 0° C. is added a 2M solution of butylmagnesium chloride in tetrahydrofurane (150 µL). The mixture is stirred at room temperature for 25 min, then warmed at 30° C. for 15 min. A second addition of butylmagnesium chloride in tetrahydrofurane (150 µL) is performed. The mixture is then diluted with diethyl ether and quenched with 0.5N hydrochloric solution. The aqueous phase is extracted with diethyl ether, then ethyl acetate. Organic phases are pooled, dried over magnesium sulfate and concentrated under reduced pressure. The residue is purified by chromatography (gradient heptane/ethyl acetate from 99/1 to 90/10). The product is then refluxed in methanol and concentrated to give 2-[(3-butylphenyl)(1-methylpiperidin-4-yloxy)methyl]benzothiazole.

TLC (eluent: $CH_2Cl_2$/MeOH 90/10): Rf=0.30

80B

To a solution of 3-[benzothiazol-2-yl(1-methylpiperidin-4-yloxy)methyl]phenol (318 mg) in pyridine (74 µL) and dichloromethane (3 mL) cooled at −5° C. is added trifluoromethanesulfonic anhydride (152 µL). The mixture is stirred for 1 h, then allowed to warm to room temperature. The organic phase is washed with water, dried over magnesium sulfate and concentrated under reduced pressure. The residue is purified by chromatography (gradient heptane/ethyl acetate from 95/5 to 50/50) to give trifluoromethanesulfonic acid 3-[benzothiazol-2-yl(1-methylpiperidin-4-yloxy)methyl] phenyl ester used without further purification.

Following compounds are prepared using general methods described in example 21A, 21C and 1B:

| Example | Product |
|---------|---------|
| 82 | [benzothiazol-2-yl(3-bromophenyl)methyl](1-methylpiperidin-4-yl)amine |

$^1$H NMR (DMSO d$^6$): 9.21 (sl, 1H), 8.02 (d, 1H), 7.85 (d, 1H), 7.52-7.20 (m, 6H), 5.39 (s, 1H), 3.45-3.30 (m, 1H), 3.05-2.80 (m, 2H), 2.75-2.55 (m, 2H), 2.65 (s, 3H), 2.25-1.85 (m, 2H), 1.80-1.45 (m, 2H)

Example 117

2-[(3-iodophenyl)(1-methylpiperidin-4-yloxy)methyl]benzothiazole enantiomer A

A solution of racemic 2-[(3-iodophenyl)(1-methylpiperidin-4-yloxy)methyl]-benzothiazole (10 mg/mL) in a mixture of heptane/isopropanol (80/20) containing diethylamine (0.1%) is injected (20×100 µL) onto an analytical Chiralpak AD-H, 250×4.6 mm column. Elution is performed with a mixture of heptane/isopropanol (80/20) containing diethylamine (0.1%) at a flow of 1 mL/min. Products are detected at 220 nm.

The first enantiomer has a retention time of 6.0 min.

Collection affords 2-[(3-iodophenyl)(1-methylpiperidin-4-yloxy)methyl]benzothiazole enantiomer A with a chromatographic enantiomeric purity of 97.3%.

Example 118

2-[(3-iodophenyl)(1-methylpiperidin-4-yloxy)methyl]benzothiazole enantiomer B The second enantiomer has a retention time of 7.0 min.
Collection affords 2-[(3-iodophenyl)(1-methylpiperidin-4-yloxy)methyl]benzothiazole enantiomer B with a chromatographic enantiomeric purity of 99.7%.

Example 126

3-[(1H-benzimidazol-2-yl)(1-methylpiperidin-4-ylamino)methyl]phenol

A solution of {(1H-benzimidazol-2-yl)[3-(tetrahydropyran-2-yloxy)phenyl]methyl}(1-methylpiperidin-4-yl)amine (example 120, 500 mg) in ethanol (5 mL) is treated with aqueous 37% hydrochloric acid at room temperature for one night. The mixture is then neutralized with an aqueous saturated sodium hydrogen carbonate solution and extracted with ethyl acetate. The pooled organic extracts are dried over magnesium sulfate and concentrated under reduced pressure. The residue is purified by column chromatography (gradient dichloromethane/methanol/ammonia from 90/10/0.5 to 80/20/0.5) to give 3-[(1H-benzimidazol-2-yl)(1-methylpiperidin-4-ylamino)methyl]phenol as a white solid melting at 230° C.

Example 131

[(1H-benzimidazol-2-yl)(3-nitrophenyl)methyl](1-methylpiperidin-4-yl)amine

131A

To a solution of [(1H-benzimidazol-2-yl)(3-nitrophenyl)methylene](1-methylpiperidin-4-yl)amine (1.1 g) in methanol (50 mL) at 0° C. is added sodium cyanoborohydride, then dropwise acetic acid (0.19 mL). The reaction mixture is allowed to reach room temperature and stirred at that temperature overnight.
Cold water (70 mL) is added as well as concentrated hydrochloric acid to reach pH 1. Then a concentrated sodium hydroxide solution is added to reach pH 10. The aqueous phase is extracted with dichloromethane. The pooled organic extracts are dried over magnesium sulfate and concentrated under reduced pressure. The residue is purified by chromatography (gradient dichloromethane/methanol from 99/1 to 95/5) to afford [(1H-benzimidazol-2-yl)(3-nitrophenyl)methyl](1-methylpiperidin-4-yl)amine melting at 254° C.

131B

[(1H-benzimidazol-2-yl)(3-nitrophenyl)methylene](1-methylpiperidin-4-yl)amine can be prepared according to the method described in example 37B.
Further examples can be prepared according to the described general methods:

| Example | Product | General methods | TLC |
| --- | --- | --- | --- |
| 22 | 2-[(3-allyloxyphenyl)(1-methylpiperidin-4-yloxy)methyl]benzothiazole, hydrochloride | 1A, 1B | 0.41(C) |
| 32 | 2-[(2,3-dihydrobenzofuran-5-yl)(1-methylpiperidin-4-yloxy)methyl]benzothiazole, oxalate | 1A, 1B | 0.32(C) |
| 71 | trifluoromethanesulfonic acid 3-[benzothiazol-2-yl(1-methylpiperidin-4-yloxy)methyl]phenyl ester | 1A, 1B | 0.50(D) |
| 101 | [benzothiazol-2-yl(3-benzyloxyphenyl)-methyl](1-methylpiperidin-4-yl)amine, oxalate | 91A, 1B | 0.17(C) |
| 134 | {(1H-benzimidazol-2-yl)[3-(2-ethoxyethoxy)-phenyl]methyl}(1-methylpiperidin-4-yl)amine | 59A, 59B | 0.26(A) |
| 135 | [(1H-benzimidazol-2-yl)(3-pent-4-enyloxyphenyl)methyl](1-methylpiperidin-4-yl)amine | 59A, 59B | 0.16(A) |
| 178 | 2-{(1-methylpiperidin-4-yloxy)[3-(3,3,3-trifluoro-propoxy)phenyl]methyl}-benzothiazole, oxalate | 1A, 168B | 0.67(D) |
| 196 | 2-{(1-methylpiperidin-4-yloxy)[3-(3-nitro-benzyloxy)phenyl]methyl}benzothiazole, oxalate | 1A, 1B | 0.17(B) |
| 270 | 1-{3-[benzothiazol-2-yl(1-methylpiperidin-4-yloxy)methyl]benzyloxy}propan-2-one, oxalate | 1A, 168B* | 0.32(A) |
| 297 | 2-[benzo[1,3]dioxol-5-yl(1-methylpiperidin-4-yloxy)methyl]-1H-benzimidazole | 272A, 272B | 0.22(D) |
| 301 | 4-{3-[benzothiazol-2-yl(1-methylpiperidin-4-yloxy)methyl]phenoxy}butylamine, oxalate | 371A, 371B, 272A, 1B | 0.08(B) |
| 328 | 4-(2-{3-[benzothiazol-2-yl(1-methylpiperidin-4-yloxy)methyl]phenoxy}ethyl)piperazine-1-carboxylic acid tert-butyl ester | 370A, 272A, 1B | 0.69(D) |
| 330 | 2-{(1-methylpiperidin-4-yloxy)[3-(2-piperazin-1-yl-ethoxy)phenyl]methyl}benzothiazole, oxalate | 423A, 370A, 272A, 1B | 0.26(D) |

| Example | Product | General methods | TLC |
|---|---|---|---|
| 361 | (2-{3-[(1H-benzimidazol-2-yl)(1-methyl-piperidin-4-yloxy)methyl]phenoxy}-ethylamino)acetic acid tert-butyl ester, oxalate | 370A, 272A, 1B | 0.51(D) |

Eluent A: $CH_2Cl_2$/MeOH/$NH_4OH$ 90/10/0.5
Eluent B: $CH_2Cl_2$/MeOH/$NH_4OH$ 95/5/0.5
Eluent C: $CH_2Cl_2$/MeOH 90/10
Eluent D: $CH_2Cl_2$/MeOH/$NH_4OH$ 90/10/1
*in the case of ketone-containing substituents, it is judicious to protect the carbonyl function (as an acetal for example) prior to the Grignard preparation

Example 147

2-[(1-methylpiperidin-4-yloxy)(3-pyrazol-1-ylphenyl)methyl]benzothiazole, oxalate To a solution of 2-[(3-Bromophenyl)(1-methylpiperidin-4-yloxy)methyl]benzothiazole (208 mg) in N,N-dimethylformamide (1 mL) are added pyrazole (68 mg), cesium carbonate (401 mg) and copper(I) iodide (19 mg). The tube is evacuated, filled with argon and sealed. After stirring at 120° C. for 48 h, the mixture is diluted with water and ammonia solution then extracted with ethyl acetate. The pooled organic extracts are dried over magnesium sulfate and concentrated under reduced pressure. The residue is purified by chromatography (gradient dichloromethane/methanol/ammonia from 100/0/0 to 95/5/0.5). The residue is added to a solution of oxalic acid (1 molar equivalent) and the residual precipitate is filtered and dried to afford 2-[(1-methylpiperidin-4-yloxy)(3-pyrazol-1-ylphenyl)methyl]benzothiazole oxalate melting at 89° C.

Example 148

2-[(3-benzylsulfanylphenyl)(1-methylpiperidin-4-yloxy)methyl]benzothiazole

A screw-cap tube is charged with 2-[(3-bromophenyl)(1-methylpiperidin-4-yloxy)methyl]benzothiazole (208 mg), palladium bis(dibenzylideneacetone) (14 mg), Xantphos (14 mg), benzyl mercaptan (59 µL), diisopropylethylamine (174 µL) and 1,4-dioxane (2 mL). The tube is evacuated, filled with argon and sealed. After stirring at 120° C. for 15 h, the mixture is diluted with ethyl acetate and water and the aqueous phase is extracted with ethyl acetate. The pooled organic extracts are dried over magnesium sulfate and concentrated under reduced pressure. The residue is purified by chromatography (gradient dichloromethane/methanol/ammonia from 100/0/0 to 95/5/0.5). The residual yellowish oil is re-crystallized from hot acetonitrile to give 2-[(3-benzylsulfanylphenyl)(1-methylpiperidin-4-yloxy)methyl]benzothiazole melting at 195° C.

Further examples can be prepared according to the above described general method:

| Example | Product |
|---|---|
| 158 | 2-{3-[benzothiazol-2-yl(1-methylpiperidin-4-yloxy)methyl]phenylsulfanyl}ethanol |

$^1$H NMR: 7.98 (d, 1H), 7.88 (d, 1H), 7.57 (s, 1H), 7.47-7.27 (m, 5H), 5.88 (s, 1H), 3.75 (t, 2H), 3.65 (m, 1H), 3.12 (t, 2H), 2.70-2.81 (m, 2H), 2.30 (s, 3H), 1.7-2.4 (m, 7H)

| | |
|---|---|
| 159 | 2-[(3-ethylsulfanylphenyl)(1-methylpiperidin-4-yloxy)methyl]benzothiazole |

$^1$H NMR: 7.98 (d, 1H), 7.88 (d, 1H), 7.50-7.30 (m, 3H), 7.30-7.10 (m, 3H), 5.83 (s, 1H), 3.93 (m, 1H), 3.25-3.00 (m, 4H), 2.95 (q, 2H), 2.67 (s, 3H), 2.50-2.30 (m, 2H), 2.20-2.00 (m, 2H), 1.30 (t, 3H)

| | |
|---|---|
| 160 | {3-[benzothiazol-2-yl(1-methylpiperidin-4-yloxy)methyl]phenylsulfanyl}acetic acid methyl ester |

$^1$H NMR: 7.98 (d, 1H), 7.87 (d, 1H), 7.62 (s, 1H), 7.50-7.29 (m, 5H), 5.85 (s, 1H), 4.02 (s, 1H), 3.74-3.65 (m, 5H), 3.4-3.2 (m, 4H), 2.79 (s, 3H), 2.6-2.4 (m, 2H), 2.25-2.05 (m, 2H)

| | |
|---|---|
| 201 | 2-[(1-methylpiperidin-4-yloxy)(3-methylsulfanyl-phenyl)methyl]benzothiazole |

$^1$H NMR: 7.97 (d, 1H), 7.87 (d, 1H), 7.50-7.10 (m, 6H), 5.89 (s, 1H), 3.70-3.58 (m, 1H), 2.62-2.78 (m, 2H), 2.48 (s, 3H) 2.23 (s, 3H), 2.23-2.10 (m, 2H), 2.00-1.7 (m, 4H)

| | |
|---|---|
| 233 | 2-{(1-methylpiperidin-4-yloxy)[3-(2-pyrazin-2-yl-ethylsulfanyl)phenyl]methyl}benzothiazole |

$^1$H NMR: 8.47 (m, 1H), 8.40 (m, 1H), 7.96 (d, 1H), 7.85 (d, 1H), 7.53 (s, 1H), 7.45-7.27 (m, 6H), 5.88 (s, 1H), 3.8-3.60 (m, 1H), 3.34 (t, 2H), 3.09 (t, 2H), 2.82-2.75 (m, 2H), 2.34 (s, 3H), 2.50-2.20 (m, 2H), 2.1-1.70 (m, 4H)

| | |
|---|---|
| 239 | (1-{3-[benzothiazol-2-yl(1-methylpiperidin-4-yloxy)methyl]phenylsulfanylmethyl}-cyclopropyl)acetic acid methyl ester |

$^1$H NMR: 7.97 (d, 1H), 7.87 (d, 1H), 7.53 (s, 1H), 7.48-7.24 (m, 5H), 5.87 (s, 1H), 3.7-3.5 (m, 4H), 3.08 (s, 2H), 2.80-2.65 (m, 2H), 2.46 (s, 2H), 2.30 (s, 3H), 2.32-2.2 (m, 2H), 2.10-1.75 (m, 4H), 0.50 (m, 4H)

| | |
|---|---|
| 254 | 3-{3-[benzothiazol-2-yl(1-methylpiperidin-4-yloxy)methyl]phenylsulfanyl}propan-1-ol |

$^1$H NMR: 7.96 (d, 1H), 7.87 (d, 1H), 7.57 (s, 1H), 7.46-7.24 (m, 5H), 5.88 (s, 1H), 3.8-3.65 (m, 3H), 3.28-3.15 (m, 1H), 3.07-2.97 (m, 1H), 2.87-2.70 (m, 2H), 2.34 (s, 3H), 2.45-2.25 (m, 2H), 2.20-1.75 (m, 7H)

| Example | Product |
|---|---|
| 255 | 1-{3-[benzothiazol-2-yl(1-methylpiperidin-4-yloxy)methyl]phenylsulfanyl}propan-2-ol |

¹H NMR: 8.06 (d, 1H), 7.91 (d, 1H), 7.46-7.24 (m, 6H), 6.09 (s, 1H), 5.5-4.0 (sl, 1H), 3.85-3.70 (m, 2H), 3.28-3.07 (m, 2H), 3.07-2.85 (m, 4H), 2.63 (s, 3H), 2.18-1.70 (m, 4H), 1.11 (d, 3H)

| | |
|---|---|
| 256 | 4-{3-[benzothiazol-2-yl(1-methylpiperidin-4-yloxy)methyl]phenylsulfanyl}butan-1-ol |

¹H NMR: 7.97 (d, 1H), 7.87 (d, 1H), 7.50-7.24 (m, 6H), 5.88 (s, 1H), 3.77-3.60 (m, 3H), 3.00-2.90 (m, 2H), 2.85-2.70 (m, 2H), 2.33 (s, 3H), 2.41-2.20 (m, 2H), 2.20-1.60 (m, 9H)

Example 150

2-[(3-benzylsulfanylphenyl)(1-methylpiperidin-4-yloxy)methyl]-1H-benzimidazole A screw-cap tube is charged with 2-[(3-bromophenyl)(1-methylpiperidin-4-yloxy)methyl]-1H-benzimidazole (200 mg), palladium bis(dibenzylideneacetone) (14 mg), Xantphos (14 mg), benzyl mercaptan (59 µL), Diisopropylethylamine (174 µL) and 1,4-dioxane (2 mL). The tube is evacuated, filled with argon and sealed. After stirring at 120° C. for 24 h, the mixture is diluted with ethyl acetate and water and the aqueous phase is extracted with ethyl acetate. The pooled organic extracts are dried over magnesium sulfate and concentrated under reduced pressure. The residue is purified by chromatography (gradient dichloromethane/methanol/ammonia from 100/0/0 to 95/5/0.5) to afford 2-[(3-benzylsulfanylphenyl)(1-methylpiperidin-4-yloxy)methyl]-1H-benzimidazole ¹H NMR: 12.38 (sl, 1H), 7.55 (d, 1H), 7.50-7.40 (m, 2H), 7.30-7.00 (m, 10H), 5.84 (s, 1H), 4.20 (s, 2H), 3.65-3.45 (m, 1H), 3.20-3.00 (m, 2H), 2.90-2.60 (m, 2H), 2.57 (s, 3H), 2.00-1.60 (m, 4H)

Further examples can be prepared according to the above described general method:

| Example | Product |
|---|---|
| 153 | 2-[(3-ethylsulfanylphenyl)(1-methylpiperidin-4-yloxy)methyl]-1H-benzimidazole |

¹H NMR: 7.54 (sl, 1H), 7.40 (s, 1H), 7.27-7.17 (m, 6H), 5.82 (s, 1H), 3.65-3.50 (m, 1H), 2.87 (q, 2H), 2.80-2.60 (m, 2H), 2.23 (s, 3H), 2.20-1.65 (m, 6H), 1.23 (s, 3H)

| | |
|---|---|
| 154 | {3-[(1H-benzimidazol-2-yl)(1-methylpiperidin-4-yloxy)methyl]phenylsulfanyl}acetic acid methyl ester |

¹H NMR: 9.66 (sl, 1H), 7.90-7.20 (m, 8H), 5.84 (s, 1H), 3.71-3.50 (m, 6H), 2.80-2.60 (m, 2H), 2.28 (s, 3H), 2.27-1.65 (m, 6H)

| | |
|---|---|
| 157 | 2-{3-[(1H-benzimidazol-2-yl)(1-methylpiperidin-4-yloxy)methyl]phenylsulfanyl}ethanol |

¹H NMR: 9.76 (sl, 1H), 7.72 (s, 1H), 7.52 (s, 1H), 7.42 (s, 1H) 7.30-7.15 (m, 5H), 5.84 (s, 1H), 3.74 (t, 2H), 3.57-3.51 (m, 1H), 3.10 (t, 2H), 2.75-2.55 (m, 2H), 2.24 (s, 3H), 2.10-1.60 (m, 7H)

| | |
|---|---|
| 173 | 2-[[3-(furan-2-ylmethylsulfanyl)phenyl](1-methylpiperidin-4-yloxy)methyl]-1H-benzimidazole |

¹H NMR: 12.36 (sl, 1H), 7.54-7.44 (m, 4H), 7.26 (m, 3H), 7.18-7.10 (m, 2H), 6.22-6.15 (m, 2H), 5.83 (s, 1H), 4.20 (s, 2H), 3.35-3.50 (m, 1H), 3.0-2.8 (m, 2H), 2.36 (s, 3H), 2.0-1.8 (m, 2H), 1.8-1.6 (m, 2H), 1.25-1.05 (m, 2H)

| | |
|---|---|
| 202 | 2-[(1-methylpiperidin-4-yloxy)(3-methylsulfanyl-phenyl)methyl]-1H-benzimidazole |

¹H NMR: 7.65-7.52 (m, 2H), 7.36 (s, 1H), 7.30-7.10 (m, 5H), 5.85 (s, 1H), 3.97-3.85 (m, 1H), 3.47-3.30 (m, 2H), 3.20-2.90 (m, 2H), 2.69 (s, 3H), 2.43 (s, 3H), 2.38-2.0 (m, 4H)

| | |
|---|---|
| 215 | 2-[(3-tert-butylsulfanylphenyl)(1-methylpiperidin-4-yloxy)methyl]-1H-benzimidazole |

¹H NMR: 9.51 (sl, 1H), 7.67 (s, 1H), 7.55-7.40 (m, 4H), 7.38-7.20 (m, 3H), 5.88 (s, 1H), 3.70-3.55 (m, 1H), 2.85-2.70 (m, 2H), 2.29 (s, 3H), 2.28-2.10 (m, 2H), 2.05-1.70 (m, 4H), 1.25 (s, 9H)

| | |
|---|---|
| 232 | 2-{(1-methylpiperidin-4-yloxy)[3-(2-pyrazin-2-yl-ethylsulfanyl)phenyl]methyl}-1H-benzimidazole |

¹H NMR: 10.24 (sl, 1H), 8.48 (m, 1H), 8.41 (m, 2H), 7.73 (sl, 1H), 7.51 (s, 1H), 7.33 (sl, 1H) 7.27-7.15 (m, 5H), 5.85 (s, 1H), 3.70-3.60 (m, 1H), 3.34 (t, 2H), 3.09 (t, 2H), 1.60-1.80 (m, 2H), 2.23 (s, 3H), 2.23-1.60 (m, 6H)

| | |
|---|---|
| 248 | 4-{3-[(1H-benzimidazol-2-yl)(1-methylpiperidin-4-yloxy)methyl]phenylsulfanyl}butan-1-ol |

¹H NMR: 10.04 (sl, 1H), 7.88-7.35 (m, 3H), 7.30-7.15 (m, 5H), 5.83 (s, 1H), 3.75-3.62 (m, 2H), 3.62-3.58 (m, 1H), 2.92 (t, 2H), 2.85-2.65 (m, 2H), 2.27 (s, 3H), 2.20-2.05 (m, 2H), 2.05-1.6 (m, 9H)

| | |
|---|---|
| 288 | 3-{3-[(1H-benzimidazol-2-yl)(1-methylpiperidin-4-yloxy)methyl]phenylsulfanyl}propane-1,2-diol |

¹H NMR: 12.38 (sl, 1H), 7.52 (d, 1H), 7.40-7.40 (m, 2H) 7.30-7.0.4 (m, 5H), 5.83 (s, 1H), 5.00-4.3 (m, 3H), 3.80-4.10 (m, 4H), 2.90-2.70 (m, 2H), 2.50-2.33 (m, 1H), 2.33 (s, 3H), 2.00-1.80 (m, 2H), 1.70-1.50 (m, 2H)

| Example | Product |
|---|---|
| 295 | 6-{3-[(1H-benzimidazol-2-yl)(1-methylpiperidin-4-yloxy)methyl]phenylsulfanyl}hexan-1-ol |

$^1$H NMR: 10.08 (sl, 1H), 7.85-7.60 (m, 1H), 7.43 (sl, 2H), 7.32-7.15 (m, 5H), 5.84 (s, 1H), 3.70-3.50 (m, 3H), 2.92-2.65 (m, 4H), 2.28 (s, 3H), 2.20-1.30 (m, 14H)

Example 165

165A

5,6-dichloro-2-[(1-methylpiperidin-4-yloxy)phenylmethyl]-1H-benzimidazole

A round-bottom flask is charged with 4,5-dichlorobenzene-1,2-diamine (354 mg) and toluene (2 mL); a solution of trimethylaluminum 2M in toluene (1 mL) is added dropwise. The reaction mixture is heated at 60° C. for one hour. A solution of (1-methyl-piperidin-4-yloxy)phenylacetic acid ethyl ester in toluene (1 mL) is added dropwise and heating is pursued for one hour. The reaction mixture is cooled to room-temperature and a solution of sodium hydroxide is added dropwise to pH 10. The slurry is filtered on celite, cake washed with water (4×5 mL) and ethyl acetate (4×5 mL). After decantation, the aqueous phase is extracted with ethyl acetate. The pooled organic extracts are washed with brine, dried over magnesium sulfate and concentrated under reduced pressure. The residue is diluted with glacial acetic acid (3 mL) and the reaction mixture is heated at reflux for one hour. Acetic acid is removed on a rotary evaporator and the residue is purified by chromatography (gradient dichloromethane/methanol/ammonia from 98/2/0 to 95/5/0.5 to give 5,6-dichloro-2-[(1-methylpiperidin-4-yloxy)phenylmethyl]-1H-benzimidazole melting at 221° C.

165B

(1-Methylpiperidin-4-yloxy)phenylacetic acid ethyl ester

To a solution of 4-(Ethoxycarbonyl-phenyl-methoxy)-piperidine-1-carboxylic acid tert-butyl ester (3.4 g) in dichloromethane (25 mL) is added trifluoroacetic acid (18 mL). After 30 minutes at room temperature, the volatiles are removed under reduced pressure. Water (30 mL) is added and the solution is basified by adding a solution of saturated sodium carbonate to pH 10. The aqueous phase is extracted with dichloromethane. The pooled organic extracts are dried over magnesium sulfate and concentrated under reduced pressure to give (1-methylpiperidin-4-yloxy)phenylacetic acid ethyl ester used without further purification.

165C (1-Methylpiperidin-4-yloxy)phenylacetic acid ethyl ester obtained above is dissolved in 1,4-dioxane (40 mL) and 40% aqueous solution of formaldehyde (4 mL) as well as a 1 molar solution of sodium hypophosphorous acid (46 mL); The reaction mixture is heated to 80° C. overnight. 1,4-dioxane is removed under reduced pressure and the residual solution is basified by adding a solution of saturated sodium carbonate to pH 10. The aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.2 to 95/5/0.5) to afford (1-methylpiperidin-4-yloxy)phenylacetic acid ethyl ester.

$^1$H NMR: 7.50-7.45 (m, 2H), 7.38-7.20 (m, 3H), 5.00 (s, 1H), 4.18 (q, 2H), 3.55-3.40 (m, 1H), 2.83-2.65 (m, 2H), 2.28 (s, 3H), 2.25-2.08 (m, 2H), 2.05-1.65 (m, 4H), 1.22 (t, 3H)

165D 4-(Ethoxycarbonylphenylmethoxy)piperidine-1-carboxylic acid tert-butyl ester To a solution of diazophenylacetic acid ethyl ester (2.55 g) in 1,2-dichloroethane is added 4-hydroxypiperidine-1-carboxylic acid tert-butyl ester (5.4 g). The flask is evacuated and filled with argon. Rhodium(II) acetate-dimer (60 mg) is added to the reaction mixture. Evolution of nitrogen occurs until the end of the reaction (about 1 hour). The solvent is removed under reduced pressure. The residue is purified by chromatography (gradient heptane/ethyl acetate from 95/5 to 80/20) to give 4-(ethoxy-carbonylphenylmethoxy)piperidine-1-carboxylic acid tert-butyl ester.

$^1$H NMR: 7.52-7.28 (m, 5H), 5.01 (s, 1H), 4.15 (q, 2H), 3.90-3.70 (m, 2H), 3.68-3.55 (m, 1H), 3.18-3.00 (m, 2H), 2.00-1.50 (m, 4H), 1.44 (s, 9H), 1.26 (t, 3H)

165E

Diazophenylacetic Acid Ethyl Ester

To a solution of ethyl phenylacetate (3.28 g) in acetonitrile (60 mL) is added para-toluenesulfonylazide (4.53 g). The reaction mixture is cooled to 0° C. and 1,8-diazabicyclo [5.4.0]undec-7-ene (3.9 mL) is added dropwise. The reaction mixture is kept at 5° C. overnight. Solvent is removed to dryness and the residue is purified by chromatography (gradient petroleum ether/dichloromethane from 90/10 to 80/20) to give diazophenylacetic acid ethyl ester;

$^1$H NMR: 7.48-7.58 (m, 2H), 7.45-7.30 (m, 2H), 7.22-7.10 (m, 1H), 4.35 (q, 2H), 1.30 (t, 3H)

Example 172

3-[(1H-benzimidazol-2-yl)(1-methylpiperidin-4-yloxy)methyl]benzonitrile

To a solution of 2-[(3-bromophenyl)(1-methylpiperidin-4-yloxy)methyl]benzothiazole (200 mg) in N,N-dimethylformamide (2.5 mL) and water (0.2 mL) are added copper(I) cyanide (180 mg), bis(dibenzylidenacetone)palladium (14.3 mg) and Xantphos (14.4 mg). The tube is evacuated, filled with argon and sealed. After stirring at 120° C. for 48 h, the mixture is diluted with water then extracted with ethyl acetate. The pooled organic extracts are washed with water, brine, dried over magnesium sulfate and concentrated under reduced pressure. The residue is purified by chromatography (gradient dichloromethane/methanol/ammonia from 100/0/0 to 92.5/7.5/0.75) to afford 3-[(1H-benzimidazol-2-yl)(1-methylpiperidin-4-yloxy)methyl]benzonitrile $^1$H NMR: 9.75 (sl, 1H), 7.82 (s, 1H), 7.80-7.62 (m, 2H), 7.57 (d, 1H), 7.50-7.20 (m, 4H), 5.89 (s, 1H), 3.60-3.40 (m, 1H), 2.75-2.55 (m, 2H), 2.25 (s, 3H), 2.20-1.60 (m, 6H)

Example 188

4-[benzothiazol-2-yl(3-bromo-phenyl)methoxy]-1,1-dimethylpiperidinium

To a solution of 2-[(3-bromophenyl)(1-methylpiperidin-4-yloxy)methyl]benzothiazole (100 mg) in acetonitrile is added iodomethane (1 molar equivalent) and the reaction mixture is refluxed for 1 hour. Solvent is removed under reduced pressure to dryness, the residue is triturated with diethylether, filtered, the cake is washed with diethylether and dried to give 4-[benzothiazol-2-yl(3-bromo-phenyl)methoxy]-1,1-dimethylpiperidinium melting at 95° C.

Example 189

2-(3-{3-[(1H-benzimidazol-2-yl)(1-methylpiperidin-4-yloxy)methyl]phenyl}prop-2-ynyl)isoindole-1,3-dione A screw-cap tube is charged with 2-[(3-iodophenyl)(1-methylpiperidin-4-yloxy)methyl]-1H-benzimidazole (200 mg), dichloro-bis(triphenylphosphine) palladium(II) (9.2 mg), copper(I) iodide (16.4 mg), N-propargylphthalimide (400 mg), diethylamine (310 μL) and N,N-dimethylformamide (2 mL). The tube is evacuated, filled with argon and sealed. After stirring at room-temperature for 24 h, the mixture is diluted with water and the aqueous phase is extracted with ethyl acetate. The pooled organic extracts are washed with water, dried over magnesium sulfate and concentrated under reduced pressure. The residue is purified by chromatography (gradient dichloromethane/methanol/ammonia from 98/2/0.2 to 95/5/0.5 to give 2-(3-{3-[(1H-benzimidazol-2-yl)(1-methylpiperidin-4-yloxy)methyl]phenyl}prop-2-ynyl)isoindole-1,3-dione.

$^1$H NMR: 9.52 (sl, 1H), 7.91-7.15 (m, 12H), 5.81 (s, 1H), 4.66 (s, 2H), 3.65-3.55 (m, 1H), 2.85-2.65 (m, 2H), 2.28 (s, 3H), 2.30-2.05 (m, 2H), 2.05-1.60 (m, 4H)

Following compounds are prepared analogously:

| Example | Product |
|---|---|
| 227 | 3-{3-[benzothiazol-2-yl(1-methylpiperidin-4-yloxy)methyl]phenyl}prop-2-yn-1-ol |
| | $^1$H NMR: 7.96 (d, 1H), 7.85 (d, 1H), 7.51 (s, 1H), 7.55-7.23 (m, 5H), 5.89 (s, 1H), 4.46 (s, 2H), 3.70-3.55 (m, 1H), 2.78-2.62 (m, 2H), 2.27 (s, 3H), 2.27-2.08 (m, 2H), 2.05-1.70 (m, 4H) |
| 236 | 4-{3-[benzothiazol-2-yl(1-methylpiperidin-4-yloxy)methyl]phenyl}but-3-yn-1-ol |
| | $^1$H NMR: 7.97 (d, 1H), 7.87 (d, 1H), 7.58 (s, 1H), 7.47-7.27 (m, 5H), 5.87 (s, 1H), 3.88-3.65 (m, 3H), 2.95-2.80 (m, 2H), 2.67 (t, 2H), 2.39 (s, 3H), 2.45-2.30 (m, 2H), 2.18 (s, 1H), 2.17-1.80 (m, 4H) |
| 237 | 5-{3-[benzothiazol-2-yl(1-methylpiperidin-4-yloxy)methyl]phenyl}pent-4-yn-1-ol hydrochloride |
| | $^1$H NMR (DMSO-d$^6$): 9.79 (sl, 1H), 8.07 (d, 1H), 7.92 (d, 1H), 7.50-7.30 (m, 5H), 6.12 (d, 1H), 3.92-3.70 (m, 1H), 3.50-2.95 (m, 6H), 2.76 and 2.67 (d, 3H), 2.48-2.35 (m, 2H), 2.30 1.60 (m, 6H) |

Example 194

3-{3-[(1H-benzimidazol-2-yl)(1-methylpiperidin-4-yloxy)methyl]phenyl}prop-2-ynylamine

194A

A solution of 2-(3-{3-[(1H-benzimidazol-2-yl)(1-methylpiperidin-4-yloxy)methyl]-phenyl}prop-2-ynyl)isoindole-1,3-dione (70 mg) and hydrazine hydrate (70 μL) in ethanol (0.7 mL) is stirred a room temperature for 3 hours. Ethanol is removed under reduced pressure and 1N hydrochloric acid in water is added to the organic residue and stirred for 5 minutes. The mixture is filtered, cake washed with ethyl acetate. The filtrate is extracted by dichloromethane. The pooled organic extracts are dried over magnesium sulfate and concentrated under reduced pressure The residue purified by chromatography (dichloromethane/methanol/ammonia from 90/10/1) to afford 3-{3-[(1H-benzimidazol-2-yl)(1-methylpiperidin-4-yloxy)methyl]phenyl}prop-2-ynylamine melting at 101° C.

194B 2-(3-{3-[(1H-benzimidazol-2-yl)(1-methylpiperidin-4-yloxy)methyl]phenyl}prop-2-ynyl)isoindole-1,3-dione is prepared according to general procedure 189.

Following compounds are prepared analogously:

| Example | Product |
|---|---|
| 282 | 4-{3-[benzothiazol-2-yl(1-methylpiperidin-4-yloxy)methyl]phenyl}but-3-ynylamine |
| | $^1$H NMR: 7.98 (d, 1H), 7.88 (d, 1H), 7.58 (s, 1H), 7.52-7.25 (m, 5H), 5.86 (s, 1H), 3.82-3.68 (m, 1H), 2.95-2.70 (m, 2H), 2.68-2.50 (m, 4H), 2.47 (s, 3H), 2.40-1.75 (m, 6H) |

-continued

| Example | Product |
|---|---|
| 286 | 4-{3-[(1H-benzimidazol-2-yl)(1-methylpiperidin-4-yloxy)methyl]phenyl}but-3-ynylamine |
| | ¹H NMR: 9.50 (sl, 1H), 7.72 (sl, 1H), 7.55-7.20 (m, 7H), 5.84 (s, 1H), 3.65-3.55 (m, 1H), 2.91 (t, 2H), 2.80-2.65 (m, 2H), 2.54 (t, 2H), 2.26 (s, 3H), 2.18-1.60 (m, 6H) |
| 287 | e5-{3-[benzothiazol-2-yl(1-methylpiperidin-4-yloxy)methyl]phenyl}pent-4-ynylamine |
| | ¹H NMR: 7.97 (d, 1H), 7.87 (d, 1H), 7.56 (s, 1H), 7.46-7.24 (m, 5H), 5.87 (s, 1H), 3.71-3.56 (m, 1H), 2.95-2.82 (m, 2H), 2.82-2.66 (m, 2H), 2.47 (t, 2H), 2.29 (s, 3H), 2.28-2.18 (m, 2H), 2.10-1.70 (m, 8H) |
| 337 | 6-{3-[(1H-benzimidazol-2-yl)(1-methylpiperidin-4-yloxy)methyl]phenyl}hex-5-ynylamine |
| | ¹H NMR: 7.70-7.45 (m, 3H), 7.40-7.10 (m, 5H), 5.84 (s, 1H), 3.60-3.55 (m, 2H), 3.32-3.17 (m, 1H), 2.80-2.60 (m, 4H), 2.45-2.30 (m, 2H), 2.24 (s, 3H), 2.18-1.50 (m, 10H) |

Example 195

2-[(3-ethynylphenyl)(1-methylpiperidin-4-yloxy)methyl]-1H-benzimidazole

195A

To a solution of 2-[(3-trimethylsilylethynylphenyl)(1-methylpiperidin-4-yloxy)methyl]-1H-benzimidazole (205 mg) in methanol (2 mL) is added potassium carbonate (81 mg). The reaction mixture is stirred at room temperature for 4 hours, then methanol is removed under reduced pressure. The residue is dissolved in water and extracted with ethyl acetate. The organic phase is dried on magnesium sulphate and solvent is removed under reduced pressure to give 2-[(3-ethynylphenyl)(1-methylpiperidin-4-yloxy)methyl]-1H-benzimidazole ¹H NMR: 9.42 (sl, 1H), 7.80-7.70 (m, 1H), 7.62 (s, 1H), 7.48-7.36 (m, 3H) 7.34-7.20 (m, 3H), 5.86 (s, 1H), 3.65-3.48 (m, 1H), 3.07 (s, 1H), 2.78-2.65 (m, 2H), 2.25 (s, 3H), 2.20-1.60 (m, 6H)

195B

2-[(3-trimethylsilylethynylphenyl)(1-methylpiperidin-4-yloxy)methyl]-1H-benzimidazole can be obtained using general method described in example 189.

Example 198

2-{(1-methylpiperidin-4-yloxy)[3-(1H-[1,2,3]triazol-4-yl)phenyl]methyl}-1H-benzimidazole To a solution of 2-[(3-(ethynylphenyl)(1-methylpiperidin-4-yloxy)methyl]-1H-benzimidazole (110 mg) in methanol (2 mL) and N,N-dimethylformamide (0.7 mL) in a screw-cap tube is added L). The reaction mixture□copper(I) iodide (3.2 mg) and azidotrimethylsilane (56 is heated at 100° C. overnight, then solvents are removed under reduced pressure. The residue is dissolved in water and ammonia solution is added to pH10; the aqueous phase is extracted with dichloromethane. The organic phase is dried on magnesium sulphate and solvent is removed under reduced pressure to give 2-{(1-methylpiperidin-4-yloxy)[3-(1H-[1,2,3]triazol-4-yl)phenyl]methyl}-1H-benzimidazole.

¹H NMR: 7.98 (s, 1H), 7.86 (s, 1H), 7.80-7.50 (m, 3H), 7.48-7.30 (m, 2H), 7.29-7.15 (m, 2H), 5.95 (s, 1H), 3.68-3.50 (m, 1H), 2.96-2.89 (m, 1H), 2.85-2.65 (m, 2H), 2.26 (s, 3H), 2.20-1.70 (m, 6H)

Example 199

3-[benzothiazol-2-yl(1-methylpiperidin-4-yloxy)methyl]benzoic acid methyl ester, oxalate A solution of 3-[benzothiazol-2-yl(1-methylpiperidin-4-yloxy)methyl]benzonitrile (109 mg, example 197) in methanol (5 mL) is treated with a flow of hydrogen chloride while refluxing for 4 h. After stirring at room temperature for one night, the mixture is concentrated under reduced pressure and the residue purified over silica gel (dichloromethane/methanol/ammonia 95/5/0.5) to afford 3-[benzothiazol-2-yl(1-methylpiperidin-4-yloxy)methyl]benzoic acid methyl ester which is then converted into its oxalate salt in acetone to give 3-[benzothiazol-2-yl(1-methylpiperidin-4-yloxy)methyl]benzoic acid methyl ester, oxalate melting at 93° C.

Example 200

2-[(1-methylpiperidin-4-yloxy)phenyl-methyl]-3H-benzimidazol-4-ylamine

To a solution of DMF (44 mg) in L). As soon as □1,2-dichloroethane (2.5 mL) is added dropwise oxalylchloride (51 the gas evolution ceased, the volatiles are removed under reduced pressure. To the residue are added 1,2-dichloroethane (2.5 mL) and (1-methylpiperidin-4-yloxy)phenylacetic acid (125 mg). The reaction mixture is stirred at room temperature for 1 hour, then 1,2-diamino-3-nitrobenzene is added and the mixture is stirred overnight. Water is added and the solution is basified by adding a solution of saturated sodium carbonate to pH 10. The aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.2 to 95/5/0.5).

To the residual solid in ethanol (4.5 mL) is added tin(II) dichloride. The reaction mixture is refluxed for 2 hours. The solution is basified by adding a solution of 10N sodium hydroxide to pH 6. The aqueous phase is extracted with chloroform. The pooled organic extracts are dried over magnesium sulfate and concentrated under reduced pressure. The residue is dissolved in acetic acid and the reaction mixture is refluxed for 3 hours. Acetic acid is removed, methanol (1 mL) and 12N hydrochloric acid are added to the residue. The reaction mixture is heated to 60° C. for 1 hour.

The solution is basified by adding a solution of saturated sodium carbonate to pH 10. The aqueous phase is extracted with ethyl acetate. The pooled organic extracts are dried over magnesium sulfate and concentrated under reduced pressure.

The residue is purified by chromatography (gradient dichloromethane/methanol/ammonia from 98/2/0.2 to 90/10/1) to afford 2-[(1-methylpiperidin-4-yloxy)phenyl-methyl]-3H-benzimidazol-4-ylamine melting at 96.7° C.

Example 203

2-[(3-methanesulfonylphenyl)(1-methylpiperidin-4-yloxy)methyl]benzothiazole

To a solution of 2-[(1-methylpiperidin-4-yloxy)(3-methylsulfanylphenyl)methyl]-benzothiazole (100 mg) in methanol (2 mL) and water (1 mL) at 0° C. is added portionwise Oxone® (400 mg) over 1 hour.

The mixture is diluted with water. The aqueous phase is extracted with ethyl acetate. The pooled organic extracts are washed with water, dried over magnesium sulfate and concentrated under reduced pressure. The residue is purified by chromatography (gradient dichloromethane/methanol from 98/2 to 90/10) to afford 2-[(3-methanesulfonylphenyl)(1-methylpiperidin-4-yloxy)methyl]benzothiazole.

$^1$H NMR: 8.17 (s, 1H), 7.97 (d, 1H), 7.90-7.83 (m, 3H), 7.60-7.39 (m, 3H), 6.00 (s, 1H), 3.72-3.60 (m, 1H), 3.06 (s, 3H), 2.82-2.75 (m, 2H), 2.28 (s, 3H), 2.28-2.10 (m, 2H), 2.05-1.70 (m, 4H)

Example 206

3-[benzothiazol-2-yl(1-methylpiperidin-4-yloxy)methyl]benzoic acid ethyl ester, oxalate 3-[benzothiazol-2-yl(1-methylpiperidin-4-yloxy)methyl]benzoic acid ethyl ester, oxalate melting at 104° C. can be prepared as described in example 199.

Example 207

{3-[benzothiazol-2-yl(1-methylpiperidin-4-yloxy)methyl]phenyl}methanol, oxalate

A solution of 3-[benzothiazol-2-yl(1-methylpiperidin-4-yloxy)methyl]benzoic acid ethyl ester (0.55 g, example 206) in tetrahydrofurane (10 mL) is treated with lithium aluminum hydride (76 mg) at room temperature for 1 h. Two other additions of lithium aluminum hydride (76 mg each) allow a complete conversion. The mixture is then hydrolyzed with water (178 μL), 5% sodium hydroxide (178 μL) and water (535 μL), filtered through a pad of clarcel and concentrated under reduced pressure. The residue is purified over silica gel (dichloromethane/methanol/ammonia 95/5/0.5) to afford {3-[benzothiazol-2-yl(1-methylpiperidin-4-yloxy)methyl]phenyl}methanol which is then converted into its oxalate salt in acetone to give {3-[benzothiazol-2-yl(1-methylpiperidin-4-yloxy)methyl]phenyl}methanol, oxalate.

$^1$H NMR (DMSO-d6): 8.06 (d, 1H), 7.90 (d, 1H), 7.50-7.20 (m, 6H), 6.09 (s, 1H), 4.47 (s, 2H), 3.75 (m, 1H), 3.16 (m, 2H), 2.98 (m, 2H), 2.64 (s, 3H), 2.10-1.75 (m, 4H).

Example 208

3-{3-[benzothiazol-2-yl(1-methylpiperidin-4-yloxy)methyl]phenyl}propionic acid tert-butyl ester A screw-cap tube is charged with 2-[(3-bromophenyl)(1-methylpiperidin-4-yloxy)methyl]benzothiazole (208 mg), palladium(II) acetate (3 mg), RuPhos® (12 mg), potassium 3-trifluoroboratopropionate tert-butyl ester (118 mg), potassium carbonate (207 mg), water (2.5 mL) and toluene (2.5 mL). The tube is evacuated, filled with argon and sealed. After stirring at 120° C. overnight, the mixture is diluted with ethyl acetate and water and the aqueous phase is extracted with ethyl acetate. The pooled organic extracts are dried over magnesium sulfate and concentrated under reduced pressure. The residue is purified by chromatography (gradient dichloromethane/methanol from 100/0 to 95/5) to afford 3-{3-[benzothiazol-2-yl(1-methylpiperidin-4-yloxy)methyl]phenyl}propionic acid tert-butyl ester.

$^1$H NMR: 7.97 (d, 1H), 7.86 (s, 1H), 7.45-7.22 (m, 5H), 7.12 (d, 1H), 5.89 (s, 1H), 3.72-3.58 (m, 1H), 2.87 (t, 2H), 2.78-2.65 (m, 2H), 2.53 (t, 2H), 2.29 (s, 3H), 2.28-2.10 (m, 2H), 2.08-1.72 (m, 4H), 1.39 (s, 9H)

Example 210

2-[(1-methylpiperidin-4-yloxy)phenylmethyl]-3H-benzimidazol-4-ol

To a solution of (1-methylpiperidin-4-yloxy)phenylacetic acid (250 mg) in acetonitrile (5 mL) are added 2,3-diaminophenol (125 mg), 2-chloro-1-methylpyridinium iodide (255 mg) and dropwise diisopropylethylamine (0.44 mL). The reaction mixture is stirred at room temperature for 3 hours. Solvent is removed under reduced pressure. Water is added to the residue and the solution is basified by adding a solution of saturated sodium carbonate to pH 10. The aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.2 to 90/10/1).

The residue is dissolved in acetic acid (2 mL) and the reaction mixture is refluxed for 24 hours. Acetic acid is removed under reduced pressure. Water is added to the residue and the solution is basified by adding a solution of saturated sodium carbonate to pH 10. The aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.2 to 90/10/1). The residual solid is re-crystalized from hot toluene to give 2-[(1-methylpiperidin-4-yloxy)phenylmethyl]-3H-benzimidazol-4-ol melting at 170.5° C.

Example 211

[benzothiazol-2-yl(4'-methoxybiphenyl-3-yl)methyl](1-methylpiperidin-4-yl)amine, dioxalate

211A

[benzothiazol-2-yl(4'-methoxybiphenyl-3-yl)methyl](1-methylpiperidin-4-yl)amine, dioxalate melting at 130° C. can be prepared according to general procedure 91A from benzothiazol-2-yl(4'-methoxybiphenyl-3-yl)methanol.

211B

A mixture of benzothiazol-2-yl(3-bromophenyl)methanol (200 mg), 4-methoxy-phenylboronic acid (142 mg), tetrakis(triphenylphosphine)palladium (50 mg), potassium carbonate (259 mg), water (4 mL), ethanol (1 mL) and toluene (9 mL) is purged with argon and refluxed for one night. After cooling at room temperature, the mixture is diluted with water and diethylether. The organic phase is dried over magnesium sulfate and concentrated under reduced pressure. The residue is purified by column chromatography (heptane/ethyl acetate 2/1) to afford benzothiazol-2-yl(4'-methoxybiphenyl-3-yl)methanol as a beige solid.

Example 217

3-{3-[benzothiazol-2-yl(1-methylpiperidin-4-yloxy)methyl]phenyl}acrylonitrile

To a solution of 2-[(3-Iodophenyl)(1-methylpiperidin-4-yloxy)methyl]benzimidazole (230 mg) in tetrahydrofuran (2.5 mL) in a screw-capped tube are added acrylonitrile (0.15 mL), triethylamine (2.5 mL) and tetrakis(triphenylphosphine)palladium. The tube is evacuated, filled with argon, sealed and heated at 70° C. for 18 h. Solvent and volatiles are removed under reduced pressure and the residue is purified by chromatography (gradient dichloromethane/methanol/ammonia from 100/0/0 to 95/5/0.5 to give 3-{3-[benzothiazol-2-yl(1-methylpiperidin-4-yloxy)methyl]phenyl}acrylonitrile.

$^1$H NMR: 7.98 (d, 1H), 7.88 (d, 1H), 7.65-7.55 (m, 2H), 7.55-7.35 (m, 5H), 5.92 (d, 1H), 5.88 (s, 1H), 4.00-3.90 (m, 1H), 3.25-2.95 (m, 4H), 2.65 (s, 3H), 2.50-2.35 (m, 2H), 2.25-2.00 (m, 2H)

Following compounds are prepared analogously:

| Example | Product |
|---|---|
| 205 | 3-{3-[benzothiazol-2-yl(1-methylpiperidin-4-yloxy)methyl]phenyl}acrylic acid tert-butyl ester |

$^1$H NMR: 7.98 (d, 1H), 7.87 (s, 1H), 7.68 (s, 1H), 7.60-7.36 (m, 6H), 6.37 (d, 1H), 5.93 (s, 1H), 3.72-3.59 (m, 1H), 2.80-2.65 (m, 2H), 2.29 (s, 3H), 2.28-2.10 (m, 2H), 2.05-1.60 (m, 4H), 1.74 (s, 9H).

| | |
|---|---|
| 209 | 2-[[3-(2-benzenesulfonylvinyl)phenyl](1-methylpiperidin-4-yloxy)methyl]benzothiazole |

$^1$H NMR: 8.02-7.92 (m, 3H), 7.98 (d, 1H), 7.75-7.35 (m, 9H), 7.30-7.15 (m, 1H), 6.90 (d, 1H), 5.88 (s, 1H), 4.10-3.95 (m, 1H), 3.45-3.25 (m, 4H), 2.76 (s, 3H), 2.70-2.45 (m, 2H), 2.35-2.10 (m, 2H)

| | |
|---|---|
| 212 | 2-[[3-(2-methanesulfonylvinyl)phenyl](1-methylpiperidin-4-yloxy)methyl]benzothiazole |

$^1$H NMR: 7.99 (d, 1H), 7.88 (s, 1H), 7.78-7.59 (m, 3H), 7.55-7.38 (m, 4H), 6.92 (d, 1H), 5.94 (s, 1H), 3.78-3.62 (m, 1H), 3.03 (s, 3H), 2.87-2.70 (m, 2H), 2.32 (s, 3H), 2.40-2.13 (m, 2H), 2.10-1.75 (m, 4H)

Example 219

3-[benzothiazol-2-yl(1-methylpiperidin-4-yloxy)methyl]-N-benzyl-N-methylbenzamide A screw-capped tube is charged with 2-[(3-bromo-phenyl)(1-methylpiperidin-4-yloxy)methyl]benzothiazole (example 27, 400 mg), N-benzylmethylamine (178 μL), 1,8-diazabicyclo(5.4.0)undec-7-ene (100 μL), trans-di-μ-acetatobis[2-(di-o-tolyl-phosphino)benzyl]dipalladium(II) (22 mg), tri-tert-butylphosphonium tetrafluoroborate (17 mg), molybdenum hexacarbonyl (127 mg) and tetrahydrofurane (3 mL). The tube is sealed and heated at 125° C. for 10 min. The reaction was allowed to cool to room temperature and concentrated under reduced pressure. The residue is purified over silica gel (gradient dichloromethane/methanol/ammonia from 98/2/0.5 to 95/5/0.5) to afford 3-[benzothiazol-2-yl(1-methylpiperidin-4-yloxy)methyl]-N-benzyl-N-methylbenzamide which is then converted into its oxalate salt in acetone to give 3-[benzothiazol-2-yl(1-methylpiperidin-4-yloxy)methyl]-N-benzyl-N-methylbenzamide, oxalate melting at 103° C.

Example 224

3-[(1H-benzimidazol-2-yl)(1-methylpiperidin-4-yloxy)methyl]phenylamine

224A

To a solution of 2-[(1-methylpiperidin-4-yloxy)(3-nitrophenyl)methyl]-1H-benzimidazole (110 mg) in ethanol is added tin(II)dichloride (340 mg). The reaction mixture is refluxed for 2 hours. The solution is basified by adding a solution of 10N sodium hydroxide to pH 10. The aqueous phase is extracted with chloroform. The pooled organic extracts are dried over magnesium sulfate and concentrated under reduced pressure. The residue is purified by chromatography (gradient dichloromethane/methanol/ammonia from 98/2/0.2 to 90/10/1) to give 3-[(1H-benzimidazol-2-yl)(1-methylpiperidin-4-yloxy)methyl]phenylamine melting at 100° C.

224 B

2-[(1-Methylpiperidin-4-yloxy)(3-nitrophenyl)methyl]-1H-benzimidazole can be prepared according to the method described in example 165.

Example 228

3-{3-[benzothiazol-2-yl(1-methylpiperidin-4-yloxy)methyl]phenoxymethyl}-phenylamine, oxalate A suspension of 2-{(1-methylpiperidin-4-yloxy)[3-(3-nitro-benzyloxy)phenyl]-methyl}benzothiazole (example 196, 55 mg) and tin(II) chloride dihydrate (250 mg) in ethanol (2 mL) is refluxed for 1 h. The cooled mixture is diluted with dichloromethane and aqueous 1N sodium hydroxide. The organic phase is dried over magnesium sulfate and concentrated under reduced pressure to afford 3-{3-[benzothiazol-2-yl(1-methylpiperidin-4-yloxy)methyl]phenoxymethyl}-phenylamine which is then converted into its oxalate salt in acetone to give 3-{3-[benzothiazol-2-yl(1-methylpiperidin-4-yloxy)methyl]phenoxymethyl}-phenylamine, oxalate as an orange solid. TLC of the base (eluent: CH$_2$Cl$_2$/MeOH/NH$_4$OH 95/5/0.5): Rf=0.14.

Example 229

2-{3-[benzothiazol-2-yl(1-methylpiperidin-4-yloxy)methyl]phenylsulfanyl}ethanol enantiomer A A solution of racemic 2-{3-[benzothiazol-2-yl(1-methylpiperidin-4-yloxy)methyl]phenylsulfanyl}ethanol (10 mg/mL) in a mixture of heptane/isopropanol (75/25) containing diethylamine (0.1%) is injected (20×100 μL) onto an analytical Chiralcel OD-H, 250×4.6 mm column. Elution is performed with a mixture of heptane/isopropanol (80/20) containing diethylamine (0.1%) at a flow of 1 mL/min. Products are detected at 220 nm.

The first enantiomer has a retention time of 7.0 min.

Collection affords 2-{3-[benzothiazol-2-yl(1-methylpiperidin-4-yloxy)methyl]phenylsulfanyl}ethanol enantiomer A with a chromatographic enantiomeric purity of 100.0%.

Example 230

2-{3-[benzothiazol-2-yl(1-methylpiperidin-4-yloxy)methyl]phenylsulfanyl}ethanol enantiomer B The second enantiomer has a retention time of 9.4 min.

Collection affords 2-{3-[benzothiazol-2-yl(1-methylpiperidin-4-yloxy)methyl]phenylsulfanyl}ethanol enantiomer B with a chromatographic enantiomeric purity of 97.8%.

Example 231

2-[(3-azidophenyl)(1-methylpiperidin-4-yloxy)methyl]-1H-benzimidazole

231A

To a solution of 3-[(1H-benzimidazol-2-yl)(1-methylpiperidin-4-yloxy)methyl]-phenylamine (57 mg) in methanol (3 mL) are added at 0° C. copper(II) sulphate and a solution of trifluoromethanesulfonylazide (freshly prepared from sodium azide (220 mg) and trifluoromethanesulfonic anhydride (200 mg)) in dichloromethane.

The reaction mixture is stirred overnight at 4° C. Volatiles are removed under reduced pressure. Water is added to the residue and the solution is basified by adding a solution of saturated sodium carbonate to pH 10. The aqueous phase is extracted with dichloromethane. The pooled organic extracts are dried over magnesium sulfate and concentrated under reduced pressure. The residue is purified by chromatography (gradient dichloromethane/methanol/ammonia from 98/2/0.2 to 90/10/1) to give 2-[(3-azidophenyl)(1-methylpiperidin-4-yloxy)methyl]-1H-benzimidazole melting at 53° C.

231B

To a solution of 2-[(1-Methyl-piperidin-4-yloxy)-(3-nitrophenyl)-methyl]-1Hbenzimidazole (110 mg) in ethanol (5 mL) is added Tin(II)dichloride-dihydrate (340 mg). The reaction mixture is heated at reflux for 2 hours. Water is added to the mixture as well as sodium hydroxide 1N solution to pH 10. The solution is extracted with chloroform. The pooled organic phases are dried with magnesium sulphate and concentrated under reduced pressure. The residue is purified by chromatography (gradient dichloromethane/methanol/ammonia from 98/2/0.2 to 90/10/1) to give 3-[(1H-benzimidazol-2-yl)(1-methylpiperidin-4-yloxy)methyl]phenylamine that is used without further purification.

Example 234

{3-[benzothiazol-2-yl(1-methylpiperidin-4-yloxy)methyl]phenyl}benzyl-amine, dioxalate A screw-capped tube is charged with 2-[(3-iodophenyl)(1-methylpiperidin-4-yloxy)methyl]benzothiazole (example 41, 190 mg), copper(I) iodide (4 mg), ethylene glycol (45 μL), potassium carbonate (173 mg), benzylamine (54 μL), and propan-2-ol (1 mL). The tube is evacuated, filled with argon and sealed. After stirring at 80° C. for 15 h, the mixture is diluted with ethyl acetate and water and the aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.5 to 95/5/0.5). The base is converted into its dioxalate salt in acetone to give {3-[benzothiazol-2-yl(1-methylpiperidin-4-yloxy)methyl]phenyl}benzyl-amine, dioxalate melting at 75° C.

Example 258

3-{3-[benzothiazol-2-yl(1-methylpiperidin-4-yloxy)methyl]phenoxy}propan-1-ol, oxalate A screw-capped tube is charged with 2-[(3-iodophenyl)(1-methylpiperidin-4-yloxy)methyl]benzothiazole (example 41, 150 mg), copper(I) iodide (6.5 mg), 3,4,7,8-tetramethyl-1,10-phenanthroline (16.3 mg), cesium carbonate (223 mg), propan-1,3-diol (74 mg), ground 4 Å molecular sieves (80 mg) and toluene (4 mL). The tube is evacuated, filled with argon and sealed. After stirring at 90° C. for 24 h, the mixture is diluted with dichloromethane, water and ammonia. After filtration and decantation, the aqueous phase is extracted with dichloromethane. The pooled organic extracts are dried over magnesium sulfate and concentrated under reduced pressure. The residue is purified by chromatography (gradient dichloromethane/methanol/ammonia from 98/2/0.5 to 95/5/0.5). The base is converted into its oxalate salt in acetone to give 3-{3-[benzothiazol-2-yl(1-methylpiperidin-4-yloxy)methyl]phenoxy}propan-1-ol, oxalate melting at 79° C.

Example 240

2-{(1-methylpiperidin-4-yloxy)[3-(2-[1,2,3]triazol-2-yl-ethylsulfanyl)phenyl]-methyl}benzothiazole

240A

To a solution of 1,2,3-triazole (36.5 mg) in N,N-dimethylformamide (1 mL) is added a dispersion of sodium hydride 60% in mineral oil (1 molar equivalent). The reaction mixture is stirred at room temperature for 15 minutes, then a solution of methanesulfonic acid 2-{3-[benzothiazol-2-yl(1-methylpiperidin-4-yloxy)methyl]phenylsulfanyl}ethyl ester (85 mg) in N,N-dimethylformamide (1 mL) is added. The reaction mixture is stirred at 60° C. overnight. Water is added and the aqueous phase is extracted by ethyl acetate. The organic phase is dried over magnesium sulfate and concentrated under reduced pressure. The residue is purified by column chromatography (gradient dichloromethane/methanol/ammonia 100/0/0 to 90/10/1) to afford 2-{(1-methylpiperidin-4-yloxy)[3-(2-[1,2,3]triazol-2-yl-ethylsulfanyl)phenyl]methyl}benzothiazole.

$^1$H NMR: 7.97 (d, 1H), 7.87 (d, 1H), 7.65-7.25 (m, 8H), 5.90 (s, 1H), 4.62 (t, 2H), 3.75-3.60 (m, 1H), 3.44 (t, 2H), 2.82-2.65 (m, 2H), 2.29 (s, 3H), 2.45-2.15 (m, 2H), 2.10-1.70 (m, 4H)

and

2-{(1-methylpiperidin-4-yloxy)[3-(2-[1,2,3]triazol-1-yl-ethylsulfanyl)phenyl]methyl}-benzothiazole

$^1$H NMR: 7.95 (d, 1H), 7.87 (d, 1H), 7.86 (s, 1H), 7.61 (s, 1H), 7.56 (s, 1H), 7.51-7.25 (m, 5H), 5.90 (s, 1H), 4.52 (t,

2H), 3.75-3.60 (m, 1H), 3.39 (t, 2H), 2.82-2.65 (m, 2H), 2.31 (s, 3H), 2.35-2.15 (m, 2H), 2.08-1.70 (m, 4H).

240B

Methanesulfonic acid 2-{3-[benzothiazol-2-yl(1-methylpiperidin-4-yloxy)methyl]phenylsulfanyl}ethyl ester To a solution of 2-{3-[benzothiazol-2-yl(1-methyl piperidin-4-yloxy)-methyl]phenylsulfanyl}ethanol (400 mg) in dichloromethane (5 mL) is added methanesulfonylchloride (1.25 molar equivalent) in dichloromethane (1.5 mL) and triethylamine (1.5 molar equivalent). The reaction mixture is stirred overnight at room temperature. Volatiles are removed under reduced pressure to dryness. Water is added and the aqueous phase is extracted by diethylether. The organic phase is dried over magnesium sulfate and concentrated. The residue is purified by column chromatography (dichloromethane/methanol from 98/2) to afford methanesulfonic acid 2-{3-[benzothiazol-2-yl(1-methylpiperidin-4-yloxy)methyl]phenylsulfanyl}ethyl ester that will be used without further purification.

Example 245

2-[(1-methylpiperidin-4-yloxy)(3-vinyl-phenyl)methyl]-1H-benzimidazole

In a screw-cap tube are placed 2-[(3-bromophenyl)(1-methylpiperidin-4-yloxy)methyl]benzimidazole (200 mg), potassium vinyltrifluoroborate (72 mg), 1,1-bis(diphenylphosphino)ferrocene-dichloro-palladium (7.5 mg) and n-propanol (3 mL). The reaction mixture is degassed and purged with argon. The mixture is heated at reflux for 48 h. Water and ammonia solution are added and the aqueous phase is extracted by ethyl acetate. The organic phase is dried over magnesium sulfate and concentrated. The residue is purified by column chromatography (gradient dichloromethane/methanol from 95/5 to 90/10 then dichloromethane/methanol/ammonia 90/10/0.1) to give 2-[(1-methylpiperidin-4-yloxy)(3-vinyl-phenyl)methyl]-1H-benzimidazole.

$^1$H NMR: 7.68-7.55 (m, 2H), 7.48 (s, 1H), 7.45-7.33 (m, 3H), 7.33-7.20 (m, 2H), 6.65 (dd, 1H), 5.83 (s, 1H), 5.75 (d, 1H), 5.26 (d, 1H), 3.88-3.75 (m, 1H), 3.28-3.10 (m, 2H), 3.05-2.75 (m, 2H), 2.63 (s, 3H), 2.30-1.95 (m, 4H)

Example 249

2-{3-[(1H-benzimidazol-2-yl)(1-methylpiperidin-4-yloxy)methyl]phenylsulfanyl}-ethylamine

249A

To a solution of N-tert-butoxycarbonyl-2-{3-[(1H-benzimidazol-2-yl)(1-methylpiperidin-4-yloxy)methyl]phenylsulfanyl}ethylamine in dichloromethane (2 mL) is added trifluoroacetic acid (0.5 ml) at room temperature. The mixture is stirred at room temperature for 24 h. Water is added and the mixture is basified by adding a solution of sodium hydroxide. The aqueous phase is extracted by ethyl acetate. The organic phase is washed by water, then dried over magnesium sulfate and concentrated. The residue is triturated in diisopropylether to give 2-{3-[(1H-benzimidazol-2-yl)(1-methylpiperidin-4-yloxy)methyl]phenylsulfanyl}ethylamine.

$^1$H NMR: 7.80-7.65 (m, 1H), 7.51 (s, 1H), 7.48-7.15 (m, 7H), 5.85 (s, 1H), 3.65-3.53 (m, 1H), 3.08-2.95 (m, 2H), 2.95-2.80 (m, 2H), 2.80-2.60 (m, 2H), 2.25 (s, 3H), 2.18-1.62 (m, 6H)

249B

N-tert-butoxycarbonyl-2-{3[(1H-benzimidazol-2-yl)(1-methylpiperidin-4-yloxy)methyl]phenylsulfanyl}ethylamine could be prepared using method described in example 150A.

Example 252

2-[(1-methylpiperidin-4-yloxy)-p-tolylmethyl]-1H-benzimidazole enantiomer A

A solution of 2-[(1-methylpiperidin-4-yloxy)-p-tolylmethyl]-1H-benzimidazole (10 mg/mL) in methanol containing diethylamine (0.1%) is injected (17×100 μL) onto an analytical Ceramospher chiral RU-1, 250×4.6 mm column. Elution is performed with a mixture of heptane/isopropanol (80/20) containing diethylamine (0.1%) at a flow of 1 mL/min. Products are detected at 220 nm.

The first enantiomer has a retention time of 10.4 min.

Collection affords 2-[(1-methylpiperidin-4-yloxy)-p-tolylmethyl]-1H-benzimidazole enantiomer A with a chromatographic enantiomeric purity of 90%.

Example 253

2-[(1-methylpiperidin-4-yloxy)-p-tolylmethyl]-1H-benzimidazole enantiomer B

The second enantiomer has a retention time of 13.7 min.

Collection affords 2-[(1-methylpiperidin-4-yloxy)-p-tolylmethyl]-1H-benzimidazole enantiomer B with a chromatographic enantiomeric purity of 90%.

Example 259

2-{3-[benzothiazol-2-yl(1-methylpiperidin-4-yloxy)methyl]phenylsulfanyl}-N-methylacetamide

259A

To a solution of methylamine hydrochloride (76 mg) in toluene (2 mL) is added a 2N solution of trimethylaluminum in toluene. The reaction mixture is heated at 60° C. for 1 hour. Then a solution of {3-[(benzothiazol-2-yl)(1-methylpiperidin-4-yloxy)-methyl]phenylsulfanyl}acetic acid methyl ester (50 mg) in toluene (1 mL) is added. The reaction mixture is heated at 60° C. for 24 hours. Water is added to the reaction mixture, pH is adjusted to 10 with a solution of sodium hydroxide, and the mixture is filtered on celite. The filtrate is extracted with ethyl acetate. The pooled organic extracts are dried over magnesium sulfate and concentrated under reduced pressure. The residue is purified by chromatography (toluene/acetone/triethylamine 80/20/0.2) to give 2-{3-[benzothiazol-2-yl(1-methylpiperidin-4-yloxy)methyl]phenylsulfanyl}-N-methylacetamide.

$^1$H NMR (DMSO-d$^6$): 8.12-7.97 (m, 2H), 7.89 (d, 1H), 7.52-7.22 (m, 6H), 5.90 (s, 1H), 3.60 (s, 2H), 3.59-3.45 (m, 1H), 2.62-2.40 (m, 5H), 2.03 (s, 3H), 2.03-1.82 (m, 4H), 1.82-1.45 (m, 4H)

259B

{3-[(benzothiazol-2-yl)(1-methylpiperidin-4-yloxy)methyl]phenylsulfanyl}acetic acid methyl ester can be obtained using method described in example 150.

Example 260

2-{(1-methylpiperidin-4-yloxy)[3-(2H-pyrazol-3-yl)phenyl]methyl}benzothiazole

260A

A solution of 2-((1-Methyl-piperidin-4-yloxy)-{3-[2-(2-trimethylsilanyl-ethoxymethyl)-2H-pyrazol-3-yl]-phenyl}-methylybenzothiazole (500 mg) in 5N hydrochloric acid (4 mL) is stirred overnight at room temperature. 30% sodium hydroxide solution is added to reach pH 10, and the reaction is diluted with water. The aqueous phase is extracted with ethyl acetate. The pooled organic extracts are dried over magnesium sulfate and concentrated under reduced pressure. The residue is purified by chromatography (gradient dichloromethane/methanol from 100/0 to 90/10) to afford 2-{(1-methylpiperidin-4-yloxy)[3-(2H-pyrazol-3-yl)phenyl]methyl}benzothiazole melting at 90° C.

260B 2-((1-Methyl-piperidin-4-yloxy)-{3-[2-(2-trimethylsilanyl-ethoxymethyl)-2H-pyrazol-3-yl]-phenyl}-methyl)-benzothiazole can be prepared according to the method described in example 53.

Example 264

{3-[benzothiazol-2-yl(1-methylpiperidin-4-yloxy)methyl]phenylsulfanyl}acetic acid hydrazide To a solution of {3-[(benzothiazol-2-yl)(1-methylpiperidin-4-yloxy)methyl]phenylsulfanyl}acetic acid methyl ester (30 mg) in absolute ethanol (1 mL) is added hydrazine hydrate (0.1 mL). The reaction mixture is heated at 80° C. for 18 hours. Solvent and volatiles are removed under reduced pressure. The residue is purified by chromatography (gradient dichloromethane/methanol from 95/5 to 80/20) to give {3-[benzothiazol-2-yl(1-methylpiperidin-4-yloxy)methyl]phenylsulfanyl}acetic acid hydrazide.

$^1$H NMR (DMSO-d$^6$): 10.30 and 10.15 (two singlets, 1H), 8.05 (d, 1H), 7.89 (d, 1H), 7.50-7.20 (m, 6H), 5.99 (s, 1H), 3.89 (d, 2H), 3.58-3.45 (m, 1H), 2.75-2.50 (m, 2H), 2.09 (s, 3H), 2.08-1.95 (m, 2H), 1.90-1.50 (m, 6H)

Example 268

2-(1-{3-[benzothiazol-2-yl(1-methylpiperidin-4-yloxy)methyl]phenylsulfanylmethyl}-cyclopropyl)ethanol

268A

To a solution of 1-{3-[benzothiazol-2-yl(1-methylpiperidin-4-yloxy)methyl]phenylsulfanylmethyl}cyclopropanecarboxylic acid methyl ester (56 mg) in tetrahydrofuran (5 mL) is added lithium aluminumhydride (25 mg) at 0° C. The reaction mixture is allowed to reach room temperature and ethyl acetate (2 mL) is added. After stirring for 5 minutes, a half-saturated aqueous solution of sodium carbonate (6 mL) is added. The aqueous phase is extracted with ethyl acetate. The pooled organic extracts are dried over magnesium sulfate and concentrated under reduced pressure. The residue is purified by chromatography (gradient dichloromethane/methanol/ammonia from 100/0/0 to 95/5/0.5) to afford 2-(1-{3-[benzothiazol-2-yl(1-methylpiperidin-4-yloxy)methyl]phenylsulfanylmethyl}cyclopropyl)ethanol.

$^1$H NMR: 7.97 (d, 1H), 7.87 (d, 1H), 7.56 (s, 1H), 7.52-7.22 (m, 5H), 5.86 (s, 1H), 3.72 (t, 2H), 3.72-3.58 (m, 1H), 2.98 (dd, 2H), 2.82-2.78 (m, 2H), 2.27 (s, 3H), 2.27-2.10 (m, 3H), 2.10-1.75 (m, 4H), 1.78 (t, 2H), 0.44 (m, 4H)

268B

1-{3-[benzothiazol-2-yl(1-methylpiperidin-4-yloxy)methyl]phenylsulfanylmethyl}-cyclopropanecarboxylic acid methyl ester can be obtained according to the method described in example 150.

Further examples can be prepared according to the above described general method:

| Example | Product |
|---|---|
| 257 | 2-(1-{3-[(1H-benzimidazol-2-yl)(1-methylpiperidin-4-yloxy)methyl]phenylsulfanylmethyl}-cyclopropyl)ethanol<br>$^1$H NMR: 10.0 (sl, 1H), 7.60 (s, 1H), 7.80-7.35 (m, 2H), 7.32-7.15 (m, 5H), 5.82 (s, 1H), 3.75 (t, 2H), 3.68-3.50 (m, 1H), 3.01 (dd, 2H), 2.90-2.70 (m, 2H), 2.30 (s, 3H), 2.27-2.10 (m, 2H), 2.10-1.75 (m, 5H), 1.67 (t, 2H), 0.45 (m, 4H) |

Example 275

1-(3-{3-[benzothiazol-2-yl(1-methylpiperidin-4-yloxy)methyl]phenyl}prop-2-ynyloxy)-propan-2-one, oxalate A screw-capped tube is charged with 2-[(3-iodophenyl)(1-methylpiperidin-4-yloxy)methyl]benzothiazole (example 41, 300 mg), copper(I) iodide (10 mg), tetrakis palladium (36 mg), triethylamine (0.33 mL), 1-methyl-2-pyrrolidinone (1.3 mL), and 1-prop-2-ynyloxypropan-2-one (109 mg). The tube is evacuated, filled with argon and sealed. After stirring at 80° C. for one night, the mixture is diluted with ethyl acetate and water and the aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.5 to 95/5/0.5). The base is converted into its oxalate salt in acetone to give 1-(3-{3-

[benzothiazol-2-yl(1-methylpiperidin-4-yloxy)methyl]phenyl}prop-2-ynyloxy)-propan-2-one, oxalate. TLC of the base (eluent: CH$_2$Cl$_2$/MeOH/NH$_4$OH 95/5/0.5): Rf=0.18.

Example 276

1-(3-{3-[benzothiazol-2-yl(1-methylpiperidin-4-yloxy)methyl]phenyl}prop-2-ynyloxy)-propan-2-ol, oxalate A solution of 1-(3-{3-[benzothiazol-2-yl(1-methylpiperidin-4-yloxy)methyl]phenyl}prop-2-ynyloxy)-propan-2-one (example 275, 140 mg) in methanol (20 mL) is treated with sodium borohydride (30 mg) at 0° C., stirred 1 h at 0° C. and 2 h at room temperature. The mixture is then diluted with water and extracted with ethyl acetate. The pooled organic extracts are dried over magnesium sulfate and concentrated under reduced pressure. Purification of the residue by chromatography (gradient dichloromethane/methanol/ammonia from 98/2/0.5 to 95/5/0.5) affords the pure base that is then converted into its oxalate salt in acetone to give 1-(3-{3-[benzothiazol-2-yl(1-methylpiperidin-4-yloxy)methyl]phenyl}prop-2-ynyloxy)-propan-2-ol, oxalate. TLC of the base (eluent: CH$_2$Cl$_2$/MeOH/NH$_4$OH 95/5/0.5): Rf=0.12.

Example 278

N-(2-{3-[(1H-benzimidazol-2-yl)(1-methylpiperidin-4-yloxy)methyl]phenylsulfanyl}ethyl)guanidine

278A

To a solution of 2-{3-[(1H-benzimidazol-2-yl)(1-methylpiperidin-4-yloxy)-methyl]phenylsulfanyl}ethylamine (130 mg) in acetonitrile (2 mL) is added N,N'-bis-Boc-guanylpyrazole (112 mg) and diisopropylethylamine (0.066 mL) at room temperature. The mixture is heated at 50° C. for 5 h. Water is added and the aqueous phase is extracted by ethyl acetate. The organic phase is dried over magnesium sulfate and concentrated. The residue is purified by chromatography (gradient dichloromethane/methanol/ammonia from 95/5/0 to 90/10/0 then 90/10/1).

The residue is then dissolved in 6N aqueous hydrochloric acid (1.5 mL) and the solution is stirred overnight at room temperature. The reaction mixture is neutralized to pH7 by adding dropwise 30% sodium hydroxide solution. The solvent is removed under reduced pressure and the residue is triturated with a (dichloromethane/methanol)(95/5) and filtered. The filtrate is evaporated under reduced pressure to give N-(2-{3-[(1H-benzimidazol-2-yl)(1-methylpiperidin-4-yloxy)methyl]phenylsulfanyl}ethyl)guanidine as the dihydrochloride salt.

m/z: [M+H]$^+$=439.0

278B

2-{3-[(1H-benzimidazol-2-yl)(1-methylpiperidin-4-yloxy)methyl]phenylsulfanyl}-ethylamine can be prepared as described in example 249.

Following compounds are prepared analogously:

| Example | Product |
|---|---|
| 394 | 4-{3-[(1H-benzimidazol-2-yl)(1-methylpiperidin-4-yloxy)methyl]phenyl}piperidine-1-carboxamidine hydrochloride |
| | $^1$H NMR (DMSO-d$^6$): 7.48-7.38 (m, 2H), 7.34 (s, 1H), 7.32-7.20 (m, 2H), 7.17-7.00 (m, 3H), 5.78 (s, 1H), 3.98 (sl, 1H), 3.92 (sl, 1H), 2.88-2.50 (m, 4H), 2.07 (s, 3H), 2.00-1.75 (m, 4H), 1.75-1.45 (m, 6H). |

Example 293

4-{3-[(1H-benzimidazol-2-yl)(1-methylpiperidin-4-yloxy)methyl]phenyl}butylamine, dichlorhydrate

293A

To a solution of 4-{3-[(1H-benzimidazol-2-yl)(1-methylpiperidin-4-yloxy)-methyl]phenyl}but-3-ynylamine (50 mg) in methanol (2.5 mL) is added platinum oxide (8 mg). The flask is purged with argon then put under one atmosphere of hydrogen. The reaction mixture is stirred overnight at room temperature then filtered on celite, cake washed with methanol. The solvent is removed under reduced pressure to give 4-{3-[(1H-benzimidazol-2-yl)(1-methylpiperidin-4-yloxy)methyl]phenyl}butylamine.

m/z: [M+H]$^+$=393.1; [M+Na]$^+$=415.2

293B

4-{3-[(1H-benzimidazol-2-yl)(1-methylpiperidin-4-yloxy)methyl]phenyl}but-3-ynylamine can be prepared according to general method in example 194.

Following compounds are prepared analogously:

| Example | Product |
|---|---|
| 238 | 4-{3-[benzothiazol-2-yl(1-methylpiperidin-4-yloxy)methyl]phenyl}butan-1-ol |
| | $^1$H NMR: 7.98 (d, 2H), 7.87 (d, 1H), 7.50-7.25 (m, 6H), 7.13 (d, 1H), 5.88 (s, 1H), 3.81-3.70 (m, 1H), 7.70-7.60 (m, 2H), 3.98-2.80 (m, 2H), 2.65 (t, 2H), 2.43 (s, 3H), 2.22-1.50 (m, 10H), 1.34 (t, 1H) |
| 396 | 2-{(1-methylpiperidin-4-yloxy)[3-(2-piperidin-4-yl-ethyl)phenyl]methyl}-1H-benzimidazole |

-continued

| Example | Product |
|---------|---------|
| | ¹H NMR: 7.65-7.50 (m, 2H), 7.35-7.15 (m, 5H), 7.03 (d, 1H), 5.85 (s, 1H), 3.75 (t, 2H), 3.65-3.50 (m, 1H), 3.45-3.30 (m, 2H), 2.90-2.65 (m, 4H), 2.58-2.45 (m, 2H), 2.28 (s, 3H), 2.28-2.10 (m, 2H), 2.10-1.65 (m, 5H), 1.65-1.35 (m, 4H) |

Following compounds are prepared according to the general methods:

| Example | Product | General methods | m/z |
|---------|---------|-----------------|-----|
| 98 | {3'-[benzothiazol-2-yl(1-methylpiperidin-4-yloxy)methyl]biphenyl-3-yl}acetonitrile, oxalate | 53 | [M + H]+ = 454.2 |
| 139 | 2-[(3'-fluorobiphenyl-3-yl)(1-methylpiperidin-4-yloxy)methyl]benzothiazole | 53 | [M + H]⁺ = 433.1 |
| 140 | 2-[(1-methylpiperidin-4-yloxy)(4'-trifluoromethylbiphenyl-3-yl)methyl]benzothiazole | 53 | [M + H]⁺ = 483.2 |
| 141 | 2-[(1-methylpiperidin-4-yloxy)(2',3',4'-trifluorobiphenyl-3-yl)methyl]benzothiazole | 53 | [M + H]⁺ = 468.6 |
| 143 | {3'-[benzothiazol-2-yl(1-methylpiperidin-4-yloxy)-methyl]biphenyl-4-yl}carbamic acid tert-butyl ester | 53 | [M + H]⁺ = 530.2 |
| 320 | N-(3-{3-[(1H-benzimidazol-2-yl)(1-methylpiperidin-4-yloxy)methyl]phenyl}propyl)guanidine, trihydrochloride | 278A, 249, 149A | [M + H]⁺ = 421.0 |
| 321 | N-(3-{3-[(1H-benzimidazol-2-yl)(1-methylpiperidin-4-yloxy)methyl]phenyl}propyl)guanidine, trihydrochloride | 278A, 249, 149A | [M + H]⁺ = 421.2 [M + Na]⁺ = 443.2 |
| 344 | 6-{3-[(1H-benzimidazol-2-yl)(1-methylpiperidin-4-yloxy)methyl]phenyl}hexylamine | 293, 194 | [M + H]⁺ = 421.2 |
| 346 | N-(6-{3-[(1H-benzimidazol-2-yl)(1-methylpiperidin-4-yloxy)methyl]phenyl}hex-5-ynyl)guanidine, hydrochloride | 278A, 249, 149A | [M + H]⁺ = 459.2 |
| 355 | N-(6-{3-[(1H-benzimidazol-2-yl)(1-methylpiperidin-4-yloxy)methyl]phenyl}hexyl)guanidine, trihydrochloride | 278A, 249, 149A | [M + H]⁺ = 463.2 [M + Na]⁺ = 485.3 |
| 358 | N-(5-{3-[(1H-benzimidazol-2-yl)(1-methylpiperidin-4-yloxy)methyl]phenyl}pent-4-ynyl)guanidine, hydrochloride | 278A, 249, 149A | [M + H]⁺ = 445.2 [M + Na]⁺ = 467.3 |
| 372 | N-(4-{3-[benzothiazol-2-yl(1-methylpiperidin-4-yloxy)methyl]phenyl}but-3-ynyl)guanidine, dihydrochloride | 278A, 249, 149A | [M + H]⁺ = 448.1 |
| 393 | N-(4-{3-[(1H-benzimidazol-2-yl)(1-methylpiperidin-4-yloxy)methyl]phenyl}but-3-ynyl)guanidine, hydrochloride | 278A, 249, 149A | [M + H]⁺ = 431.1 |
| 397 | N-(5-{3-[(1H-benzimidazol-2-yl)(1-methylpiperidin-4-yloxy)methyl]phenyl}pentyl)guanidine, hydrochloride | 278A, 249, 149A | [M + H]⁺ = 449.2 [M + Na]⁺ = 471.2 |
| 418 | N-(3-{3-[(1H-benzimidazol-2-yl)(1-methylpiperidin-4-yloxy)methyl]phenyl}prop-2-ynyl)guanidine, hydrochloride | 278A, 249, 149A | [M + H]⁺ = 417.1 |
| 426 | 3-{3-[(1H-benzimidazol-2-yl)(1-methylpiperidin-4-yloxy)methyl]phenylethynyl}azetidine-1-carboxamidine | 278A, 249, 149A | [M + H]⁺ = 443.1 [M + Na]⁺ = 465.4 |

Example 298

(2-{3-[(1H-benzimidazol-2-yl)(1-methylpiperidin-4-yloxy)methyl]phenylsulfanyl}-ethyl)urea

298A

To a solution of 2-{3-[(1H-benzimidazol-2-yl)(1-methylpiperidin-4-yloxy)-methyl]phenylsulfanyl}ethylamine (50 mg) in ethanol (0.5 mL) in a screw-cap tube is added potassium cyanate (15 mg). The reaction mixture is heated at 80° C. for 24 hours. The mixture is diluted water, basified to pH 9 by adding of an aqueous saturated solution of sodium carbonate and extracted with ethyl acetate. The pooled organic extracts are dried over magnesium sulfate and concentrated under reduced pressure. The residue is purified by chromatography (gradient dichloromethane/methanol/ammonia from 95/5/0.5 to 90/10/1) to afford (2-{3-[(1H-benzimidazol-2-yl)(1-methylpiperidin-4-yloxy)methyl]phenylsulfanyl}ethyl)urea melting at 136° C.

298B

2-{3-[(1H-benzimidazol-2-yl)(1-methylpiperidin-4-yloxy)methyl]phenylsulfanyl}-ethylamine can be prepared according to the method described in example 249.

Following compounds are prepared analogously:

| Example | Product |
|---------|---------|
| 299 | (2-{3-[(1H-benzimidazol-2-yl)(1-methylpiperidin-4-yloxy)methyl]phenyl-sulfanyl}ethyl)(4,5-dihydrothiazol-2-yl)amine |
| | ¹H NMR (DMSO-d⁶): 12.37 (sl, 1H), 7.53-7.38 (m, 3H), 7.27-6.95 (m, 5H), 5.80 (s, 1H), 3.80 (t, 2H), 3.45-3.00 (m, 7H), 2.65-2.50 (m, 2H), 2.07 (s, 3H), 2.00-1.75 (m, 4H), 1.65-1.45 (m, 2H) |
| 317 | (2-{3-[(1H-benzimidazol-2-yl)(1-methylpiperidin-4-yloxy)methyl]-phenylsulfanyl}ethyl)(4,5-dihydro-1H-imidazol-2-yl)amine |
| | ¹H NMR (DMSO-d⁶): 12.90 (sl, 1H), 10.80 and 10.40 (sl, 1H), 8.58-8.42 (m, 1H), 7.53-7.38 (m, 3H), 7.27-6.95 (m, 5H), 5.93 (s, 1H), 3.80 (t, 2H), 3.45-3.00 (m, 7H), 2.65-2.50 (m, 2H), 2.07 (s, 3H), 2.00-1.75 (m, 4H), 1.65-1.45 (m, 2H) |

-continued

| Example | Product |
|---|---|
| 347 | 1-(2-{3-[(1H-benzimidazol-2-yl)(1-methylpiperidin-4-yloxy)methyl]phenylsulfanyl}ethyl)-3-isopropylthiourea
$^1$H NMR: 10.43 (sl, 1H), 7.72-7.50 (m, 3H), 7.35-7.20 (m, 5H), 6.45-6.15 (m, 2H), 5.83 (s, 1H), 4.05-3.50 (m, 4H), 3.45-3.05 (m, 2H), 3.00-2.75 (m, 2H), 2.39 (s, 3H), 2.20-1.75 (m, 4H), 1.22 (m, 1H), 1.02 (d, 3H), 0.91 (d, 3H) |

Example 305

5-{3-[benzothiazol-2-yl(1-methylpiperidin-4-yloxy)methyl]phenylsulfanyl}pentylamine, oxalate

305A 2-(5-{3-[(1H-Benzimidazol-2-yl)(1-methylpiperidin-4-yloxy)methyl]phenylsulfanyl}-pentyl)isoindole-1,3-dione (200 mg) is dissolved in ethanol (1 mL) and hydrazine hydrate (0.1 mL) is added. The reaction mixture is stirred at room temperature overnight. The mixture is evaporated to dryness and the residue is purified by chromatography (gradient dichloromethane/methanol/ammonia from 98/2/0.2 to 90/10/1). The residue is added to oxalic acid (1 equivalent) in acetone (0.5 ml), and the precipitate is filtered and dry to give 5-{3-[benzothiazol-2-yl(1-methylpiperidin-4-yloxy)methyl]phenylsulfanyl}pentylamine, oxalate melting at 201° C.

305B 2-(5-{3-[(1H-Benzimidazol-2-yl)(1-methylpiperidin-4-yloxy)methyl]phenylsulfanyl}-pentyl)isoindole-1,3-dione A screw-cap tube is charged with 2-[(3-bromophenyl)(1-methylpiperidin-4-yloxy)methyl]benzothiazole (200 mg), palladium bis(dibenzylideneacetone) (14 mg), Xantphos (14 mg), thioacetic acid 5-(1,3-dioxo-1,3-dihydro-isoindol-2-yl)-pentyl ester (209 mg), diisopropylethylamine (170 µL), potassium phosphate (105 mg), water (0.05 mL) and 1,4-dioxane (2 mL). The tube is evacuated, filled with argon and sealed. After stirring at 120° C. for 48 h, solvents are removed under reduced pressure. The residual solution is basified by adding a solution of saturated sodium carbonate to pH 10 and the aqueous phase is extracted with ethyl acetate. The pooled organic extracts are dried over magnesium sulfate and concentrated under reduced pressure. The residue is purified by chromatography (gradient dichloromethane/methanol/ammonia from 100/0/0 to 95/5/0.5) to give 2-(5-{3-[(1H-benzimidazol-2-yl)(1-methylpiperidin-4-yloxy)methyl]phenylsulfanylpentyl)isoindole-1,3-dione that is used without further purification.

Example 307

N-tert-butoxycarbonyl-N'-(4-{3-[(1H-benzimidazol-2-yl)(1-methylpiperidin-4-yloxy)methyl]phenyl}but-3-ynyl)guanidine

307A

To a solution of 4-{3-[(1H-benzimidazol-2-yl)(1-methylpiperidin-4-yloxy)-methyl]phenyl}but-3-ynylamine (290 mg) in acetonitrile (4.5 mL) is added N,N'-bis-Boc-guanylpyrazole (255 mg) and diisopropylethylamine (0.15 mL) at room temperature. The mixture is heated at 50° C. overnight. Water is added and the aqueous phase is extracted by ethyl acetate. The organic phase is dried over magnesium sulfate and concentrated. The residue is purified by chromatography (gradient dichloromethane/methanol/ammonia from 95/5/0 to 90/10/0 then 90/10/1).

A part of the residue (100 mg) is then dissolved in 1,2-dichloroethane (2 mL); phenol (149 mg) and chlorotrimethylsilane (0.2 mL) are added and the solution is heated at 50° C. for 20 h. Solvent and volatiles are removed under reduced pressure. The residue is purified by chromatography (gradient dichloromethane/methanol/ammonia from 95/5/0 to 90/10/0 then 90/10/1) to give N-tert-butoxycarbonyl-N'-(4-{3-[(1H-benzimidazol-2-yl)(1-methylpiperidin-4-yloxy)methyl]phenyl}but-3-ynyl)guanidine.

$^1$H NMR: 7.54 (sl, 2H), 7.32 (s, 1H), 7.27-7.19 (m, 6H), 5.67 (s, 1H), 3.70-3.52 (m, 1H), 3.52-3.32 (m, 2H), 2.85-2.65 (m, 2H), 2.61 (t, 2H), 2.24 (s, 3H), 2.20-2.02 (m, 2H), 1.92-1.50 (m, 4H), 1.49 (t, 9H)

307B

4-{3-[(1H-benzimidazol-2-yl)(1-methylpiperidin-4-yloxy)methyl]phenyl}but-3-ynylamine can be prepared as described in example 194A.

Example 315

2-{(1-methylpiperidin-4-yloxy)[3-(4-[1,2,3]triazol-2-yl-butoxy)phenyl]methyl}-benzothiazole, oxalate

315A

60% in oil sodium hydride (20 mg) is washed with pentane and diluted with anhydrous N,N-dimethylformamide (5 mL). 1H-1,2,3-triazole is then added. After stirring at room temperature for 15 min, the mixture is treated with 2[[3-(4-chloro-butoxy)phenyl]-(1-methyl-piperidin-4-yloxy)methyl]benzothiazole (223 mg) and warmed at 60° C. for one night. The mixture is then poured into water and extracted with diethylether. The pooled organic extracts are dried over magnesium sulfate and concentrated under reduced pressure. Purification of the residue by chromatography (gradient dichloromethane/methanol/ammonia from 98/2/0.5 to 90/10/0.5) affords the pure base that is then converted into its oxalate salt in acetone to give 2-{(1-methylpiperidin-4-yloxy)[3-(4-[1,2,3]triazol-2-yl-butoxy)phenyl]methyl}benzothiazole, oxalate. TLC of the base (eluent: CH$_2$Cl$_2$/MeOH/NH$_4$OH 90/10/0.5): Rf=0.30.

315B

2[[3-(4-Chlorobutoxy)phenyl](1-methylpiperidin-4-yloxy)methyl]benzothiazole can be prepared according to the described general methods 272A and 1B.

Example 316

2-{(1-methylpiperidin-4-yloxy)[3-(4-[1,2,4]triazol-1-yl-butoxy)phenyl]methyl}-benzothiazole, oxalate 2-{(1-methylpiperidin-4-yloxy)[3-(4-[1,2,4]triazol-1-yl-butoxy)phenyl]methyl}-benzothiazole, oxalate can be prepared according general procedure 315A. TLC of the base (eluent: CH$_2$Cl$_2$/MeOH/NH$_4$OH 90/10/0.5): Rf=0.22.

Example 318

N-(2-{3-[(1H-benzimidazol-2-yl)(1-methylpiperidin-4-yloxy)methyl]phenylsulfanyl}-ethyl)-N'-cyanoguanidine

318A

To a solution of 2-{3-[(1H-benzimidazol-2-yl)(1-methylpiperidin-4-yloxy)-methyl]phenylsulfanyl}ethylamine (50 mg) in isopropanol (1 mL) in a screw-cap tube is added diphenylcyanocarbonimidate (30 mg). The reaction mixture is stirred at room temperature overnight. Solvent is removed under reduced pressure and the residual solid is dried. This solid is dissolved in ethanol (2 mL) saturated with ammonia gas in a screw-cap tube. The tube is sealed and the reaction mixture is heated to 80° C. for 2 hours. The solvent and volatiles are removed under reduced pressure. The residue is purified by chromatography (gradient dichloromethane/methanol/ammonia from 98/2/0.2 to 90/10/1) to afford N-(2-{3-[(1H-benzimidazol-2-yl)(1-methylpiperidin-4-yloxy)methyl]phenylsulfanyl}ethyl)-N'-cyanoguanidine melting at 65° C.

318B

2-{3-[(1H-benzimidazol-2-yl)(1-methylpiperidin-4-yloxy)methyl]phenylsulfanyl}-ethylamine can be prepared according to the method described in example 249.

Example 338

2-{(1-methylpiperidin-4-yloxy)[3-(1,2,3,6-tetrahydro-pyridin-4-yl)phenyl]methyl}-1H-benzimidazole

338A

To a solution of 4-{3-[(1H-benzimidazol-2-yl)(1-methylpiperidin-4-yloxy)methyl]phenyl}-3,6-dihydro-2H-pyridine-1-carboxylic acid tert-butyl ester (407 mg) in dichloromethane (2 mL) is added trifluoroacetic acid (1 mL). After 2 hours at room temperature, volatiles are removed under reduced pressure. The mixture is diluted with water, basified to pH 10 by adding of an aqueous saturated solution of sodium carbonate and extracted with ethyl acetate. The pooled organic extracts are dried over magnesium sulfate and concentrated under reduced pressure. The residue is purified by chromatography (gradient dichloromethane/methanol/ammonia from 100/0/0 to 85/15/1.5) to afford 2-{(1-methylpiperidin-4-yloxy)[3-(1,2,3,6-tetrahydro-pyridin-4-yl)phenyl]methyl}-1H-benzimidazole.

$^1$H NMR: 10.0 (sl, 1H), 7.60 (s, 1H), 7.70-7.45 (m, 2H), 7.40-7.20 (m, 5H), 6.06 (s, 1H), 5.87 (s, 1H), 3.50 (t, 2H), 3.65-3.45 (m, 1H), 3.08 (d, 2H), 2.80-2.75 (m, 2H), 2.60-2.22 (m, 3H), 2.26 (s, 3H), 2.20-1.65 (m, 6H)

338A

4-{3-[(1H-Benzimidazol-2-yl)(1-methylpiperidin-4-yloxy)methyl]phenyl}-3,6-dihydro-2H-pyridine-1-carboxylic acid tert-butyl ester can be prepared according to the procedure described in example 53.

Example 359

4-{3-[benzothiazol-2-yl(1-methylpiperidin-4-yloxy)methyl]phenylsulfanyl}butylamine, oxalate

359A (4-{3-[Benzothiazol-2-yl-(1-methyl-piperidin-4-yloxy)-methyl]-phenylsulfanyl}-butyl)-carbamic acid tert-butyl ester (140 mg) is dissolved in dichloromethane (1 mL) and trifluoroacetic acid (0.4 mL) is added. The reaction mixture is stirred at room temperature for 1 hour. The mixture is evaporated to dryness. The residue is basified by adding a solution of saturated sodium carbonate to pH 10 and the aqueous phase is extracted with dichloromethane. The pooled organic extracts are dried over magnesium sulfate and concentrated under reduced pressure. The residue is purified by chromatography (gradient dichloromethane/methanol/ammonia from 100/0/0 to 90/10/1). The residue is added to oxalic acid (1 equivalent) in acetone (0.5 ml), and the precipitate is filtered and dry to give 4-{3-[benzothiazol-2-yl(1-methylpiperidin-4-yloxy)methyl]phenylsulfanyl}butylamine, oxalate melting at 108° C.

359B (4-{3-[(1H-Benzimidazol-2-yl)(1-methylpiperidin-4-yloxy)methyl]phenylsulfanyl}butyl)-carbamic acid tert-butyl ester A screw-cap tube is charged with 2-[(3-bromophenyl)(1-methylpiperidin-4-yloxy)methyl]benzothiazole (200 mg), palladium bis(dibenzylideneacetone) (14 mg), Xantphos (14 mg), thioacetic acid S-(4-tert-butoxycarbonylaminobutyl) ester (180 mg), potassium phosphate (200 mg), water (0.01 mL) and 1,4-dioxane (2 mL). The tube is evacuated, filled with argon and sealed. After stirring at 120° C. for 48 h, solvents are removed under reduced pressure. The residue is basified by adding a solution of saturated sodium carbonate to pH 10 and the aqueous phase is extracted with ethyl acetate. The pooled organic extracts are dried over magnesium sulfate and concentrated under reduced pressure. The residue is purified by chromatography (gradient dichloromethane/methanol/ammonia from 100/0/0 to 95/5/0.5) to give (4-{3-[(1H-benzimidazol-2-yl)-(1-methylpiperidin-4-yloxy)methyl]phenylsulfanyl}butyl)carbamic acid tert-butyl ester that is used without further purification.

Example 376

2-[(1-methylpiperidin-4-yloxy)(3-piperidin-4-ylethynyl-phenyl)methyl]-1H-benzimidazole

376A

To a solution of 4-{3-[(1H-benzimidazol-2-yl)(1-methylpiperidin-4-yloxy)-methyl]phenylethynyl}piperidine-1-carboxylic acid tert-butyl ester (160 mg) in 1,2-dichloroethane (10 mL) are added phenol (940 mg) and chlorotrimethylsilane (1.26 mL). The reaction mixture is heated to 100° C. for 30 minutes. Volatiles are removed under reduced pressure. The residue is purified by chromatography (gradient dichloromethane/methanol/ammonia from 100/0/0 to 85/15/1.5) to afford 2-[(1-methylpiperidin-4-yloxy)(3-piperidin-4-ylethynyl-phenyl)methyl]-1H-benzimidazole.

¹H NMR: 9.80 (sl, 1H), 7.50 (s, 1H), 7.80-7.50 (m, 2H), 7.45-7.20 (m, 5H), 5.84 (s, 1H), 3.65-3.50 (m, 1H), 3.25-3.10 (m, 2H), 2.90-2.35 (m, 7H), 2.25 (s, 3H), 2.20-1.65 (m, 9H)

376B

4-{3-[(1H-Benzimidazol-2-yl)(1-methylpiperidin-4-yloxy)methyl]phenylethynyl}-piperidine-1-carboxylic acid tert-butyl ester can be prepared according to the procedure described in example 189.

Example 384

5-{3-[benzothiazol-2-yl(1-methylpiperidin-4-yloxy)methyl]phenyl}pent-4-en-1-ol

384A

To a solution of Acetic acid 5-{3-[benzothiazol-2-yl(1-methylpiperidin-4-yloxy)methyl]phenyl}pent-4-enyl ester (150 mg) in a mixture of water (1 mL), 1,4-dioxane (1 mL) and methanol (1 mL) is added 1N sodium hydroxide solution (0.6 mL). The reaction mixture is stirred at room temperature for 2 hours. After neutralization to pH 7 with addition of 1N hydrochloric acid, the reaction mixture is extracted with dichloromethane. The pooled organic extracts are dried over magnesium sulfate and concentrated under reduced pressure. The residue is purified by chromatography (gradient dichloromethane/methanol/ammonia from 95/5/0.5 to 90/10/1) to afford 5-{3-[benzothiazol-2-yl(1-methylpiperidin-4-yloxy)methyl]phenyl}pent-4-en-1-ol.

¹H NMR: 7.97 (d, 1H), 7.86 (dd, 1H), 7.53-7.24 (m, 6H), 6.32 (dd, 1H), 6.27 (dd, 1H) 5.30 (s, 1H), 3.71 (t, 2H), 3.77-3.60 (m, 1H), 3.00-2.90 (m, 2H), 2.80-2.68 (m, 2H), 2.30 (s, 3H), 2.37-2.15 (m, 4H), 2.20-1.55 (m, 5H)

384B

Acetic acid 5-{3-[benzothiazol-2-yl-(1-methyl-piperidin-4-yloxy)-methyl]-phenyl}-pent-4-enyl ester can be prepared according to the method described in example 53.

Following examples can be prepared analogously:

| Example | Product | General methods |
|---|---|---|
| 156 | 2-[[3-(2,5-difluorobenzyloxy)phenyl](1-methylpiperidin-4-yloxy)methyl]benzothiazole, oxalate | 1A, 168B |
| | ¹H NMR of the base (CDCl₃): 7.96 (d, 1H), 7.85 (d, 1H), 6.90-7.50 (m, 9H), 5.86 (s, 1H), 5.10 (s, 2H), 3.83 (m, 1H), 2.97 (m, 2H), 2.83 (m, 2H), 2.61 (s, 3H), 2.20 (m, 2H), 1.93 (m, 2H). | |
| 263 | 2-{3-[benzothiazol-2-yl(1-methylpiperidin-4-yloxy)methyl]phenylsulfanyl}acetamide | 259A, 150 |
| | ¹H NMR (DMSO-d⁶): 8.03 (s, 1H), 7.86 (d, 1H), 7.61 (sl, 1H), 7.48-7.18 (m, 6H), 7.11 (sl, 1H), 5.95 (s, 1H), 3.57 (s, 2H), 3.57-3.45 (m, 1H), 2.62-2.40 (m, 2H), 2.07 (s, 3H), 2.07-1.72 (m, 4H), 1.70-1.35 (m, 2H) | |
| 309 | N-tert-butoxycarbonyl-N'-(4-{3-[(1H-benzimidazol-2-yl)(1-methylpiperidin-4-yloxy)methyl]phenyl}butyl)guanidine | 307A, 194A |
| | ¹H NMR: 7.65-7.55 (m, 2H), 7.38 (s, 1H), 7.30-7.15 (m, 4H), 7.01 (d, 1H), 5.79 (s, 1H), 3.70-3.55 (m, 1H), 3.18-2.95 (m, 4H), 2.55-2.30 (m, 4H), 2.44 (s, 3H), 2.15-1.95 (m, 2H), 1.95-1.70 (m, 2H), 1.65-1.50 (m, 4H), 1.49 (s, 9H) | |
| 313 | N-tert-butoxycarbonyl-N'-(3-{3-[(1H-benzimidazol-2-yl)(1-methylpiperidin-4-yloxy)methyl]phenyl}propyl)amine | 307A, 194A |
| | ¹H NMR: 7.68-7.58 (m, 2H), 7.52 (s, 1H), 7.30-7.15 (m, 4H), 7.01 (d, 1H), 5.79 (s, 1H), 3.85-3.70 (m, 1H), 3.45-3.18 (m, 4H), 2.78-2.50 (m, 4H), 2.62 (s, 3H), 2.20-1.60 (m, 6H), 1.46 (s, 9H) | |
| 335 | N-tert-butoxycarbonyl-N'-(-{3-[(1H-benzimidazol-2-yl)(1-methylpiperidin-4-yloxy)methyl]phenyl}pentyl)guanidine, hydrochloride | 307A, 194A |
| | ¹H NMR: 8.95 (sl, 1H), 7.68-7.58 (m, 2H), 7.41 (s, 1H), 7.32-7.15 (m, 4H), 7.01 (d, 1H), 5.78 (s, 1H), 3.92-3.82 (m, 1H), 3.70-3.25 (m, 4H), 3.20-2.70 (m, 4H), 2.81 (s, 3H), 2.52 (t, 2H), 2.30-1.85 (m, 4H), 1.70-1.50 (m, 2H), 1.49 (s, 9H), 1.35-1.20 (m, 2H) | |
| 336 | N-tert-butoxycarbonyl-N'-(3-{3-[(1H-benzimidazol-2-yl)(1-methylpiperidin-4-yloxy)methyl]phenyl}prop-2-ynyl)guanidine | 307A, 194A |
| | ¹H NMR: 7.68-7.58 (m, 2H), 7.41 (s, 1H), 7.32-7.15 (m, 4H), 7.01 (d, 1H), 5.78 (s, 1H), 4.27 (s, 2H), 3.92-3.82 (m, 1H), 3.10-2.80 (m, 2H), 2.37 (s, 3H), 2.65-2.30 (m, 2H), 2.15-1.90 (m, 2H), 1.90-1.65 (m, 2H), 1.46 (s, 9H) | |
| 345 | N-tert-butoxycarbonyl-N'-(6-{3-[(1H-benzimidazol-2-yl)(1-methylpiperidin-4-yloxy)methyl]phenyl}hex-5-ynyl)guanidine | 307A, 194A |
| | ¹H NMR (DMSO-d⁶): 10.91 (sl, 1H), 8.71 (sl, 1H), 7.65-7.48 (m, 2H), 7.48-7.15 (m, 6H), 6.00 (s, 1H), 3.80 (s, 1H), 3.00-2.82 (m, 2H), 2.75 (m, 2H), 3.63 (m, 2H), 2.43 (s, 3H), 2.15-2.05 (m, 2H), 1.98-1.75 (m, 2H), 1.75-1.55 (m, 6H), 1.44 (s, 9H) | |
| 351 | 4-(3-{3-[benzothiazol-2-yl(1-methylpiperidin-4-yloxy)methyl]phenoxy}propyl)piperazine-1-carboxylic acid tert-butyl ester, oxalate | 370A, 272A and 1B |
| | ¹H NMR of the base (CDCl₃): 7.96 (d, 1H), 7.82 (d, 1H), 7.50-7.20 (m, 3H), 7.07 (m, 2H), 6.79 (d, 1H), 5.86 (s, 1H), 3.97 (t, 2H), 3.60 (m, 1H), 3.40 (m, 4H), 2.67 (m, 2H), 2.48 (t, 2H), 2.36 (m, 4H), 2.23 (s, 3H), 2.13 (m, 2H), 2.00-1.70 (m, 6H), 1.44 (s, 9H) | |
| 353 | 4-{3-[(1H-benzimidazol-2-yl)(1-methylpiperidin-4-yloxy)methyl]phenyl}-3,6-dihydro-2H-pyridine-1-carboxamidine, hydrochloride | 376A, 189 |
| | ¹H NMR (DMSO-d⁶): 10.7 and 10.45 (sl, 1H), 7.68-7.50 (m, 1H), 7.50-7.35 (m, 2H), 7.28-7.10 (m, 5H), 6.20 (s, 1H), 5.95 (d, 1H), 4.06 (s, 2H), 3.79 (s, 1H), 3.58 (t, 2H), 3.05-2.80 (m, 2H), 2.74 (s, 2H), 2.65-2.50 (m, 2H), 2.48 (s, 3H), 2.25-2.05 (m, 2H), 2.00-1.75 (m, 2H) | |
| 357 | N-tert-butoxycarbonyl-N'-(5-{3-[(1H-benzimidazol-2-yl)(1-methylpiperidin-4-yloxy)methyl]phenyl}pent-4-ynyl)guanidine | 307A, 194A |
| | ¹H NMR (DMSO-d⁶): 12.55 (sl, 1H), 8.67 (sl, 1H), 7.68-7.40 (m, 2H), 7.40-7.25 (m, 3H), 7.20-7.05 (m, 3H), 5.86 (s, 1H), 3.78-3.50 (m, 1H), 3.10-2.80 (m, 2H), 2.75-2.50 (m, 4H), 2.46 (s, 3H), 2.20-1.65 (m, 8H), 1.42 (s, 9H) | |

| Example | Product | General methods |
|---|---|---|
| 383 | 2-{(1-methylpiperidin-4-yloxy)[3-(pyrrolidin-3-yloxy)phenyl]methyl}benzothiazole, dioxalate | 258 |

$^1$H NMR of the base (CDCl$_3$): 7.98 (d, 1H), 7.87 (d, 1H), 7.46-7.20 (m, 3H), 7.09 (m, 2H), 6.80 (d, 1H), 5.89 (s, 1H), 4.83 (m, 1H), 3.63 (m, 2H), 3.17 (m, 1H), 3.00-2.85 (m, 2H), 2.68 (m, 2H), 2.28 (s, 3H), 2.20-1.70 (m, 8H)

| | | |
|---|---|---|
| 390 | 5-{3-[(benzothiazol-2-yl)(1-methylpiperidin-4-yloxy)methyl]phenyl}pent-4-en-1-ol | 384A, 53 |

$^1$H NMR: 7.97 (d, 1H), 7.86 (dd, 1H), 7.54 (s, 1H), 7.50-7.25 (m, 4H), 7.19 (d, 1H), 6.43 (dd, 1H), 6.27 (dd, 1H) 5.94 (s, 1H), 5.73 (dd, 1H), 3.77-3.60 (m, 3H), 2.87-2.70 (m, 2H), 2.55-2.20 (m, 2H), 2.33 (s, 3H), 2.20-1.65 (m, 7H)

Example 385

3-amino-4-(2-{3-[(1H-benzimidazol-2-yl)(1-methylpiperidin-4-yloxy)methyl]phenylsulfanyl}ethylamino)-cyclobut-3-ene-1,2-dione

385A

To a solution of 2-{3-[(1H-benzimidazol-2-yl)(1-methylpiperidin-4-yloxy)-methyl]phenylsulfanyl}ethylamine (150 mg) in diethylether (10 mL) is added L). The reaction mixture is stirred at □3,4-diethoxy-3-cyclobutene-1,2-dione (56 room temperature for 1 hour. The mixture is filtered, washed with diethylether and dried. The residue is dissolved in ethanol (2 mL) saturated with ammonia gas in a screw-capped tube. The tube is sealed and the reaction mixture is heated to 80° C. for 2 hours. The solvent and volatiles are removed under reduced pressure. The residue is purified by chromatography (gradient dichloromethane/methanol/ammonia from 98/2/0.2 to 90/10/1) to afford 3-amino-4-(2-{3-[(1H-benzimidazol-2-yl)(1-methylpiperidin-4-yloxy)methyl]phenylsulfanyl}ethylamino)-cyclobut-3-ene-1,2-dione melting at 161° C.

385B

2-{3-[(1H-benzimidazol-2-yl)(1-methylpiperidin-4-yloxy)methyl]phenylsulfanyl}-ethylamine can be prepared according to the method described in example 249.

Example 386

[[3-(6-aminohex-1-ynyl)phenyl](1H-benzimidazol-2-yl)methyl](1-methylpiperidin-4-yl)amine

386A

A solution of 2-(5-{3-[(1H-benzimidazol-2-yl)(1-methylpiperidin-4-ylamino)-methyl]phenyl}pent-4-ynyl)isoindole-1,3-dione (230 mg) and hydrazine hydrate (120 µL) in ethanol (3 mL) is stirred a room temperature for one night. The mixture is then concentrated under reduced pressure and the residue purified by chromatography (dichloromethane/methanol/ammonia from 90/10/0.5) to afford [[3-(6-aminohex-1-ynyl)phenyl](1H-benzimidazol-2-yl)methyl](1-methylpiperidin-4-yl)amine melting at 79° C.

386B 2-(5-{3-[(1H-Benzimidazol-2-yl)(1-methylpiperidin-4-ylamino)methyl]phenyl}pent-4-ynyl)isoindole-1,3-dione can be prepared according to general procedure 275 starting from [(1H-benzimidazol-2-yl)(3-iodo-phenyl)methyl](1-methylpiperidin-4-yl)amine.

Example 398

2-[{3-[3-(3H-imidazol-4-yl)propylsulfanyl]phenyl}(1-methylpiperidin-4-yloxy)methyl]-1H-benzimidazole

398A

To a solution of 2-((1-methylpiperidin-4-yloxy){3-[3-(1-trityl-1H-imidazol-4-yl)propylsulfanyl]phenyl}methyl)-1H-benzimidazole (200 mg) in 1,2-dichloroethane (7 mL) are added phenol (270 mg) and chlorotrimethylsilane (0.37 mL). The reaction mixture is heated at reflux overnight. Volatiles are removed under reduced pressure and the residue is purified by chromatography (gradient dichloromethane/methanol/ammonia from 98/2/0.2 to 90/10/1) to give 2-[{3-[3-(3H-imidazol-4-yl)propylsulfanyl]phenyl}(1-methylpiperidin-4-yloxy)methyl]-1H-benzimidazole.

$^1$H NMR: 7.72-7.40 (m, 4H), 7.25-7.15 (m, 5H), 6.82 (s, 1H), 5.84 (s, 1H), 3.60-3.45 (m, 1H), 3.00-2.65 (m, 6H), 2.25 (s, 3H), 2.15-1.60 (m, 8H)

398B 2-((1-Methylpiperidin-4-yloxy){3-[3-(1-trityl-1H-imidazol-4-yl)propylsulfanyl]phenyl}-methyl)-1H-benzimidazole can be prepared according to the method described in example 359A.

Example 401

N-acetyl-N'-(2-{3-[(1H-benzimidazol-2-yl)(1-methylpiperidin-4-yloxy)methyl]phenylsulfanyl}ethyl)guanidine

401A

To a solution of N-(2-{3-[(1H-benzimidazol-2-yl)(1-methylpiperidin-4-yloxy)-methyl]phenylsulfanyl}ethyl)guanidine.dihydrochloride (100 mg) in dry acetonitrile (1 mL) is added acetic anhydride (64 mg) et 4-dimethylaminopyridine (51 mg). After 24 hours at room temperature, solvent and volatiles are removed under reduced pressure. The residue is purified by chromatography (toluene/acetone/triethylamine 50/50/1 then gradient dichloromethane/methanol/ammonia from 95/5/0.5 to 90/10/1) to give N-acetyl-N'-(2-{3-[(1H-benzimidazol-2-yl)(1-methylpiperidin-4-yloxy)methyl]phenylsulfanyl}ethyl)guanidine.

$^1$H NMR (DMSO-d$^6$): 12.40 (sl, 1H), 7.55-7.40 (m, 1H), 7.40-7.20 (m, 3H), 7.20-7.05 (m, 4H), 5.81 (s, 1H), 3.50-3.05 (m, 3H), 2.65-2.55 (m, 2H), 2.46 (s, 3H), 2.07 (s, 3H), 2.02-1.72 (m, 4H), 1.68-1.45 (m, 4H).

401B

N-(2-{3-[(1H-benzimidazol-2-yl)(1-methylpiperidin-4-yloxy)methyl]phenylsulfanyl}-ethyl)guanidine can be obtained according to the method described in example 278.

Example 403

1-{3-[benzothiazol-2-yl(1-methylpiperidin-4-yloxy) methyl]phenyl}azetidin-3-ol, oxalate A screw-capped tube is charged with 2-[(3-iodophenyl)(1-methylpiperidin-4-yloxy)methyl]benzothiazole (example 41, 150 mg), copper(I) iodide (15 mg), deanol (1 mL), potassium carbonate (306 mg), azetidin-3-ol, hydrochloride (88 mg). The tube is evacuated, filled with argon and sealed. After stirring at 60° C. for 100 h, the mixture is diluted with dichloromethane, water and ammonia. After decantation, the aqueous phase is extracted with dichloromethane. The pooled organic extracts are dried over magnesium sulfate and concentrated under reduced pressure. The residue is purified by chromatography (gradient dichloromethane/methanol/ammonia from 95/5/0.5 to 90/10/0.5). The base is converted into its oxalate salt in acetone to give 1-{3-[benzothiazol-2-yl(1-methylpiperidin-4-yloxy)methyl]phenyl}azetidin-3-ol, oxalate melting at 117° C.

Example 411

1-{3-[benzothiazol-2-yl(1-methylpiperidin-4-yloxy) methyl]phenyl}piperidin-4-ol, oxalate A solution of acetic acid 1-{3-[benzothiazol-2-yl(1-methylpiperidin-4-yloxy)methyl]phenyl}piperidin-4-yl ester (example 413, 100 mg) and aqueous 1N sodium hydroxide in methanol (1 mL) is stirred at room temperature for 30 min. The mixture is diluted water and extracted with dichloromethane. The pooled organic extracts are dried over magnesium sulfate and concentrated under reduced pressure. The residue is purified by chromatography (gradient dichloromethane/methanol/ammonia from 95/5/0.5 to 90/10/0.5). The base is converted into its oxalate salt in acetone to give 1-{3-[benzothiazol-2-yl(1-methylpiperidin-4-yloxy)methyl] phenyl}piperidin-4-ol, oxalate melting at 110° C.

Example 412

2-[{3-[2-(1H-imidazol-4-yl)ethyl]phenyl}(1-methylpiperidin-4-yloxy)methyl]-1H-benzimidazole

412A

To a solution of 2-{(1-methylpiperidin-4-yloxy)[3-(1-trityl-1H-imidazol-4-ylethynyl)phenyl]methyl}-1H-benzimidazole (260 mg) in 1,2-dichloroethane (7 mL) are added phenol (374 mg) and chlorotrimethylsilane (0.51 mL). The reaction mixture is heated at reflux overnight. Volatiles are removed under reduced pressure and the residue is purified by chromatography (gradient dichloromethane/methanol from 95/5 to 90/10 then dichloromethane/methanol/ammonia 90/10/1).

The residue is then dissolved in methanol (3 mL) and palladium on charcoal (8 mg). is added. The flask is purged with argon then put under one atmosphere of hydrogen. The reaction mixture is stirred overnight at room temperature then filtered on celite, cake washed with methanol. The solvent is removed under reduced pressure to give 2-[{3-[2-(1H-imidazol-4-yl)ethyl]phenyl}(1-methylpiperidin-4-yloxy)methyl]-1H-benzimidazole.

$^1$H NMR (methanol-d$^4$): 7.65-7.55 (m, 3H), 7.40-7.15 (m, 6H), 6.70 (s, 1H), 5.85 (s, 1H), 3.80-3.70 (m, 1H), 3.28-3.10 (m, 2H), 3.05-2.75 (m, 6H), 2.64 (s, 3H), 2.15-1.85 (m, 4H).

412B

2-{(1-Methylpiperidin-4-yloxy)[3-(1-trityl-1H-imidazol-4-ylethynyl)phenyl]methyl}-1H-benzimidazole can be prepared according to the method described in example 189.

Example 416

2-{(1-methylpiperidin-4-yloxy)[3-(5-[1,2,3]triazol-2-yl-pent-1-ynyl)phenyl]methyl}-1H-benzimidazole

416A

To a solution of 1,2,3-triazole (66 mg) in DMF (0.6 mL) is added sodium hydride (25 mg). After gas evolution ceased, 2[[3-(5-chloropent-1-ynyl)phenyl](1-methylpiperidin-4-yloxy)methyl]-1H-benzimidazole (50 mg) and a catalytic quantity of n-tetrabutylammonium iodide are added. After stirring overnight at room temperature, the solvent is removed under reduced pressure to dryness. The residue is purified by chromatography (dichloromethane/methanol/ammonia 90/10/1) to afford 2-{(1-methylpiperidin-4-yloxy)[3-(5-[1,2,3]triazol-2-yl-pent-1-ynyl)phenyl]methyl}-1H-benzimidazole.

$^1$H NMR: 9.43 (sl, 1H), 7.83-7.68 (m, 1H), 7.60 (s, 2H), 7.52 (s, 1H), 7.50-7.20 (m, 6H), 5.84 (s, 1H), 4.61 (t, 2H), 3.68-3.50 (m, 1H), 2.88-2.70 (m, 2H), 2.46 (t, 2H), 2.30 (s, 3H), 2.38-2.10 (m, 4H), 2.10-1.65 (m, 6H).

416B

2[[3-(5-Chloropent-1-ynyl)phenyl](1-methylpiperidin-4-yloxy)methyl]-1H-benzimidazole can be obtained according to the synthetic method described in example 189.

Following compounds are prepared analogously:

| Example | Product |
|---|---|
| 417 | 2-{(1-methylpiperidin-4-yloxy)[3-(5-[1,2,3]triazol-1-ylpent-1-ynyl)phenyl]methyl}-1H-benzimidazole |
| | $^1$H NMR: 9.77 (sl, 1H), 7.83-7.68 (m, 1H), 7.70 (s, 1H), 7.61 (s, 1H), 7.52 (s, 1H), 7.50-7.35 (m, 2H), 7.35-7.20 (m, 4H), 5.84 (s, 1H), 4.58 (t, 2H), 3.70-3.55 (m, 1H), 2.90-2.75 (m, 2H), 2.47 (t, 2H), 2.32 (s, 3H), 2.40-2.15 (m, 4H), 2.15-1.70 (m, 4H) |
| 409 | 2-[[3-(5-imidazol-1-ylpent-1-ynyl)phenyl](1-methylpiperidin-4-yloxy)methyl]-1H-benzimidazole |
| | $^1$H NMR: 10.90 (sl, 1H), 7.85-7.68 (m, 1H), 7.69 (s, 1H), 7.60 (s, 1H), 7.37 (dt, 1H), 7.40-7.20 (m, 5H), 7.11 (s, 1H), 7.00 (s, 1H), 5.84 (s, 1H), 4.17 (t, 2H), 3.68-3.50 (m, 1H), 2.88-2.70 (m, 2H), 2.48 (t, 2H), 2.30 (s, 3H), 2.29-1.90 (m, 4H), 1.90-1.50 (m, 4H) |

Example 421

5-{3-[(1H-benzimidazol-2-yl)(1-methylpiperidin-4-yloxy)methyl]phenyl}pent-4-enylamine

421A

To a solution of 5-{3-[(1H-benzimidazol-2-yl)(1-methylpiperidin-4-yloxy)-methyl]phenyl}pent-4-ynylamine (200 mg) in N,N-dimethylformamide (1.8 mL) are added water (0.05 mL), potassium hydroxide (42 mg) and palladium(II) acetate. The tube is evacuated, filled with argon and sealed. After stirring at 120° C. for 24 h, the mixture is filtered on celite, and the solvent removed under reduced pressure.diluted with water and the aqueous phase is extracted with ethyl acetate. The pooled organic extracts are washed with water, dried over magnesium sulfate and concentrated under reduced pressure. The residue is purified by chromatography (gradient dichloromethane/methanol/ammonia from 90/10/0 to 90/10/1) to give 5-{3-[(1H-benzimidazol-2-yl)(1-methylpiperidin-4-yloxy)methyl]phenyl}pent-4-enylamine.

$^1$H NMR: 7.75-7.58 (m, 2H), 7.42-7.10 (m, 6H), 6.45 (d, 1H), 5.90 (s, 1H), 5.72 (dt, 1H), 3.68-3.50 (m, 1H), 2.95-2.85 (m, 2H), 2.85-2.65 (m, 2H), 2.50-2.35 (m, 2H), 2.25 (s, 3H), 2.25-1.65 (m, 8H),

421B

5-{3-[(1H-benzimidazol-2-yl)(1-methylpiperidin-4-yloxy)methyl]phenyl}pent-4-ynylamine can be synthesized according to the procedure described in example 194.

Example 423

1-{3-[benzothiazol-2-yl(1-methylpiperidin-4-yloxy)methyl]phenyl}pyrrolidin-3-ylamine, dioxalate

423A

A solution of crude (1-{3-[benzothiazol-2-yl-(1-methylpiperidin-4-yloxy)methyl]phenyl}pyrrolidin-3-yl)carbamic acid tert-butyl ester (289 mg) in dichloromethane (3 mL) and trifluoroacetic acid (2.5 mL) is stirred at room temperature for one night. The mixture is concentrated under reduced pressure, diluted with ethyl acetate, washed with aqueous 1N sodium hydroxide, dried over magnesium sulfate and concentrated under reduced pressure. The residue is purified by chromatography (gradient dichloromethane/methanol/ammonia from 95/5/0.5 to 80/20/0.5). The base is converted into its dioxalate salt in acetone to give 1-{3-[benzothiazol-2-yl(1-methylpiperidin-4-yloxy)methyl]phenyl}pyrrolidin-3-ylamine, dioxalate melting at 145° C.

423B

A screw-capped tube is charged with 2-[(3-iodophenyl)(1-methylpiperidin-4-yloxy)methyl]benzothiazole (example 41, 200 mg), copper(I) iodide (7 mg), 2-isobutyrylcyclohexanone (25 mg), cesium carbonate (280 mg), 3-(Boc-amino)pyrrolidine (160 mg) and anhydrous N,N-dimethylformamide (1 mL). The tube is evacuated, filled with argon and sealed. After stirring at 55° C. for 4 days, the mixture is diluted with ethyl acetate, water and ammonia. After decantation, the aqueous phase is extracted with ethyl acetate. The pooled organic extracts are dried over magnesium sulfate and concentrated under reduced pressure. The residue is purified by chromatography (gradient dichloromethane/methanol/ammonia from 98/2/0.5 to 95/5/0.5). to afford (1-{3-[benzothiazol-2-yl-(1-methylpiperidin-4-yloxy)methyl]phenyl}pyrrolidin-3-yl)carbamic acid tert-butyl ester.

Example 432

432A 2-(5-{3-[(1H-Benzimidazol-2-yl)(1-methylpiperidin-4-yloxy)methyl]phenylsulfanyl}-pentyl)isoindole-1,3-dione To a solution of 5-{3-[(1H-benzimidazol-2-yl)(1-methylpiperidin-4-yloxy)methyl]phenylsulfanyl}pentan-1-ol (35 mg) in tetrahydrofuran are added triphenylphosphine (31 mg) and phthalimide (18 mg). The reaction mixture is cooled to 0° C. and diethyl azodicarboxylate (31 µL) is added. The reaction mixture is stirred at 0° C. for 30 minute. The mixture is evaporated to dryness and the residue is purified by chromatography (gradient dichloromethane/methanol/ammonia from 98/2/0.2 to 95/5/0.5) to give 2-(5-{3-[(1H-benzimidazol-2-yl)(1-methylpiperidin-4-yloxy)methyl]phenylsulfanyl}pentyl)isoindole-1,3-dione (example 305B).

432B

5-{3-[(1H-Benzimidazol-2-yl)(1-methylpiperidin-4-yloxy)methyl]phenylsulfanyl}pentan-1-ol can be prepared according to the method described in example 150.

Preparation of Starting Materials

1-Bromo-3-(2-fluoroethoxy)benzene is prepared from 3-bromophenol and 2-fluoroethanol using standard Mitsunobu protocol.

1-Bromo-3-(3-fluoropropoxy)benzene is prepared from 3-bromophenol and 3-fluoropropanol using standard Mitsunobu protocol.

2-[2-(3-Bromophenoxy)ethyl]-6,6-dimethylbicyclo[3.1.1]hept-2-ene is prepared from 3-bromophenol and 2-(6,6-dimethylbicyclo[3.1.1]hept-2-en-2-yl)ethanol using standard Mitsunobu protocol.

Example 436

N-(2-aminoethyl)-2-{3-[(1H-benzimidazol-2-yl)(1-methylpiperidin-4-yloxy)methyl]phenylsulfanyl}acetamide The compound is made from example 154 and ethylenediamine using method described in example 264. $^1$H NMR: 7.68-7.48 (m, 2H), 7.35-6.95 (m, 8H), 5.89 (s, 1H), 3.83-3.50 (m, 3H), 3.50-3.35 (m, 1H), 3.25-3.10 (m, 1H), 2.82-2.62 (m, 3H), 2.59-2.45 (m, 1H), 2.26 (s, 3H), 2.24-1.95 (m, 3H), 1.92-1.50 (m, 5H).

Example 437

N-(2-{3-[(5-fluoro-1H-benzimidazol-2-yl)(1-methylpiperidin-4-yloxy)methyl]phenylsulfanyl}ethyl)guanidine

437A

To a solution of 2-{3-[(5-fluoro-1H-benzimidazol-2-yl)(1-methylpiperidin-4-yloxy)methyl]phenylsulfanyl}ethylamine (example 437B, 230 mg) in acetonitrile (15 mL) is added is added N,N'-bis-Boc-guanylpyrazole (172 mg) and diisopropylethylamine (1 equivalent) at room temperature. The mixture is stirred at room temperature for 3 h. The solvent and volatiles are removed under reduced pressure. The residue is purified by chromatography on silica gel (gradient dichloromethane/methanol from 100/0 to 95/5). The residue is then dissolved in 5N aqueous hydrochloric acid (8 mL) and the solution is stirred overnight at room temperature. The solvent and volatiles are removed under reduced pressure and the residue is triturated with diethyl ether and filtered to afford N-(2-{3-[(5-fluoro-1H-benzimidazol-2-yl)(1-methylpiperidin-4-yloxy)methyl]phenylsulfanyl}ethyl) guanidine trihydrochloride as a white crystalline solid melting at 170° C.

437B

2-{3-[(5-Fluoro-1H-benzimidazol-2-yl)(1-methylpiperidin-4-yloxy)methyl]phenylsulfanyl}ethylamine To a solution of (2-{3-[(5-fluoro-1H-benzimidazol-2-yl)(1-methylpiperidin-4-yloxy)methyl]phenylsulfanyl}ethyl) carbamic acid tert-butyl ester (example 437C, 386 mg) in chloroform (10 mL) are added phenol (750 mg) and chlorotrimethylsilane (814 mg). The mixture is heated at reflux for 2 h. The solvent and volatiles are removed under reduced pressure. The residue is basified by adding a solution of 1N sodium hydroxide. The aqueous phase is extracted by ethyl acetate. The organic phase is washed by water, then dried over magnesium sulfate and concentrated. The residue is purified by chromatography on silica gel (gradient dichloromethane/methanol/ammonia from 100/0/0 to 90/10/1) to give 2-{3-[(5-fluoro-1H-benzimidazol-2-yl)(1-methylpiperidin-4-yloxy)methyl]phenylsulfanyl}ethylamine.
$^1$H NMR: 8.5-9 (sl, 1H), 7.53 (s, 1H), 7.32-7.20 (m, 5H), 7.08-6.98 (m, 1H), 5.84 (s, 1H), 3.70-3.50 (m, 1H), 3.08-3.04 (m, 2H), 3.00-2.88 (m, 2H), 2.87-2.70 (m, 2H), 2.33 (s, 3H), 2.30-1.60 (m, 8H).

437C (2-{3-[(5-Fluoro-1H-benzimidazol-2-yl)(1-methylpiperidin-4-yloxy)methyl]phenylsulfanyl}ethyl)carbamic acid tert-butyl ester A screw-capped tube is charged with 2-[(3-bromophenyl)(1-methylpiperidin-4-yloxy)methyl]-5-fluoro-1H-benzimidazole (example 437D, 418 mg), palladium bis(dibenzylideneacetone) (30 mg), Xantphos (30 mg), (2-mercaptoethyl) carbamic acid tert-butyl ester (1 equivalent), diisopropylethylamine (180 µL) and 1,4-dioxane (6 mL). The tube is evacuated, filled with argon and sealed. After stirring at 120° C. overnight, the mixture is diluted with ethyl acetate and water and the aqueous phase is extracted with ethyl acetate. The pooled organic extracts are dried over magnesium sulfate and concentrated under reduced pressure. The residue is purified by chromatography (gradient dichloromethane/methanol from 98/2 to 95/5) to afford (2-{3-[(5-fluoro-1H-benzimidazol-2-yl)(1-methylpiperidin-4-yloxy)methyl]phenylsulfanyl}ethyl)carbamic acid tert-butyl ester.
$^1$H NMR: 11.07 (sl, 1H), 7.69-7.59 (m, 1H), 7.39-7.36 (m, 1H), 7.30-7.15 (m, 2H), 7.04-6.91 (m, 2H), 5.83 (s, 1H), 5.30 (sl, 1H), 4.20 (s, 2H), 3.65-3.40 (m, 3H), 3.30-3.05 (m, 2H), 2.80-2.65 (m, 2H), 2.27 (s, 3H), 2.25-1.75 (m, 6H), 1.55 (s, 9H).

437D

2-[(3-Bromophenyl)(1-methylpiperidin-4-yloxy)methyl]-5-fluoro-1H-benzimidazole

A mixture of (3-bromophenyl)(5-fluoro-1H-benzimidazol-2-yl)methanol (example 437E, 3.30 g) and 1-methylpiperidin-4-ol (2.37 g) in methanesulfonic acid (10 mL) is heated overnight in a sealed tube at a temperature close to 140° C. The mixture is cooled back to room temperature, poured into water which is then made alkaline with concentrated sodium hydroxide solution. The aqueous phase is extracted with ethyl acetate. Pooled extracts are dried over magnesium sulfate, concentrated under reduced pressure. The residue is purified by column chromatography over silica gel (gradient dichloromethane/methanol/ammonia from 100/0/0 to 90/10/1) to afford 2-[(3-bromophenyl)(1-methylpiperidin-4-yloxy)methyl]-5-fluoro-1H-benzimidazole. $^1$H NMR: 9.92 (sl, 1H), 7.60 (s, 1H), 7.55-6.85 (m, 6H), 5.80 (s, 1H), 3.65-3.50 (m, 1H), 2.80-2.65 (m, 2H), 2.34 (s, 3H), 2.15-1.65 (m, 6H).

437E (3-Bromophenyl)(5-fluoro-1H-benzimidazol-2-yl)methanol could be synthesized using the method described in example 449B.

Example 438

438A

5-{3-[(5-fluoro-1H-benzimidazol-2-yl)(1-methylpiperidin-4-yloxy)methyl]phenyl}pent-4-ynylamine oxalate A solution of 2-(5-{3-[(5-fluoro-1H-benzimidazol-2-yl)(1-methylpiperidin-4-yloxy)methyl]phenyl}pent-4-ynyl) isoindole-1,3-dione (example 438B, 170 mg) and hydrazine hydrate (200 µL) in ethanol (2.5 mL) is stirred a room temperature overnight. Water is added and the aqueous phase is extracted by diethyl ether. The pooled organic extracts are dried over magnesium sulfate and concentrated under reduced pressure. The residue is purified by chromatography (dichloromethane/methanol/ammonia from 95/5/0.5 to 90/10/1)) to afford the free base. One equivalent of oxalic acid in acetone is added to the free base to afford 5-{3-[(5-fluoro-1H-benzimidazol-2-yl)(1-methylpiperidin-4-yloxy)methyl]phenyl}pent-4-ynylamine oxalate as a white crystalline solid melting at 150° C.

438B 2-(5-{3-[(5-Fluoro-1H-benzimidazol-2-yl)(1-methylpiperidin-4-yloxy)methyl]phenyl}pent-4-ynyl) isoindole-1,3-dione A screw-capped tube is charged with 2-[(3-bromophenyl)(1-methylpiperidin-4-yloxy)methyl]-5-fluoro-1H-benzimidazole (example 437D, 418 mg), PEPPSi-sono catalyst (19 mg), copper (I) iodide (38 mg), N-pentynylphthalimide (428 mg), diethylamine (880 µL) and N,N-dimethylformamide (1.5 mL). The tube is evacuated, filled with argon and sealed. The reaction mixture is stirred at 80° C. overnight. As the reaction is not completed, PEPPSi-sono catalyst (10 mg) and N-pentynylphthalimide (214 mg) are added, and the reaction mixture is heated at 80° C. for 24 h. The mixture is diluted with water and the aqueous phase is extracted with ethyl acetate. The pooled organic extracts are washed with water, dried over magnesium sulfate and concentrated under reduced pressure. The residue is purified by chromatography (gradient dichloromethane/methanol from 98/2/to 90/10) to give 2-(5-{3-[(5-fluoro-1H-benzimidazol-2-yl)(1-methylpiperidin-4-yloxy)methyl]phenyl}pent-4-ynyl)isoindole-1,3-dione. $^1$H NMR: 9.65 (sl, 1H), 7.84-7.65 (m, 4H), 7.54 (s, 1H), 7.48-6.95 (m, 4H), 5.84 (s, 1H), 3.90 (t, 2H, J=6.9 Hz), 3.65-3.50 (m, 1H), 2.85-2.70 (m, 2H), 2.52 (t, 2H, J=7.0 Hz), 2.32 (s, 3H), 2.28-1.50 (m, 8H).

| Example | Product | General methods |
|---|---|---|
| 439 | 6-{3-[(5-fluoro-1H-benzimidazol-2-yl)(1-methylpiperidin-4-yloxy)methyl]phenyl}hex-5-ynylamine oxalate<br>mp = 146° C. | 438 |
| 440 | 4-{3-[(5-fluoro-1H-benzimidazol-2-yl)(1-methylpiperidin-4-yloxy)methyl]phenyl-sulfanyl}butylamine oxalate<br>mp = 160° C. | 432, 150 |
| 441 | N-(3-{3-[(1H-benzimidazol-2-yl)(1-methylpiperidin-4-yloxy)methyl]phenyl-sulfanyl}propyl)guanidine, dihydrochloride<br>mp = 318° C. | 278, 432, 150 |

Example 443

1-{3-[benzothiazol-2-yl(1-methylpiperidin-4-yloxy)methyl]-phenyl}pyrrolidin-3-one, oxalate To a solution of oxalyl chloride (317 µL) in dichloromethane (8 mL) at −78° C. is added DMSO (517 µL). After 15 min, a solution of 1-{3-[benzothiazol-2-yl(1-methylpiperidin-4-yloxy)methyl]phenyl}pyrrolidin-3-ol (example 406, 958 mg) in dichloromethane (18 mL) is slowly added at the same temperature. After 45 min triethylamine (2 mL) is added and the mixture allowed to warm to room temperature. After hydrolysis with aqueous saturated ammonium chloride, the organic phase is dried over magnesium sulfate and concentrated under reduced pressure. Purification of the residue by chromatography over silica gel(dichloromethane/methanol/ammonia 98/2/0.5) affords the pure base that is then converted into its oxalate salt in acetone to give 1-{3-[benzothiazol-2-yl(1-methylpiperidin-4-yloxy)methyl]phenyl}pyrrolidin-3-one, oxalate melting at 105° C.

| Example | Product | General methods |
|---|---|---|
| 444 | N-(4-{3-[(1H-benzimidazol-2-yl)(1-methylpiperidin-4-yloxy)methyl]phenylsulfanyl}butyl)guanidine, dihydrochloride<br>¹H NMR: (methanol-d₄): 7.65-7.50 (m, 2H), 7.45 (s, 1H), 7.40-7.15 (m, 5H), 5.84 (s, 1H), 3.70-3.55 (m, 1H), 3.10 (t, 2H, J = 6.6 Hz), 3.00-2.80 (m, 4H), 2.5-2.30 (m, 5H), 2.08-1.75 (m, 4H), 1.70-1.55 (m, 4H). | 278, 432, 150 |
| 445 | 5-{3-[(1H-benzimidazol-2-yl)(1-methylpiperidin-4-yloxy)methyl]phenylsulfanyl}pentan-1-ol<br>¹H NMR (methanol-d₄): 9.90 (sl, 1H), 7.75-7.70 (m, 1H), 7.42-7.35 (m, 2H), 7.32-7.15 (m, 5H), 5.84 (s, 1H), 3.70-3.48 (m, 3H), 2.89 (t, 2H, J = 6.6 Hz), 2.80-2.62 (m, 2H), 2.24 (s, 3H), 2.15-1.42 (m, 12H). | 359B |
| 446 | N-(2-{3-[(1H-benzimidazol-2-yl)(1-methylpiperidin-4-yloxy)methyl]phenylsulfanyl}ethyl)-N-(2,2-dimethylpropionyl)guanidine<br>¹H NMR: 12.34 (sl; 1H), 7.51 (d, 1H, J = 6.75 Hz), 7.48-7.40 (m, 2H), 7.30-7.20 (m, 3H), 7.20-7.05 (m, 2H), 6.65 (sl, 1H), 5.81 (s, 1H), 3.50-3.25 (m, 3H), 3.18-3.05 (m, 2H), 2.07 (m, 3H), 2.00-1.75 (m, 4H), 1.65-1.45 (m, 2H), 1.00 (s, 9H). | 401 |
| 447 | 2-[(1-methylpiperidin-4-yloxy)(4-nitrophenyl)methyl]-1H-benzimidazole<br>mp = 90° C. | 165C, B, 210, 165D |

Example 448

2-{(1-methylpiperidin-4-yloxy)[3-(pyridin-3-yloxy)phenyl]methyl}benzothiazole, oxalate A screw-capped tube is charged with 2-[(3-iodophenyl)(1-methylpiperidin-4-yloxy)methyl]benzothiazole (example 441, 500 mg), copper(I) iodide (9 mg), 2,2,6,6-tetramethylheptane-3,5-dione (37 mg), cesium carbonate (701 mg), 3-hydroxypyridine (125 mg), powdered 4A molecular sieves (200 mg) and anhydrous N,N-dimethylformamide (1 mL). The tube is evacuated, filled with argon and sealed. After stirring at 95° C. for 2 days, the mixture is diluted with ethyl acetate, water and ammonia. After decantation, the aqueous phase is extracted with ethyl acetate. The pooled organic extracts are dried over magnesium sulfate and concentrated under reduced pressure. The residue is purified by chromatography over silica gel (gradient dichloromethane/methanol/ammonia from 98/2/0.5 to 95/5/0.5). to afford the pure base that is then converted into its oxalate salt in acetone to give 2-{(1-methylpiperidin-4-yloxy)[3-(pyridin-3-yloxy)phenyl]methyl}benzothiazole, oxalate melting at 78° C.

Example 449

2-[(3-bromophenyl)(1-methylpyrrolidin-3-ylmethoxy)methyl]-5-fluoro-1H-benzimidazole, oxalate

449A

2-[(3-bromophenyl)(1-methylpyrrolidin-3-ylmethoxy)methyl]-5-fluoro-1H-benzimidazole is prepared from 3-bromophenyl(5-fluoro-1H-benzimidazol-2-yl)methanol and pyrrolidin-3-ylmethanol according to general procedures 165C and 272A. Conversion into its oxalate salt in acetone gives 2-[(3-bromophenyl)(1-methylpyrrolidin-3-ylmethoxy)methyl]-5-fluoro-1H-benzimidazole, oxalate melting at 70° C.

449B

A mixture of (3-bromophenyl)hydroxyacetic acid (3.7 g) and 4-fluoro-ortho-phenylenediamine (2 g) in 5N aqueous hydrochloric solution (3.2 mL) is heated under reflux for 15 h and cooled back to room temperature. The mixture is basified with concentrated sodium hydroxide and extracted with ethyl acetate. The organic phase is then dried over magnesium sulfate and concentrated under reduced pressure. The residue is purified by chromatography over silica gel (gradient dichloromethane/methanol/ammonia from 98/2/0.5 to 90/10/0.5) to afford the pure 3-bromophenyl(5-fluoro-1H-benzimidazol-2-yl)methanol.

Example 455

4-[(1H-benzimidazol-2-yl)(1-methylpiperidin-4-yloxy)methyl]aniline

To a solution of 2-[(1-methylpiperidin-4-yloxy)(4-nitrophenyl)methyl]-1H-benzimidazole (example 447, 200 mg) in methanol (5 mL) and a solution of 5N hydrochloric acid in isopropanol (0.2 mL) is added 10% palladium on carbon (50 mg). The flask is evacuated and filled with hydrogen (balloon) and stirred overnight at room temperature. The reaction mixture is filtered on celite and the solvents are evaporated under reduced pressure to dryness. The residual solid is triturated twice with diethyl ether and the solid is filtered and dry to afford 4-[(1H-benzimidazol-2-yl)(1-methylpiperidin-4-yloxy)methyl]aniline hydrochloride as a cream-colored solid melting at 185° C.

The following example is made using the same method:

| Example | Product | mp |
|---------|---------|-----|
| 456 | 4-[(1H-benzimidazol-2-yl)(piperidin-4-yloxy)methyl]aniline, hydrochloride | 190° C. |

The following example are made using the method of example 436

| Example | Product |
|---------|---------|
| 459 | N-(2-amino-ethyl)-2-{3-[(5-fluoro-1H-benzimidazol-2-yl)(1-methylpiperidin-4-yloxy)methyl]phenylsulfanyl}acetamide |

$^1$H NMR: 7.70-7.52 (m, 2H), 7.50-6.90 (m, 7H), 5.85 (s, 1H), 4.75 (s, 2H), 3.85-3.45 (m, 3H), 3.45-3.30 (m, 1H), 3.25-3.05 (m, 1H), 2.80-2.60 (m, 3H), 2.57-2.42 (m, 1H), 2.25 (s, 3H), 2.20-1.95 (m, 3H), 1.90-1.55 (m, 3H).

Example 460

1-{3-[benzothiazol-2-yl(1-methylpiperidin-4-yloxy)methyl]phenyl}-3-trifluoromethylpyrrolidin-3-ol, oxalate A solution of 1-{3-[benzothiazol-2-yl(1-methylpiperidin-4-yloxy)methyl]phenyl}pyrrolidin-3-one (example 443, 170 mg) in tetrahydrofuran (3 mL) is treated with cesium fluoride (612 mg) and trifluoromethyltrimethylsilane (595 μL). After stirring for 2 h, the mixture is hydrolyzed with 1N aqueous hydrochloric acid for one night. The reaction mixture is then concentrated under reduced pressure and the residue purified by chromatography over silica gel (dichloromethane/methanol/ammonia 98/2/0.5) to afford the pure base that is then converted into its oxalate salt in acetone to give 1-{3-[benzothiazol-2-yl(1-methylpiperidin-4-yloxy)methyl]phenyl}-3-trifluoromethylpyrrolidin-3-ol, oxalate. 1H NMR of the base (CDCl3): 7.96 (d, 1H), 7.86 (d, 1H), 7.45-7.20 (m, 3H), 6.91 (d, 1H), 6.73 (s, 1H), 6.51 (d, 1H), 5.85 (s, 1H), 3.77-3.30 (m, 5H), 2.69 (m, 2H), 2.36 (m, 1H), 2.25 (s, 3H), 2.20-1.70 (m, 7H).

Example 468

2-[[3-(4,5-dihydro-1H-imidazol-2-ylmethylsulfanyl)phenyl](1-methylpiperidin-4-yloxy)methyl]-1H-benzimidazole To a solution of triphenylphosphine oxide (2.2 mmoles) in 4 mL CH$_2$Cl$_2$ cooled at 0° C. is added dropwise trifluoromethanesulfonyl anhydride (310 mg, 1.1 mmoles). The reaction mixture is stirred at 0° C. for 30 minutes, then a solution of N-(2-aminoethyl)-2-{3-[(1H-benzimidazol-2-yl)(1-methylpiperidin-4-yloxy)methyl]phenylsulfanyl}acetamide (Example 436) (250 mg, 0.55 mmole) in 2 mL CH$_2$Cl$_2$ is added dropwise. The reaction mixture is allowed to reach room temperature and stirred for 1.5 h. The organic phase is washed with 1N sodium hydroxide solution, then dried over magnesium sulfate and concentrated. The residue is purified by chromatography on silica gel (gradient dichloromethane/methanol/ammonia from 100/0/0 to 80/20/2). The residue is then dissolved in acetone and one equivalent of oxalic acid is added. Acetone is removed under reduced pressure to afford 2-[[3-(4,5-dihydro-1H-imidazol-2-ylmethylsulfanyl)phenyl](1-methylpiperidin-4-yloxy)methyl]-1H-benzimidazole melting at 62° C. (déc.); MS, [M+H]$^+$=436.1.

The following example is made using the same method

| Example | Product | mp |
|---------|---------|-----|
| 463 | 2-[[3-(4,5-dihydro-1H-imidazol-2-ylmethylsulfanyl)phenyl](1-methylpiperidin-4-yloxy)methyl]-5-fluoro-1H-benzimidazole | 80° C. |

Example 469

2-[(3-bromophenyl)(1-methylpiperidin-4-yloxy)methyl]-5,6-difluoro-1H-benzimidazole

469A

2-[(3-bromophenyl)(1-methylpiperidin-4-yloxy)methyl]-5,6-difluoro-1H-benzimidazole is prepared from 3-bromophenyl(5,6-difluoro-1H-benzimidazol-2-yl)methanol according to general procedure 272A, solid melting at 70° C.

469B

A mixture of (3-bromophenyl)hydroxyacetic acid (809 mg) and 4,5-difluoro-ortho-phenylenediamine (500 mg) in 5N aqueous hydrochloric solution (2 mL) is heated under reflux for 15 h and cooled back to room temperature. The mixture is basified with concentrated sodium hydroxide and extracted with ethyl acetate. The organic phase is then dried over magnesium sulfate and concentrated under reduced pressure. The residue is purified by trituration in dichloromethane to afford the pure 3-bromophenyl(5,6-difluoro-1H-benzimidazol-2-yl)methanol.

Example 472

2-[(3-iodophenyl)(1-methylpiperidin-4-yloxy)methyl]-1-methyl-1H-benzimidazole, dioxalate A solution of 2-[(3-iodophenyl)(1-methylpiperidin-4-yloxy)methyl]-1H-benzimidazole (example 51, 260 mg) in anhydrous acetonitrile (10 mL) is treated with 60% sodium hydride (47 mg) for 1 h at room temperature. The mixture is then cooled to 0° C. and iodomethane (36 μL) is introduced. After stirring for 15 h, dilution with water and extraction with ethyl acetate, the organic phase is dried over magnesium sulfate and concentrated under reduced pressure. The residue is purified by chromatography over silica gel (gradient dichloromethane/methanol/ammonia from 95/5/0.5 to 90/10/

0.5) to afford the pure base that is then converted into its dioxalate salt in acetone to give 2-[(3-iodophenyl)(1-methylpiperidin-4-yloxy)methyl]-1-methyl-1H-benzimidazole, dioxalate, melting at 76° C.

Example 479

2-amino-5-{3-[(1H-benzimidazol-2-yl)(1-methylpiperidin-4-yloxy)methyl]phenylsulfanylmethyl}-1,5-dihydroimidazol-4-one

479A 2-amino-5-{3-[(1H-benzimidazol-2-yl)(1-methylpiperidin-4-yloxy)methyl]phenylsulfanylmethyl}-1,5-dihydroimidazol-4-one To a solution of 3-{3-[(1H-benzimidazol-2-yl)(1-methylpiperidin-4-yloxy)methyl]phenylsulfanyl}-2-(N,N'-bis-tert-butoxycarbonyl)guanidinopropionic acid methyl ester (260 mg) in dichloromethane (2.6 mL) is added dropwise trifluoroacetic acid (1 mL). The reaction mixture is stirred at room temperature for 28 h.
Solvents are removed under reduced pressure. The residue is basified by adding 1N sodium hydroxide, and the solution is evaporated to dryness. The residue is purified by chromatography on silica gel (gradient dichloromethane/methanol/ammonia from 90/10/0 to 90/10/1). The residual solid is triturated in hot ethyl acetate, cooled down to room temperature and filtered. The solid is washed with ethyl acetate; then dried to afford 2-amino-5-{3-[(1H-benzimidazol-2-yl)(1-methylpiperidin-4-yloxy)methyl]phenylsulfanyl-methyl}-1,5-dihydroimidazol-4-one.
MS, [M+H]$^+$=465.1; [M+Na]$^+$=487.1.

479B

3-{3-[(1H-Benzimidazol-2-yl)(1-methylpiperidin-4-yloxy)methyl]phenylsulfanyl}-2-(N,N'-bis-tert-butoxycarbonyl)guanidinopropionic acid methyl ester The compound is synthesized from Example 479C using the method described at example 307A; mixture of diastereomers. $^1$H NMR: 11.35 and 11.13 (sl, 1H), 10.25 and 10.06 (sl, 1H), 9.04 and 8.90 (d, 1H, J=7.5 Hz), 7.82-7.70 (m, 2H), 7.52-7.18 (m, 6H), 5.89 and 5.84 (s, 1H), 5.58-5.30 (m, 1H), 5.25-5.90 (m, 1H), 4.65-4.40 (m, 1H), 3.82-3.05 (m, 6H), 2.95-2.75 (m, 2H), 2.38 (sl, 3H), 2.252-1.60 (m, 6H), 1.60-1.30 (m, 18H).

479C

2-Amino-3-{3-[(1H-benzimidazol-2-yl)(1-methylpiperidin-4-yloxy)methyl]phenylsulfanyl}propionic acid methyl ester The compound is synthesized from example 479D using the method described in example 437B; mixture of diastereomers. $^1$H NMR: 9.74 and 9.67 (sl, 1H), 7.80-7.55 (m, 2H), 7.48-7.15 (m, 7H), 5.84 (s, 1H), 3.75-3.50 (m, 3H), 3.42-3.15 (m, 3H), 2.90-2.70 (m, 2H), 2.40-2.15 (m, 5H), 2.10-1.70 (m, 6H).

479D

3-{3-[(1H-Benzimidazol-2-yl)(1-methylpiperidin-4-yloxy)methyl]phenylsulfanyl}-2-tert-butoxycarbonylaminopropionic acid methyl ester The compound is synthesized from 2-[(3-bromophenyl)(1-methylpiperidin-4-yloxy)methyl]-1H-benzimidazole (example 72A) and N-Boc-Cysteine methyl ester using the method described in example 150; mixture of diastereomers. $^1$H NMR: 10.66 and 9.83 (sl, 1H), 7.90-7.70 (m, 2H), 7.50-7.35 (m, 2H), 7.35-7.18 (m, 5H), 5.87 and 5.85 (s, 1H), 5.58-5.30 (m, 1H), 4.65-4.40 (m, 1H), 3.70-3.20 (m, 6H), 2.82-2.62 (m, 2H), 2.28 and 2.26 (s, 3H), 2.22-1.65 (m, 6H), 1.53 and 1.45 (s, 9H).

Example 481

2-[(3-bromophenyl)(1-methylpiperidin-4-yloxy)methyl]-5,6,7-trifluoro-1H-benzimidazole

481A

2-[(3-bromophenyl)(1-methylpiperidin-4-yloxy)methyl]-5,6,7-trifluoro-1H-benzimidazole, solid melting at 140° C., is prepared according to general procedure 165C from 2-[(3-bromophenyl)(piperidin-4-yloxy)methyl]-5,6,7-trifluoro-1H-benzimidazole.

481B

To a solution of 4-[(3-bromophenyl)carboxymethoxy]piperidine-1-carboxylic acid tert-butyl ester (general procedure 165D+saponification)(1 g) in acetonitrile (10 mL) are added 3,4,5-trifluorobenzene-1,2-diamine (470 mg), 2-chloro-1-methylpyridinium iodide (802 mg) and dropwise diisopropylethylamine (1.1 mL). The reaction mixture is stirred at room temperature for 2 hours. Solvent is removed under reduced pressure and the residue diluted with ethyl acetate. The organic phase is washed with water, dried over magnesium sulfate and concentrated under reduced pressure. The residue is purified by chromatography over silica gel (gradient dichloromethane/methanol/ammonia from 98/2/0.2 to 90/10/1) to get 4-[(6-amino-2,3,4-trifluorophenylcarbamoyl)(3-bromophenyl)methoxy]piperidine-1-carboxylic acid tert-butyl ester. This intermediate is dissolved in acetic acid (15 mL) and the reaction mixture is refluxed for 3 hours. Acetic acid is removed under reduced pressure. Water is added to the residue and the solution is basified by adding a solution of saturated sodium hydrogencarbonate to pH 10. The aqueous phase is extracted with ethyl acetate. The pooled organic extracts are dried over magnesium sulfate and concentrated under reduced pressure. The residue is purified by chromatography over silica gel (gradient dichloromethane/methanol/ammonia from 98/2/0.2 to 90/10/1) to yield 2-[(3-bromophenyl)(piperidin-4-yloxy)methyl]-5,6,7-trifluoro-1H-benzimidazole.

Example 497

1-(2-ethoxyethyl)-2-[(3-iodophenyl)(1-methylpiperidin-4-yloxy)methyl]-1H-benzimidazole, dioxalate A solution of 2-[(3-iodophenyl)(1-methylpiperidin-4-yloxy)methyl]-1H-benzimidazole (example 51, 260 mg) in anhydrous acetonitrile (10 mL) is treated with 60% sodium hydride (47 mg) for 30 min at room temperature. 1-Bromo- 2-ethoxyethane (84 μL) is then introduced. After warming at 60° C. for 8 h, dilution with water and extraction with diethylether, the organic phase is dried over magnesium sulfate and concentrated under reduced pressure. The residue is purified by chromatography over silica gel (gradient dichloromethane/methanol/ammonia from 98/2/0.5 to 95/5/0.5) to afford the pure base that is then converted into its dioxalate salt in acetone to give 1-(2-ethoxyethyl)-2-[(3-iodophenyl)(1-methylpiperidin-4-yloxy)methyl]-1H-benzimidazole, dioxalate, melting at 88° C.

Example 505

505A

5-{3-[(1H-benzimidazol-2-yl)(1-methylpiperidin-4-yloxy)methyl]benzylidene}-2-iminoimidazolidin-4-one To a solution of 3-[(1H-benzimidazol-2-yl)(1-methylpiperidin-4-yloxy)methyl]-benzaldehyde (example 505C, 200 mg) in a mixture of ethanol-water (8:2) (3 mL) is added thiohydantoin (70 mg) and piperidine (57 μL). The reaction mixture is heated at 55° C. for 5 h. Ethanol is removed under reduced pressure. Water is added and the reaction mixture is extracted by ethyl acetate. The organic phase is washed by water, then dried over magnesium sulfate and concentrated. The residue is purified by chromatography on silica gel (gradient dichloromethane/methanol from 95/5 to 90/10). The residue is dissolved in methanol (6 mL) and 30% solution of aqueous ammonia (1.1 mL) and tert-butylhydroperoxide (90 μL) are added. The reaction mixture is stirred at room temperature for two days. The reaction mixture is evaporated to dryness. The residue is purified by chromatography on silica gel (gradient dichloromethane/methanol/ammonia from 90/10/0.1 to 70/30/0.1) to give 5-{3-[(1H-benzimidazol-2-yl)(1-methylpiperidin-4-yloxy)methyl]benzylidene}-2-iminoimidazolidin-4-one. MS, [M+H]$^+$=431.1; [M+Na]$^+$=453.1

505B

3-[(1H-Benzimidazol-2-yl)(1-methylpiperidin-4-yloxy)methyl]benzaldehyde

To a solution of 3-[(1H-benzimidazol-2-yl)(1-methylpiperidin-4-yloxy)methyl]-benzonitrile (example 172, 740 mg) in 80% aqueous formic acid (3 mL) is added platinum(IV) oxide (48 mg). The reaction mixture is heated at 60° C. for 7 h, then at room temperature for 2 days. As the reaction is not complete, 80% aqueous formic acid (3 mL) and platinum (IV) oxide (48 mg) are added and the reaction mixture is heated at 60° C. overnight. Water is added and the reaction mixture is filtered on celite. The phase is basified by adding a solution of 1N sodium hydroxide and extracted by ethyl acetate. The organic phase is washed by water, then dried over magnesium sulfate and concentrated to give 3-[(1H-benzimidazol-2-yl)(1-methylpiperidin-4-yloxy)methyl]benzaldehyde. $^1$H NMR: 9.99 (s, 1H), 9.67 (sl, 1H), 8.01 (s, 1H), 7.85-7.65 (m, 2H), 7.60-7.40 (m, 2H), 7.32-7.15 (m, 3H), 5.95 (s, 1H), 3.65-3.50 (m, 1H), 2.82-2.65 (m, 2H), 2.26 (s, 3H), 2.20-1.65 (m, 6H).

Example 507

4-{3-[(1H-benzimidazol-2-yl)(1-methylazetidin-3-yl-methoxy)methyl]-phenylsulfanyl}butylamine, oxalate. Compound made from example 506 using methods described in examples 150, 432. $^1$H NMR (methanol-d$_4$)(base): 7.65-7.40 (m, 3H), 7.40-7.10 (m, 5H), 5.69 (s, 1H), 3.785-3.40 (m, 4H), 3.40-3.10 (m, 5H), 2.44 (s, 3H), 1.80-1.45 (m, 3H), 1.35-1.10 (m, 2H), 1.00-1.75 (m, 1H).

Example 525

2-[(2-fluoro-5-trifluoromethoxyphenyl)(1-methylpiperidin-4-yloxy)methyl]benzoxazole, oxalate

525A

2-[(2-fluoro-5-trifluoromethoxyphenyl)(1-methylpiperidin-4-yloxy)methyl]benzoxazole, oxalate (solid melting at 103° C.) is prepared according to general procedure 272A.

525B

A mixture of (2-fluoro-5-trifluoromethoxyphenyl)hydroxyacetic acid (prepared according to 72C) (2.4 g), orthoaminophenol (1.03 g) in xylene (25 mL) is refluxed for 4 h with a Dean-Stark apparatus and concentrated under reduced pressure. Purification by chromatography on silica gel (gradient dichloromethane/methanol/ammonia from 100/0/0 to 98/2/0.5) to afford the pure benzoxazol-2-yl(2-fluoro-5-trifluoromethoxyphenyl)methanol.

Example 528

528A

2-[(1-methylpiperidin-4-yloxy)(3-methylsulfanylmethylphenyl)methyl]-1H-benzimidazole To a solution of {3-[(1H-benzimidazol-2-yl)(1-methylpiperidin-4-yloxy)methyl]phenyl}methanol (example 528B, 320 mg) in dichloromethane (3 mL) is added triethylamine (0.16 mL). The reaction mixture is cooled to 0° C., and methanesulfonyl chloride (84 μL) is added dropwise. The reaction mixture is stirred at room temperature for 3 h, then cooled to 0° C. and sodium thiomethoxide (191 mg) is added. After one night at room temperature, methanol (2 mL) is added to help solubilizing the suspension. The reaction mixture is stirred at room temperature overnight. Water is added and the aqueous phase is extracted by dichloromethane. The organic phase is washed by water, then dried over magnesium sulfate and concentrated. The residue is purified by chromatography on silica gel (gradient dichloromethane/methanol/ammonia from 90/10/0 to 90/10/0.1 then 80/20/0.1), followed by a purification by preparative thin-layer chromatography (dichloromethane/methanol/ammonia from 90/10/0.1) to give 2-[(1-methylpiperidin-4-yloxy)(3-methylsulfanylmethylphenyl)methyl]-1H-benzimidazole. MS, [M+H]$^+$=382.1;

528B

{3-[(1H-Benzimidazol-2-yl)(1-methylpiperidin-4-yloxy)methyl]phenyl}methanol

To a solution of 3-[(1H-benzimidazol-2-yl)(1-methylpiperidin-4-yloxy)methyl]benzaldehyde (example 505B, 310 mg) in methanol (4 mL) is added portionwise sodium borohydride (50 mg). The reaction mixture is stirred at room temperature for 15 minutes then heated at reflux for 3 h. Methanol is removed under reduced pressure. Water is added and the aqueous phase is extracted by ethyl acetate. The organic phase is washed by water, then dried over magnesium sulfate and concentrated to give {3-[(1H-benzimidazol-2-yl)(1-methylpiperidin-4-yloxy)methyl]-phenyl}methanol. $^1$H NMR: 9.85 (sl, 1H), 7.78-7.65 (m, 1H), 7.50-7.12 (m, 7H), 5.87 (s, 1H), 4.64 (s, 2H), 3.62-3.45 (m, 1H), 2.78-2.58 (m, 2H), 2.22 (s, 3H), 2.15-1.50 (m, 6H).

Example 530

530A

2-[(3-bromophenyl)(1-methyl-1,2,3,6-tetrahydropyridin-4-ylsulfanyl)methyl]-1H-benzimidazole To a solution of 1,2-phenylenediamine (213 mg) in toluene (2 mL) is added dropwise a solution of 2M trimethylaluminium in toluene (1 ml). The reaction mixture is heated at 75° C. for 2 hours then a solution of (3-bromophenyl)(1-methyl-1,2,3,6-tetrahydropyridin-4-ylsulfanyl)acetic acid methyl ester (example 530B, 358 mg) in toluene (2 mL) is added, and the heating is continued at 75° C. for 3 hours. Water is added and the reaction mixture is made alkaline by adding 1N sodium hydroxide. The aqueous phase is extracted by ethyl acetate. The organic phase is washed by water, brine, then dried over magnesium sulfate and concentrated. The residue is the dissolved in acetic acid (5 mL) and the reaction mixture is refluxed for 3 hours. The solvent is removed under reduced pressure. Water is added and the reaction mixture is made alkaline by adding 2N sodium hydroxide. The aqueous phase is extracted by ethyl acetate. The organic phase is washed by water, brine, then dried over magnesium sulfate and concentrated. The residual solid is triturated with acetonitrile, filtered and the solid is washed with diethyl ether to give 2-[(3-bromophenyl)(1-methyl-1,2,3,6-tetrahydropyridin-4-ylsulfanyl)methyl]-1H-benzimidazole melting at 189° C.

530B

(3-Bromophenyl)(1-methyl-1,2,3,6-tetrahydropyridin-4-ylsulfanyl)acetic acid methyl ester To a solution of 4-[(3-bromophenyl)methoxycarbonylmethylsulfanyl]-1-methylpyridinium iodide (example 530C, 480 mg) in methanol (5 mL) is added portionwise sodium borohydride (2 equivalents). The mixture is refluxed for one hour then concentrated to dryness. Water is added and the aqueous phase is extracted by ethyl acetate. The organic phase is washed by water, brine, then dried over magnesium sulfate and concentrated to give (3-Bromophenyl)(1-methyl-1,2,3,6-tetrahydropyridin-4-ylsulfanyl)acetic acid methyl ester. $^1$H NMR: 7.62 (s, 1H), 7.50-7.35 (m, 2H), 7.30-7.15 (m, 1H), 5.75 (sl, 1H), 4.77 (s, 1H), 3.76 (s, 3H), 3.10-2.98 (m, 2H), 2.68-2.55 (m, 2H), 2.45-2.25 (m, 5H).

530C

4-[(3-Bromophenyl)methoxycarbonylmethylsulfanyl]-1-methylpyridinium iodide

To a solution of (3-bromophenyl)(pyridin-4-ylsulfanyl)acetic acid methyl ester (example 530D, 2.2 g) in acetonitrile (50 mL) is added iodomethane (1.2 equivalent) and the mixture is stirred over-the-weekend at room temperature. The solid is filtered and washed with diethyl ether to give 4-[(3-Bromophenyl)methoxycarbonylmethylsulfanyl]-1-methylpyridinium iodide. $^1$H NMR (dmso-d$_6$): 8.75-8.65 (m, 2H), 7.98-7.88 (m, 2H), 7.78 (s, 1H), 7.63-7.51 (m, 2H), 7.42-7.30 (m, 1H), 6.20 (s, 1H), 4.13 (s, 3H), 3.70 (s, 3H).

530D

(3-Bromophenyl)(pyridin-4-ylsulfanyl)acetic acid methyl ester

To a solution of dimethylsulfoxonium ylide and 3-bromophenylacetic acid methyl ester (example 530E, 3 g) in dichloroethane (50 mL) are added 4-mercaptopyridine (2 equivalents) and [Ir(COD)Cl]$_2$ (20 mg). The reaction mixture is refluxed overnight then concentrated to dryness under reduced pressure. The residue is purified by chromatography on silica gel (heptane/ethyl acetate 1/1) to give (3-Bromophenyl)(pyridin-4-ylsulfanyl)acetic acid methyl ester. $^1$H NMR: 8.50-8.35 (m, 2H), 7.68 (s, 1H), 7.55-7.45 (m, 2H), 7.35-7.20 (m, 1H), 7.20-7.05 (m, 2H), 5.08 (s, 1H), 3.77 (s, 3H).

530E

Dimethylsulfoxonium ylide of 3-Bromophenylacetic acid methyl ester

To a solution of (3-bromophenyl)diazoacetic acid methyl ester (synthesized according to the method described in example 165E, 7.5 g) in dimethylsulfoxide (35 mL) is added copper(II)cyanide (150 mg), and the mixture is heated at 60° C. for 1 h, with evolution of nitrogen. The solvent is removed under reduced pressure. Water is added and the reaction mixture is extracted by ethyl acetate. The organic phase is washed by water, brine, then dried over magnesium sulfate and concentrated. The residual solid is triturated with diisopropyl ether, filtered and dried to give the dimethylsulfoxonium ylide of 3-bromophenylacetic acid methyl ester. $^1$H NMR: 7.47 (s, 1H), 7.45-7.35 (m, 1H), 7.30-7.12 (m, 2H), 3.63 (s, 3H), 3.45 (s, 6H)

Example 533

2-[(2-fluoro-4-methylphenyl)(1-methylpiperidin-4-yloxy)methyl]-1H-benzimidazole, enantiomer B A solution of racemic 2-[(2-fluoro-4-methylphenyl)(1-methylpiperidin-4-yloxy)methyl]-1H-benzimidazole (10 mg/mL) in a mixture of heptane/isopropanol (90/10) containing diethylamine (0.1%) is injected (30×100 μL) onto an analytical Chiralpak AD-H, 250×4.6 mm column. Elution is performed with a mixture of heptane/isopropanol (90/10) containing diethylamine (0.1%) at a flow of 1 mL/min. Products are detected at 210 nm. The enantiomer B has a retention time of 13.2 min. Collection affords 2-[(2-fluoro-4-methylphenyl)(1-methylpiperidin-4-yloxy)methyl]-1H-benzimidazole enantiomer B with a chromatographic enantiomeric purity of 97.4%.

Example 534

2-[(2,6-difluoro-3-methoxyphenyl)(1-methylpiperidin-4-yloxy)methyl]-1H-benzimidazole

534A

2-[(2,6-Difluoro-3-methoxyphenyl)(1-methylpiperidin-4-yloxy)methyl]-1H-benzimidazole (solid melting at 185° C.)

is prepared according to general procedure 172A from (1H-benzimidazol-2-yl)(2,6-difluoro-3-methoxyphenyl)methanol.

534B

A solution of (2,6-difluoro-3-methoxyphenyl)[1-(2-trimethylsilylethoxymethyl)-1H-benzimidazol-2-yl]methanol (1.4 g) in tetrahydrofuran (20 mL) is refluxed for 15 h with tetrabutylammonium fluoride (10 mL of a 1M solution in tetrahydrofuran). The mixture is then concentrated under reduced pressure and purified by chromatography over silica gel (gradient dichloromethane/methanol from 100/0 to 95/5) to afford the pure (1H-benzimidazol-2-yl)-(2,6-difluoro-3-methoxyphenyl)methanol.

534C

To a solution of 2,4-difluoro-1-methoxybenzene (156 mg) in tetrahydrofuran (5 mL) at −78° C. is added a 2M solution of lithium diisopropylamide in THF (540 µL). After stirring for 45 min a solution of 1-(2-trimethylsilylethoxymethyl)-1H-benzimidazole-2-carbaldehyde (which can be prepared according to US2003/220341 or U.S. Pat. No. 6,476,041 for example) (300 mg) in tetrahydrofuran (5 mL) is added at −78° C. and the reaction mixture allowed to warm to room temperature. After hydrolysis with aqueous saturated ammonium chloride and extraction with ethyl acetate, the organic phase is dried over magnesium sulfate and concentrated under reduced pressure. The residue is purified by chromatography over silica gel (gradient dichloromethane/methanol from 100/0 to 95/5) to afford (2,6-difluoro-3-methoxyphenyl)[1-(2-trimethylsilylethoxymethyl)-1H-benzimidazol-2-yl]methanol.

Example 549 ethyl (6-{3-[(1-methyl-1H-benzimidazol-2-yl)(1-methylpiperidin-4-yloxy)methyl]phenyl}hex-5-ynyl)carbamate, oxalate To a cooled solution of 6-{3-[(1-methyl-1H-benzimidazol-2-yl)(1-methylpiperidin-4-yloxy)methyl]phenyl}hex-5-ynylamine (example 480, 22 mg) in dichloromethane is added ethyl chloroformate (1 eq). After stirring at room temperature, the organic phase is washed with aqueous sodium hydroxide, dried over magnesium sulfate and concentrated under reduced pressure. The residue is purified by chromatography over silica gel (gradient dichloromethane/methanol from 100/0 to 90/10) to afford the pure base that is then converted into its oxalate salt in acetone to give ethyl (6-{3-[(1-methyl-1H-benzimidazol-2-yl)(1-methylpiperidin-4-yloxy)methyl]phenyl}hex-5-ynyl)carbamate, oxalate melting at 90° C.

Example 550

2-[(1H-indol-6-yl)(1-methylpiperidin-4-yloxy)methyl]-1H-benzimidazole, oxalate

550A

2-[(1-Benzenesulfonyl-1H-indol-6-yl)(1-methyl-piperidin-4-yloxy)methyl]-1H-benzimidazole (150 mg) and sodium hydroxide (excess) in methanol are refluxed for 3 h. The reaction mixture is then concentrated under reduced pressure, diluted with water and extracted with dichloromethane. The organic phase is dried over magnesium sulfate and concentrated under reduced pressure. The residue is purified by chromatography over silica gel (gradient dichloromethane/methanol/ammonia from 100/0/0 to 80/20/2) to afford the pure base that is then converted into its oxalate salt in acetone to give 2-[(1H-indol-6-yl)(1-methylpiperidin-4-yloxy)methyl]-1H-benzimidazole, oxalate, melting at 170° C.

550B

2-[(1-Benzenesulfonyl-1H-indol-6-yl)(1-methyl-piperidin-4-yloxy)methyl]-1H-benzimidazole is prepared according to general procedures 172A and 172B from 1-benzenesulfonyl-1H-indole-6-carbaldehyde.

Example 556

2-[benzo[b]thiophen-6-yl(1-methylpiperidin-4-yloxy)methyl]-1H-benzimidazole, oxalate

556A

2-[Benzo[b]thiophen-6-yl(1-methylpiperidin-4-yloxy)methyl]-1H-benzimidazole, oxalate melting at 160° C. is prepared according to general procedures 272A and 534B from benzo[b]thiophen-6-yl[1-(2-trimethylsilylethoxymethyl)-1H-benzimidazol-2-yl]methanol.

556B

To a suspension of magnesium (86 mg) in tetrahydrofuran is added a solution of 6-bromobenzo[b]thiophene (which can be prepared according to WO2006/107784) (500 mg) in tetrahydrofuran. After reflux for 3 h, a solution of 1-(2-trimethylsilylethoxymethyl)-1H-benzimidazole-2-carbaldehyde (which can be prepared according to US2003/220341 or U.S. Pat. No. 6,476,041 for example) (635 mg) in tetrahydrofuran is added to the Grignard reagent at room temperature. After stirring for 12 h, the reaction mixture is treated with diluted hydrochloric acid and the organic phase is dried over magnesium sulfate and concentrated under reduced pressure. The residue is purified by chromatography over silica gel (gradient dichloromethane/methanol from 100/0 to 90/10) to afford benzo[b]thiophen-6-yl[1-(2-trimethylsilylethoxymethyl)-1H-benzimidazol-2-yl]methanol.

Example 559

2-[(2,6-difluoro-4-methylphenyl)(1-methylpiperidin-4-yloxy)methyl]-1H-benzimidazole, enantiomer B A solution of racemic 2-[(2,6-difluoro-4-methylphenyl)(1-methylpiperidin-4-yloxy)methyl]-1H-benzimidazole (example 523) (10 mg/mL) in a mixture of heptane/isopropanol (90/10) containing diethylamine (0.1%) is injected (30×100 µL) onto an analytical Chiralpak AD-H, 250×4.6 mm column. Elution is performed with a mixture of heptane/isopropanol (90/10) containing diethylamine (0.1%) at a flow of 1 mL/min. Products are detected at 210 nm. The enantiomer B has a retention time of 13.9 min. Collection affords 2-[(2,6-difluoro-4-methylphenyl)(1-methylpiperidin-4-yloxy)methyl]-1H-benzimidazole, enantiomer B with a chromatographic enantiomeric purity of 99.3%

Example 561

2-[(1H-benzimidazol-2-yl)(1-methylpiperidin-4-yloxy)methyl]phenol

561A

2-[(1H-benzimidazol-2-yl)(1-methylpiperidin-4-yloxy) methyl]phenol (solid melting at 118-120° C.) is prepared from 2-[(1H-benzimidazol-2-yl)hydroxymethyl]phenol according to general procedure 1A.

561B

To a solution of 1-pyrrolidin-1-ylmethyl-1H-benzimidazole (6 g) in tetrahydrofuran (40 mL) at −78° C., is added a 2.3M solution of butyllithium in hexanes (13 mL). The mixture is stirred for 25 minutes. Salicaldehyde (1.82 g) is then dropwise introduced at −78° C. After 1 h at the same temperature, the mixture is allowed to warm to room temperature and hydrolyzed with aqueous saturated ammonium chloride. After 1 h, the mixture is extracted with ethyl acetate. Pooled extracts are washed with brine, dried over magnesium sulfate and concentrated under reduced pressure. The residue is purified by trituration in dichloromethane to afford 2-[(1H-benzimidazol-2-yl)hydroxymethyl]phenol.

Example 562

2-[(6-{3-[(1H-benzimidazol-2-yl)(1-methylpiperidin-4-yloxy)methyl]-4-fluorophenyl}hex-5-ynylimino)phenylmethyl]phenol A mixture of 6-{3-[(1H-benzimidazol-2-yl)(1-methylpiperidin-4-yloxy)methyl]-4-fluorophenyl}hex-5-ynylamine, oxalate (example 557, 70 mg), 2-hydroxybenzophenone (30 mg) in ethanol (4 mL) is refluxed for 4 h. The mixture is then cooled, diluted with water and extracted with ethyl acetate. Pooled extracts are dried over magnesium sulfate and concentrated under reduced pressure. The residue is purified by chromatography over silica gel (gradient dichloromethane/methanol/ammonia from 100/0/0 to 90/10/0.5) to afford 2-[(6-{3-[(1H-benzimidazol-2-yl)(1-methylpiperidin-4-yloxy)methyl]-4-fluorophenyl}hex-5-ynylimino)phenylmethyl]phenol. TLC (Eluent: $CH_2Cl_2$/MeOH/$NH_4OH$ 95/5/0.5) Rf=0.15.

Example 563

5-(6-{3-[(1H-benzimidazol-2-yl)(1-methylpiperidin-4-yloxy)methyl]-4-fluorophenyl}hex-5-ynylimino)-2-methylcyclopent-1-enol A mixture of 6-{3-[(1H-benzimidazol-2-yl)(1-methylpiperidin-4-yloxy)methyl]-4-fluorophenyl}hex-5-ynylamine, oxalate (example 557, 50 mg), 3-methyl-1,2-cyclopentanedione (11.8 mg) in ethanol (2 mL) is refluxed for 2 h. The mixture is then cooled, diluted with water and 1N sodium hydroxide and extracted with ethyl acetate. Pooled extracts are dried over magnesium sulfate and concentrated under reduced pressure. The residue is purified by chromatography over silica gel (gradient dichloromethane/methanol/ammonia from 100/0/0.5 to 95/5/0.5) to afford 5-(6-{3-[(1H-benzimidazol-2-yl)(1-methylpiperidin-4-yloxy)methyl]-4-fluorophenyl}hex-5-ynylimino)-2-methylcyclopent-1-enol. TLC (Eluent: $CH_2Cl_2$/MeOH/$NH_4OH$ 95/5/0.5) Rf=0.30.

Example 564

2-[(3-bromophenyl)(1-methylpiperidin-4-yloxy)methyl]-1H-benzimidazole, enantiomer B Resolution of racemic 2-[(3-bromophenyl)(1-methylpiperidin-4-yloxy)methyl]-1H-benzimidazole (example 78) with (1R)-(−)-10-camphorsulfonic acid (0.45 eq) in ethyl acetate affords after several recrystallizations enantiopure 2-[(3-bromophenyl)(1-methylpiperidin-4-yloxy)methyl]-1H-benzimidazole, enantiomer B (solid melting at 85° C.). HPLC analysis: analytical Chiralpak AD-H, 250×4.6 mm column. Elution is performed with a mixture of heptane/isopropanol (90/10) containing diethylamine (0.1%) at a flow of 1 mL/min. The enantiomer B has a retention time of 10.4 min.

Example 565

5-{3-[(1H-benzimidazol-2-yl)(1-methylpiperidin-4-yloxy)methyl]phenyl}pent-4-ynylamine, enantiomer A 5-{3-[(1H-Benzimidazol-2-yl)(1-methylpiperidin-4-yloxy)methyl]phenyl}pent-4-ynylamine, enantiomer A (melting at 84° C.) is prepared according to general procedures 194 and 189 from 2-[(3-bromophenyl)(1-methylpiperidin-4-yloxy)methyl]-1H-benzimidazole, enantiomer A (prepared according example 564 with (1S)-(+)-camphorsulfonic acid).

Example 566

5-{3-[(1H-benzimidazol-2-yl)(1-methylpiperidin-4-yloxy)methyl]phenyl}pent-4-ynylamine, enantiomer B 5-{3-[(1H-Benzimidazol-2-yl)(1-methylpiperidin-4-yloxy)methyl]phenyl}pent-4-ynylamine, enantiomer B (melting at 82° C.) is prepared according to general procedures 194 and 189 from 2-[(3-bromophenyl)(1-methylpiperidin-4-yloxy)methyl]-1H-benzimidazole, enantiomer B (example 564).

Example 567

2-[(3-bromophenyl)(1-methylpiperidin-4-yloxy)methyl]-5-fluoro-1H-benzimidazole, enantiomer A Resolution of racemic 2-[(3-bromophenyl)(1-methylpiperidin-4-yloxy)methyl]-5-fluoro-1H-benzimidazole with (1S)-(+)-10-camphorsulfonic acid (0.5 eq) in ethyl acetate affords after several recrystallizations 2-[(3-bromophenyl)(1-methylpiperidin-4-yloxy)methyl]-5-fluoro-1H-benzimidazole, enantiomer A (solid melting at 89° C.). HPLC analysis: analytical Chiralpak AD-H, 250×4.6 mm column. Elution is performed with a mixture of heptane/isopropanol (90/10) containing diethylamine (0.1%) at a flow of 1 mL/min. The enantiomer A has a retention time of 8.2 min. e.e.=93.5%

Example 568

2-[(3-bromophenyl)(1-methylpiperidin-4-yloxy)methyl]-5-fluoro-1H-benzimidazole, enantiomer B Resolution of racemic 2-[(3-bromophenyl)(1-methylpiperidin-4-yloxy)methyl]-5-fluoro-1H-benzimidazole with (1R)-(−)-10-camphorsulfonic acid (0.5 eq) in ethyl acetate affords after several recrystallizations 2-[(3-bromophenyl)(1-methylpiperidin-4-yloxy)methyl]-5-fluoro-1H-benzimidazole, enantiomer B (solid melting at 89° C.). HPLC analysis: analytical Chiralpak AD-H, 250×4.6 mm column. Elution is performed with a mixture of heptane/isopropanol (90/10) containing diethylamine (0.1%) at a flow of 1 mL/min. The enantiomer B has a retention time of 10.3 min. e.e.=95.5%

Example 578

2-[(1H-benzimidazol-2-yl)(1-methylpiperidin-4-yloxy)methyl]-4-methylphenol

A mixture of 2-[(1H-benzimidazol-2-yl)hydroxymethyl]-4-methylphenol (prepared according to procedure 561B) (360 mg), methanesulfonic acid (500 μL) and 1-methyl-4-piperidinol (500 mg) in 1,2-dichloroethane (20 mL) and N-methylpyrrolidinone (2 mL) is warmed at 90° C. for 2 h. After cooling at 0° C., the mixture is diluted with water and dichloromethane and concentrated sodium hydroxide slowly added up to pH 9. Organic phase is then dried over magnesium sulfate and concentrated under reduced pressure. The residue is purified by chromatography over silica gel (gradient dichloromethane/methanol/ammonia from 100/0/0.5 to 80/20/0.5) to afford 2-[(1H-benzimidazol-2-yl)(1-methylpiperidin-4-yloxy)methyl]-4-methylphenol, melting at 151° C.

For the other examples prepared according this general procedure, it can be advantageous to rise the temperature progressively after having mixed the different reagents and to observe when etherification occurs. Once the right temperature has been found, reaction may be continued up to adequate conversion. Use of N-methylpyrrolidinone can be optional depending of the solubility of the mixture. Additional equivalents of methanesulfonic acid can be used for a better conversion if necessary.

Example 626

2-[(1H-benzimidazol-2-yl)(1-methylpiperidin-4-yloxy)methyl]phenol enantiomer A

2-[(1H-Benzimidazol-2-yl)(1-methylpiperidin-4-yloxy)methyl]phenol enantiomer A is prepared by separation on Chiralpak AD-H from racemic 2-[(1H-benzimidazol-2-yl)(1-methylpiperidin-4-yloxy)methyl]phenol (example 561). HPLC analysis: Chiralpak AD-H, 250×4.6 mm column. Elution is performed with a mixture of heptane/isopropanol (90/10) containing diethylamine (0.1%) at a flow of 1 mL/min. The enantiomer A has a retention time of 18.8 min. e.e.=100%

Example 627

2-[(1H-benzimidazol-2-yl)(1-methylpiperidin-4-yloxy)methyl]phenol enantiomer B

2-[(1H-Benzimidazol-2-yl)(1-methylpiperidin-4-yloxy)methyl]phenol enantiomer B is prepared by separation on Chiralpak AD-H from racemic 2-[(1H-benzimidazol-2-yl)(1-methylpiperidin-4-yloxy)methyl]phenol (example 561). HPLC analysis: Chiralpak AD-H, 250×4.6 mm column. Elution is performed with a mixture of heptane/isopropanol (90/10) containing diethylamine (0.1%) at a flow of 1 mL/min. The enantiomer B has a retention time of 34.3 min. e.e.=100%

Example 628

6-[(1Hbenzimidazol-2-yl)(1-methylpiperidin-4-yloxy)methyl]-2-fluoro-3-methylphenol enantiomer A By analogy with example 626 from racemic 6-[(1H-benzimidazol-2-yl)(1-methylpiperidin-4-yloxy)methyl]-2-fluoro-3-methylphenol (example 601). HPLC analysis: Chiralpak AD-H, 250×4.6 mm column. Elution is performed with a mixture of heptane/isopropanol (90/10) containing diethylamine (0.1%) at a flow of 1 mL/min. The enantiomer A has a retention time of 15.8 min.

Example 629

6-[(1H-benzimidazol-2-yl)(1-methylpiperidin-4-yloxy)methyl]-2-fluoro-3-methylphenol enantiomer B By analogy with example 627 from racemic 6-[(1H-benzimidazol-2-yl)(1-methylpiperidin-4-yloxy)methyl]-2-fluoro-3-methylphenol (example 601). HPLC analysis: Chiralpak AD-H, 250×4.6 mm column. Elution is performed with a mixture of heptane/isopropanol (90/10) containing diethylamine (0.1%) at a flow of 1 mL/min. The enantiomer B has a retention time of 19.9 min.

Example 630

6-[(1H-benzimidazol-2-yl)(1-methylpiperidin-4-yloxy)methyl]-2,3-difluorophenol enantiomer A By analogy with example 626 from racemic 6-[(1H-benzimidazol-2-yl)(1-methylpiperidin-4-yloxy)methyl]-2,3-difluorophenol (example 625). HPLC analysis: Chiralpak AD-H, 250×4.6 mm column. Elution is performed with a mixture of heptane/isopropanol (90/10) containing diethylamine (0.1%) at a flow of 1 mL/min. The enantiomer A has a retention time of 13.4 min.

Example 631

6-[(1H-benzimidazol-2-yl)(1-methylpiperidin-4-yloxy)methyl]-2,3-difluorophenol enantiomer B By analogy with example 627 from racemic 6-[(1H-benzimidazol-2-yl)(1-methylpiperidin-4-yloxy)methyl]-2,3-difluorophenol (example 625). HPLC analysis: Chiralpak AD-H, 250×4.6 mm column. Elution is performed with a mixture of heptane/isopropanol (90/10) containing diethylamine (0.1%) at a flow of 1 mL/min. The enantiomer B has a retention time of 15.3 min.

Further examples can be prepared according to the described general methods:

| Example | Product | General methods | Melting point |
| --- | --- | --- | --- |
| 442 | 5-{3-[(1H-benzimidazol-2-yl)(1-methylpiperidin-4-yloxy)methyl]-4-fluorophenyl}pent-4-ynylamine, dioxalate | 194, 189, 425 | 139° C. |

-continued

| Example | Product | General methods | Melting point |
|---|---|---|---|
| 453 | 3-{3-[benzothiazol-2-yl(1-methylpiperidin-4-yloxy)methyl]phenoxy}cyclopentylamine, oxalate | 194, 432A, 258 | 91° C. |
| 454 | 2-{[3-(3-fluoropyrrolidin-1-yl)phenyl](1-methylpiperidin-4-yloxy)methyl}benzothiazole, oxalate | 423B | 103° C. |
| 462 | 5-{3-[(5-fluoro-1H-benzimidazol-2-yl)(1-methylpyrrolidin-3-ylmethoxy)methyl]phenyl}pent-4-ynylamine, oxalate | 194, 189, 449 | 200° C. |
| 464 | 2-[(3-bromophenyl)(1-methylpyrrolidin-3-ylmethoxy)methyl]benzothiazole, oxalate (one epimer) | 165C, 1A, 1B | 68° C. |
| 465 | 2-[(3-bromophenyl)(1-methylpyrrolidin-3-ylmethoxy)methyl]benzothiazole, oxalate (50/50 mixture of two epimers) | 165C, 1A, 1B | 68° C. |
| 466 | 2-{(1-methylpiperidin-4-yloxy)[3-(octahydrocyclopenta[c]pyrrol-5-yloxy)phenyl]methyl}benzothiazole, dioxalate | 249, 258 | 70° C. |
| 467 | (1-{3-[benzothiazol-2-yl(1-methylpiperidin-4-yloxy)methyl]phenyl}pyrrolidin-3-yl)methylamine, dioxalate | 249, 423B | 216° C. |
| 470 | 4-{3-[(5,6-difluoro-1H-benzimidazol-2-yl)(1-methylpiperidin-4-yloxy)methyl]phenylsulfanyl}butan-1-ol | 150, 469 | 60° C. |
| 471 | 2-{3-[benzothiazol-2-yl(1-methylpiperidin-4-yloxy)methyl]phenyl}octahydrocyclopenta[c]pyrrol-5-ylamine, dioxalate | 194, 432A, 423B | 126° C. |
| 475 | 2-{[3-(3-fluoropropoxy)phenyl](1-methylpiperidin-4-yloxy)methyl}-1H-benzimidazole, oxalate | 272A, 272B | 106° C. |
| 476 | 2-{[3-(2-fluoroethoxy)phenyl](1-methylpiperidin-4-yloxy)methyl}-1H-benzimidazole, oxalate | 272A, 272B | 136° C. |
| 477 | 4-{3-[benzothiazol-2-yl(1-methylpiperidin-4-yloxy)methyl]phenoxy}cyclohexylamine, oxalate | 194, 432A, 258 | 95° C. |
| 480 | 6-{3-[(1-methyl-1H-benzimidazol-2-yl)(1-methylpiperidin-4-yloxy)methyl]phenyl}hex-5-ynylamine, dioxalate | 194, 189, 472 | 113° C. |
| 482 | 1-{3-[benzothiazol-2-yl(1-methylpiperidin-4-yloxy)methyl]phenyl}pyrrolidin-2-ylmethylamine, oxalate | 194, 432A, 423B | 145° C. |
| 483 | (1-{3-[benzothiazol-2-yl(1-methylpiperidin-4-yloxy)methyl]phenyl}pyrrolidin-3-yl)(methyl)amine, oxalate | 249, 423B | 115° C. |
| 484 | (1-{3-[benzothiazol-2-yl(1-methylpiperidin-4-yloxy)methyl]phenyl}pyrrolidin-3-yl)(dimethyl)amine, oxalate | 423B | 106° C. |
| 485 | 2-{[3-(5-methylhexahydropyrrolo[3,4-c]pyrrol-2-yl)phenyl](1-methylpiperidin-4-yloxy)methyl}benzothiazole, dioxalate | 423B | 131° C. |
| 486 | 2-[(2-fluoro-5-methoxyphenyl)(1-methylpiperidin-4-yloxy)methyl]-1H-benzimidazole, oxalate | 272A, 272B | 105° C. |
| 487 | 3-[(1H-benzimidazol-2-yl)(1-methylpiperidin-4-yloxy)methyl]-4-fluorophenol, oxalate | 272A, 272B | 135° C. |
| 489 | 2-{[2-fluoro-5-(2-fluoroethoxy)phenyl](1-methylpiperidin-4-yloxy)methyl}-1H-benzimidazole, oxalate | 272A, 272B | 109° C. |
| 490 | 2-[(2-fluoro-5-methylphenyl)(1-methylpiperidin-4-yloxy)methyl]-1H-benzimidazole, oxalate | 272A, 272B | 132° C. |
| 493 | 4-{3-[(1-methylpiperidin-4-yloxy)(5,6,7-trifluoro-1H-benzimidazol-2-yl)methyl]phenylsulfanyl}butylamine, oxalate | 305A, 305B, 481 | 110° C. |
| 495 | 4-{3-[(5,6-difluoro-1H-benzimidazol-2-yl)(1-methylpiperidin-4-yloxy)methyl]phenylsulfanyl}butylamine, oxalate | 305A, 305B, 469 | 180° C. |
| 500 | 6-(3-{[1-(2-ethoxyethyl)-1H-benzimidazol-2-yl](1-methylpiperidin-4-yloxy)methyl}phenyl)hex-5-ynylamine, dioxalate | 194, 189, 497 | 103° C. |
| 501 | 6-(3-{[1-(2-methoxyethyl)-1H-benzimidazol-2-yl](1-methylpiperidin-4-yloxy)methyl}phenyl)hex-5-ynylamine, dioxalate | 194, 189, 497 | 109° C. |
| 508 | 2-{[3-(3-fluoropropylsulfanyl)phenyl](1-methylpiperidin-4-yloxy)methyl}-1H-benzimidazole, dioxalate | 150 | 85° C. |
| 509 | 5-fluoro-2-[(2-fluoro-5-trifluoromethoxyphenyl)(1-methylpiperidin-4-yloxy)methyl]-1H-benzimidazole, oxalate | 272A, 272B | 70° C. |

-continued

| Example | Product | General methods | Melting point |
|---|---|---|---|
| 510 | 4,5,6-trifluoro-2-[(2-fluoro-5-trifluoromethoxyphenyl)(1-methylpiperidin-4-yloxy)methyl]-1H-benzimidazole | 272A, 272B | 75° C. |
| 511 | 5,6-difluoro-2-[(2-fluoro-5-trifluoromethoxyphenyl)(1-methylpiperidin-4-yloxy)methyl]-1H-benzimidazole | 272A, 272B | 9° C. |
| 522 | 2-{[2-fluoro-5-(2,2,2-trifluoroethoxy)phenyl](1-methylpiperidin-4-yloxy)methyl}-1H-benzimidazole | 272A, 272B | 204° C. |
| 523 | 2-[(2,6-difluoro-4-methylphenyl)(1-methylpiperidin-4-yloxy)methyl]-1H-benzimidazole | 272A, 272B | 211° C. |
| 524 | 2-[(2-chloro-5-trifluoromethoxyphenyl)(1-methylpiperidin-4-yloxy)methyl]-1H-benzimidazole, oxalate | 272A, 272B | 107° C. |
| 526 | 2-[(2-fluoro-5-trifluoromethoxyphenyl)(1-methylpiperidin-4-yloxy)methyl]benzothiazole, oxalate | 272A, 1B | 95° C. |
| 527 | 2-[(4-chloro-2,6-difluorophenyl)(1-methylpiperidin-4-yloxy)methyl]-1H-benzimidazole | 272A, 272B | 195° C. |
| 529 | 7-fluoro-2-[(2-fluoro-5-trifluoromethoxyphenyl)(1-methylpiperidin-4-yloxy)methyl]-1H-benzimidazole, oxalate | 165C, 165A | 135° C. |
| 531 | 2-[(2,6-difluoro-4-methylphenyl)(1-methylpiperidin-4-yloxy)methyl]benzothiazole, oxalate | 272A, 168B | 125° C. |
| 532 | 2-[(4-chloro-2,6-difluorophenyl)(1-methylpiperidin-4-yloxy)methyl]benzothiazole, oxalate | 272A, 1B | 158° C. |
| 535 | 2-[(3-ethoxy-2,6-difluorophenyl)(1-methylpiperidin-4-yloxy)methyl]-1H-benzimidazole | 534 | 130° C. |
| 536 | 2-[(2,6-difluoro-4-methylphenyl)(1-methylpiperidin-4-yloxy)methyl]benzoxazole, oxalate | 525 | 114° C. |
| 537 | 2-[(1-methylpiperidin-4-yloxy)(4-trifluoromethylphenyl)methyl]-1H-benzimidazole | 272A, 272B | 86° C. |
| 540 | 2-[(2-fluoro-4-trifluoromethylphenyl)(1-methylpiperidin-4-yloxy)methyl]-1H-benzimidazole | 272A, 272B | 91° C. |
| 541 | 2-[(2,4-dimethylphenyl)(1-methylpiperidin-4-yloxy)methyl]-1H-benzimidazole | 272A, 272B | 120° C. |
| 542 | 2-[(3-methoxyphenyl)(1-methylpiperidin-4-yloxy)methyl]-1H-benzimidazole | 272A, 272B | 83° C. |
| 543 | 2-[chroman-7-yl(1-methylpiperidin-4-yloxy)methyl]-1H-benzimidazole | 272A, 272B | 128° C. |
| 545 | 2-[(2-fluoro-4-methylphenyl)(1-methylpiperidin-4-yloxy)methyl]benzoxazole, oxalate | 525 | 110° C. |
| 547 | 2-[(3,5-bis-trifluoromethylphenyl)(1-methylpiperidin-4-yloxy)methyl]-1H-benzimidazole, oxalate | 272A, 272B | 130° C. |
| 548 | 5-fluoro-2-[(2-fluoro-4-methylphenyl)(1-methylpiperidin-4-yloxy)methyl]-1H-benzimidazole | 272A, 272B | 90° C. |
| 551 | 2-[(2,3-difluoro-4-methylphenyl)(1-methylpiperidin-4-yloxy)methyl]-1H-benzimidazole | 272A, 272B | 80° C. |
| 552 | 2-[(3-chloro-4-methylphenyl)(1-methylpiperidin-4-yloxy)methyl]-1H-benzimidazole | 272A, 272B | 86° C. |
| 553 | ethyl 2-[(2-fluoro-5-trifluoromethoxyphenyl)(1-methylpiperidin-4-yloxy)methyl]benzimidazole-1-carboxylate, oxalate | 549 | 118° C. |
| 554 | 2-[(3-fluoro-4-methylphenyl)(1-methylpiperidin-4-yloxy)methyl]-1H-benzimidazole | 272A, 272B | 92° C. |
| 555 | 2-[(5-bromo-2-fluorophenyl)(1-methylpiperidin-4-yloxy)methyl]-1H-benzimidazole | 272A, 272B | 232° C. |
| 557 | 6-{3-[(1H-benzimidazol-2-yl)(1-methylpiperidin-4-yloxy)methyl]-4-fluorophenyl}hex-5-ynylamine, oxalate | 194, 189, 555 | 195° C. |
| 558 | 5-{4-fluoro-3-[(5-fluoro-1H-benzimidazol-2-yl)(1-methylpiperidin-4-yloxy)methyl]phenyl}pent-4-ynylamine | 194, 189, 272A, 272B | 90° C. |
| 560 | ethyl (5-{3-[(1H-benzimidazol-2-yl)(1-methylpiperidin-4-yloxy)methyl]-4-fluorophenyl}pent-4-ynyl)carbamate | 549, 442 | 87° C. |
| 569 | 2-[(1H-benzimidazol-2-yl)(1-methylpiperidin-4-yloxy)methyl]-4-chlorophenol | 272A, 561B | 185° C. |
| 570 | ethyl (5-{4-fluoro-3-[(5-fluoro-1H-benzimidazol-2-yl)(1-methylpiperidin-4-yloxy)methyl]phenyl}pent-4-ynyl)carbamate | 189, 272A, 272B | 95° C. |
| 571 | 2-[(1H-benzimidazol-2-yl)(1-methylpiperidin-4-yloxy)methyl]-4-trifluoromethoxyphenol | 272A, 561B | 132° C. |
| 572 | 2-[(1H-benzimidazol-2-yl)(1-methylpiperidin-4-yloxy)methyl]-4-fluorophenol | 272A, 561B | 142° C. |
| 573 | 2-[(1H-benzimidazol-2-yl)(1-methylpiperidin-4-yloxy)methyl]-4-methoxyphenol | 1A, 561B | 146° C. |

-continued

| Example | Product | General methods | Melting point |
|---|---|---|---|
| 574 | 2-[(1H-benzimidazol-2-yl)(1-methylpiperidin-4-yloxy)methyl]-5-methylphenol | 1A, 561B | 145° C. |
| 575 | 2-[(1H-benzimidazol-2-yl)(1-methylpiperidin-4-yloxy)methyl]-4-bromophenol | 272A, 561B | 145° C. |
| 576 | 2-[(1H-benzimidazol-2-yl)(1-methylpiperidin-4-yloxy)methyl]-4-ethoxyphenol | 272A, 561B | 213° C. |
| 577 | 2-[(1H-indol-7-yl)(1-methylpiperidin-4-yloxy)methyl]-1H-benzimidazole | 550A, 1A, 272B | 110° C. |
| 579 | 2-[(1H-benzimidazol-2-yl)(1-methylpiperidin-4-yloxy)methyl]-4,6-difluorophenol | 272A, 561B | 142° C. |
| 580 | 2-[(1H-benzimidazol-2-yl)(1-methylpiperidin-4-yloxy)methyl]-4,6-dichlorophenol | 272A, 561B | 161° C. |
| 581 | 2-[(1H-benzimidazol-2-yl)(1-methylpiperidin-4-yloxy)methyl]-6-fluorophenol | 578 | 145° C. |
| 582 | 2-[(1H-benzimidazol-2-yl)(1-methylpiperidin-4-yloxy)methyl]-3-fluorophenol | 578 | 129° C. |
| 583 | 2-[(1H-benzimidazol-2-yl)(1-methylpiperidin-4-yloxy)methyl]-4,5-difluorophenol | 272A, 561B | 198° C. |
| 584 | 2-[(1H-benzimidazol-2-yl)(1-methylpiperidin-4-yloxy)methyl]-5-fluorophenol | 578 | 140° C. |
| 585 | 2-[(1H-benzimidazol-2-yl)(1-methylpiperidin-4-yloxy)methyl]-5-chlorophenol | 578 | 142° C. |
| 586 | 2-[(1H-benzimidazol-2-yl)(1-methylpiperidin-4-yloxy)methyl]-6-methylphenol | 578 | 111° C. |
| 587 | 2-[(1H-benzimidazol-2-yl)(1-methylpiperidin-4-yloxy)methyl]-4-methylsulfanylphenol | 578 | 138° C. |
| 588 | 2-[(1H-benzimidazol-2-yl)(1-methylpiperidin-4-yloxy)methyl]-4-ethylsulfanylphenol | 578 | 116° C. |
| 589 | 3-[(1H-benzimidazol-2-yl)(1-methylpiperidin-4-yloxy)methyl]biphenyl-4-ol | 578 | 140° C. |
| 590 | 2-[(1H-benzimidazol-2-yl)(1-methylpiperidin-4-yloxy)methyl]-4-tert-butylphenol | 272A, 561B | 139° C. |
| 591 | 2-[(1H-benzimidazol-2-yl)(1-methylpiperidin-4-yloxy)methyl]-4-propylphenol | 578 | 120° C. |
| 592 | 2-[(1H-benzimidazol-2-yl)(1-methylpiperidin-4-yloxy)methyl]-6-methoxyphenol | 578 | 112° C. |
| 593 | 2-[(1H-benzimidazol-2-yl)(1-methy-piperidin-4-yloxy)methyl]-3-fluoro-5-methylphenol | 578 | 136° C. |
| 594 | 2-[(1H-benzimidazol-2-yl)(1-methylpiperidin-4-yloxy)methyl]-3-chlorophenol | 272A, 561B | 145° C. |
| 595 | 2-[(1H-benzimidazol-2-yl)(1-methylpiperidin-4-yloxy)methyl]-6-fluoro-4-methylphenol | 272A, 561B | 144° C. |
| 596 | 2-[(1H-benzimidazol-2-yl)(1-methylpiperidin-4-yloxy)methyl]-4-benzylphenol | 272A, 561B | 120° C. |
| 598 | 2-[(1H-benzimidazol-2-yl)(1-methylpiperidin-4-yloxy)methyl]-4-trifluoromethylphenol | 578 | 135° C. |
| 599 | 2-[(1H-benzimidazol-2-yl)(1-methylpiperidin-4-yloxy)methyl]-4-chloro-6-fluorophenol | 272A, 561B | 146° C. |
| 600 | 2-[(1H-benzimidazol-2-yl)(1-methylpiperidin-4-yloxy)methyl]-5-fluoro-3-methylphenol | 272A, 561B | 146° C. |
| 601 | 6-[(1H-benzimidazol-2-yl)(1-methylpiperidin-4-yloxy)methyl]-2-fluoro-3-methylphenol | 272A, 561B | 148° C. |
| 602 | 6-[(1H-benzimidazol-2-yl)(1-methylpiperidin-4-yloxy)methyl]indan-5-ol | 578 | 152° C. |
| 603 | 2-[(1H-benzimidazol-2-yl)(1-methylpiperidin-4-yloxy)methyl]-4-propoxyphenol | 578 | 120° C. |
| 604 | 2-[(1H-benzimidazol-2-yl)(1-methylpiperidin-4-yloxy)methyl]-4-(1-methyl-1-phenylethyl)phenol | 272A, 561B | 130° C. |
| 605 | 2-[(1H-benzimidazol-2-yl)(1-methylpiperidin-4-yloxy)methyl]-4-(2-fluoroethoxy)phenol | 578 | 222° C. |
| 606 | 2-[(1H-benzimidazol-2-yl)(1-methylpiperidin-4-yloxy)methyl]-4-(3-fluoropropoxy)phenol | 578 | 114° C. |
| 607 | 2-[(1H-benzimidazol-2-yl)(1-methylpiperidin-4-yloxy)methyl]-4-fluoro-6-methylphenol | 272A, 561B | 111° C. |
| 608 | 2-[(1H-benzimidazol-2-yl)(1-methylpiperidin-4-yloxy)methyl]-6-fluoro-4-methoxyphenol | 272A, 561B | 132° C. |
| 609 | 2-[(1H-benzimidazol-2-yl)(1-methylpiperidin-4-yloxy)methyl]-4-phenoxyphenol | 578 | 140° C. |
| 610 | 2-[(1H-benzimidazol-2-yl)(1-methylpiperidin-4-yloxy)methyl]-4-fluoro-6-methoxyphenol | 578 | 108° C. |
| 611 | 2-[(1H-benzimidazol-2-yl)(1-methylpiperidin-4-yloxy)methyl]-4,5-dimethylphenol | 578 | 139° C. |
| 612 | 2-[(1H-benzimidazol-2-yl)(1-methylpiperidin-4-yloxy)methyl]-4-(3-fluoropropylsulfanyl)phenol | 578 | 128° C. |
| 613 | 2-[(1H-benzimidazol-2-yl)(1-methylpiperidin-4-yloxy)methyl]-4-fluoro-5-methylphenol | 1A, 561B | 102° C. |

-continued

| Example | Product | General methods | Melting point |
|---|---|---|---|
| 614 | 2-[(1H-benzimidazol-2-yl)(1-methylpiperidin-4-yloxy)methyl]-4-(2-fluoroethylsulfanyl)phenol | 578 | 127° C. |
| 615 | 3-[(1H-benzimidazol-2-yl)(1-methylpiperidin-4-yloxy)methyl]-2-hydroxybiphenyl | 578 | 129° C. |
| 616 | 2-[(1H-benzimidazol-2-yl)(1-methylpiperidin-4-yloxy)methyl]-6-ethylphenol | 578 | 105° C. |
| 617 | 2-[(1H-benzimidazol-2-yl)(1-methylpiperidin-4-yloxy)methyl]-5-trifluoromethylphenol | 272A, 561B | 144° C. |
| 618 | 2-[(1H-benzimidazol-2-yl)(1-methylpiperidin-4-yloxy)methyl]-4-hydroxyphenol | 1A, 561B | 189° C. |
| 619 | 2-[(1H-benzimidazol-2-yl)(1-methylpiperidin-4-yloxy)methyl]-5,6,7,8-tetrahydro-1-naphthol | 578 | 125° C. |
| 620 | 2-[(1H-benzimidazol-2-yl)(1-methylpiperidin-4-yloxy)methyl]-6-trifluoromethoxyphenol | 578 | 126° C. |
| 621 | 2-[(1H-benzimidazol-2-yl)(1-methylpiperidin-4-yloxy)methyl]-5-trifluoromethoxyphenol | 578 | 133° C. |
| 622 | 6-[(1H-benzimidazol-2-yl)(1-methylpiperidin-4-yloxy)methyl]-2-fluoro-3,4-dimethylphenol | 578 | 163° C. |
| 623 | 6-[(1H-benzimidazol-2-yl)(1-methylpiperidin-4-yloxy)methyl]-3-fluoro-2-methylphenol | 578 | 97° C. |
| 624 | 6-[(1H-benzimidazol-2-yl)(1-methylpiperidin-4-yloxy)methyl]-2,4-difluoro-3-methylphenol | 578 | 146° C. |
| 625 | 6-[(1H-benzimidazol-2-yl)(1-methylpiperidin-4-yloxy)methyl]-2,3-difluorophenol | 578 | 184° C. |

Further examples can be prepared according to the described general methods:

| Example | Product | General methods | TLC |
|---|---|---|---|
| 450 | (1-{3-[benzothiazol-2-yl(1-methylpiperidin-4-yloxy)methyl]phenyl}-azetidin-3-yl)dimethylamine, oxalate | 165C, 249, 423B | 0.22(A) |
| 452 | 1-{3-[(1H-benzimidazol-2-yl)(1-methylpiperidin-4-yloxy)methyl]phenyl}pyrrolidin-3-ol, oxalate | 423B | 0.18(D) |
| 461 | 2-{(1-methylpiperidin-4-yloxy)[3-(pyrrolidin-3-yloxy)phenyl]methyl}-1H-benzimidazole, dioxalate | 272A, 272B, 258 | 0.04(D) |
| 496 | 2-[(5-chloro-2-fluorophenyl)(1-methylpiperidin-4-yloxy)methyl]-1H-benzimidazole, oxalate | 272A, 272B | 0.14(B) |
| 498 | 2-[(2-fluoro-5-trifluoromethylphenyl)(1-methylpiperidin-4-yloxy)methyl]-1H-benzimidazole, oxalate | 272A, 272B | 0.25(A) |
| 503 | 6-{3-[(1-ethyl-1H-benzimidazol-2-yl)(1-methylpiperidin-4-yloxy)methyl]phenyl}hex-5-ynylamine, oxalate | 194, 189, 472 | 0.08(E) |
| 504 | 2-[(2-fluoro-5-methoxyphenyl)(1-methylpyrrolidin-3-ylmethoxy)methyl]-1H-benzimidazole, oxalate | 165C, 449A | 0.33(E) |
| 517 | 2-[(1-methylpiperidin-4-yloxy)(3-trifluoromethylsulfanylphenyl)methyl]-1H-benzimidazole, oxalate | 272A, 272B | 0.36(A) |
| 518 | 2-[(4-fluoro-3-trifluoromethoxyphenyl)(1-methylpiperidin-4-yloxy)methyl]-1H-benzimidazole, oxalate | 272A, 272B | 0.32(A) |
| 519 | 2-[(2-fluoro-5-propoxyphenyl)(1-methylpiperidin-4-yloxy)methyl]-1H-benzimidazole, oxalate | 272A, 272B | 0.33(A) |
| 597 | 4-[(1H-benzimidazol-2-yl)(1-methylpiperidin-4-yloxy)methyl]phenol | 578 | 0.20(A) |

Eluent A: $CH_2Cl_2$/MeOH/$NH_4OH$ 90/10/0.5
Eluent B: $CH_2Cl_2$/MeOH/$NH_4OH$ 95/5/0.5
Eluent C: $CH_2Cl_2$/MeOH 90/10
Eluent D: $CH_2Cl_2$/MeOH/$NH_4OH$ 90/10/1
Eluent E: $CH_2Cl_2$/MeOH/$NH_4OH$ 80/20/0.5

Further examples can be prepared according to the described general methods:

| Example | Product | General methods |
|---|---|---|
| 491 | 2-{[3-(3,3-difluoropyrrolidin-1-yl)phenyl](1-methylpiperidin-4-yloxy)methyl}-1H-benzimidazole, dioxalate | 272A, 272B |

$^1$H NMR of the base (CDCl$_3$): 9.90 (sl, 1H), 7.69 (sl, 1H), 7.18 (m, 3H), 6.86 (d, 1H), 6.64 (s, 1H), 6.43 (d, 1H), 5.80 (s, 1H), 3.65-3.35 (m, 5H), 2.67 (m, 2H), 2.38 (m, 3H), 2.22 (s, 3H), 2.20-1.60 (m, 5H)

| | | |
|---|---|---|
| 492 | 2-{[3-(5-fluorohexahydrocyclopenta[c]pyrrol-2-yl)phenyl](1-methylpiperidin-4-yloxy)methyl}benzothiazole, dioxalate | 423B |

$^1$H NMR of the base (CDCl$_3$): 7.96 (d, 1H), 7.85 (d, 1H), 7.15-7.50 (m, 3H), 6.90 (d, 1H), 6.80 (s, 1H), 6.57 (d, 1H), 5.85 (s, 1H), 5.25 (d, 1H), 3.66 (m, 1H), 3.33 (m, 2H), 3.17 (m, 2H), 3.00 (m, 2H), 2.73 (m, 2H), 2.30 (s, 3H), 2.40-1.60 (m, 10H).

| | | |
|---|---|---|
| 451 | 6-{3-[(1H-benzimidazol-2-yl)(1-methylpiperidin-4-yloxy)methyl]phenylsulfanyl}hexylamine, oxalate | 432, 150 |

$^1$H NMR (base): 7.65-7.48 (m, 2H), 7.43 (s, 1H), 7.30-7.15 (m, 5H), 5.85 (s, 1H), 3.60-3.45 (m, 1H), 2.86 (t, 2H, J = 7.1 Hz), 2.78-2.60 (m, 4H), 2.23 (s, 3H), 2.18-1.50 (m, 10H), 1.50-1.20 (m, 2H).

| | | |
|---|---|---|
| 457 | 5-{3-[(1H-benzimidazol-2-yl)(1-methylpiperidin-4-yloxy)methyl]phenylsulfanylmethyl}oxazolidin-2-one<br>mp = 109° C. | 359B |
| 458 | N-(6-{3-[(1H-benzimidazol-2-yl)(1-methylpiperidin-4-yloxy)methyl]phenylsulfanyl}hexyl)guanidine, dihydrochloride | 278, 432, 150 |

$^1$H NMR (dmso-d$_6$): 7.65-7.48 (m, 2H), 7.43 (s, 1H), 7.30-7.15 (m, 5H), 5.85 (s, 1H), 3.60-3.45 (m, 1H), 2.86 (t, 2H, J = 7.1 Hz), 2.78-2.60 'm, 4H), 2.23 (s, 3H), 2.18-1.50 (m, 10H), 1.50-1.20 (m, 2H).

| | | |
|---|---|---|
| 473 | 4-{3-[(1H-benzimidazol-2-yl)(1-methylpiperidin-4-yloxy)methyl]phenylsulfanyl}but-2-enylamine<br>MS, [M = H]$^+$ = 423.2 | 437B, 359B, |
| 474 | 4-{3-[(1H-benzimidazol-2-yl)(1-methylpiperidin-4-yloxy)methyl]phenylsulfanyl}but-2-enylamine, oxalate | 437B, 359B, |
| 478 | N-(2-{3-[(1H-benzimidazol-2-yl)(1-methylpiperidin-4-yloxy)methyl]phenylsulfanyl}ethyl)-N-isobutyrylguanidine<br>MS, [M + H]$^+$ = 509.2; [M + Na]$^+$ = 531.1 | 401 |
| 488 | 3-{3-[(1H-benzimidazol-2-yl)(1-methylpiperidin-4-yloxy)methyl]phenyl}allylamine<br>mp = 183° C.; MS, [M + H]$^+$ = 377.3; [M + Na]$^+$ = 399.1 | 437B, 53 |
| 494 | cis-2-{3-[(1H-benzimidazol-2-yl)(1-methylpiperidin-4-yloxy)methyl]phenylsulfanylmethyl}cyclopropylmethylamine<br>mp = 99° C.; MS, [M + H]$^+$ = 437.1; [M + Na]$^+$ = 459.2 | 437B, 359B |
| 499 | N-(3-{3-[(1H-benzimidazol-2-yl)(1-methylpiperidin-4-yloxy)methyl]phenyl}allyl)guanidine, trihydrochloride<br>MS, [M + H]$^+$ = 419.2; [M + Na]$^+$ = 441.3 | 278, 437B, 359B |
| 502 | 2-[(azetidin-3-ylmethoxy)(3-bromophenyl)methyl]-1H-benzimidazole<br>mp = 104° C. | 210, 165D, E |
| 506 | 2-[(3-bromophenyl)(1-methylazetidin-3-ylmethoxy)methyl]-1H-benzimidazole | 165C, 437B, 210, 165D, E |

MS, $^{79}$Br [M + H]$^+$ = 386.1; [M + Na]$^+$ = 408.0; MS, $^{80}$Br [M + H]$^+$ = 388.0; [M + Na]$^+$ = 410.0

| | | |
|---|---|---|
| 512 | 2-[(2,6-difluorophenyl)(1-methylpiperidin-4-yloxy)methyl]-1H-benzimidazole<br>mp = 210° C. | 272A, 1B |
| 513 | 2-[(2-fluoro-4-methylphenyl)(1-methylpiperidin-4-yloxy)methyl]-1H-benzimidazole<br>mp = 85° C. | 272A, 1B |
| 514 | 2-[(5-ethylsulfanyl-2-fluorophenyl)(1-methylpiperidin-4-yloxy)methyl]-1H-benzimidazole<br>mp = 90° C. | 150, 272A, 1B |
| 515 | 2-[(azetidin-3-ylmethoxy)(2-fluoro-5-trifluoromethoxyphenyl)methyl]-1H-benzimidazole, oxalate | 165B, A, D, E |

$^1$H NMR (base): 7.57-7.62 (m, 2H), 7.38-7.52 (m, 1H), 7.25-7.11 (m, 4H), 6.07 (s, 1H), 3.99-3.90 (m, 2H), 3.80-3.74 (m, 2H), 3.64-3.51 (m, 2H), 2.88-3.00 (m, 1H).

| | | |
|---|---|---|
| 516 | 2-[(2-fluoro-5-trifluoromethoxyphenyl)(1-methylazetidin-3-ylmethoxy)methyl]-1H-benzimidazole, oxalate | 165C, B, A, D, E |

$^1$H NMR (base): 7.65-7.48 (m, 2H), 7.38-7.33 (m, 1H), 7.25-7.10 (m, 4H), 6.04 (s, 1H), 3.89-3.70 (m, 2H), 3.44-3.48 (m, 1H), 3.32-3.38 (m, 3H), 2.52-2.76 (m, 1H), 2.44 (m, 3H)

| | | |
|---|---|---|
| 520 | 2-[(3-ethylsulfanyl-2,6-difluorophenyl)(1-methylpiperidin-4-yloxy)methyl]-1H-benzimidazole<br>mp = 150° C. | 150, 272A, 1B |
| 521 | 2-[(2,2-difluorobenzo[1,3]dioxol-5-yl)(1-methylpiperidin-4-yloxy)methyl]-1H-benzimidazole<br>MS, [M + H]$^+$ = 402.1 | 272A, 1B |
| 538 | 2-[(piperidin-4-yloxy)thiophen-3-ylmethyl]-1H-benzimidazole | 165B, A, D, E |

$^1$H NMR: 9.50 (sl, 1H), 7.75 (sl, 1H), 7.48 (sl, 1H), 7.38-7.22 (m, 5H), 7.12-7.05 (m, 1H), 5.98 (s, 1H), 3.75-3.60 (m, 1H), 3.20-3.05 (m, 2H), 2.72-2.55 (m, 2H), 2.10-1.85 (m, 2H), 1.70-1.45 (m, 2H)

-continued

| Example | Product | General methods |
|---|---|---|
| 539 | 2-[(1-methylpiperidin-4-yloxy)thiophen-3-ylmethyl]-1H-benzimidazole | 165C, B, A, D, E |
| | MS, [M + H]$^+$ = 328.03 | |
| 544 | 2-[(piperidin-4-yloxy)thiophen-2-ylmethyl]-1H-benzimidazole | 165B, A, D, E |
| | mp = 185° C. | |
| 546 | 2-[(1-methylpiperidin-4-yloxy)thiophen-2-ylmethyl]-1H-benzimidazole | 165C, B, A, D, E |
| | mp = 85° C. | |

Preparation of Starting Materials

Salicaldehydes can be prepared from the corresponding phenols according to following procedures (non exhaustive):
- with paraformaldehyde, magnesium chloride and triethylamine according *J. Med. Chem.*, 2006, 49 (26), pp 7731-7739.
- protection of phenol with a tetrahydropyranyl (THP) group followed by metalation and addition of dimethylformamide and final THP deprotection according to WO2009/089057
- with the Reimer-Tiemann procedure *Org. React.* 1982, 28, 2)
- with hexamethylenetetramine (Duff reaction, *Organic Syntheses* Coll. Vol. 10, p. 96; Vol. 75, p. 1)

Biological Data

In Vitro Evaluation of Compounds

Membrane Preparation

SH-SY5Y cells stably expressing human H4 receptor are grown until sub-confluence and centrifuged at 300 g 15 minutes at 4° C. Pellets are resuspended in buffer I Tris-HCl 50 mM, MgCl$_2$ 10 mM, NaCl 140 mM, pH=7.4 supplemented by Leupeptin 10 μg/mL, Phenyl Methyl Sulphonyl Fluoride (PMSF) 0.1 mM, Aprotinin 2 μg/mL and Pepstatin 2 μM (or a 1/50 dilution of a mix of protease inhibitors). The obtained suspension is stirred gently and submitted to a 25-26×g mechanic pressure exerted through a syringe. The cell lysate is then centrifuged at 300 g 15 minutes at 4° C. in order to eliminate nucleus and cell scraps. The obtained supernatant is then centrifuged at 48000 g for 30 minutes at 4° C. The final pellet is resuspended in buffer I with a potter homogenizer. Aliquots are frozen in liquid nitrogen and stored until use at −80° C. Protein content is measured by the Bradford method.

GTPγ [$^{35}$S] Binding

Defreezed membranes are diluted at a final concentration of 5 μg/180 μL/well in buffer I supplemented by GDP 10 μM and distributed in 96 well polystyrene microplate. GTPγ [$^{35}$S] labelled ligand (0.2-0.3 nM) is added for additional 30 minutes. After transfer in a Millipore GF/C HTS® microplate, the filtration of the reactional mix is followed by a three times 250 μl wash to stop the reaction.

The filter-bound radioactivity is measured in a liquid scintillation counter Microbeta TRILUX® with 50 μl of scintillation fluid.

GTPγ [$^{35}$S] dependent binding activity is determined in vitro for Histamine, Imetit, R(−)-alpha-methyl-histamine and all our compounds.

Compounds can also be tested against Histamine or Imetit to evaluate their antagonist potential. Results are expressed with IC50 and Ki values.

Membrane Preparation

CHO cells stably expressing human H4 receptor were grown until sub-confluence and centrifuged at 300 g 15 minutes at 4° C. Pellets were resuspended in buffer I Tris-HCl 50 mM, MgCl$_2$ 10 mM, NaCl 140 mM, pH=7.4 supplemented by a 1/50 dilution of a mix of protease inhibitors. The obtained suspension is stirred gently and submitted to a 25-26×g mechanic pressure exerted through a syringe. The cell lysate is then centrifuged at 300 g 15 minutes at 4° C. in order to eliminate nucleus and cell scraps. The obtained supernatant was then centrifuged at 48000 g for 30 minutes at 4° C. The final pellet is resuspended in buffer I with a potter homogenizer. Aliquots were frozen in liquid nitrogen and stored until use at −80° C. Protein content is measured by the Bradford method.

[$^3$H]Histamine Binding

Defreezed membranes were diluted at a final concentration of 20 μg/180 μL/well in a binding buffer containing 50 mM Tris/HCl, 0.5 mM EDTA, pH=7.4 and distributed in 96 well polystyrene microplate. [$^3$H] Histamine labelled ligand (10-15 nM) is added for 60 minutes with compounds at room temperature under continuous stirring. Non specific binding was estimated in the presence of 10 μM BP1.2404 (JNJ 7777120). The reaction was terminated by filtration through GF/B filters pre-soaked 2 hours at 4° C. in 1% polyethyleneimine. Filters were rinsed 3 times with 250 μl of ice cold incubation binding buffer.

The filter-bound radioactivity was measured in a liquid scintillation counter Microbeta TRILUX® with 50 μl of scintillation fluid.

The hH4 binding investigated by use of [$^3$H] Histamine give a Bmax ~1 pmole/mg prot and a Kd ~9 nM.

Racemates described hereabove have been evaluated in the GTPγ [$^{35}$S] assay or in the [$^3$H] histamine binding assay and have been found active with a Ki or IC50 under 1000 nM.

| Example | Activity |
|---|---|
| 1 | B |
| 2 | A |
| 3 | B |
| 4 | A |
| 5 | B |
| 6 | B |
| 7 | B |
| 8 | C |
| 9 | C |
| 10 | C |
| 11 | C |
| 12 | B |
| 13 | B |
| 14 | A |
| 15 | B |
| 16 | C |
| 17 | A |
| 18 | B |
| 19 | B |
| 20 | B |
| 21 | B |

-continued

| Example | Activity |
|---|---|
| 22 | C |
| 23 | C |
| 24 | A |
| 25 | C |
| 26 | C |
| 27 | C |
| 28 | B |
| 29 | A |
| 30 | B |
| 31 | C |
| 32 | B |
| 33 | B |
| 34 | B |
| 35 | A |
| 36 | B |
| 37 | A |
| 38 | B |
| 39 | B |
| 40 | C |
| 41 | C |
| 42 | C |
| 43 | B |
| 44 | A |
| 45 | C |
| 46 | B |
| 47 | C |
| 48 | B |
| 49 | A |
| 50 | C |
| 51 | C |
| 52 | A |
| 53 | B |
| 54 | B |
| 55 | C |
| 56 | B |
| 57 | C |
| 58 | B |
| 59 | C |
| 60 | C |
| 61 | C |
| 62 | C |
| 63 | B |
| 64 | A |
| 65 | C |
| 66 | A |
| 67 | C |
| 68 | B |
| 69 | C |
| 70 | B |
| 71 | B |
| 73 | B |
| 74 | B |
| 75 | C |
| 76 | B |
| 77 | B |
| 78 | B |
| 79 | B |
| 80 | B |
| 81 | B |
| 82 | B |
| 83 | B |
| 84 | A |
| 85 | B |
| 86 | B |
| 87 | B |
| 88 | C |
| 89 | B |
| 90 | B |
| 91 | C |
| 92 | B |
| 93 | B |
| 94 | C |
| 95 | C |
| 96 | B |
| 97 | B |
| 98 | B |
| 99 | B |

-continued

| Example | Activity |
|---|---|
| 100 | B |
| 101 | C |
| 102 | C |
| 103 | B |
| 104 | C |
| 105 | C |
| 106 | B |
| 107 | C |
| 108 | B |
| 109 | B |
| 110 | B |
| 111 | C |
| 112 | A |
| 113 | C |
| 114 | B |
| 115 | B |
| 116 | B |
| 117 | C |
| 118 | C |
| 119 | B |
| 120 | A |
| 121 | B |
| 122 | B |
| 123 | A |
| 124 | C |
| 125 | C |
| 126 | B |
| 127 | B |
| 128 | B |
| 129 | C |
| 130 | B |
| 131 | B |
| 132 | B |
| 133 | B |
| 134 | B |
| 135 | B |
| 136 | B |
| 137 | B |
| 138 | B |
| 139 | C |
| 140 | B |
| 141 | B |
| 142 | B |
| 143 | B |
| 144 | C |
| 145 | B |
| 146 | B |
| 147 | B |
| 148 | B |
| 149 | C |
| 150 | B |
| 151 | B |
| 152 | C |
| 153 | C |
| 154 | B |
| 155 | B |
| 156 | C |
| 157 | B |
| 158 | C |
| 159 | C |
| 160 | C |
| 161 | C |
| 162 | C |
| 163 | C |
| 164 | B |
| 165 | B |
| 166 | C |
| 167 | C |
| 168 | B |
| 169 | A |
| 170 | B |
| 171 | C |
| 172 | B |
| 173 | B |
| 174 | B |
| 175 | B |
| 176 | C |

| Example | Activity |
|---------|----------|
| 177 | B |
| 178 | B |
| 179 | B |
| 180 | C |
| 181 | C |
| 182 | C |
| 183 | B |
| 184 | B |
| 185 | C |
| 186 | A |
| 187 | C |
| 188 | C |
| 189 | B |
| 190 | B |
| 191 | B |
| 192 | B |
| 193 | B |
| 194 | B |
| 195 | B |
| 196 | C |
| 197 | C |
| 198 | C |
| 199 | B |
| 200 | B |
| 201 | C |
| 202 | C |
| 203 | A |
| 204 | B |
| 205 | A |
| 206 | B |
| 207 | A |
| 208 | B |
| 209 | B |
| 210 | A |
| 211 | B |
| 212 | A |
| 213 | B |
| 214 | B |
| 215 | B |
| 216 | B |
| 217 | B |
| 218 | C |
| 219 | A |
| 220 | C |
| 221 | B |
| 222 | B |
| 223 | B |
| 224 | B |
| 225 | B |
| 226 | B |
| 227 | C |
| 228 | C |
| 229 | C |
| 231 | B |
| 232 | A |
| 233 | B |
| 234 | B |
| 235 | A |
| 236 | B |
| 237 | B |
| 238 | A |
| 239 | A |
| 240 | B |
| 241 | B |
| 242 | A |
| 243 | B |
| 244 | B |
| 245 | B |
| 246 | B |
| 247 | B |
| 248 | B |
| 249 | B |
| 250 | B |
| 251 | A |
| 252 | A |
| 253 | C |
| 254 | C |
| 255 | C |
| 256 | C |
| 257 | A |
| 258 | B |
| 259 | B |
| 260 | C |
| 261 | B |
| 262 | B |
| 263 | A |
| 264 | B |
| 265 | B |
| 266 | B |
| 267 | C |
| 268 | B |
| 269 | C |
| 270 | A |
| 271 | C |
| 272 | A |
| 273 | A |
| 274 | B |
| 275 | B |
| 276 | C |
| 277 | B |
| 278 | C |
| 279 | A |
| 280 | B |
| 281 | A |
| 282 | A |
| 283 | C |
| 284 | B |
| 285 | A |
| 286 | B |
| 287 | C |
| 288 | A |
| 289 | C |
| 290 | B |
| 291 | B |
| 292 | B |
| 293 | B |
| 294 | C |
| 295 | B |
| 296 | B |
| 297 | B |
| 298 | A |
| 299 | A |
| 300 | B |
| 301 | C |
| 302 | C |
| 303 | B |
| 304 | C |
| 305 | C |
| 306 | B |
| 307 | A |
| 308 | B |
| 309 | B |
| 310 | B |
| 311 | B |
| 312 | B |
| 313 | B |
| 314 | C |
| 315 | A |
| 316 | B |
| 317 | A |
| 318 | C |
| 319 | C |
| 320 | C |
| 321 | C |
| 322 | A |
| 323 | A |
| 324 | B |
| 325 | C |
| 326 | C |
| 327 | B |
| 328 | C |
| 330 | B |
| 331 | B |
| 332 | A |

-continued

| Example | Activity |
|---|---|
| 333 | B |
| 334 | B |
| 335 | B |
| 336 | B |
| 337 | C |
| 338 | B |
| 339 | B |
| 340 | C |
| 341 | B |
| 342 | B |
| 343 | B |
| 344 | B |
| 345 | B |
| 346 | B |
| 347 | A |
| 348 | A |
| 349 | B |
| 350 | A |
| 351 | A |
| 352 | B |
| 353 | B |
| 354 | C |
| 355 | B |
| 356 | A |
| 357 | B |
| 358 | C |
| 359 | C |
| 360 | A |
| 361 | A |
| 362 | A |
| 363 | B |
| 364 | A |
| 365 | B |
| 366 | C |
| 367 | B |
| 368 | C |
| 369 | A |
| 370 | A |
| 371 | C |
| 372 | C |
| 373 | C |
| 374 | C |
| 375 | A |
| 376 | A |
| 377 | B |
| 378 | A |
| 379 | A |
| 380 | B |
| 381 | C |
| 382 | C |
| 383 | B |
| 384 | B |
| 385 | B |
| 386 | C |
| 387 | C |
| 388 | A |
| 389 | B |
| 390 | C |
| 391 | A |
| 392 | A |
| 393 | C |
| 394 | A |
| 395 | B |
| 396 | A |
| 397 | B |
| 398 | B |
| 399 | B |
| 400 | C |
| 401 | B |
| 402 | B |
| 403 | B |
| 404 | B |
| 405 | B |
| 406 | C |
| 407 | C |
| 408 | B |
| 409 | B |

-continued

| Example | Activity |
|---|---|
| 410 | B |
| 411 | A |
| 412 | A |
| 413 | B |
| 414 | B |
| 415 | B |
| 416 | B |
| 417 | A |
| 418 | C |
| 419 | A |
| 421 | C |
| 422 | C |
| 423 | B |
| 424 | B |
| 425 | C |
| 426 | B |
| 427 | B |
| 428 | B |
| 429 | B |
| 430 | C |
| 431 | C |
| 433 | C |
| 435 | C |
| 436 | C |
| 437 | C |
| 438 | C |
| 439 | C |
| 440 | C |
| 441 | C |
| 442 | C |
| 443 | C |
| 444 | B |
| 445 | B |
| 446 | B |
| 447 | A |
| 448 | B |
| 449 | C |
| 450 | A |
| 451 | B |
| 452 | B |
| 453 | C |
| 454 | C |
| 455 | C |
| 456 | A |
| 457 | C |
| 458 | B |
| 459 | C |
| 460 | A |
| 461 | B |
| 462 | B |
| 463 | A |
| 464 | C |
| 465 | C |
| 466 | C |
| 467 | C |
| 468 | B |
| 469 | A |
| 470 | B |
| 471 | B |
| 472 | B |
| 473 | C |
| 474 | C |
| 475 | B |
| 476 | C |
| 477 | A |
| 478 | B |
| 479 | C |
| 480 | B |
| 481 | A |
| 482 | C |
| 483 | B |
| 484 | C |
| 485 | A |
| 486 | C |
| 487 | C |
| 488 | A |
| 489 | C |

| Example | Activity |
|---|---|
| 490 | B |
| 491 | A |
| 492 | A |
| 493 | C |
| 494 | C |
| 495 | C |
| 496 | B |
| 497 | A |
| 498 | B |
| 499 | C |
| 500 | B |
| 501 | B |
| 502 | A |
| 503 | B |
| 504 | C |
| 505 | A |
| 506 | B |
| 507 | C |
| 508 | C |
| 509 | C |
| 510 | B |
| 511 | B |
| 512 | C |
| 513 | C |
| 514 | C |
| 515 | A |
| 516 | B |
| 517 | C |
| 518 | A |
| 519 | C |
| 520 | B |
| 521 | A |
| 522 | C |
| 523 | C |
| 524 | B |
| 525 | B |
| 526 | C |
| 527 | C |
| 528 | B |
| 529 | B |
| 530 | A |
| 531 | C |
| 532 | B |
| 533 | C |
| 534 | B |
| 535 | B |
| 536 | C |
| 537 | A |
| 538 | A |
| 539 | B |
| 540 | B |
| 541 | C |
| 542 | C |
| 543 | C |
| 544 | A |
| 545 | B |
| 546 | B |
| 547 | A |
| 548 | C |
| 549 | A |
| 550 | C |
| 551 | B |
| 552 | B |
| 553 | A |
| 554 | B |
| 555 | C |
| 556 | C |
| 557 | C |
| 558 | C |
| 559 | C |
| 560 | B |
| 561 | C |
| 562 | C |
| 563 | B |
| 564 | C |
| 565 | B |
| 566 | C |
| 567 | B |
| 568 | C |
| 569 | C |
| 570 | B |
| 571 | C |
| 572 | C |
| 573 | B |
| 574 | C |
| 575 | C |
| 576 | C |
| 577 | B |
| 578 | C |
| 579 | A |
| 580 | A |
| 581 | C |
| 582 | C |
| 583 | B |
| 584 | C |
| 585 | C |
| 586 | C |
| 587 | C |
| 588 | C |
| 589 | A |
| 590 | A |
| 591 | B |
| 592 | B |
| 593 | C |
| 594 | C |
| 595 | B |
| 596 | C |
| 597 | A |
| 598 | B |
| 599 | B |
| 600 | C |
| 601 | C |
| 602 | B |
| 603 | B |
| 604 | B |
| 605 | C |
| 606 | B |
| 607 | A |
| 608 | B |
| 609 | B |
| 610 | A |
| 611 | C |
| 612 | C |
| 613 | C |
| 614 | C |
| 615 | B |
| 616 | C |
| 617 | C |
| 618 | C |
| 619 | B |
| 620 | C |
| 621 | C |
| 622 | B |
| 623 | C |
| 624 | C |
| 625 | C |
| 627 | C |

A: Ki or IC50 <1000 nM
B: Ki or IC50 <300 nM
C: Ki or IC50 <30 nM

The invention claimed is:
1. A combination of a compound of formula (I) and one or more therapeutic agent(s),
  wherein said compound of formula (I) being:

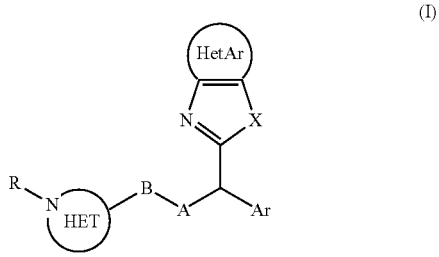

wherein:
X represents NR', S or O;
HetAr represents a phenyl or heteroaryl, optionally substituted with one or more substituents chosen from halogen, OR" alkyl, cyano, NR"R"', —COR", —COOR", —CONR"R"', aryl, -alkylaryl;
R represents a lower alkyl or H
R' represents H, lower alkyl, alkoxyalkyl or alkoxycarbonyl;
R", R"' identical or different independently represent H or alkyl;
HET representing a non aromatic monocyclic heterocycle containing at least one nitrogen atom, which is linked to R;
B represents a single bond or an -alkyl- group;
A represents O, NH or S;
Ar is a mono or polycyclic aromatic or a mono or polycyclic heteroaromatic which can be optionally substituted with one or more of:
halo; azido; cyano; hydroxy; nitro;
alkyl; alkoxy; alkylsulfanyl; alkenyl; alkynyl; alkenyloxy; alkenyloxy; alkenylsulfanyl; alkynylsulfanyl; cycloalkoxy; cyloalkylalkyl;
  whose alkyl, alkenyl, alkynyl or cycloalkyl part can be substituted with one or more of halo, hydroxy, polyhydroxy, alkoxy, hydroxyalkoxy, cyano, amino, aminoalkyl, alkylamino, dialkylamino, aminoalkylamino, aminoalkylaminocarbonyl, alkoxycarbonylamino, diarylmethylimino (where aryl is optionally substituted with one or more of hydroxy or halo), cycloalkenylimino (where cylalkenyl is optionally substituted with one or more of alkyl, OH), alkylsulfanyl, alkylsulfinyl, alkylsulfonyl, cycloalkyl, polycycloalkyl, cycloalkenyl, polycycloalkenyl, guanidino, alkylcarbonylguanidino, acylguanidino, cyanoguanidino, alkoxycarbonylguanidino, alkoxycarbonyl, alkoxycarbonylalkylamino, alkoxycarbonylalkylcycloalkyl, alkoxycarbonylheterocyclyl, aminocarbonyl, alkylaminocarbonyl, alkylcarbonyl, alkylcarbonylalkoxy, aryloxy, arylsulfanyl, arylsulfinyl, arylsulfonyl, heteroaryl, heterocyclyl (heterocyclyl being optionally substituted with one or more of oxo, amino, imino), heteroaryloxy, heterocyclyloxy, heteroarylamino, heterocyclylamino, hydrazinocarbonyl, hydroxyalkylcycloalkyl, N-alkyl(thioureido), phthalimido, ureido, oxocycloalkenylamino substituted with amino, carbamimidoylheterocyclyl;
amino; alkylamino; alkylcarbonyl; alkoxycarbonyl; alkylsulfanyl; alkylsulfinyl; alkylsulfonyl; alkylsulfonyloxy whose alkyl can be substituted with one or more of halo;
aminocarbonyl which can be N-substituted with one or two of alkyl, aryl, arylalkyl;
aryl; arylalkyl; aryloxy; arylalkoxy; arylalkylamino; arylalkylsulfanyl; heteroaryl; heteroaryloxy
  whose aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, alkylsulfinyl, alkylsulfonyl, nitro, cyanoalkyl, or fused with a non aromatic heterocycle;
heterocyclyl; heterocyclyloxy; heterocyclylalkoxy
  whose heterocycle can be substituted with one or more of halogenoalkyl, acylamino, acyloxy, amino, alkyl, alkylamino, dialkylamino, aminoalkyl, oxo, carbamimidoyl, halo, hydroxy, hydroxyalkyl, hydroxymethyl, alkoxcarbonyl;
or
fused with a non aromatic heterocycle (optionally substituted with one or more of halogens) or carbocycle;
as well as their enantiomers, diastereomers, mixtures thereof and pharmaceutically acceptable salts, tautomers, hydrates and solvates; and
wherein said one or more therapeutic agent(s) selected from the group consisting of:
Histamine $H_1$, $H_2$ or $H_3$ receptor antagonists,
Leukotriene antagonists,
5-Lipoxygenase (5-LO) inhibitors or 5-lipoxygenase activating protein (FLAP) antagonists
$CX_1$- and $\alpha_2$-adrenoceptor agonist vasoconstrictor sympathomimetic agents for decongestant use,
Xanthines, such as theophylline and aminophylline,
Steroidal and non-steroidal antiinflammatories, such as sodium cromoglycate and nedocromil sodium,
Ketotifen,
COX-1 inhibitors (NSAIDs) and COX-2 selective inhibitors,
Immunosuppressants, and
mucolytics or anti-tussive agents.
2. The combination according to claim 1, wherein the $H_1$ receptor antagonist is selected from the group consisting of cetirizine, desloratadine, bepotastine and doxepin.
3. The combination according to claim 1, wherein:
X represents NR' or S;
HetAr represents a phenyl, optionally substituted with one or more substituents chosen from hydrogen, halogen, amino, alkyl;
R represents H or a lower alkyl;
R' represents H, alkyl, alkoxyalkyl, alkoxycarbonyl;
HET representing a non aromatic 5 or 6 membered heterocycle containing one nitrogen atom, which is linked to R;
B represents a single bond or a —CH$_2$— group;
A represents O, NH or S;
Ar is a thienyl, phenyl or naphtyl or 5 to 6 membered heteroaromatic where the phenyl can be optionally substituted with one or more of:
halo; azido; cyano; hydroxy; nitro; alkyl;
alkoxy; alkylsulfanyl; alkenyl; alkenylsulfanyl; alkynyl; alkenyloxy; alkenyloxy; cycloalkoxy; cyloalkylalkyl
  whose alkyl, alkenyl, alkynyl or or cycloalkyl part can be substituted with one or more of halo, hydroxy, alkoxy, hydroxyalkoxy, cyano, amino, aminoalkyl, alkylamino, aminoalkylamino, dialkylamino, aminoalkylaminocarbonyl, alkoxycarbonylamino, diarylmethylimino (where aryl is optionally substituted with one or more of hydroxy or halo), cycloalkenylimino (where cylalkenyl is optionally substituted with one or more of alkyl, OH), alkylsulfanyl, alkylsulfonyl, cycloalkyl, (poly)cycloalkenyl, guanidino, alkylcarbonylguanidino, acylguanidino, alkoxycarbonylguanidino, alkoxycarbonyl, alkoxycarbonylalkylamino, alkoxycarbonylheterocyclyl, aminocarbonyl, alkylaminocarbonyl, alkylcarbonyl, alkylcarbonylalkoxy, aryloxy, arylsulfonyl, heteroaryl, heterocyclyl (heterocyclyl being optionally substituted with one or more of oxo, amino, imino), heterocyclylamino, hydrazinocarbonyl, N-alkyl(thioureido), phthalimido, ureido, oxocycloalkenylamino substituted with amino, carbamimidoylheterocyclyl;

amino; alkylamino; alkylcarbonyl; alkoxycarbonyl; alkylsulfanyl; alkylsulfonyl; alkylsulfonyloxy
whose alkyl can be substituted with one or more of halo;
aminocarbonyl which can be N-substituted with one or two of alkyl, aryl, arylalkyl;
aryl; arylalkyl; aryloxy; arylalkoxy; arylalkylsulfanyl; heteroaryl; heteroaryloxy
  whose aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, nitro, cyanoalkyl, or is fused with a non aromatic heterocycle;
heterocyclyloxy; heterocyclylalkoxy; heterocyclyl
  whose heterocycle can be substituted with one or more of halo, halogenoalkyl, acylamino, acyloxy, amino, alkyl, alkylamino, dialkylamino, aminoalkyl, oxo, carbamimidoyl, hydroxy, hydroxyalkyl;
or
fused with a non aromatic heterocycle (optionally substituted with one or more of halogens) or carbocycle;
as well as their enantiomers, diastereomers, mixtures thereof and pharmaceutically acceptable salts, tautomers, hydrates and solvates.

4. The combination according to claim 1, wherein X represents NH or S.

5. The combination according to claim 1, wherein HetAr is phenyl.

6. The combination according to claim 1, wherein R represents methyl.

7. The combination according to claim 1, wherein B represents a single bond.

8. The combination according to claim 1, wherein Ar is a phenyl which can be optionally substituted with one or more of:

halo; azido; cyano; hydroxy; nitro; alkyl;
alkoxy; alkylsulfanyl; alkenyl; alkynyl; alkenyloxy; alkenyloxy;
  whose alkyl; alkenyl or alkynyl part can be substituted with one or more of halo, hydroxy, alkoxy, hydroxyalkoxy, cyano, amino, alkylamino, aminoalkylamino, alkylsulfanyl, alkylsulfonyl, cycloalkyl, (poly)cycloalkenyl, guanidino, acylguanidino, alkoxycarbonylguanidino, alkoxycarbonyl, alkoxycarbonylalkylamino, alkoxycarbonylheterocyclyl, aminocarbonyl, alkylaminocarbonyl, alkylcarbonyl, alkylcarbonylalkoxy, aryloxy, arylsulfonyl, heteroaryl, heterocyclyl, heterocyclylamino, hydrazinocarbonyl, N-alkyl(thioureido), phthalimido, ureido, oxocycloalkenylamino substituted with amino, carbamimidoylheterocyclyl;
amino; alkylamino; alkylcarbonyl; alkoxycarbonyl; alkylsulfanyl; alkylsulfonyl; alkylsulfonyloxy
whose alkyl can be substituted with one or more of halo;
aminocarbonyl which can be N-substituted with one or two of alkyl, aryl, arylalkyl; aryl; aryloxy; arylalkoxy; arylalkylsulfanyl; heteroaryl
  whose aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, nitro, cyanoalkyl, or is fused with a non aromatic heterocycle; heterocyclyloxy; heterocyclylalkoxy
  whose heterocycle can be substituted with one or more of acylamino, acyloxy, amino, alkyl, carbamimidoyl, hydroxy, hydroxyalkyl;
or fused with a non aromatic heterocycle.

9. The combination according to claim 1, wherein the compound of formula (I) is selected from the group consisting of:

2-[(1-methylpiperidin-4-yloxy)phenylmethyl]benzothiazole
2-[(1-methylpyrrolidin-3-yloxy)phenylmethyl]benzothiazole
2-[(4-fluorophenyl)(1-methylpiperidin-4-yloxy)methyl]benzothiazole
2-[(4-chlorophenyl)(1-methylpiperidin-4-yloxy)methyl]benzothiazole
2-[(3-fluorophenyl)(1-methylpiperidin-4-yloxymethyl]benzothiazole
2-[(2-fluorophenyl)(1-methylpiperidin-4-yloxy)methyl]benzothiazole
2-[(1-methylpiperidin-4-yloxy)-p-tolylmethyl]benzothiazole
2-[(1-methylpiperidin-4-yloxy)(m-tolyl)methyl]benzothiazole
(benzothiazol-2-yl-phenylmethyl)(1-methylpiperidin-4-yl)amine
2-[(2,3-dihydrobenzo[1,4]dioxin-6-yl)(1-methylpiperidin-4-yloxy)methyl]benzothiazole
2-[(3-methoxyphenyl)(1-methylpiperidin-4-yloxy)methyl]benzothiazole
2-[(2,4-difluorophenyl)(1-methylpiperidin-4-yloxy)methyl]benzothiazole
2-[(1-methylpiperidin-4-yloxy)thiophen-2-ylmethyl]benzothiazole
2-[(4-methoxyphenyl)(1-methylpiperidin-4-yloxy)methyl]benzothiazole
2-[(3,5-difluorophenyl)(1-methylpiperidin-4-yloxy)methyl]benzothiazole
2-[(1-methylpiperidin-4-yloxy)thiophen-3-ylmethyl]benzothiazole
2-[(1-methylpiperidin-4-yloxy)naphthalen-1-ylmethyl]benzothiazole
2-[(1-methylpiperidin-4-yloxy)naphthalen-2-ylmethyl]benzothiazole
2-[(1-methylpiperidin-4-yloxy)(5-methylthiophen-2-yl)methyl]benzothiazole
2-[benzo[1,3]dioxol-5-yl(1-methylpiperidin-4-yloxy)methyl]benzothiazole
[(benzothiazol-2-yl)(m-tolyl)methyl](1-methylpiperidin-4-yl)amine
2-[(3-allyloxyphenyl)(1-methylpiperidin-4-yloxy)methyl]benzothiazole
2-[(1-methylpiperidin-4-yloxy)(3-trifluoromethoxyphenyl)methyl]benzothiazole
2-[(1-methylpiperidin-4-yloxy)(4-trifluoromethoxyphenyl)methyl]benzothiazole
[benzothiazol-2-yl(3-methoxyphenyl)methyl](1-methylpiperidin-4-yl)amine 2-[(1-methylpiperidin-4-yloxy)(3-propoxy-phenyl)methyl]benzothiazole
2-[(3-bromo-phenyl)(1-methylpiperidin-4-yloxy)methyl]benzothiazole
2-[(1-methylpiperidin-4-yloxy)(3-phenoxy-phenyl)methyl]benzothiazole
5-methyl-2-[(1-methylpiperidin-4-yloxy)phenylmethyl]benzothiazole
2-[(1-methylpiperidin-4-yloxy)phenylmethyl]-1H-benzimidazole
2-[(1-methylpiperidin-4-yloxy)(3-trifluoromethylphenyl)methyl]benzothiazole
2-[(2,3-dihydrobenzofuran-5-yl)(1-methylpiperidin-4-yloxy)methyl]benzothiazole
5-fluoro-2-[(1-methylpiperidin-4-yloxy)phenylmethyl]benzothiazole
2-[(4-fluoro-3-methylphenyl)(1-methylpiperidin-4-yloxy)methyl]benzothiazole
[benzothiazol-2-yl(4-fluoro-3-methyl-phenyl)methyl](1-methylpiperidin-4-yl)amine
(benzothiazol-2-yl-p-tolylmethyl)(1-methylpiperidin-4-yl)amine
[(benzofuran-2-yl)(benzothiazol-2-yl)methyl](1-methylpiperidin-4-yl)amine
2-[(3-fluoro-5-methylphenyl)(1-methylpiperidin-4-yloxy)methyl]benzothiazole
[(1H-benzimidazol-2-yl)phenylmethyl](1-methylpiperidin-4-yl)amine
2-[(3-fluoro-5-methoxyphenyl)(1-methylpiperidin-4-yloxy)methyl]benzothiazole
2-[(3-iodophenyl)(1-methylpiperidin-4-yloxy)methyl]benzothiazole
[benzothiazol-2-yl(3-propoxyphenyl)methyl](1-methylpiperidin-4-yl)amine
[benzothiazol-2-yl(3-fluoro-5-methoxyphenyl)methyl](1-methylpiperidin-4-yl)amine
[benzothiazol-2-yl(3-fluoro-5-methylphenyl)methyl](1-methylpiperidin-4-yl)amine
2-[(3-benzyloxyphenyl)(1-methylpiperidin-4-yloxy)methyl]benzothiazole
2-[benzofuran-5-yl(1-methylpiperidin-4-yloxy)methyl]benzothiazole
2-[(3-ethoxyphenyl)(1-methylpiperidin-4-yloxy)methyl]benzothiazole
[benzothiazol-2-yl(3-iodophenyl)methyl](1-methylpiperidin-4-yl)amine
2-[(1-methylpiperidin-4-yloxy)(3-propoxyphenyl)methyl]-1H-benzimidazole
[(1H-benzimidazol-2-yl)(3-propoxyphenyl)methyl](1-methylpiperidin-4-yl)amine
2-[(3-iodophenyl)(1-methylpiperidin-4-yloxy)methyl]-1H-benzimidazole
(benzothiazol-2-ylpyridin-3-ylmethyl)(1-methylpiperidin-4-yl)amine
2-[biphenyl-3-yl(1-methylpiperidin-4-yloxy)methyl]benzothiazole
{3'-[benzothiazol-2-yl(1-methylpiperidin-4-yloxymethyl]biphenyl-3-yl}methanol
2-[(3-isopropoxyphenyl)(1-methylpiperidin-4-yloxy)methyl]benzothiazole
[benzothiazol-2-yl(3-propoxyphenyl)methyl](1-methylpiperidin-4-yl)amine
[benzothiazol-2-yl(3-propoxyphenyl)methyl](1-methylpiperidin-4-yl)amine
[benzothiazol-2-yl(1H-pyrrol-2-yl)methyl](1-methylpiperidin-4-yl)amine
[(1H-benzimidazol-2-yl)(3-trifluoromethylphenyl)methyl](1-methylpiperidin-4-yl)amine
[(1H-benzimidazol-2-yl)(3-trifluoromethoxyphenyl)methyl](1-methylpiperidin-4-yl)amine
[(1H-benzimidazol-2-yl)(3-ethylphenyl)methyl](1-methylpiperidin-4-yl)amine
3-[benzothiazol-2-yl(1-methylpiperidin-4-yloxy)methyl]phenol
2-[(1-methylpiperidin-4-yloxy)(3-pyridin-3-ylphenyl)methyl]benzothiazole
[(1H-benzimidazol-2-yl)(3-bromophenyl)methyl](1-methylpiperidin-4-yl)amine
[(1H-benzimidazol-2-yl)(3-benzyloxyphenyl)methyl](1-methylpiperidin-4-yl)amine
[(1H-benzimidazol-2-yl)(3-isopropylphenyl)methyl](1-methylpiperidin-4-yl)amine
[(1H-benzimidazol-2-yl)(3-isobutoxyphenyl)methyl](1-methylpiperidin-4-yl)amine
{(1H-benzimidazol-2-yl)[3-(3-methylbutoxy)phenyl]methyl}(1-methylpiperidin-4-yl)amine
[(1H-benzimidazol-2-yl)(3-butoxyphenyl)methyl](1-methylpiperidin-4-yl)amine
[(1H-benzimidazol-2-yl)(3-methoxyphenyl)methyl](1-methylpiperidin-4-yl)amine
trifluoromethanesulfonic acid 3-[benzothiazol-2-yl(1-methylpiperidin-4-yloxy)methyl]phenyl ester
trifluoromethanesulfonic acid 3-[benzothiazol-2-yl(1-methylpiperidin-4-yloxy)methyl]phenyl ester
[(1H-benzimidazol-2-yl)(3-cyclohexyl methoxyphenyl)methyl](1-methylpiperidin-4-yl)amine
[(1H-benzimidazol-2-yl)(3-fluorophenyl)methyl](1-methylpiperidin-4-yl)amine
[(1H-benzimidazol-2-yl)(3-methylsulfanylphenyl)methyl](1-methylpiperidin-4-yl)amine
[(1H-benzimidazol-2-yl)(3-hexylphenyl)methyl](1-methylpiperidin-4-yl)amine
[(1H-benzimidazol-2-yl)(3-isopropoxyphenyl)methyl](1-methylpiperidin-4-yl)amine
2-[(3-bromophenyl)(1-methylpiperidin-4-yloxy)methyl]-1H-benzimidazole
3'-[benzothiazol-2-yl(1-methylpiperidin-4-yloxy)methyl]biphenyl-3-ylamine
2-[(3-butylphenyl)(1-methylpiperidin-4-yloxy)methyl]benzothiazole
2-[biphenyl-3-yl(1-methylpiperidin-4-yloxy)methyl]-1H-benzimidazole
[benzothiazol-2-yl(3-bromophenyl)methyl](1-methylpiperidin-4-yl)amine
[(1H-benzimidazol-2-yl)(3-ethoxyphenyl)methyl](1-methylpiperidin-4-yl)amine
[(1H-benzimidazol-2-yl)(m-tolyl)methyl](1-methylpiperidin-4-yl)amine
[(1H-benzimidazol-2-yl)(3-phenoxyphenyl)methyl](1-methylpiperidin-4-yl)amine
{3'-[(1H-benzimidazol-2-yl)(1-methylpiperidin-4-yloxy)methyl]biphenyl-3-yl}methanol
3'-[(1H-benzimidazol-2-yl)(1-methylpiperidin-4-yloxy)methyl]biphenyl-3-ylamine
[benzothiazol-2-yl(3-isopropoxyphenyl)methyl](1-methylpiperidin-4-yl)amine
2-[(1-methylpiperidin-4-yloxy)(3-pyridin-3-ylphenyl)methyl]-1H-benzimidazole
1-{3-[(1H-benzimidazol-2-yl)(1-methylpiperidin-4-ylamino)methyl]phenyl}ethanone
[benzothiazol-2-yl(3-butoxyphenyl)methyl](1-methylpiperidin-4-yl)amine 2-[(3-butoxyphenyl)(1-methylpiperidin-4-yloxy)methyl]
benzothiazole
[benzothiazol-2-yl(3-cyclohexylmethoxyphenyl)methyl]
(1-methylpiperidin-4-yl)amine
[(1H-benzimidazol-2-yl)biphenyl-3-ylmethyl](1-methylpiperidin-4-yl)amine
[(1H-benzimidazol-2-yl)(3-pentyloxyphenyl)methyl](1-methylpiperidin-4-yl)amine
2-[(2'-methoxybiphenyl-3-yl)(1-methylpiperidin-4-yloxy)methyl]benzothiazole
2-[(1-methylpiperidin-4-yloxy)(3'-nitrobiphenyl-3-yl)methyl]benzothiazole
{3'-[benzothiazol-2-yl(1-methylpiperidin-4-yloxy)methyl]biphenyl-3-yl}acetonitrile
2-[(3'-methoxybiphenyl-3-yl)(1-methylpiperidin-4-yloxy)methyl]benzothiazole
2-[(4'-methoxybiphenyl-3-yl)(1-methylpiperidin-4-yloxy)methyl]benzothiazole
[benzothiazol-2-yl(3-benzyloxyphenyl)methyl](1-methylpiperidin-4-yl)amine
(benzothiazol-2-ylbiphenyl-3-ylmethyl)(1-methylpiperidin-4-yl)amine
{(1H-benzimidazol-2-yl)[3-(4-fluorobenzyloxy)phenyl]methyl}(1-methylpiperidin-4-yl)amine
[(1H-benzimidazol-2-yl)(3-benzylsulfanylphenyl)methyl](1-methylpiperidin-4-yl)amine
{(1H-benzimidazol-2-yl)[3-(3-fluorobenzyloxy)phenyl]methyl}(1-methylpiperidin-4-yl)amine
{(1H-benzimidazol-2-yl)[3-(2-phenoxyethoxy)phenyl]methyl}(1-methylpiperidin-4-yl)amine
[benzothiazol-2-yl(3-benzylsulfanylphenyl)methyl](1-methylpiperidin-4-yl)amine
1-{3'-[(1H-benzimidazol-2-yl)(1-methylpiperidin-4-yloxy)methyl]biphenyl-4-yl}ethanone
2-[(3'-fluoro-biphenyl-3-yl)(1-methylpiperidin-4-yloxy)methyl]-1H-benzimidazole
1-{3'-[(1H-benzimidazol-2-yl)(1-methylpiperidin-4-yloxy)methyl]biphenyl-3-yl}ethanone
[benzothiazol-2-yl(3-methylsulfanylphenyl)methyl](1-methylpiperidin-4-yl)amine
[(3-allyloxyphenyl)(1H-benzimidazol-2-yl)methyl](1-methylpiperidin-4-yl)amine
{(1H-benzimidazol-2-yl)[3-(2-fluorobenzyloxy)phenyl]methyl}(1-methylpiperidin-4-yl)amine
2-[(1-methylpiperidin-4-yloxy)(2'-methylsulfanylbiphenyl-3-yl)methyl]-1H-benzimidazole
2-[(4'-fluorobiphenyl-3-yl)(1-methylpiperidin-4-yloxy)methyl]-1H-benzimidazole
2-[(1-methylpiperidin-4-yloxy)(3'-methylsulfanylbiphenyl-3-yl)methyl]-1H-benzimidazole
2-[(3-iodophenyl)(1-methylpiperidin-4-yloxy)methyl]benzothiazole
2-[(3-iodophenyl)(1-methylpiperidin-4-yloxy)methyl]benzothiazole
2-[(1-methylpiperidin-4-yloxy)(4'-trifluoromethylbiphenyl-3-yl)methyl]-1H-benzimidazole
{(1H-benzimidazol-2-yl)[3-(tetrahydropyran-2-yloxy)phenyl]methyl}(1-methylpiperidin-4-yl)amine
2-[(2'-chlorobiphenyl-3-yl)(1-methylpiperidin-4-yloxy)methyl]-1H-benzimidazole
2-[(3',4'-dichlorobiphenyl-3-yl)(1-methylpiperidin-4-yloxy)methyl]-1H-benzimidazole
{3'-[(1H-benzimidazol-2-yl)(1-methylpiperidin-4-yloxy)methyl]biphenyl-2-yl}methanol
{(1H-benzimidazol-2-yl)[3-(4-methoxybenzyloxy)phenyl]methyl}(1-methylpiperidin-4-yl)amine
{(1H-benzimidazol-2-yl)[3-(3-methoxybenzyloxy)phenyl]methyl}(1-methylpiperidin-4-yl)amine
3-[(1H-benzimidazol-2-yl)(1-methylpiperidin-4-ylamino)methyl]phenol
{3'-[benzothiazol-2-yl(1-methylpiperidin-4-yloxy)methyl]biphenyl-2-yl}methanol
2-[(1-methylpiperidin-4-yloxy)(3'-methylsulfanylbiphenyl-3-yl)methyl]benzothiazole
{(1H-benzimidazol-2-yl)[3-(2-methylbenzyloxy)phenyl]methyl}(1-methylpiperidin-4-yl)amine
{(1H-benzimidazol-2-yl)[3-(4-methylbenzyloxy)phenyl]methyl}(1-methylpiperidin-4-yl)amine
[(1H-benzimidazol-2-yl)(3-nitrophenyl)methyl](1-methylpiperidin-4-yl)amine
[(3-azidophenyl)(1H-benzimidazol-2-yl)methyl](1-methylpiperidin-4-yl)amine
2-[(3',4'-dichlorobiphenyl-3-yl)(1-methylpiperidin-4-yloxy)methyl]benzothiazole
{(1H-benzimidazol-2-yl)[3-(2-ethoxyethoxy)phenyl]methyl}(1-methylpiperidin-4-yl)amine
[(1H-benzimidazol-2-yl)(3-pent-4-enyloxyphenyl)methyl](1-methylpiperidin-4-yl)amine
2-[(4'-fluorobiphenyl-3-yl)(1-methylpiperidin-4-yloxy)methyl]benzothiazole
2-[(2'-fluorobiphenyl-3-yl)(1-methylpiperidin-4-yloxy)methyl]benzothiazole
{3'-[(1H-benzimidazol-2-yl)(1-methylpiperidin-4-yloxy)methyl]biphenyl-4-yl}carbamic acid tert-butyl ester
2-[(3'-fluorobiphenyl-3-yl)(1-methylpiperidin-4-yloxy)methyl]benzothiazole
2-[(1-methylpiperidin-4-yloxy)(4'-trifluoromethylbiphenyl-3-yl)methyl]benzothiazole
2-[(1-methylpiperidin-4-yloxy)(2',3',4'-trifluorobiphenyl-3-yl)methyl]benzothiazole
2-[(2'-fluorobiphenyl-3-yl)(1-methylpiperidin-4-yloxy)methyl]-1H-benzimidazole
{3'-[benzothiazol-2-yl(1-methylpiperidin-4-yloxy)methyl]biphenyl-4-yl}carbamic acid tert-butyl ester
[(1H-benzimidazol-2-yl)(3-furan-2-ylphenyl)methyl](1-methylpiperidin-4-yl)amine
[(1H-benzimidazol-2-yl)(3-but-3-enyloxyphenyl)methyl](1-methylpiperidin-4-yl)amine
{(1H-benzimidazol-2-yl)[3-(4-methylpentyloxy)phenyl]methyl}(1-methylpiperidin-4-yl)amine
2-[(1-methylpiperidin-4-yloxy)(3-pyrazol-1-ylphenyl)methyl]benzothiazole
2-[(3-benzylsulfanylphenyl)(1-methylpiperidin-4-yloxy)methyl]benzothiazole
{(1H-benzimidazol-2-yl)[3-(2,5-difluoro-benzyloxy)phenyl]methyl}(1-methylpiperidin-4-yl)amine
2-[(3-benzylsulfanylphenyl)(1-methylpiperidin-4-yloxy)methyl]-1H-benzimidazole
2-[(2-chlorophenyl)(1-methylpiperidin-4-yloxy)methyl]-1H-benzimidazole
2-[(3-ethylphenyl)(1-methylpiperidin-4-yloxy)methyl]benzothiazole
2-[(3-ethylsulfanylphenyl)(1-methylpiperidin-4-yloxy)methyl]-1H-benzimidazole
{3-[(1H-benzimidazol-2-yl)(1-methylpiperidin-4-yloxy)methyl]phenylsulfanyl}acetic acid methyl ester
2-[(3-fluorophenyl)(1-methylpiperidin-4-yloxy)methyl]-1H-benzimidazole
2[[3-(2,5-difluorobenzyloxy)phenyl](1-methylpiperidin-4-yloxy)methyl]benzothiazole
2-{3-[(1H-benzimidazol-2-yl)(1-methylpiperidin-4-yloxy)methyl]phenylsulfanyl}ethanol 2-{3-[benzothiazol-2-yl(1-methylpiperidin-4-yloxy)methyl]phenylsulfanyl}ethanol
2-[(3-ethylsulfanylphenyl)(1-methylpiperidin-4-yloxy)methyl]benzothiazole
{3-[benzothiazol-2-yl(1-methylpiperidin-4-yloxy)methyl]phenylsulfanyl}acetic acid methyl ester
2[[3-(2,3-difluorobenzyloxy)phenyl](1-methylpiperidin-4-yloxy)methyl]benzothiazole
{(1H-benzimidazol-2-yl)[3-(2,3-difluoro-benzyloxy)phenyl]methyl}(1-methylpiperidin-4-yl)amine
2[[3-(2-fluoroethoxy)phenyl](1-methylpiperidin-4-yloxy)methyl]benzothiazole
2-[(1-methylpiperidin-4-yloxy)(m-tolyl)methyl]-1H-benzimidazole
5,6-dichloro-2-[(1-methylpiperidin-4-yloxy)phenyl-methyl]-1H-benzimidazole
5-fluoro-2-[(1-methylpiperidin-4-yloxy)phenyl-methyl]-1H-benzimidazole
2-[(2-fluorophenyl)(1-methylpiperidin-4-yloxy)methyl]-1H-benzimidazole
2-[(1-methylpiperidin-4-yloxy)(3-pent-4-enyloxy-phenyl)methyl]benzothiazole
2-{(1-methylpiperidin-4-yloxy)[3-(4,4,4-trifluoro-butoxy)phenyl]methyl}benzothiazole
5-bromo-2-[(1-methylpiperidin-4-yloxy)phenyl-methyl]-1H-benzimidazole
2[[3-(3-fluorobenzyloxy)phenyl](1-methylpiperidin-4-yloxy)methyl]benzothiazole
3-[(1H-benzimidazol-2-yl)(1-methylpiperidin-4-yloxy)methyl]benzonitrile
2[[3-(furan-2-ylmethylsulfanyl)phenyl](1-methylpiperidin-4-yloxy)methyl]-1H-benzimidazole
((1H-benzimidazol-2-yl)-{3-[3-(2-methyl-[1,3]dioxolan-2-yl)-propoxy]phenyl}methyl)(1-methylpiperidin-4-yl)amine
{(1H-benzimidazol-2-yl)[3-(4,4,4-trifluoro-butoxy)phenyl]methyl}(1-methylpiperidin-4-yl)amine
2[[3-(3-fluoropropoxy)phenyl](1-methylpiperidin-4-yloxy)methyl]benzothiazole
2-[(1-methylpiperidin-4-yloxy)-p-tolyl-methyl]-1H-benzimidazole
2-{(1-methylpiperidin-4-yloxy)[3-(3,3,3-trifluoro-propoxy)phenyl]methyl}benzothiazole
2-[(4-fluorophenyl)(1-methylpiperidin-4-yloxy)methyl]-1H-benzimidazole
{(1H-benzimidazol-2-yl)[3-(2-fluoro-ethoxy)phenyl]methyl}(1-methylpiperidin-4-yl)amine
((1H-benzimidazol-2-yl)-{3-[2-(6,6-dimethyl-bicyclo[3.1.1]hept-2-en-2-yl)ethoxy]phenyl}methyl)(1-methylpiperidin-4-yl)amine
2-[(1-methylpiperidin-4-yloxy)(4'-trifluoromethoxy-biphenyl-3-yl)methyl]-1H-benzimidazole
2-[(4'-methoxybiphenyl-3-yl)(1-methylpiperidin-4-yloxy)methyl]-1H-benzimidazole
2-[(3-benzo[1,3]dioxol-5-ylphenyl)(1-methylpiperidin-4-yloxy)methyl]-1H-benzimidazole
2[[3-(3-methoxybenzyloxy)phenyl](1-methylpiperidin-4-yloxy)methyl]benzothiazole
5-{3-[benzothiazol-2-yl(1-methylpiperidin-4-yloxy)methyl]phenoxy}pentan-2-one
2-{(1-methylpiperidin-4-yloxy)[3-(3-trifluoromethyl-benzyloxy)phenyl]methyl}benzothiazole
4-[benzothiazol-2-yl(3-bromo-phenyl)methoxy]-1,1-dimethylpiperidinium
2-(3-{3-[(1H-benzimidazol-2-yl)(1-methylpiperidin-4-yloxy)methyl]phenyl}prop-2-ynyl)isoindole-1,3-dione
3-{3-[(1H-benzimidazol-2-yl)(1-methylpiperidin-4-yloxy)methyl]phenyl}prop-2-yn-1-ol
4-{3-[(1H-benzimidazol-2-yl)(1-methylpiperidin-4-yloxy)methyl]phenyl}but-3-yn-1-ol
5-{3-[(1H-benzimidazol-2-yl)(1-methylpiperidin-4-yloxy)methyl]phenyl}pent-4-yn-1-ol
2-[(1-methylpiperidin-4-yloxy)-o-tolyl-methyl]-1H-benzimidazole
3-{3-[(1H-benzimidazol-2-yl)(1-methylpiperidin-4-yloxy)methyl]phenyl}prop-2-ynylamine
2-[(3-ethynylphenyl)(1-methylpiperidin-4-yloxy)methyl]-1H-benzimidazole
2-{(1-methylpiperidin-4-yloxy)[3-(3-nitro-benzyloxy)phenyl]methyl}benzothiazole
3-[benzothiazol-2-yl(1-methylpiperidin-4-yloxy)methyl]benzonitrile
2-{(1-methylpiperidin-4-yloxy)[3-(1H-[1,2,3]triazol-4-yl)phenyl]methyl}-1H-benzimidazole
3-[benzothiazol-2-yl(1-methylpiperidin-4-yloxy)methyl]benzoic acid methyl ester
2-[(1-methylpiperidin-4-yloxy)phenyl-methyl]-3H-benzimidazol-4-ylamine
2-[(1-methylpiperidin-4-yloxy)(3-methylsulfanyl-phenyl)methyl]benzothiazole
2-[(1-methylpiperidin-4-yloxy)(3-methylsulfanyl-phenyl)methyl]-1H-benzimidazole
2-[(3-methanesulfonylphenyl)(1-methylpiperidin-4-yloxy)methyl]benzothiazole
2-[(4-bromophenyl)(1-methylpiperidin-4-yloxy)methyl]-1H-benzimidazole
3-{3-[benzothiazol-2-yl(1-methylpiperidin-4-yloxy)methyl]phenyl}acrylic acid tert-butyl ester
3-[benzothiazol-2-yl(1-methylpiperidin-4-yloxy)methyl]benzoic acid ethyl ester
{3-[benzothiazol-2-yl(1-methylpiperidin-4-yloxy)methyl]phenyl}methanol
3-{3-[benzothiazol-2-yl(1-methylpiperidin-4-yloxy)methyl]phenyl}propionic acid tert-butyl ester
2[[3-(2-benzenesulfonylvinyl)phenyl](1-methylpiperidin-4-yloxy)methyl]benzothiazole
2-[(1-methylpiperidin-4-yloxy)phenyl-methyl]-3H-benzimidazol-4-ol
[benzothiazol-2-yl(4'-methoxy-biphenyl-3-yl)methyl](1-methylpiperidin-4-yl)amine
2[[3-(2-methanesulfonylvinyl)phenyl](1-methylpiperidin-4-yloxy)methyl]benzothiazole
2-[(2-chloro-4-methylphenyl)(1-methylpiperidin-4-yloxy)methyl]-1H-benzimidazole
5-{3-[benzothiazol-2-yl(1-methylpiperidin-4-yloxy)methyl]phenyl}pyrimidin-2-ol
2-[(3-tert-butylsulfanylphenyl)(1-methylpiperidin-4-yloxy)methyl]-1H-benzimidazole
2-[(1-methylpiperidin-4-yloxy)(3-pyrimidin-5-yl-phenyl)methyl]benzothiazole
3-{3-[benzothiazol-2-yl(1-methylpiperidin-4-yloxy)methyl]phenyl}acrylonitrile
2-[(1-methylpiperidin-4-yloxy)(3-vinyl-phenyl)methyl]benzothiazole
3-[benzothiazol-2-yl(1-methylpiperidin-4-yloxy)methyl]-N-benzyl-N-methylbenzamide
3-[benzothiazol-2-yl(1-methylpiperidin-4-yloxy)methyl]-N-propylbenzamide
2-[(2,4-difluorophenyl)(1-methylpiperidin-4-yloxy)methyl]-1H-benzimidazole
[(1H-benzimidazol-2-yl)(4'-methoxy-biphenyl-3-yl)methyl](1-methylpiperidin-4-yl)amine 3-[benzothiazol-2-yl(1-methylpiperidin-4-yloxy)methyl]-N-methyl-N-phenylbenzamide
3-[(1H-benzimidazol-2-yl)(1-methylpiperidin-4-yloxy)methyl]phenylamine
2-[(3-chlorophenyl)(1-methylpiperidin-4-yloxy)methyl]-1H-benzimidazole
2-[(4-chlorophenyl)(1-methylpiperidin-4-yloxy)methyl]-1H-benzimidazole
3-{3-[benzothiazol-2-yl(1-methylpiperidin-4-yloxy)methyl]phenyl}prop-2-yn-1-ol
3-{3-[benzothiazol-2-yl(1-methylpiperidin-4-yloxy)methyl]phenoxymethyl}-phenylamine
2-{3-[benzothiazol-2-yl(1-methylpiperidin-4-yloxy)methyl]phenylsulfanyl}ethanol
2-{3-[benzothiazol-2-yl(1-methylpiperidin-4-yloxy)methyl]phenylsulfanyl}ethanol
2-[(3-azidophenyl)(1-methylpiperidin-4-yloxy)methyl]-1H-benzimidazole
2-{(1-methylpiperidin-4-yloxy)[3-(2-pyrazin-2-yl-ethylsulfanyl)phenyl]methyl}-1H-benzimidazole
2-{(1-methylpiperidin-4-yloxy)[3-(2-pyrazin-2-yl-ethylsulfanyl)phenyl]methyl}benzothiazole
{3-[benzothiazol-2-yl(1-methylpiperidin-4-yloxy)methyl]phenyl}benzyl-amine
3-{3-[(1H-benzimidazol-2-yl)(1-methylpiperidin-4-yloxy)methyl]phenylsulfanyl}-3-methyl-butan-1-ol
4-{3-[benzothiazol-2-yl(1-methylpiperidin-4-yloxy)methyl]phenyl}but-3-yn-1-ol
5-{3-[benzothiazol-2-yl(1-methylpiperidin-4-yloxy)methyl]phenyl}pent-4-yn-1-ol
4-{3-[benzothiazol-2-yl(1-methylpiperidin-4-yloxy)methyl]phenyl}butan-1-ol
(1-{3-[benzothiazol-2-yl(1-methylpiperidin-4-yloxy)methyl]phenylsulfanylmethyl}-cyclopropyl)acetic acid methyl ester
2-{(1-methylpiperidin-4-yloxy)[3-(2-[1,2,3]triazol-2-yl-ethylsulfanyl)phenyl]methyl}benzothiazole
2-{(1-methylpiperidin-4-yloxy)[3-(2-[1,2,3]triazol-1-yl-ethylsulfanyl)phenyl]methyl}benzothiazole
3-{3-[benzothiazol-2-yl(1-methylpiperidin-4-yloxy)methyl]phenylsulfanyl}-3-methyl-butan-1-ol
2-[(1-methylpiperidin-4-yloxy)(3-morpholin-4-yl-phenyl)methyl]benzothiazole
2-{3-[benzothiazol-2-yl(1-methylpiperidin-4-yloxy)methyl]phenoxy}ethanol
2-[(1-methylpiperidin-4-yloxy)(3-vinyl-phenyl)methyl]-1H-benzimidazole
3-{3-[(1H-benzimidazol-2-yl)(1-methylpiperidin-4-yloxy)methyl]phenylsulfanyl}propan-1-ol
1-{3-[(1H-benzimidazol-2-yl)(1-methylpiperidin-4-yloxy)methyl]phenylsulfanyl}propan-2-ol
4-{3-[(1H-benzimidazol-2-yl)(1-methylpiperidin-4-yloxy)methyl]phenylsulfanyl}butan-1-ol
2-{3-[(1H-benzimidazol-2-yl)(1-methylpiperidin-4-yloxy)methyl]phenylsulfanyl}ethylamine
2-{(1-methylpiperidin-4-yloxy)[3-(2-methylsulfanyl-ethoxy)phenyl]methyl}benzothiazole
2-[(1-methylpiperidin-4-yloxy)(2-trifluoromethoxy-phenyl)methyl]-1H-benzimidazole
2-[(1-methylpiperidin-4-yloxy)-p-tolylmethyl]-1H-benzimidazole
2-[(1-methylpiperidin-4-yloxy)-p-tolyl-methyl]-1H-benzimidazole
3-{3-[benzothiazol-2-yl(1-methylpiperidin-4-yloxy)methyl]phenylsulfanyl}propan-1-ol
1-{3-[benzothiazol-2-yl(1-methylpiperidin-4-yloxy)methyl]phenylsulfanyl}propan-2-ol
4-{3-[benzothiazol-2-yl(1-methylpiperidin-4-yloxy)methyl]phenylsulfanyl}butan-1-ol
2-(1-{3-[(1H-benzimidazol-2-yl)(1-methylpiperidin-4-yloxy)methyl]phenylsulfanylmethyl}-cyclopropyl)ethanol
3-{3-[benzothiazol-2-yl(1-methylpiperidin-4-yloxy)methyl]phenoxy}propan-1-ol
2-{3-[benzothiazol-2-yl(1-methylpiperidin-4-yloxy)methyl]phenylsulfanyl}-N-methylacetamide
2-{(1-methylpiperidin-4-yloxy)[3-(2H-pyrazol-3-yl)phenyl]methyl}benzothiazole
2-[(3-bromo-4-methylphenyl)(1-methylpiperidin-4-yloxy)methyl]-1H-benzimidazole
2-[(2-bromophenyl)(1-methylpiperidin-4-yloxy)methyl]-1H-benzimidazole
2-{3-[benzothiazol-2-yl(1-methylpiperidin-4-yloxy)methyl]phenylsulfanyl}acetamide
{3-[benzothiazol-2-yl(1-methylpiperidin-4-yloxy)methyl]phenylsulfanyl}acetic acid hydrazide
2-{(1-methylpiperidin-4-yloxy)[3-(pyridin-4-ylmethoxy)phenyl]methyl}benzothiazole
4-{3-[benzothiazol-2-yl(1-methylpiperidin-4-yloxy)methyl]phenoxy}butan-1-ol
2[[3-(furan-2-ylmethoxy)phenyl](1-methylpiperidin-4-yloxy)methyl]benzothiazole
2-(1-{3-[benzothiazol-2-yl(1-methylpiperidin-4-yloxy)methyl]phenylsulfanylmethyl}-cyclopropyl)ethanol
2-{3-[benzothiazol-2-yl(1-methylpiperidin-4-yloxy)methyl]phenylsulfanyl}ethylamine
1-{3-[benzothiazol-2-yl(1-methylpiperidin-4-yloxy)methyl]benzyloxy}propan-2-one
2-{3-[benzothiazol-2-yl(1-methylpiperidin-4-yloxy)methyl]phenoxy}ethylamine
2-[(1-methylpyrrolidin-3-yloxy)phenyl-methyl]-1H-benzimidazole
[(1H-benzimidazol-2-yl)-p-tolyl-methyl](1-methylpiperidin-4-yl)amine
2-[(3-ethylsulfanyl-4-methylphenyl)(1-methylpiperidin-4-yloxy)methyl]-1H-benzimidazole
1-(3-{3-[benzothiazol-2-yl(1-methylpiperidin-4-yloxy)methyl]phenyl}prop-2-ynyloxy)-propan-2-one
1-(3-{3-[benzothiazol-2-yl(1-methylpiperidin-4-yloxy)methyl]phenyl}prop-2-ynyloxy)-propan-2-ol
2[[3-(2-methoxyethoxy)phenyl](1-methylpiperidin-4-yloxy)methyl]benzothiazole
N-(2-{3-[(1H-benzimidazol-2-yl)(1-methylpiperidin-4-yloxy)methyl]phenylsulfanyl}ethyl)guanidine
(2-{3-[benzothiazol-2-yl(1-methylpiperidin-4-yloxy)methyl]phenoxy}ethyl)methyl-amine
2-[(1-methylpiperidin-4-yloxy)(3-trifluoromethoxy-phenyl)methyl]-1H-benzimidazole
2-[(2-chlorophenyl)(1-methylpiperidin-4-yloxy)methyl]benzothiazole
4-{3-[benzothiazol-2-yl(1-methylpiperidin-4-yloxy)methyl]phenyl}but-3-ynylamine
2-{(1-methylpiperidin-4-yloxy)[3-(pyridin-2-ylmethoxy)phenyl]methyl}benzothiazole
2-{(1-methylpiperidin-4-yloxy)[3-(pyridin-3-ylmethoxy)phenyl]methyl}benzothiazole
2-[(3-Cyclohexylmethoxyphenyl)(1-methylpiperidin-4-yloxy)methyl]benzothiazole
4-{3-[(1H-benzimidazol-2-yl)(1-methylpiperidin-4-yloxy)methyl]phenyl}but-3-ynylamine
5-{3-[benzothiazol-2-yl(1-methylpiperidin-4-yloxy)methyl]phenyl}pent-4-ynylamine
3-{3-[(1H-benzimidazol-2-yl)(1-methylpiperidin-4-yloxy)methyl]phenylsulfanyl}propane-1,2-diol 5-{3-[benzothiazol-2-yl(1-methylpiperidin-4-yloxy)methyl]phenyl}pentylamine
2-{3-[benzothiazol-2-yl(1-ethyl-piperidin-4-yloxy)methyl]phenoxy}ethylamine
2-{3-[(1H-benzimidazol-2-yl)(1-methylpiperidin-4-yloxy)methyl]phenoxy}ethylamine
6-{3-[benzothiazol-2-yl(1-methylpiperidin-4-yloxy)methyl]phenylsulfanyl}hexan-1-ol
4-{3-[(1H-benzimidazol-2-yl)(1-methylpiperidin-4-yloxy)methyl]phenyl}butylamine
5-{3-[(1H-benzimidazol-2-yl)(1-methylpiperidin-4-yloxy)methyl]phenyl}pent-4-ynylamine
6-{3-[(1H-benzimidazol-2-yl)(1-methylpiperidin-4-yloxy)methyl]phenylsulfanyl}hexan-1-ol
3-{3-[benzothiazol-2-yl(1-methylpiperidin-4-yloxy)methyl]phenyl}prop-2-ynylamine
2-[benzo[1,3]dioxol-5-yl(1-methylpiperidin-4-yloxy)methyl]-1H-benzimidazole
(2-{3-[(1H-benzimidazol-2-yl)(1-methylpiperidin-4-yloxy)methyl]phenylsulfanyl}ethyl)-urea
(2-{3-[(1H-benzimidazol-2-yl)(1-methylpiperidin-4-yloxy)methyl]phenylsulfanyl}ethyl)(4,5-dihydro-thiazol-2-yl)amine
2-[(2,3-dihydrobenzo[1,4]dioxin-6-yl)(1-methylpiperidin-4-yloxy)methyl]-1H-benzimidazole
4-{3-[benzothiazol-2-yl(1-methylpiperidin-4-yloxy)methyl]phenoxy}butylamine
N-(2-{3-[benzothiazol-2-yl(1-methylpiperidin-4-yloxy)methyl]phenylsulfanyl}ethyl)guanidine
3-{3-[(1H-benzimidazol-2-yl)(1-methylpiperidin-4-yloxy)methyl]phenyl}propylamine
N-tert-butoxycarbonyl-N'-(2-{3-[(benzothiazol-2-yl)(1-methylpiperidin-4-yloxy)methyl]phenylsulfanyl}ethyl)guanidine
5-{3-[benzothiazol-2-yl(1-methylpiperidin-4-yloxy)methyl]phenylsulfanyl}pentylamine
2-[{3-[2-(1-methyl-1H-imidazol4-yl)ethyl]phenyl}(1-methylpiperidin-4-yloxy)methyl]benzothiazole
N-tert-butoxycarbonyl-N'-(4-{3-[(1H-benzimidazol-2-yl)(1-methylpiperidin-4-yloxy)methyl]phenyl}but-3-ynyl)guanidine
N-(4-{3-[(1H-benzimidazol-2-yl)(1-methylpiperidin-4-yloxy)methyl]phenyl}butyl)guanidine
N-tert-butoxycarbonyl-N'-(4-{3-[(1H-benzimidazol-2-yl)(1-methylpiperidin-4-yloxy)methyl]phenyl}butyl)guanidine
2-{(1-methylpiperidin-4-yloxy)[3-(pyridin-2-ylmethoxy)phenyl]methyl}-1H-benzimidazole
3-{3-[benzothiazol-2-yl(1-methylpiperidin-4-yloxy)methyl]phenoxy}propylamine
5-{3-[(1H-benzimidazol-2-yl)(1-methylpiperidin-4-yloxy)methyl]phenyl}pentylamine
N-tert-butoxycarbonyl-N'-(3-{3-[(1H-benzimidazol-2-yl)(1-methylpiperidin-4-yloxy)methyl]phenyl}propyl)guanidine
3-{3-[benzothiazol-2-yl(1-methylpiperidin-4-yloxy)methyl]phenylsulfanyl}propylamine
2-{(1-methylpiperidin-4-yloxy)[3-(4-[1,2,3]triazol-2-yl-butoxy)phenyl]methyl}benzothiazole
2-{(1-methylpiperidin-4-yloxy)[3-(4-[1,2,4]triazol-1-yl-butoxy)phenyl]methyl}benzothiazole
(2-{3-[(1H-benzimidazol-2-yl)(1-methylpiperidin-4-yloxy)methyl]phenylsulfanyl}ethyl)(4,5-dihydro-1H-imidazol-2-yl)amine
N-(2-{3-[(1H-benzimidazol-2-yl)(1-methylpiperidin-4-yloxy)methyl]phenylsulfanyl}ethyl)-N'-cyanoguanidine
6-{3-[benzothiazol-2-yl(1-methylpiperidin-4-yloxy)methyl]phenyl}hex-5-ynylamine
N-(3-{3-[(1H-benzimidazol-2-yl)(1-methylpiperidin-4-yloxy)methyl]phenyl}propyl)guanidine
N-(3-{3-[(1H-benzimidazol-2-yl)(1-methylpiperidin-4-yloxy)methyl]phenyl}propyl)guanidine
2-{(1-methylpiperidin-4-yloxy)[3-(4-morpholin-4-yl-butoxy)phenyl]methyl}benzothiazole
(1-{3-[benzothiazol-2-yl(1-methylpiperidin-4-yloxy)methyl]phenyl}pyrrolidin-2-yl)methanol
(1-{3-[benzothiazol-2-yl(1-methylpiperidin-4-yloxy)methyl]phenyl}pyrrolidin-2-yl)methanol
6-{3-[benzothiazol-2-yl(1-methylpiperidin-4-yloxy)methyl]phenyl}hexylamine
4-{3-[(1H-benzimidazol-2-yl)(1-methylpiperidin-4-yloxy)methyl]phenylsulfanyl}butylamine
3-{3-[(1H-benzimidazol-2-yl)(1-methylpiperidin-4-yloxy)methyl]phenoxy}propylamine
4-(2-{3-[benzothiazol-2-yl(1-methylpiperidin-4-yloxy)methyl]phenoxy}ethyl)piperazine-1-carboxylic acid tert-butyl ester
4-(2-{3-[benzothiazol-2-yl(1-methylpiperidin-4-yloxy)methyl]phenoxy}ethyl)piperazine-1-carboxylic acid tert-butyl ester
2-{(1-methylpiperidin-4-yloxy)[3-(2-piperazin-1-yl-ethoxy)phenyl]methyl}benzothiazole
4-{3-[(1H-benzimidazol-2-yl)(1-methylpiperidin-4-yloxy)methyl]phenoxy}butylamine
2-{(1-methylpiperidin-4-yloxy)[3-(4-morpholin-4-yl-butoxy)phenyl]methyl}-1H-benzimidazole
2-{(1-methylpiperidin-4-yloxy)[3-(4-piperidin-1-yl-butoxy)phenyl]methyl}-1H-benzimidazole
2-[(2-fluoro-3-iodophenyl)(1-methylpiperidin-4-yloxy)methyl]-1H-benzimidazole
N-tert-butoxycarbonyl-N'-(-{3-[(1H-benzimidazol-2-yl)(1-methylpiperidin-4-yloxy)methyl]phenyl}pentyl)guanidine
N-tert-butoxycarbonyl-N'-(3-{3-[(1H-benzimidazol-2-yl)(1-methylpiperidin-4-yloxy)methyl]phenyl}prop-2-ynyl)guanidine
6-{3-[(1H-benzimidazol-2-yl)(1-methylpiperidin-4-yloxy)methyl]phenyl}hex-5-ynylamine
2-{(1-methylpiperidin-4-yloxy)[3-(1,2,3,6-tetrahydro-pyridin-4-yl)phenyl]methyl}-1H-benzimidazole
N-tert-butoxycarbonyl-N'-(5-{3-[(benzothiazol-2-yl)(1-methylpiperidin-4-yloxy)methyl]phenyl}pent-5-ynyl)guanidine
N-(5-{3-[benzothiazol-2-yl(1-methylpiperidin-4-yloxy)methyl]phenyl}pent-4-ynyl)guanidine
N-tert-butoxycarbonyl-N'-(6-{3-[(benzothiazol-2-yl)(1-methylpiperidin-4-yloxy)methyl]phenyl}hex-5-ynyl)guanidine
N-(6-{3-[benzothiazol-2-yl(1-methylpiperidin-4-yloxy)methyl]phenyl}hex-5-ynyl)guanidine
4-(4-{3-[(1H-benzimidazol-2-yl)(1-methylpiperidin-4-yloxy)methyl]phenoxy}butyl)piperazine-1-carboxylic acid tert-butyl ester
6-{3-[(1H-benzimidazol-2-yl)(1-methylpiperidin-4-yloxy)methyl]phenyl}hexylamine
N-tert-butoxycarbonyl-N'-(6-{3-[(1H-benzimidazol-2-yl)(1-methylpiperidin-4-yloxy)methyl]phenyl}hex-5-ynyl)guanidine
N-(6-{3-[(1H-benzimidazol-2-yl)(1-methylpiperidin-4-yloxy)methyl]phenyl}hex-5-ynyl)guanidine
1-(2-{3-[(1H-benzimidazol-2-yl)(1-methylpiperidin-4-yloxy)methyl]phenylsulfanyl}ethyl)-3-isopropyl-thiourea 2-{(1-methylpiperidin-4-yloxy)[3-(3-[1,2,4]triazol-1-yl-propoxy)phenyl]methyl}benzothiazole
2-{(1-methylpiperidin-4-yloxy)[3-(3-[1,2,3]triazol-2-yl-propoxy)phenyl]methyl}benzothiazole
2-{(1-methylpiperidin-4-yloxy)[3-(3-morpholin-4-yl-propoxy)phenyl]methyl}benzothiazole
4-(3-{3-[benzothiazol-2-yl(1-methylpiperidin-4-yloxy)methyl]phenoxy}propyl)piperazine-1-carboxylic acid tert-butyl ester
2-{3-[(1H-benzimidazol-2-yl)(1-methylpiperidin-4-yloxy)methyl]-2-fluoro-phenylsulfanyl}ethylamine
4-{3-[(1H-benzimidazol-2-yl)(1-methylpiperidin-4-yloxy)methyl]phenyl}-3,6-dihydro-2H-pyridine-1-carboxamidine
2[[3-(2-chloroethoxy)phenyl](1-methylpiperidin-4-yloxy)methyl]benzothiazole
N-(6-{3-[(1H-benzimidazol-2-yl)(1-methylpiperidin-4-yloxy)methyl]phenyl}hexyl)guanidine
2-{(1-methylpiperidin-4-yloxy)[3-(2-piperidin-1-yl-ethoxy)phenyl]methyl}-1H-benzimidazole
N-tert-butoxycarbonyl-N'-(5-{3-[(1H-benzimidazol-2-yl)(1-methylpiperidin-4-yloxy)methyl]phenyl}pent-4-ynyl)guanidine
N-(5-{3-[(1H-benzimidazol-2-yl)(1-methylpiperidin-4-yloxy)methyl]phenyl}pent-4-ynyl)guanidine
4-{3-[benzothiazol-2-yl(1-methylpiperidin-4-yloxy)methyl]phenylsulfanyl}butylamine
4-(3-{3-[(1H-benzimidazol-2-yl)(1-methylpiperidin-4-yloxy)methyl]phenoxy}propyl)piperazine-1-carboxylic acid tert-butyl ester
(2-{3-[(1H-benzimidazol-2-yl)(1-methylpiperidin-4-yloxy)methyl]phenoxy}ethylamino)acetic acid tert-butyl ester
4-(5-{3-[benzothiazol-2-yl(1-methylpiperidin-4-yloxy)methyl]phenoxy}pentyl)piperazine-1-carboxylic acid tert-butyl ester
N-(6-{3-[benzothiazol-2-yl(1-methylpiperidin-4-yloxy)methyl]phenyl}hexyl)guanidine
N-tert-butoxycarbonyl-N'-(6-{3-[(1H-benzimidazol-2-yl)(1-methylpiperidin-4-yloxy)methyl]phenyl}hexyl)guanidine
N-(5-{3-[benzothiazol-2-yl(1-methylpiperidin-4-yloxy)methyl]phenyl}pentyl)guanidine
4-{3-[benzothiazol-2-yl(1-methylpiperidin-4-yloxy)methyl]phenyl}butylamine
[[3-(4-aminobutoxy)phenyl](1H-benzimidazol-2-yl)methyl](1-methylpiperidin-4-yl)amine
3-{3-[(1H-benzimidazol-2-yl)(1-methylpiperidin-4-yloxy)methyl]phenylsulfanyl}propylamine
4-(2-{3-[(1H-benzimidazol-2-yl)(1-methylpiperidin-4-yloxy)methyl]phenoxy}ethyl)piperazine-1-carboxylic acid tert-butyl ester
(2-{3-[benzothiazol-2-yl(1-methylpiperidin-4-yloxy)methyl]phenoxy}ethylamino)acetic acid tert-butyl ester
5-{3-[benzothiazol-2-yl(1-methylpiperidin-4-yloxy)methyl]phenoxy}pentylamine
N-(4-{3-[benzothiazol-2-yl(1-methylpiperidin-4-yloxy)methyl]phenyl}but-3-ynyl)guanidine
N-(3-{3-[benzothiazol-2-yl(1-methylpiperidin-4-yloxy)methyl]phenyl}prop-2-ynyl)guanidine
N-(4-{3-[benzothiazol-2-yl(1-methylpiperidin-4-yloxy)methyl]phenyl}butyl)guanidine
(5-{3-[benzothiazol-2-yl(1-methylpiperidin-4-yloxy)methyl]phenoxy}pentylamino)acetic acid tert-butyl ester
2-[(1-methylpiperidin-4-yloxy)(3-piperidin-4-ylethynyl-phenyl)methyl]-1H-benzimidazole 2-{(1-methylpiperidin-4-yloxy)[3-(piperidin-4-yl-methoxy)phenyl]methyl}benzothiazole
2-{(1-methylpiperidin-4-yloxy)[3-(piperidin-3-yl-methoxy)phenyl]methyl}benzothiazole
2-[[3-(1-methylpiperidin-3-ylmethoxy)phenyl](1-methylpiperidin-4-yloxy)methyl]benzothiazole
2-[(1-methylpiperidin-4-yloxy)(3-piperidin-3-ylethynyl-phenyl)methyl]-1H-benzimidazole
5-{3-[(1H-benzimidazol-2-yl)(1-methylpiperidin-4-yloxy)methyl]phenylsulfanyl}pentylamine
2-{(1-methylpiperidin-4-yloxy)[3-(pyrrolidin-3-yloxy)phenyl]methyl}benzothiazole
2-{(1-methylpiperidin-4-yloxy)[3-(pyrrolidin-3-yloxy)phenyl]methyl}benzothiazole
5-{3-[benzothiazol-2-yl(1-methylpiperidin-4-yloxy)methyl]phenyl}pent-4-en-1-ol
3-amino-4-(2-{3-[(1H-benzimidazol-2-yl)(1-methylpiperidin-4-yloxy)methyl]phenylsulfanyl}ethylamino)-cyclobut-3-ene-1,2-dione
[[3-(6-aminohex-1-ynyl)phenyl](1H-benzimidazol-2-yl)methyl](1-methylpiperidin-4-yl)amine
{[3-(4-aminobutoxy)phenyl]benzothiazol-2-yl-methyl}(1-methylpiperidin-4-yl)amine
2-[(3-azetidin-3-ylethynylphenyl)(1-methylpiperidin-4-yloxy)methyl]-1H-benzimidazole
5-{3-[(1H-benzimidazol-2-yl)(1-methylpiperidin-4-yloxy)methyl]phenyl}pent-4-en-1-ol
5-{3-[benzothiazol-2-yl(1-methylpiperidin-4-yloxy)methyl]phenyl}pent-4-en-1-ol
4-(5-{3-[(1H-benzimidazol-2-yl)(1-methylpiperidin-4-yloxy)methyl]phenoxy}pentyl)piperazine-1-carboxylic acid tert-butyl ester
2-[[3-(2-azetidin-3-ylethyl)phenyl](1-methylpiperidin-4-yloxy)methyl]-1H-benzimidazole
N-(4-{3-[(1H-benzimidazol-2-yl)(1-methylpiperidin-4-yloxy)methyl]phenyl}but-3-ynyl)guanidine
4-{3-[(1H-benzimidazol-2-yl)(1-methylpiperidin-4-yloxy)methyl]phenyl}piperidine-1-carboxamidine
2-{(1-methylpiperidin-4-yloxy)[3-(2-piperidin-2-yl-ethylsulfanyl)phenyl]methyl}-1H-benzimidazole
2-{(1-methylpiperidin-4-yloxy)[3-(2-piperidin-4-yl-ethyl)phenyl]methyl}-1H-benzimidazole
N-(5-{3-[(1H-benzimidazol-2-yl)(1-methylpiperidin-4-yloxy)methyl]phenyl}pentyl)guanidine
2-[{3-[3-(3H-imidazol-4-yl)propylsulfanyl]phenyl}(1-methylpiperidin-4-yloxy)methyl]-1H-benzimidazole
N-tert-butoxycarbonyl-W-(4-{3-[(benzothiazol-2-yl)(1-methylpiperidin-4-yloxy)methyl]phenyl}but-3-ynyl)guanidine
5-{3-[(1H-benzimidazol-2-yl)(1-methylpiperidin-4-yloxy)methyl]phenoxy}pentylamine
N-acetyl-N'-(2-{3-[(1H-benzimidazol-2-yl)(1-methylpiperidin-4-yloxy)methyl]phenylsulfanyl}ethyl)guanidine
2-[[3-(azetidin-3-yloxy)phenyl](1-methylpiperidin-4-yloxy)methyl]benzothiazole
1-{3-[benzothiazol-2-yl(1-methylpiperidin-4-yloxy)methyl]phenyl}azetidin-3-ol
(1-{3-[benzothiazol-2-yl(1-methylpiperidin-4-yloxy)methyl]phenyl}pyrrolidin-3-yl)methanol
1-{3-[benzothiazol-2-yl(1-methylpiperidin-4-yloxy)methyl]phenyl}piperidin-4-ylamine
1-{3-[benzothiazol-2-yl(1-methylpiperidin-4-yloxy)methyl]phenyl}pyrrolidin-3-ol
1-{3-[benzothiazol-2-yl(1-methylpiperidin-4-yloxy)methyl]phenyl}pyrrolidin-3-ol
N-(1-{3-[benzothiazol-2-yl(1-methylpiperidin-4-yloxy)methyl]phenyl}pyrrolidin-3-yl)acetamide 2[[3-(5-imidazol-1-ylpent-1-ynyl)phenyl](1-methylpiperidin-4-yloxy)methyl]-1H-benzimidazole
2-{(1-methylpiperidin-4-yloxy)[3-(5-pyrazol-1-yl-pent-1-ynyl)phenyl]methyl}-1H-benzimidazole
1-{3-[benzothiazol-2-yl(1-methylpiperidin-4-yloxy)methyl]phenyl}piperidin-4-ol
2-[{3-[2-(1H-imidazol-4-yl)ethyl]phenyl}(1-methylpiperidin-4-yloxy)methyl]-1H-benzimidazole
acetic acid 1-{3-[benzothiazol-2-yl(1-methylpiperidin-4-yloxy)methyl]phenyl}piperidin-4-yl ester
2-[(3-bromo-phenyl)(1-methyl-pyrrolidin-3-ylmethoxy)methyl]-1H-benzimidazole
2-{(1-methylpiperidin-4-yloxy)[3-(piperidin-4-yloxy)phenyl]methyl}benzothiazole
2-{(1-methylpiperidin-4-yloxy)[3-(5-[1,2,3]triazol-2-yl-pent-1-ynyl)phenyl]methyl}-1H-benzimidazole
2-{(1-methylpiperidin-4-yloxy)[3-(5-[1,2,3]triazol-1-yl-pent-1-ynyl)phenyl]methyl}-1H-benzimidazole
N-(3-{3-[(1H-benzimidazol-2-yl)(1-methylpiperidin-4-yloxy)methyl]phenyl}prop-2-ynyl)guanidine
N1-(5-{3-[(1H-benzimidazol-2-yl)(1-methylpiperidin-4-yloxy)methyl]phenoxy}pentyl)butane-1,4-diamine
{[3-(6-aminohex-1-ynyl)phenyl]benzothiazol-2-yl-methyl}(1-methylpiperidin-4-yl)amine
5-{3-[(1H-benzimidazol-2-yl)(1-methylpiperidin-4-yloxy)methyl]phenyl}pent-4-enylamine
4-{3-[benzothiazol-2-yl(1-methylpiperidin-4-yloxy)methyl]phenoxy}but-2-en-1-ol
1-{3-[benzothiazol-2-yl(1-methylpiperidin-4-yloxy)methyl]phenyl}pyrrolidin-3-ylamine
2-[(2,5-difluorophenyl)(1-methylpiperidin-4-yloxy)methyl]-1H-benzimidazole
2-[(2-fluoro-5-iodo-phenyl)(1-methylpiperidin-4-yloxy)methyl]-1H-benzimidazole
3-{3-[(1H-benzimidazol-2-yl)(1-methylpiperidin-4-yloxy)methyl]phenylethynyl}azetidine-1-carboxamidine
4-{3-[(5-fluoro-1H-benzimidazol-2-yl)(1-methylpiperidin-4-yloxy)methyl]phenylsulfanyl}butan-1-ol
2-{3-[(5-fluoro-1H-benzimidazol-2-yl)(1-methylpiperidin-4-yloxy)methyl]phenylsulfanyl}ethylamine
1-{3-[benzothiazol-2-yl(1-methylpiperidin-4-yloxy)methyl]phenyl}pyrrolidin-3-ylamine
2-[[3-(3-fluoropyrrolidin-1-yl)phenyl](1-methylpiperidin-4-yloxy)methyl]benzothiazole
4-{3-[benzothiazol-2-yl(1-methylpiperidin-4-yloxy)methyl]phenoxy}but-2-enylamine
2-[(2-fluoro-5-trifluoromethoxyphenyl)(1-methylpiperidin-4-yloxy)methyl]-1H-benzimidazole
2-[(2-fluoro-5-trifluoromethoxyphenyl)(1-methylpiperidin-4-yloxy)methyl]-1H-benzimidazole (enantiomer A)
2-[(2-fluoro-5-trifluoromethoxyphenyl)(1-methylpiperidin-4-yloxy)methyl]-1H-benzimidazole (enantiomer B)
N-(2-aminoethyl)-2-{3-[(1H-benzimidazol-2-yl)(1-methylpiperidin-4-yloxy)methyl]phenylsulfanyl}acetamide
N-(2-{3-[(5-fluoro-1H-benzimidazol-2-yl)(1-methylpiperidin-4-yloxy)methyl]phenylsulfanyl}ethyl)guanidine
2-(5-{3-[(5-fluoro-1H-benzimidazol-2-yl)(1-methylpiperidin-4-yloxy)methyl]phenyl}pent-4-ynyl)isoindole-1,3-dione
6-{3-[(5-fluoro-1H-benzimidazol-2-yl)(1-methylpiperidin-4-yloxy)methyl]phenyl}hex-5-ynylamine oxalate
4-{3-[(5-fluoro-1H-benzimidazol-2-yl)(1-methylpiperidin-4-yloxy)methyl]phenylsulfanyl}butylamine oxalate
N-(3-{3-[(1H-benzimidazol-2-yl)(1-methylpiperidin-4-yloxy)methyl]phenylsulfanyl}propyl)guanidine, dihydrochloride
1-{3-[benzothiazol-2-yl(1-methylpiperidin-4-yloxy)methyl]phenyl}pyrrolidin-3-one, oxalate
N-(4-{3-[(1H-benzimidazol-2-yl)(1-methylpiperidin-4-yloxy)methyl]phenylsulfanyl}butyl)guanidine, dihydrochloride
5-{3-[(1H-benzimidazol-2-yl)(1-methylpiperidin-4-yloxy)methyl]phenylsulfanyl}pentan-1-ol
N-(2-{3-[(1H-benzimidazol-2-yl)(1-methylpiperidin-4-yloxy)methyl]phenylsulfanyl}ethyl)-N-(2,2-dimethylpropionyl)guanidine
2-[(1-methylpiperidin-4-yloxy)(4-nitrophenyl)methyl]-1H-benzimidazole
2-{(1-methylpiperidin-4-yloxy)[3-(pyridin-3-yloxy)phenyl]methyl}benzothiazole, oxalate
2-[(3-bromophenyl)(1-methylpyrrolidin-3-ylmethoxy)methyl]-5-fluoro-1H-benzimidazole, oxalate
4-[(1H-benzimidazol-2-yl)(1-methylpiperidin-4-yloxy)methyl]aniline
4-[(1H-benzimidazol-2-yl)(piperidin-4-yloxy)methyl]aniline, hydrochloride
N-(2-amino-ethyl)-2-{3-[(5-fluoro-1H-benzimidazol-2-yl)(1-methylpiperidin-4-yloxy)methyl]phenylsulfanyl}acetamide
1-{3-[benzothiazol-2-yl(1-methylpiperidin-4-yloxy)methyl]phenyl}-3-trifluoromethylpyrrolidin-3-ol, oxalate
2-[[3-(4,5-dihydro-1H-imidazol-2-ylmethylsulfanyl)phenyl](1-methylpiperidin-4-yloxy)methyl]-1H-benzimidazole
2-[[3-(4,5-dihydro-1H-imidazol-2-ylmethylsulfanyl)phenyl](1-methylpiperidin-4-yloxy)methyl]-5-fluoro-1H-benzimidazole
2-[(3-bromophenyl)(1-methylpiperidin-4-yloxy)methyl]-5,6-difluoro-1H-benzimidazole
2-[(3-iodophenyl)(1-methylpiperidin-4-yloxy)methyl]-1-methyl-1H-benzimidazole, dioxalate
2-amino-5-{3-[(1H-benzimidazol-2-yl)(1-methylpiperidin-4-yloxy)methyl]phenylsulfanylmethyl}-1,5-dihydroimidazol-4-one
2-[(3-bromophenyl)(1-methylpiperidin-4-yloxy)methyl]-5,6,7-trifluoro-1H-benzimidazole
1-(2-ethoxyethyl)-2-[(3-iodophenyl)(1-methylpiperidin-4-yloxy)methyl]-1H-benzimidazole, dioxalate
3-[(1H-benzimidazol-2-yl)(1-methylpiperidin-4-yloxy)methyl]benzaldehyde
4-{3-[(1H-benzimidazol-2-yl)(1-methylazetidin-3-ylmethoxy)methyl]phenylsulfanyl}butylamine, oxalate
2-[(2-fluoro-5-trifluoromethoxyphenyl)(1-methylpiperidin-4-yloxy)methyl]benzoxazole, oxalate
{3-[(1H-benzimidazol-2-yl)(1-methylpiperidin-4-yloxy)methyl]phenyl}methanol. dimethylsulfoxonium ylide of 3-bromophenylacetic acid methyl ester
2-[(2-fluoro-4-methylphenyl)(1-methylpiperidin-4-yloxy)methyl]-1H-benzimidazole, enantiomer B
2-[(2,6-difluoro-3-methoxyphenyl)(1-methylpiperidin-4-yloxy)methyl]-1H-benzimidazole
ethyl (6-{3-[(1-methyl-1H-benzimidazol-2-yl)(1-methylpiperidin-4-yloxy)methyl]phenyl}hex-5-ynyl)carbamate, oxalate
2-[(1H-indol-6-yl)(1-methylpiperidin-4-yloxy)methyl]-1H-benzimidazole, oxalate
2-[benzo[b]thiophen-6-yl(1-methylpiperidin-4-yloxy)methyl]-1H-benzimidazole, oxalate
2-[(2,6-difluoro-4-methylphenyl)(1-methylpiperidin-4-yloxy)methyl]-1H-benzimidazole, enantiomer B 2-[(1H-benzimidazol-2-yl)(1-methylpiperidin-4-yloxy)methyl]phenol 2-[(1H-benzimidazol-2-yl)hydroxymethyl]phenol 2-[(6-{3-[(1H-benzimidazol-2-yl)(1-methylpiperidin-4-yloxy)methyl]-4-fluorophenyl}hex-5-ynylimino)phenylmethyl]phenol 5-(6-{3-[(1H-benzimidazol-2-yl)(1-methylpiperidin-4-yloxy)methyl]-4-fluorophenyl}hex-5-ynylimino)-2-methylcyclopent-1-enol 2-[(3-bromophenyl)(1-methylpiperidin-4-yloxy)methyl]-1H-benzimidazole, enantiomer B 5-{3-[(1H-benzimidazol-2-yl)(1-methylpiperidin-4-yloxy)methyl]phenyl}pent-4-ynylamine, enantiomer A 5-{3-[(1H-benzimidazol-2-yl)(1-methylpiperidin-4-yloxy)methyl]phenyl}pent-4-ynylamine, enantiomer B 2-[(3-bromophenyl)(1-methylpiperidin-4-yloxy)methyl]-5-fluoro-1H-benzimidazole, enantiomer A 2-[(3-bromophenyl)(1-methylpiperidin-4-yloxy)methyl]-5-fluoro-1H-benzimidazole, enantiomer B 2-[(1H-benzimidazol-2-yl)(1-methylpiperidin-4-yloxy)methyl]-4-methylphenol 2-[(1H-benzimidazol-2-yl)(1-methylpiperidin-4-yloxy)methyl]phenol enantiomer A 2-[(1H-benzimidazol-2-yl)(1-methylpiperidin-4-yloxy)methyl]phenol enantiomer B 6-[(1H-benzimidazol-2-yl)(1-methylpiperidin-4-yloxy)methyl]-2-fluoro-3-methylphenol enantiomer A 6-[(1H-benzimidazol-2-yl)(1-methylpiperidin-4-yloxy)methyl]-2-fluoro-3-methylphenol enantiomer B 6-[(1H-benzimidazol-2-yl)(1-methylpiperidin-4-yloxy)methyl]-2,3-difluorophenol enantiomer A 6-[(1H-benzimidazol-2-yl)(1-methylpiperidin-4-yloxy)methyl]-2,3-difluorophenol enantiomer B 5-{3-[(1H-benzimidazol-2-yl)(1-methylpiperidin-4-yloxy)methyl]-4-fluorophenyl}pent-4-ynylamine, dioxalate 3-{3-[benzothiazol-2-yl(1-methylpiperidin-4-yloxy)methyl]phenoxy}cyclopentylamine, oxalate 2-{[3-(3-fluoropyrrolidin-1-yl)phenyl](1-methylpiperidin-4-yloxy)methyl}benzothiazole, oxalate 5-{3-[(5-fluoro-1H-benzimidazol-2-yl)(1-methylpyrrolidin-3-ylmethoxy)methyl]phenyl}pent-4-ynylamine, oxalate 2-[(3-bromophenyl)(1-methylpyrrolidin-3-ylmethoxy)methyl]benzothiazole, oxalate (one epimer)

2-[(3-bromophenyl)(1-methylpyrrolidin-3-ylmethoxy)methyl]benzothiazole, oxalate (50/50 mixture of two epimers)

2-{(1-methylpiperidin-4-yloxy)[3-(octahydrocyclopenta[c]pyrrol-5-yloxy)phenyl]methyl}benzothiazole, dioxalate (1-{3-[benzothiazol-2-yl(1-methylpiperidin-4-yloxy)methyl]phenyl}pyrrolidin-3-yl)methylamine, dioxalate 4-{3-[(5,6-difluoro-1H-benzimidazol-2-yl)(1-methylpiperidin-4-yloxy)methyl]phenylsulfanyl}butan-1-ol 2-{3-[benzothiazol-2-yl(1-methylpiperidin-4-yloxy)methyl]phenyl}octahydrocyclopenta[c]pyrrol-5-ylamine, dioxalate 2-{[3-(3-fluoropropoxy)phenyl](1-methylpiperidin-4-yloxy)methyl}-1H-benzimidazole, oxalate 2-{[3-(2-fluoroethoxy)phenyl](1-methylpiperidin-4-yloxy)methyl}-1H-benzimidazole, oxalate 4-{3-[benzothiazol-2-yl(1-methylpiperidin-4-yloxy)methyl]phenoxy}cyclohexylamine, oxalate 6-{3-[(1-methyl-1H-benzimidazol-2-yl)(1-methylpiperidin-4-yloxy)methyl]phenyl}hex-5-ynylamine, dioxalate 1-{3-[benzothiazol-2-yl(1-methylpiperidin-4-yloxy)methyl]phenyl}pyrrolidin-2-ylmethylamine, oxalate (1-{3-[benzothiazol-2-yl(1-methylpiperidin-4-yloxy)methyl]phenyl}pyrrolidin-3-yl)(methyl)amine, oxalate (1-{3-[benzothiazol-2-yl(1-methylpiperidin-4-yloxy)methyl]phenyl}pyrrolidin-3-yl)(dimethyl)amine, oxalate 2-{[3-(5-methylhexahydropyrrolo[3,4-c]pyrrol-2-yl)phenyl](1-methylpiperidin-4-yloxy)methyl}benzothiazole, dioxalate 2-[(2-fluoro-5-methoxyphenyl)(1-methylpiperidin-4-yloxy)methyl]-1H-benzimidazole, oxalate 3-[(1H-benzimidazol-2-yl)(1-methylpiperidin-4-yloxy)methyl]-4-fluorophenol, oxalate 2-{[2-fluoro-5-(2-fluoroethoxy)phenyl](1-methylpiperidin-4-yloxy)methyl}-1H-benzimidazole, oxalate 2-[(2-fluoro-5-methylphenyl)(1-methylpiperidin-4-yloxy)methyl]-1H-benzimidazole, oxalate 4-{3-[(1-methylpiperidin-4-yloxy)(5,6,7-trifluoro-1H-benzimidazol-2-yl)methyl]phenylsulfanyl}butylamine, oxalate 4-{3-[(5,6-difluoro-1H-benzimidazol-2-yl)(1-methylpiperidin-4-yloxy)methyl]phenylsulfanyl}butylamine, oxalate 6-(3-{[1-(2-ethoxyethyl)-1H-benzimidazol-2-yl](1-methylpiperidin-4-yloxy)methyl}phenyl)hex-5-ynylamine, dioxalate 6-(3-{[1-(2-methoxyethyl)-1H-benzimidazol-2-yl](1-methylpiperidin-4-yloxy)methyl}phenyl)hex-5-ynylamine, dioxalate 2-{[3-(3-fluoropropylsulfanyl)phenyl](1-methylpiperidin-4-yloxy)methyl}-1H-benzimidazole, dioxalate 5-fluoro-2-[(2-fluoro-5-trifluoromethoxyphenyl)(1-methylpiperidin-4-yloxy)methyl]-1H-benzimidazole, oxalate 4,5,6-trifluoro-2-[(2-fluoro-5-trifluoromethoxyphenyl)(1-methylpiperidin-4-yloxy)methyl]-1H-benzimidazole 5,6-difluoro-2-[(2-fluoro-5-trifluoromethoxyphenyl)(1-methylpiperidin-4-yloxy)methyl]-1 H-benzimidazole 2-{[2-fluoro-5-(2,2,2-trifluoroethoxy)phenyl](1-methylpiperidin-4-yloxy)methyl}-1H-benzimidazole 2-[(2,6-difluoro-4-methylphenyl)(1-methylpiperidin-4-yloxy)methyl]-1H-benzimidazole 2-[(2-chloro-5-trifluoromethoxyphenyl)(1-methylpiperidin-4-yloxy)methyl]-1H-benzimidazole, oxalate 2-[(2-fluoro-5-trifluoromethoxyphenyl)(1-methylpiperidin-4-yloxy)methyl]benzothiazole, oxalate 2-[(4-chloro-2,6-difluorophenyl)(1-methylpiperidin-4-yloxy)methyl]-1H-benzimidazole 7-fluoro-2-[(2-fluoro-5-trifluoromethoxyphenyl)(1-methylpiperidin-4-yloxy)methyl]-1H-benzimidazole, oxalate 2-[(2,6-difluoro-4-methylphenyl)(1-methylpiperidin-4-yloxy)methyl]benzothiazole, oxalate 2-[(4-chloro-2,6-difluorophenyl)(1-methylpiperidin-4-yloxy)methyl]benzothiazole, oxalate 2-[(3-ethoxy-2,6-difluorophenyl)(1-methylpiperidin-4-yloxy)methyl]-1H-benzimidazole 2-[(2,6-difluoro-4-methylphenyl)(1-methylpiperidin-4-yloxy)methyl]benzoxazole, oxalate 2-[(1-methylpiperidin-4-yloxy)(4-trifluoromethylphenyl)methyl]-1H-benzimidazole 2-[(2-fluoro-4-trifluoromethylphenyl)(1-methylpiperidin-4-yloxy)methyl]-1H-benzimidazole 2-[(2,4-dimethylphenyl)(1-methylpiperidin-4-yloxy)methyl]-1H-benzimidazole 2-[(3-methoxyphenyl)(1-methylpiperidin-4-yloxy)methyl]-1H-benzimidazole 2-[chroman-7-yl(1-methylpiperidin-4-yloxy)methyl]-1H-benzimidazole
2-[(2-fluoro-4-methylphenyl)(1-methylpiperidin-4-yloxy)methyl]benzoxazole, oxalate
2-[(3,5-bis-trifluoromethylphenyl)(1-methylpiperidin-4-yloxy)methyl]-1H-benzimidazole, oxalate
5-fluoro-2-[(2-fluoro-4-methylphenyl)(1-methylpiperidin-4-yloxy)methyl]-1H-benzimidazole
2-[(2,3-difluoro-4-methylphenyl)(1-methylpiperidin-4-yloxy)methyl]-1H-benzimidazole
2-[(3-chloro-4-methylphenyl)(1-methylpiperidin-4-yloxy)methyl]-1H-benzimidazole
ethyl 2-[(2-fluoro-5-trifluoromethoxyphenyl)(1-methylpiperidin-4-yloxy)methyl]benzimidazole-1-carboxylate, oxalate
2-[(3-fluoro-4-methylphenyl)(1-methylpiperidin-4-yloxy)methyl]-1H-benzimidazole
2-[(5-bromo-2-fluorophenyl)(1-methylpiperidin-4-yloxy)methyl]-1H-benzimidazole
6-{3-[(1H-benzimidazol-2-yl)(1-methylpiperidin-4-yloxy)methyl]-4-fluorophenyl}hex-5-ynylamine, oxalate
5-{4-fluoro-3-[(5-fluoro-1H-benzimidazol-2-yl)(1-methylpiperidin-4-yloxy)methyl]phenyl}pent-4-ynylamine
ethyl (5-{3-[(1H-benzimidazol-2-yl)(1-methylpiperidin-4-yloxy)methyl]-4-fluorophenyl}pent-4-ynyl)carbamate
2-[(1H-benzimidazol-2-yl)(1-methylpiperidin-4-yloxy)methyl]-4-chlorophenol
ethyl (5-{4-fluoro-3-[(5-fluoro-1H-benzimidazol-2-yl)(1-methylpiperidin-4-yloxy)methyl]phenyl}pent-4-ynyl)carbamate
2-[(1H-benzimidazol-2-yl)(1-methylpiperidin-4-yloxy)methyl]-4-trifluoromethoxyphenol
2-[(1H-benzimidazol-2-yl)(1-methylpiperidin-4-yloxy)methyl]-4-fluorophenol
2-[(1H-benzimidazol-2-yl)(1-methylpiperidin-4-yloxy)methyl]-4-methoxyphenol
2-[(1H-benzimidazol-2-yl)(1-methylpiperidin-4-yloxy)methyl]-5-methylphenol
2-[(1H-benzimidazol-2-yl)(1-methylpiperidin-4-yloxy)methyl]-4-bromophenol
2-[(1H-benzimidazol-2-yl)(1-methylpiperidin-4-yloxy)methyl]-4-ethoxyphenol
2-[(1H-indol-7-yl)(1-methylpiperidin-4-yloxy)methyl]-1H-benzimidazole
2-[(1H-benzimidazol-2-yl)(1-methylpiperidin-4-yloxy)methyl]-4,6-difluorophenol
2-[(1H-benzimidazol-2-yl)(1-methylpiperidin-4-yloxy)methyl]-4,6-dichlorophenol
2-[(1H-benzimidazol-2-yl)(1-methylpiperidin-4-yloxy)methyl]-6-fluorophenol
2-[(1H-benzimidazol-2-yl)(1-methylpiperidin-4-yloxy)methyl]-3-fluorophenol
2-[(1H-benzimidazol-2-yl)(1-methylpiperidin-4-yloxy)methyl]-4,5-difluorophenol
2-[(1H-benzimidazol-2-yl)(1-methylpiperidin-4-yloxy)methyl]-5-fluorophenol
2-[(1H-benzimidazol-2-yl)(1-methylpiperidin-4-yloxy)methyl]-5-chlorophenol
2-[(1H-benzimidazol-2-yl)(1-methylpiperidin-4-yloxy)methyl]-6-methylphenol
2-[(1H-benzimidazol-2-yl)(1-methylpiperidin-4-yloxy)methyl]-4-methylsulfanylphenol
2-[(1H-benzimidazol-2-yl)(1-methylpiperidin-4-yloxy)methyl]-4-ethylsulfanylphenol
3-[(1H-benzimidazol-2-yl)(1-methylpiperidin-4-yloxy)methyl]biphenyl-4-ol
2-[(1H-benzimidazol-2-yl)(1-methylpiperidin-4-yloxy)methyl]-4-tert-butyl phenol
2-[(1H-benzimidazol-2-yl)(1-methylpiperidin-4-yloxy)methyl]-4-propylphenol
2-[(1H-benzimidazol-2-yl)(1-methylpiperidin-4-yloxy)methyl]-6-methoxyphenol
2-[(1H-benzimidazol-2-yl)(1-methy-piperidin-4-yloxy)methyl]-3-fluoro-5-methylphenol
2-[(1H-benzimidazol-2-yl)(1-methylpiperidin-4-yloxy)methyl]-3-chlorophenol
2-[(1H-benzimidazol-2-yl)(1-methylpiperidin-4-yloxy)methyl]-6-fluoro-4-ethylphenol
2-[(1H-benzimidazol-2-yl)(1-methylpiperidin-4-yloxy)methyl]-4-benzylphenol
2-[(1H-benzimidazol-2-yl)(1-methylpiperidin-4-yloxy)methyl]-4-trifluoromethylphenol
2-[(1H-benzimidazol-2-yl)(1-methylpiperidin-4-yloxy)methyl]-4-chloro-6-fluorophenol
2-[(1H-benzimidazol-2-yl)(1-methylpiperidin-4-yloxy)methyl]-5-fluoro-3-methylphenol
6-[(1H-benzimidazol-2-yl)(1-methylpiperidin-4-yloxy)methyl]-2-fluoro-3-methylphenol
6-[(1H-benzimidazol-2-yl)(1-methylpiperidin-4-yloxy)methyl]indan-5-ol
2-[(1H-benzimidazol-2-yl)(1-methylpiperidin-4-yloxy)methyl]-4-propoxyphenol
2-[(1H-benzimidazol-2-yl)(1-methylpiperidin-4-yloxy)methyl]-4-(1-methyl-1-phenylethyl)phenol
2-[(1H-benzimidazol-2-yl)(1-methylpiperidin-4-yloxy)methyl]-4-(2-fluoroethoxy)phenol
2-[(1H-benzimidazol-2-yl)(1-methylpiperidin-4-yloxy)methyl]-4-(3-fluoropropoxy)phenol
2-[(1H-benzimidazol-2-yl)(1-methylpiperidin-4-yloxy)methyl]-4-fluoro-6-methylphenol
2-[(1H-benzimidazol-2-yl)(1-methylpiperidin-4-yloxy)methyl]-6-fluoro-4-methoxyphenol
2-[(1H-benzimidazol-2-yl)(1-methylpiperidin-4-yloxy)methyl]-4-phenoxyphenol
2-[(1H-benzimidazol-2-yl)(1-methylpiperidin-4-yloxy)methyl]-4-fluoro-6-methoxyphenol
2-[(1H-benzimidazol-2-yl)(1-methylpiperidin-4-yloxy)methyl]-4,5-dimethylphenol
2-[(1H-benzimidazol-2-yl)(1-methylpiperidin-4-yloxy)methyl]-4-(3-fluoropropylsulfanyl)phenol
2-[(1H-benzimidazol-2-yl)(1-methylpiperidin-4-yloxy)methyl]-4-fluoro-5-methylphenol
2-[(1H-benzimidazol-2-yl)(1-methylpiperidin-4-yloxy)methyl]-4-(2-fluoroethylsulfanyl)phenol
3-[(1H-benzimidazol-2-yl)(1-methylpiperidin-4-yloxy)methyl]-2-hydroxybiphenyl
2-[(1H-benzimidazol-2-yl)(1-methylpiperidin-4-yloxy)methyl]-6-ethylphenol
2-[(1H-benzimidazol-2-yl)(1-methylpiperidin-4-yloxy)methyl]-5-trifluoromethylphenol
2-[(1H-benzimidazol-2-yl)(1-methylpiperidin-4-yloxy)methyl]-4-hydroxyphenol
2-[(1H-benzimidazol-2-yl)(1-methylpiperidin-4-yloxy)methyl]-5,6,7,8-tetrahydro-1-naphthol
2-[(1H-benzimidazol-2-yl)(1-methylpiperidin-4-yloxy)methyl]-6-trifluoromethoxyphenol
2-[(1H-benzimidazol-2-yl)(1-methylpiperidin-4-yloxy)methyl]-5-trifluoromethoxyphenol
6-[(1H-benzimidazol-2-yl)(1-methylpiperidin-4-yloxy)methyl]-2-fluoro-3,4-dimethylphenol 6-[(1H-benzimidazol-2-yl)(1-methylpiperidin-4-yloxy)methyl]-3-fluoro-2-methylphenol 6-[(1H-benzimidazol-2-yl)(1-methylpiperidin-4-yloxy)methyl]-2,4-difluoro-3-methylphenol 6-[(1H-benzimidazol-2-yl)(1-methylpiperidin-4-yloxy)methyl]-2,3-difluorophenol (1-{3-[benzothiazol-2-yl(1-methylpiperidin-4-yloxy)methyl]phenyl}-azetidin-3-yl)dimethylamine, oxalate 1-{3-[(1H-benzimidazol-2-yl)(1-methylpiperidin-4-yloxy)methyl]phenyl}pyrrolidin-3-ol, oxalate 2-{(1-methylpiperidin-4-yloxy)[3-(pyrrolidin-3-yloxy)phenyl]methyl}-1H-benzimidazole, dioxalate 2-[(5-chloro-2-fluorophenyl)(1-methylpiperidin-4-yloxy)methyl]-1H-benzimidazole, oxalate 2-[(2-fluoro-5-trifluoromethylphenyl)(1-methylpiperidin-4-yloxy)methyl]-1H-benzimidazole, oxalate 6-{3-[(1-ethyl-1H-benzimidazol-2-yl)(1-methylpiperidin-4-yloxy)methyl]phenyl}hex-5-ynylamine, oxalate 2-[(2-fluoro-5-methoxyphenyl)(1-methylpyrrolidin-3-ylmethoxy)methyl]-1H-benzimidazole, oxalate 2-[(1-methylpiperidin-4-yloxy)(3-trifluoromethylsulfanylphenyl)methyl]-1H-benzimidazole, oxalate 2-[(4-fluoro-3-trifluoromethoxyphenyl)(1-methylpiperidin-4-yloxy)methyl]-1H-benzimidazole, oxalate 2-[(2-fluoro-5-propoxyphenyl)(1-methylpiperidin-4-yloxy)methyl]-1H-benzimidazole, oxalate 4-[(1H-benzimidazol-2-yl)(1-methylpiperidin-4-yloxy)methyl]phenol 2-{[3-(3,3-difluoropyrrolidin-1-yl)phenyl](1-methylpiperidin-4-yloxy)methyl}-1H-benzimidazole, dioxalate 2-{[3-(5-fluorohexahydrocyclopenta[c]pyrrol-2-yl)phenyl](1-methylpiperidin-4-yloxy)methyl}benzothiazole, dioxalate 6-{3-[(1H-benzimidazol-2-yl)(1-methylpiperidin-4-yloxy)methyl]phenylsulfanyl}hexylamine, oxalate 5-{3-[(1H-benzimidazol-2-yl)(1-methylpiperidin-4-yloxy)methyl]phenylsulfanylmethyl}oxazolidin-2-one N-(6-{3-[(1H-benzimidazol-2-yl)(1-methylpiperidin-4-yloxy)methyl]phenylsulfanyl}hexyl)guanidine, dihydrochloride 4-{3-[(1H-benzimidazol-2-yl)(1-methylpiperidin-4-yloxy)methyl]phenylsulfanyl}but-2-enylamine 4-{3-[(1H-benzimidazol-2-yl)(1-methylpiperidin-4-yloxy)methyl]phenylsulfanyl}but-2-enylamine, oxalate N-(2-{3-[(1H-benzimidazol-2-yl)(1-methylpiperidin-4-yloxy)methyl]phenylsulfanyl}ethyl)-N-isobutyrylguanidine 3-{3-[(1H-benzimidazol-2-yl)(1-methylpiperidin-4-yloxy)methyl]phenyl}allylamine cis-2-{3-[(1H-benzimidazol-2-yl)(1-methylpiperidin-4-yloxy)methyl]phenylsulfanylmethyl}cyclopropylmethylamine N-(3-{3-[(1H-benzimidazol-2-yl)(1-methylpiperidin-4-yloxy)methyl]phenyl}allyl)guanidine, trihydrochloride 2-[(azetidin-3-ylmethoxy)(3-bromophenyl)methyl]-1H-benzimidazole 2-[(3-bromophenyl)(1-methylazetidin-3-ylmethoxy)methyl]-1H-benzimidazole 2-[(2,6-difluorophenyl)(1-methylpiperidin-4-yloxy)methyl]-1H-benzimidazole 2-[(2-fluoro-4-methylphenyl)(1-methylpiperidin-4-yloxy)methyl]-1H-benzimidazole 2-[(5-ethylsulfanyl-2-fluorophenyl)(1-methylpiperidin-4-yloxy)methyl]-1H-benzimidazole 2-[(azetidin-3-ylmethoxy)(2-fluoro-5-trifluoromethoxyphenyl)methyl]-1H-benzimidazole, oxalate 2-[(2-fluoro-5-trifluoromethoxyphenyl)(1-methylazetidin-3-ylmethoxy)methyl]-1H-benzimidazole, oxalate 2-[(3-ethylsulfanyl-2,6-difluorophenyl)(1-methylpiperidin-4-yloxy)methyl]-1H-benzimidazole 2-[(2,2-difluorobenzo[1,3]dioxol-5-yl)(1-methylpiperidin-4-yloxy)methyl]-1H-benzimidazole 2-[(piperidin-4-yloxy)thiophen-3-ylmethyl]-1H-benzimidazole 2-[(1-methylpiperidin-4-yloxy)thiophen-3-ylmethyl]-1H-benzimidazole 2-[(piperidin-4-yloxy)thiophen-2-ylmethyl]-1H-benzimidazole 2-[(1-methylpiperidin-4-yloxy)thiophen-2-ylmethyl]-1H-benzimidazole as well as their enantiomers, diastereomers, mixtures thereof and pharmaceutically acceptable salts, free forms, tautomers, hydrates and solvates.

\* \* \* \* \*